(12) United States Patent
Wu et al.

(10) Patent No.: US 8,946,266 B2
(45) Date of Patent: Feb. 3, 2015

(54) SUBSTITUTED TRIAZOLE AND IMIDAZOLE DERIVATIVES AS GAMMA SECRETASE MODULATORS

(75) Inventors: Tongfei Wu, Jette (BE); Henricus Jacobus Maria Gijsen, Breda (NL); Frederik Jan Rita Rombouts, Wilrijk (BE); François Paul Bischoff, Vosselaar (BE); Didier Jean-Claude Berthelot, Edegem (BE); Daniel Oehlrich, Malle (BE); Michel Anna Jozef De Cleyn, Lille (BE); Serge Maria Aloysius Pieters, Hulst (NL); Garrett Berlond Minne, Bissegem (BE); Adriana Ingrid Velter', Antwerp (BE); Sven Franciscus Anna Van Brandt, Lier (BE); Michel Surkyn, Merksplas (BE)

(73) Assignees: Janssen Pharmaceuticals, Inc., Titusville, NJ (US); Cellzome Limited, Brentford, Middlesex (GB)

( * ) Notice: Subject to any disclaimer, the term of this patent is extended or adjusted under 35 U.S.C. 154(b) by 22 days.

(21) Appl. No.: 13/382,659

(22) PCT Filed: Jul. 13, 2010

(86) PCT No.: PCT/EP2010/060083
§ 371 (c)(1),
(2), (4) Date: Jan. 6, 2012

(87) PCT Pub. No.: WO2011/006903
PCT Pub. Date: Jan. 20, 2011

(65) Prior Publication Data
US 2012/0135981 A1 May 31, 2012

(30) Foreign Application Priority Data

Jul. 15, 2009 (EP) .................................... 09165585
Jun. 1, 2010 (EP) .................................... 10164625

(51) Int. Cl.
| | | |
|---|---|---|
| *A61K 31/4439* | (2006.01) | |
| *C07D 401/14* | (2006.01) | |
| *C07D 233/60* | (2006.01) | |
| *C07D 403/10* | (2006.01) | |
| *C07D 405/14* | (2006.01) | |
| *C07D 471/04* | (2006.01) | |
| *C07D 487/04* | (2006.01) | |
| *C07D 498/04* | (2006.01) | |

(52) U.S. Cl.
CPC ............ *C07D 233/60* (2013.01); *C07D 401/14* (2013.01); *C07D 403/10* (2013.01); *C07D 405/14* (2013.01); *C07D 471/04* (2013.01); *C07D 487/04* (2013.01); *C07D 498/04* (2013.01)
USPC ......................... 514/341; 514/340; 546/272.4

(58) Field of Classification Search
USPC ............................... 546/272.4; 514/340, 341
See application file for complete search history.

(56) References Cited

U.S. PATENT DOCUMENTS

| | | |
|---|---|---|
| 5,767,144 A | 6/1998 | Winn et al. |
| 6,114,334 A | 9/2000 | Kerrigan et al. |
| 7,923,563 B2 | 4/2011 | Kushida et al. |
| 2002/0128319 A1 | 9/2002 | Koo et al. |
| 2006/0004013 A1 | 1/2006 | Kimura et al. |
| 2008/0280948 A1 | 11/2008 | Baumann et al. |
| 2009/0062529 A1 | 3/2009 | Kimura et al. |
| 2010/0137320 A1 | 6/2010 | Huang et al. |

FOREIGN PATENT DOCUMENTS

| | | |
|---|---|---|
| EP | 1757591 | 2/2007 |
| JP | 2003/502313 | 1/2003 |
| WO | WO 01/78721 | 10/2001 |
| WO | WO 01/87845 | 11/2001 |
| WO | WO 02/069946 | 9/2002 |
| WO | WO 2004/017963 | 3/2004 |
| WO | WO 2004/076448 | 9/2004 |

(Continued)

OTHER PUBLICATIONS

Yu et al., "Physical characterization of, etc.," PSTT, vl. 1(3), 118-127 (1998).*
Kirk-Othmer Encyclopedia of Chemical Technology, 8, pp. 95-147 (2002).*
Vippagunta et al., "Crystalline Solids", Advanced Drug Delivery Reviews 48 (2001) 3-26.*
Guillory (in Brittain ed.), "Polymorphism in Pharmaceutical Solids.," NY: Marcel Dekker, Inc., 1999, 1-2, 125-181, 183-226.*
Jain et al., "Polymorphism in Pharmacy", Indian Drugs, 1986, 23(6) 315-329.*

(Continued)

*Primary Examiner* — Patricia L Morris
(74) *Attorney, Agent, or Firm* — Baker & Hostetler LLP

(57) ABSTRACT

The present invention is concerned with novel substituted triazole and imidazole derivatives of Formula (I)

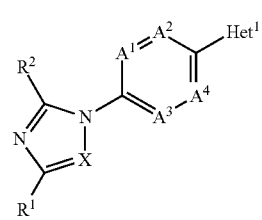

wherein $R^1$, $R^2$, $A^1$, $A^2$, $A^3$, $A^4$, X, and $Het^1$ have the meaning defined in the claims. The compounds according to the present invention are useful as gamma secretase modulators. The invention further relates to processes for preparing such novel compounds, pharmaceutical compositions comprising said compounds as an active ingredient as well as the use of said compounds as a medicament.

14 Claims, No Drawings

(56) References Cited

FOREIGN PATENT DOCUMENTS

| WO | WO 2004/110350 A2 | 12/2004 |
|---|---|---|
| WO | WO 2005/016892 | 5/2005 |
| WO | WO 2005/085245 | 9/2005 |
| WO | WO 2005/115990 | 12/2005 |
| WO | WO 2006/135667 | 12/2006 |
| WO | WO 2007/034252 | 3/2007 |
| WO | WO 2007/038314 | 4/2007 |
| WO | WO 2007/043786 | 4/2007 |
| WO | WO 2007/044895 | 4/2007 |
| WO | WO 2007/105053 | 9/2007 |
| WO | WO 2007/113276 | 10/2007 |
| WO | WO 2007/131991 | 11/2007 |
| WO | WO 2008/065199 | 6/2008 |
| WO | WO 2008/082490 | 7/2008 |
| WO | WO 2008/097538 | 8/2008 |
| WO | WO 2008/099210 | 8/2008 |
| WO | WO 2008/100412 | 8/2008 |
| WO | WO 2008/137139 | 11/2008 |
| WO | WO 2008/156580 | 12/2008 |
| WO | WO 2009/005729 A1 | 1/2009 |
| WO | WO 2009/032277 A1 | 3/2009 |
| WO | WO 2009/050227 | 4/2009 |
| WO | WO 2009/073777 A1 | 6/2009 |
| WO | WO 2009/076352 A1 | 6/2009 |
| WO | WO 2009/103652 | 8/2009 |
| WO | WO 2010/010188 | 1/2010 |
| WO | WO 2010/052199 | 5/2010 |
| WO | WO 2010/054067 | 5/2010 |
| WO | WO 2010/065310 | 6/2010 |
| WO | WO 2010/070008 | 6/2010 |
| WO | WO 2010/083141 | 7/2010 |
| WO | WO 2010/089292 | 8/2010 |
| WO | WO 2010/094647 | 8/2010 |
| WO | WO 2010/098487 | 9/2010 |
| WO | WO 2010/098488 | 9/2010 |
| WO | WO 2010/098495 | 9/2010 |
| WO | WO 2010/100606 | 9/2010 |
| WO | WO 2010/106745 | 9/2010 |
| WO | WO 2010/126745 | 11/2010 |
| WO | WO 2010/137320 | 12/2010 |
| WO | WO 2010/145883 | 12/2010 |
| WO | WO 2011/006903 | 1/2011 |
| WO | WO 2011/086098 | 7/2011 |
| WO | WO 2011/086099 | 7/2011 |
| WO | WO 2012/131539 | 4/2012 |
| WO | WO 2012/126984 | 9/2012 |
| WO | WO 2013/010904 | 1/2013 |

OTHER PUBLICATIONS

Dorwald, Side Reactions in Organic Synthesis, 2005, Wiley: VCH Weinheim Preface, pp. 1-15 & Chapter 8, pp. 279-308.*
Eriksen, J., et al. "NSAIDs and Enanatiomers of Flurbiprofen Target Gamma-Secretase and Lower A-beta-42 in vivo", Journal of Clinical Investigation, New York, NY US vol. 112, No. 3, (2003), XP002311406.
Jadhav, G., et al. "Ammonium Metavanadate: A Novel Catalyst for Synthesis of 2-Substituted Benzimidazole Derivatives", Chinese Chemical Letters, vol. 20 (2009) pp. 292-295.
Larner, A., "Secretases as Therapeutic Targets in Alzheimer's Disease: Patents 2000-2004", Exp. Opinion Ther. Patents 14, p. 1403 (2004).
Marjaux, E., et al. "γ-Secretase Inhibitors: Still in the Running as Alzheimer's Therapeutics", Drug Discovery Today: Therapeutics Strategies 1, p. 1 (2004).
Matthews, D., et al. "A Convenient Procedure for the Preparation of 4(5)-Cyanoimidazoles", Journal of Organic Chemistry, vol. 51 (1986) pp. 3228-3231.
Peretto, D., et al. "Synthesis and Biological Activity of Fluriprofen Analogues as Selective Inhibitors of 62 -Amylid 1-42 Secretion", J. Med. Chem. 48 p. 5705 (2005).
Schweisguth, F., et al. Regulation of Notch Signaling Activity, Curr. Biol. 14, p. R129 (2004).
Steiner, H., "Uncovering γ-Sucretase", Curr. Alzheimer Research 1(3), p. 175 (2004).
Tanzi, R., et al. "Twenty Years of the Alzlheimer's Disease Amyloid Hypothesis: A Genetic Perspective", Cell, vol. 120, (2005) p. 545-555.
Citron et al. "Mutant Presenilins of Alzheimer's Disease Increase Production of 42-Residue Amyloid β-Protein in Both Transfected Cells and Transgenic Mice", Nature Medicine, Jan. 1997, 3(1), 67-72.
"Crystallization", Kirk-Othmer Encyclopedia of Chemical Technology, 2002, 8, 95-147.
Dyatkin et al., "Determination of the Absolute Configuration of a Key Tricyclic Component of a Novel Vasopressin Receptor Antagonist by Use of Vibrational Circular Dichroism", Chirality, 2002, 14, 215-219.
Garofalo, "Patents Targeting Gamma-Secretase Inhibition and Modulation for the Treatment of Alzheimer's Disease: 2004-2008", Expert Opinion Ther. Patents, 2008, 18(7), 693-703.
Greene et al., "Protective Groups in Organic Synthesis", John Wiley & Sons, Inc., Third Edition, 1999, 3 pages.
Jain et al., "Polymorphism in Pharmacy", Indian Drugs, 1986, 23(6), 315-329.
Moechars et al., "Early Phenotypic Changes in Transgenic Mice That Overexpress Different Mutants of Amyloid Precursor Protein in Brain", J. Biol. Chem., 1999, 274(10), 6483-6492.
Morihara et al., "Selective Inhibition of Aβ42 Production by NSAID R-Enantiomers", Journal of Neurochemistry, 2002, 83, 1009-1012.
Oumata et al., "Roscovitine-Derived, Dual-Specificity Inhibitors of Cyclin-Dependent Kinases and Casein Kinases 1", J. Med. Chem., 2008, 51, 5229-5242.
Sechi et al., "Design and Synthesis of Novel Indole β-Diketo Acid Derivatives as HIV-1 Integrase Inhibitors", J. Med. Chem., 2004, 47, 5298-5310.
Wang et al., "Preparation of a-Chloroketones by the Chloracetate Claisen Reaction", Synlett, 2000, 6, 902-904.
Weggen et al., "A Subset of NSAIDs Lower Amyloidegenic Aβ42 Independently of Cyclooxygenase Activity", Nature, Nov. 2001, 414, 212-216.
West, "Solid State Chemistry and its Applications", Wiley, New York, 1988, 16 pages (see pp. 358 & 365).
Zettl et al., "Exploring the Chemical Space of γ-Secretase Modulators",Trends in Pharmaceutical Sciences, 2010, 31(9), 402-410.

* cited by examiner

SUBSTITUTED TRIAZOLE AND IMIDAZOLE DERIVATIVES AS GAMMA SECRETASE MODULATORS

CROSS REFERENCE TO RELATED APPLICATIONS

This application is a national stage application of Patent Application No. PCT/EP2010/060083, filed Jul. 13, 2010, which in turn claims the benefit of EPO Patent Application No. 10164625.5 filed Jun. 1, 2010 and EPO Patent Application No. 09165585.2 filed Jul. 15, 2009. The complete disclosures of the aforementioned related patent applications are hereby incorporated herein by reference for all purposes.

FIELD OF THE INVENTION

The present invention is concerned with novel substituted triazole and imidazole derivatives useful as gamma secretase modulators. The invention further relates to processes for preparing such novel compounds, pharmaceutical compositions comprising said compounds as an active ingredient as well as the use of said compounds as a medicament.

BACKGROUND OF THE INVENTION

Alzheimer's Disease (AD) is a progressive neurodegenerative disorder marked by loss of memory, cognition, and behavioral stability. AD afflicts 6-10% of the population over age 65 and up to 50% over age 85. It is the leading cause of dementia and the third leading cause of death after cardiovascular disease and cancer. There is currently no effective treatment for AD. The total net cost related to AD in the U.S. exceeds $100 billion annually.

AD does not have a simple etiology, however, it has been associated with certain risk factors including (1) age, (2) family history and (3) head trauma; other factors include environmental toxins and low levels of education. Specific neuropathological lesions in the limbic and cerebral cortices include intracellular neurofibrillary tangles consisting of hyperphosphorylated tau protein and the extracellular deposition of fibrillar aggregates of amyloid beta peptides (amyloid plaques). The major component of amyloid plaques are the amyloid beta (A-beta, Abeta or Aβ) peptides of various lengths. A variant thereof, which is the Aβ1-42-peptide (Abeta-42), is believed to be the major causative agent for amyloid formation. Another variant is the Aβ1-40-peptide (Abeta-40). Amyloid beta is the proteolytic product of a precursor protein, beta amyloid precursor protein (beta-APP or APP).

Familial, early onset autosomal dominant forms of AD have been linked to missense mutations in the β-APP and in the presenilin proteins 1 and 2. In some patients, late onset forms of AD have been correlated with a specific allele of the apolipoprotein E (ApoE) gene, and, more recently, the finding of a mutation in alpha2-macroglobulin, which may be linked to at least 30% of the AD population. Despite this heterogeneity, all forms of AD exhibit similar pathological findings. Genetic analysis has provided the best clues for a logical therapeutic approach to AD. All mutations, found to date, affect the quantitative or qualitative production of the amyloidogenic peptides known as Abeta-peptides (Aβ), specifically Aβ42, and have given strong support to the "amyloid cascade hypothesis" of AD (Tanzi and Bertram, 2005, Cell 120, 545). The likely link between Aβ peptide generation and AD pathology emphasizes the need for a better understanding of the mechanisms of Aβ production and strongly warrants a therapeutic approach at modulating Aβ levels.

The release of Aβ peptides is modulated by at least two proteolytic activities referred to as β- and γ-secretase cleavage at the N-terminus (Met-Asp bond) and the C-terminus (residues 37-42) of the Aβ peptide, respectively. In the secretory pathway, there is evidence that β-secretase cleaves first, leading to the secretion of s-APPβ (sβ) and the retention of a 11 kDa membrane-bound carboxy terminal fragment (CTF). The latter is believed to give rise to Aβ peptides following cleavage by γ-secretase. The amount of the longer isoform, Aβ42, is selectively increased in patients carrying certain mutations in a particular protein (presenilin), and these mutations have been correlated with early-onset familial AD. Therefore, Aβ42 is believed by many researchers to be the main culprit of the pathogenesis of AD.

It has now become clear that the γ-secretase activity cannot be ascribed to a single protein, but is in fact associated with an assembly of different proteins.

The gamma (γ)-secretase activity resides within a multiprotein complex containing at least four components: the presenilin (PS) heterodimer, nicastrin, aph-1 and pen-2. The PS heterodimer consists of the amino- and carboxyterminal PS fragments generated by endoproteolysis of the precursor protein. The two aspartates of the catalytic site are at the interface of this heterodimer. It has recently been suggested that nicastrin serves as a γ-secretase-substrate receptor. The functions of the other members of γ-secretase are unknown, but they are all required for activity (Steiner, 2004. Curr. Alzheimer Research 1(3): 175-181).

Thus, although the molecular mechanism of the second cleavage-step has remained elusive until now, the γ-secretase-complex has become one of the prime targets in the search for compounds for the treatment of AD.

Various strategies have been proposed for targeting γ-secretase in AD, ranging from targeting the catalytic site directly, developing substrate-specific inhibitors and modulators of γ-secretase activity (Marjaux et al., 2004. Drug Discovery Today: Therapeutic Strategies, Volume 1, 1-6). Accordingly, a variety of compounds were described that have secretases as targets (Lamer, 2004. Secretases as therapeutics targets in AD: patents 2000-2004. Expert Opin. Ther. Patents 14, 1403-1420).

Indeed, this finding was supported by biochemical studies in which an effect of certain Non-Steroidal Anti-Inflammatory Drugs (NSAIDs) on γ-secretase was shown (US 2002/0128319; Eriksen (2003) J. Clin. Invest. 112, 440). Potential limitations for the use of NSAIDs to prevent or treat AD are their inhibition activity of cyclooxygenase (COX) enzymes, which can lead to unwanted side effects, and their low CNS penetration (Peretto et al., 2005, J. Med. Chem. 48, 5705-5720). More recently the NSAID R-flurbiprofen, an enantiomer lacking Cox-inhibitory activity and related gastric toxicity, has failed in a large phase III trial since the drug did not improve thinking ability or the ability of patients to carry out daily activities significantly more than those patients with placebo.

WO-2009/032277 relates to heterocyclic compounds useful as γ-secretase modulators.

WO-2009/050227 relates to pyridazine derivatives for inhibiting beta amyloid peptide reduction.

WO-2004/110350 relates to thiazolyl derivatives and their use in modulating amyloid beta.

US20090062529 relates to multi-cyclic cinnamide derivatives effective for treatment of a neurodegenerative disease caused by amyloid-β.

Journal of Organic Chemistry; vol. 51; no. 16; p. 3228-3231; Matthews, Donald P. et al., describes synthetic procedures for the preparation of 4(5)-cyanoimidazoles, including 2-[4-(1H-imidazol-1-yl)phenyl]-4-(trifluoromethyl)-1H-Imidazole. However no use is mentioned for these compounds.

There is a strong need for novel compounds which modulate γ-secretase activity thereby opening new avenues for the treatment of AD. It is an object of the present invention to overcome or ameliorate at least one of the disadvantages of the prior art, or to provide a useful alternative. It is accordingly an object of the present invention to provide such novel compounds.

DESCRIPTION OF THE INVENTION

It has been found that the compounds of the present invention are useful as γ-secretase modulators. The compounds according to the invention and the pharmaceutically acceptable compositions thereof, may be useful in the treatment or prevention of AD.

The present invention concerns novel compounds of Formula (I):

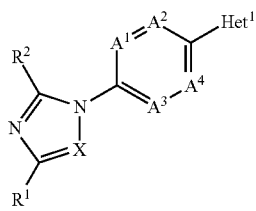

(I)

and stereoisomeric forms thereof, wherein
$R^1$ is hydrogen or $C_{1-4}$alkyl;
$R^2$ is hydrogen or $C_{1-4}$alkyl;
X is CH or N;
$A^1$ is $CR^{3a}$ or N; wherein $R^{3a}$ is hydrogen; halo; cyano; $C_{1-4}$alkyl; or $C_{1-4}$alkyloxy optionally substituted with one or more halo substituents;
$A^2$ is $CR^{3b}$ or N; wherein $R^{3b}$ is hydrogen; fluoro; or $C_{1-4}$alkyloxy;
$A^3$ and $A^4$ each independently are CH; CF; or N;
provided that no more than two of $A^1$, $A^2$, $A^3$ and $A^4$ are N;
$Het^1$ is a heterocycle, having formula (a), (b) or (c)

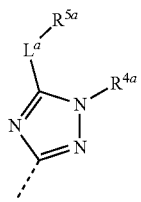

(a)

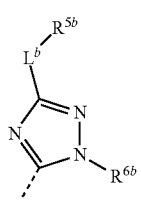

(b)

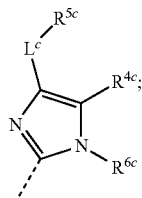

(c)

$R^{4a}$ is hydrogen; tetrahydropyranyl; tetrahydrofuranyl; piperidinyl; morpholinyl; pyrrolidinyl; $cycloC_{3-7}$alkyl; $Ar^1$; or $C_{1-6}$alkyl optionally substituted with one or more substituents each independently selected from the group consisting of halo, hydroxyl, cyano, $Ar^1$, tetrahydropyranyl, tetrahydrofuranyl, piperidinyl, morpholinyl, pyrrolidinyl, $cycloC_{3-7}$alkyl, $C_{1-6}$alkyloxy, $C_{1-6}$alkylthio, and O—$Ar^1$;
$R^{4c}$ is hydrogen; tetrahydropyranyl; tetrahydrofuranyl; piperidinyl; morpholinyl; pyrrolidinyl; $cycloC_{3-7}$alkyl; $C_{1-6}$alkyloxy; $C_{1-6}$alkylthio; $Ar^1$; or $C_{1-6}$alkyl optionally substituted with one or more substituents each independently selected from the group consisting of halo, $Ar^1$, tetrahydropyranyl, tetrahydrofuranyl, piperidinyl, morpholinyl, pyrrolidinyl, $cycloC_{3-7}$alkyl, $C_{1-6}$alkyloxy, $C_{1-6}$alkylthio, and O—$Ar^1$;
wherein in the definitions of $R^{4a}$ and $R^{4c}$ piperidinyl, morpholinyl and pyrrolidinyl may be substituted with one or more substituents each independently selected from the group consisting of $C_{2-6}$alkenyl, $C_{1-4}$acyl, halo, $C_{1-4}$alkyloxycarbonyl, and $C_{1-4}$alkyl optionally substituted with one or more halo substituents;
wherein in the definitions of $R^{4a}$ and $R^{4c}$ each $Ar^1$ independently is phenyl optionally substituted with one or more substituents each independently selected from the group consisting of halo, $C_{1-4}$alkyloxy, cyano, $NR^7R^8$, morpholinyl, and $C_{1-4}$alkyl optionally substituted with one or more halo substituents; or each $Ar^1$ independently is a 5- or 6-membered heteroaryl selected from the group consisting of furanyl, thiophenyl, pyrazolyl, oxazolyl, isoxazolyl, thiazolyl, isothiazolyl, thiadiazolyl, oxadiazolyl, pyridinyl, pyrimidinyl, pyridazinyl, and pyrazinyl, wherein said 5- or 6-membered heteroaryl is optionally substituted with one or more substituents each independently selected from the group consisting of halo, $C_{1-4}$alkyloxy, cyano, $NR^7R^8$, morpholinyl, and $C_{1-4}$alkyl optionally substituted with one or more halo substituents;
wherein in the definitions of $R^{4a}$ and $R^{4c}$ each $cycloC_{3-7}$alkyl, tetrahydropyranyl or tetrahydrofuranyl may be substituted with one or more substituents each independently selected from the group consisting of halo, $C_{1-4}$alkyloxy, cyano, and $C_{1-4}$alkyl optionally substituted with one or more halo substituents;
$R^{5a}$, $R^{5b}$ and $R^{5c}$ are hydrogen; tetrahydropyranyl; tetrahydrofuranyl; piperidinyl; morpholinyl; pyrrolidinyl; piperazinyl; hexahydro-1H-1,4-diazepin-1-yl; 1,2,3,4-tetrahydro-2-quinolinyl; 3,4-dihydro-2(1H)-isoquinolinyl; 3,4-dihydro-1(2H)-quinolinyl; 2,2-difluoro-1,3-benzodioxol-5-yl; 2,2-difluoro-1,3-benzodioxol-4-yl; 1,6-dihydro-1-methyl-6-oxo-3-pyridinyl; 1,2-dihydro-1-methyl-2-oxo-3-pyridinyl; 2,3-dihydro-4H-1,4-benzoxazin-4-yl; 3,4-dihydro-1,5-benzoxazepin-5(2H)-yl; $cycloC_{3-7}$alkyl; $Ar^2$; or $C_{1-6}$alkyl optionally substituted with one or more substituents each independently selected from the group consisting of halo, $C_{1-4}$alkyloxy, $C_{1-4}$acyl, and $C_{1-4}$alkyloxycarbonyl;

wherein in the definitions of $R^{5a}$, $R^{5b}$ and $R^{5c}$ tetrahydrofuranyl, tetrahydropyranyl, piperidinyl, morpholinyl, pyrrolidinyl, piperazinyl, hexahydro-1H-1,4-diazepin-1-yl, 1,2,3,4-tetrahydro-2-quinolinyl, 3,4-dihydro-2(1H)-isoquinolinyl, 3,4-dihydro-1(2H)-quinolinyl and cycloC$_{3-7}$alkyl may be substituted with one or more substituents each independently selected from the group consisting of C$_{2-6}$alkenyl, C$_{1-4}$acyl, halo, C$_{1-4}$alkyloxycarbonyl, C$_{1-4}$alkyl optionally substituted with one or more halo substituents, and phenyl optionally substituted with one or more substituents each independently selected from the group consisting of C$_{1-4}$alkyl and trifluoromethyl;

wherein in the definitions of $R^{5a}$, $R^{5b}$ and $R^{5c}$, $Ar^2$ is phenyl optionally substituted with one or more substituents each independently selected from the group consisting of halo, cyano, NR$^7$R$^8$, (C=O)—NR$^7$R$^8$, morpholinyl, C$_{1-4}$acyl, C$_{1-4}$alkylsulfonyl, C$_{1-4}$alkylsulfinyl, cycloC$_{3-7}$alkyl, cycloC$_{3-7}$alkyloxy, tetrahydropyranyloxy, tetrahydrofuranyloxy, C$_{1-4}$alkyloxy optionally substituted with one or more substituents each independently selected from the group consisting of halo, hydroxyl, C$_{1-4}$alkyloxy, and cyclopropyl, and C$_{1-4}$alkyl optionally substituted with one or more substituents each independently selected from the group consisting of halo, hydroxyl and C$_{1-4}$alkyloxy optionally substituted with one or more halo substituents;

or $Ar^2$ is a 5- or 6-membered heteroaryl selected from the group consisting of furanyl, thiophenyl, pyrazolyl, oxazolyl, isoxazolyl, thiazolyl, isothiazolyl, thiadiazolyl, oxadiazolyl, pyridinyl, pyrimidinyl, pyridazinyl, and pyrazinyl, wherein said 5- or 6-membered heteroaryl is optionally substituted with one or more substituents each independently selected from the group consisting of halo, C$_{1-4}$alkyloxy, cyano, NR$^7$R$^8$, morpholinyl, and C$_{1-4}$alkyl optionally substituted with one or more halo substituents;

or $Ar^2$ is quinolinyl;

$L^a$, $L^b$ and $L^c$ represent a direct bond; C$_{2-6}$alkenediyl; carbonyl; O; S; S(=O)$_p$; NR$^9$; NR$^9$—C$_{1-4}$alkanediyl; C$_{1-4}$alkanediyl-NR$^9$; NR$^{12}$—(C=O); (C=O)—NR$^{12}$; or C$_{1-6}$alkanediyl optionally substituted with one or more substituents each independently selected from the group consisting of halo and hydroxy; two geminal hydrogen atoms in said C$_{1-6}$alkanediyl may be replaced by C$_{1-6}$alkanediyl;

p represents 1 or 2;

or -$L^a$-$R^{5a}$ and $R^{4a}$; or -$L^c$-$R^{5c}$ and $R^{4c}$; can be taken together to form a bivalent radical -$L^a$-$R^{5a}$—$R^{4a}$— or -$L^c$-$R^{5c}$—$R^{4c}$—, having formula $$—(CH_2)_{m-n}—Y—(CH_2)_n— \quad (d-1)$$

$$—(CH_2)_n—Y—(CH_2)_{m-n}— \quad (d-2)$$

$$\text{-1,2-benzenediyl-}(CH_2)_r—Y—(CH_2)_{q-r}— \quad (d-3)$$

$$\text{-1,2-benzenediyl-}(CH_2)_{q-r}—Y—(CH_2)_r— \quad (d-4)$$

$$—CH=CH—CH=CH— \quad (d-5)$$

$$—CH=CH—N=CH— \quad (d-6)$$

$$—CH=N—CH=CH— \quad (d-7)$$

$$—N=CH—CH=CH— \quad (d-8); \text{ or}$$

$$—CH=CH—CH=N— \quad (d-9);$$

wherein (d-1), (d-2), (d-3) or (d-4) may be substituted on one or more CH$_2$ groups with one or two substituents each independently selected from the group consisting of hydroxyl, cyano, Ar$^3$, C$_{1-4}$acyl, and C$_{1-4}$alkyl optionally substituted with one or more substituents selected from the group consisting of halo and hydroxyl;

wherein two geminal hydrogen atoms in (d-1) or (d-2) may be replaced by C$_{2-6}$alkanediyl;

wherein (d-3) or (d-4) may be substituted on the 1,2-benzenediyl-moiety with one or more substituents each independently selected from the group consisting of halo, C$_{1-4}$alkyloxy, cyano, NR$^7$R$^8$, morpholinyl, and C$_{1-4}$alkyl optionally substituted with one or more halo substituents;

wherein (d-5), (d-6), (d-7), (d-8) or (d-9) may be substituted where possible with one or more substituents each independently selected from the group consisting of Ar$^3$, (C=O)—Ar$^3$, O—Ar$^3$, NR$^{11}$—Ar$^3$, C$_{1-4}$acyl, and C$_{1-4}$alkyl optionally substituted with one or more halo substituents;

Y represents a direct bond, NR$^{10}$ or O; wherein R$^{16}$ is hydrogen, Ar$^3$, C$_{1-4}$acyl, or C$_{1-4}$alkyl optionally substituted with one or more halo substituents;

m represents 3, 4, 5, 6 or 7;

n represents 0, 1, 2 or 3;

q represents 3, 4, 5 or 6;

r represents 0, 1, 2 or 3;

each Ar$^3$ independently represents phenyl optionally substituted with one or more substituents each independently selected from the group consisting of halo, cyano, NR$^7$R$^8$, morpholinyl, cycloC$_{3-7}$alkyl, C$_{1-4}$alkyloxy optionally substituted with one or more halo substituents, and C$_{1-4}$alkyl optionally substituted with one or more halo substituents;

or a 5- or 6-membered heteroaryl selected from the group consisting of furanyl, thiophenyl, pyrazolyl, oxazolyl, isoxazolyl, thiazolyl, isothiazolyl, thiadiazolyl, oxadiazolyl, pyridinyl, pyrimidinyl, pyridazinyl, and pyrazinyl, wherein said 5- or 6-membered heteroaryl is optionally substituted with one or more substituents each independently selected from the group consisting of halo, C$_{1-4}$alkyloxy, cyano, NR$^7$R$^8$, morpholinyl, and C$_{1-4}$alkyl optionally substituted with one or more halo substituents;

or 1,6-dihydro-1-methyl-6-oxo-3-pyridinyl or 1,2-dihydro-1-methyl-2-oxo-3-pyridinyl;

R$^{6b}$ and R$^{6c}$ represent hydrogen or methyl;

each R$^7$ independently is hydrogen, C$_{1-4}$acyl, or C$_{1-4}$alkyl;

each R$^8$ independently is hydrogen or C$_{1-4}$alkyl;

R$^9$ is hydrogen, C$_{1-4}$acyl, or C$_{1-4}$alkyl optionally substituted with one or more substituents each independently selected from the group consisting of halo and cycloC$_{3-7}$alkyl;

R$^{11}$ is hydrogen or C$_{1-4}$alkyl;

R$^{12}$ is hydrogen or methyl;

and the pharmaceutically acceptable addition salts, and the solvates thereof;

provided that the compound is not 2-[4-(1H-imidazol-1-yl)phenyl]-4-(trifluoromethyl)-1H-Imidazole.

The present invention also concerns methods for the preparation of compounds of Formula (I) and pharmaceutical compositions comprising them.

The present compounds surprisingly were found to modulate the γ-secretase activity in vitro and in vivo, and therefore may be useful in the treatment or prevention of AD, traumatic brain injury (TBI), mild cognitive impairment (MCI), senility, dementia, dementia with Lewy bodies, cerebral amyloid angiopathy, multi-infarct dementia, Down's syndrome, dementia associated with Parkinson's disease and dementia associated with beta-amyloid, preferably AD or other disorders with Beta-amyloid pathology (e.g. glaucoma).

In view of the aforementioned pharmacology of the compounds of Formula (I), it follows that they may be suitable for use as a medicament.

More especially the compounds may be suitable in the treatment or prevention of AD, cerebral amyloid angiopathy, multi-infarct dementia, dementia pugilistica or Down syndrome.

The invention also relates to a compound according to the general Formula (I), the stereoisomeric forms thereof and the pharmaceutically acceptable acid or base addition salts and the solvates thereof, for use in the modulation of γ-secretase activity.

The present invention will now be further described. In the following passages, different aspects of the invention are defined in detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION OF THE INVENTION

When describing the compounds of the invention, the terms used are to be construed in accordance with the following definitions, unless a context dictates otherwise.

Whenever the term "substituted" is used in the present invention, it is meant, unless otherwise is indicated or is clear from the context, to indicate that one or more hydrogens, in particular from 1 to 4 hydrogens, preferably from 1 to 3 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

The term "halo" or "halogen" as a group or part of a group is generic for fluoro, chloro, bromo, iodo unless otherwise is indicated or is clear from the context.

The term "$C_{1-6}$alkyl" as a group or part of a group refers to a hydrocarbyl radical of Formula $C_nH_{2n+1}$ wherein n is a number ranging from 1 to 6. $C_{1-6}$alkyl groups comprise from 1 to 6 carbon atoms, preferably from 1 to 4 carbon atoms, more preferably from 1 to 3 carbon atoms, still more preferably 1 to 2 carbon atoms. Alkyl groups may be linear or branched and may be substituted as indicated herein. When a subscript is used herein following a carbon atom, the subscript refers to the number of carbon atoms that the named group may contain. Thus, for example, $C_{1-6}$alkyl includes all linear, or branched alkyl groups with between 1 and 6 carbon atoms, and thus includes such as for example methyl, ethyl, n-propyl, i-propyl, 2-methyl-ethyl, butyl and its isomers (e.g. n-butyl, isobutyl and tert-butyl), pentyl and its isomers, hexyl and its isomers, and the like.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, preferably from 1 to 3 carbon atoms, more preferably 1 to 2 carbon atoms. $C_{1-4}$alkyl includes all linear, or branched alkyl groups with between 1 and 4 carbon atoms, and thus includes such as for example methyl, ethyl, n-propyl, 1-propyl, 2-methyl-ethyl, butyl and its isomers (e.g. n-butyl, isobutyl and tert-butyl), and the like.

The term "$C_{1-4}$acyl" alone or in combination refers to a radical containing from 1 to 4 carbon atoms in which carbonyl is bound to hydrogen or to a straight-chain or branched-chain hydrocarbon having from 1 to 3 carbon atoms. Non-limiting examples of suitable $C_{1-4}$acyl include formyl, acetyl, propionyl, butyryl and iso-butyryl. In particular $C_{1-4}$acyl is acetyl.

The term "$C_{1-6}$alkyloxy" as a group or part of a group refers to a radical having the Formula —$OR^b$ wherein $R^b$ is $C_{1-6}$alkyl. Non-limiting examples of suitable alkyloxy include methyloxy, ethyloxy, propyloxy, isopropyloxy, butyloxy, isobutyloxy, sec-butyloxy, tert-butyloxy, pentyloxy, and hexyloxy.

The term "$C_{1-4}$alkyloxy" as a group or part of a group refers to a radical having the Formula —$OR^c$ wherein $R^c$ is $C_{1-4}$alkyl. Non-limiting examples of suitable $C_{1-4}$alkyloxy include methyloxy (also methoxy), ethyloxy (also ethoxy), propyloxy, isopropyloxy, butyloxy, isobutyloxy, sec-butyloxy and tert-butyloxy.

The term "$C_{1-6}$alkylthio" refers to a straight chain or branched chain alkylthio group having from 1 to 6 carbon atoms, such as methylthio, ethylthio, propylthio, isopropylthio, butylthio, isobutylthio, sec-butylthio, tert-butylthio, pentylthio, neopentylthio, sec-pentylthio, n-pentylthio, iso-pentylthio, tert-pentylthio, hexylthio and the like.

The term "$C_{1-4}$alkylsulfonyl" refers to a straight chain or branched chain alkylsulfonyl group having from 1 to 4 carbon atoms, such as methylsulfonyl, ethylsulfonyl, propylsulfonyl, isopropylsulfonyl, butylsulfonyl, isobutylsulfonyl, sec-butylsulfonyl, tert-butylsulfonyl and the like.

The term "$C_{1-4}$alkylsulfinyl" refers to a straight chain or branched chain alkylsulfinyl group having from 1 to 4 carbon atoms, such as methylsulfinyl, ethylsulfinyl, isopropylsulfinyl, butylsulfinyl, isobutylsulfinyl, tert-butylsulfinyl and the like.

In the framework of this application, $C_{2-6}$alkenyl is a straight or branched hydrocarbon radical having from 2 to 6 carbon atoms containing a double bond such as ethenyl, propenyl, butenyl, pentenyl, 1-propen-2-yl, hexenyl and the like;

The term "cyclo$C_{3-7}$alkyl" alone or in combination, refers to a cyclic saturated hydrocarbon radical having from 3 to 7 carbon atoms. Non-limiting examples of suitable cyclo$C_{3-7}$alkyl include cyclopropyl, cyclobutyl, cyclopentyl, cyclohexyl and cycloheptyl.

The term "cyclo$C_{3-7}$alkyloxy" alone or in combination, refers to a saturated cyclo$C_{3-7}$alkyl-O—, wherein cyclo$C_{3-7}$alkyl is as defined above. Non-limiting examples of suitable cyclo$C_{3-7}$alkyl include cyclopropyloxy, cyclobutyloxy, cyclopentyloxy and cyclohexyloxy.

In a particular embodiment, cyclo$C_{3-7}$alkyl is restricted to cyclo$C_{3-6}$alkyl. In another particular embodiment cyclo$C_{3-7}$alkyloxy is restricted to cyclo$C_{3-6}$alkyloxy.

The term "$C_{1-4}$alkanediyl" as a group or part of a group defines bivalent straight or branched chained saturated hydrocarbon radicals having from 1 to 4 carbon atoms such as, for example, methylene or methanediyl, ethan-1,2-diyl, propan-1,3-diyl, propan-1,2-diyl, butan-1,4-diyl and the like.

The term "$C_{1-6}$alkanediyl" as a group or part of a group defines bivalent straight or branched chained saturated hydrocarbon radicals having from 1 to 6 carbon atoms such as, for example, methylene or methanediyl, ethan-1,2-diyl, ethan-1,1-diyl or ethylidene, propan-1,3-diyl, propan-1,2-diyl, butan-1,4-diyl, pentan-1,5-diyl, pentan-1,1-diyl, hexan-1,6-diyl, 2-methylbutan-1,4-diyl, 3-methylpentan-1,5-diyl and the like.

The term "$C_{2-6}$alkanediyl" as a group or part of a group defines bivalent straight or branched chained saturated hydrocarbon radicals having from 2 to 6 carbon atoms such as, for example, ethan-1,2-diyl, ethan-1,1-diyl or ethylidene, propan-1,3-diyl, propan-1,2-diyl, butan-1,4-diyl, pentan-1,5-diyl, pentan-1,1-diyl, hexan-1,6-diyl, 2-methylbutan-1,4-diyl, 3-methylpentan-1,5-diyl and the like.

In a particular embodiment, $C_{2-6}$alkanediyl is selected from the group consisting of ethan-1,2-diyl, propan-1,3-diyl, butan-1,4-diyl, pentan-1,5-diyl and hexan-1,6-diyl.

In a particular embodiment, $C_{1-4}$alkanediyl, $C_{1-6}$alkanediyl and $C_{2-6}$alkanediyl defines bivalent straight chained saturated hydrocarbon radicals.

The term "$C_{2-6}$alkenediyl" as a group or part of a group defines bivalent straight and branched chain hydrocarbon radicals containing one double bond and having from 2 to 6 carbon atoms such as, for example, 1,2-ethenediyl, 2-propenediyl, 3-butenediyl, 2-pentenediyl, 3-pentenediyl, 3-methyl-2-butenediyl, and the like.

In a particular embodiment, $C_{2-6}$alkenediyl defines bivalent straight chain hydrocarbon radicals containing one double bond and having from 2 to 6 carbon atoms.

The term "thiophenyl" is equivalent to "thienyl".

The term "oxopyridinyl" defines partially hydrogenated pyridinyl derivatives substituted with oxo such as, for example, 1,6-dihydro-6-oxo-3-pyridinyl and 1,2-dihydro-2-oxo-3-pyridinyl. Said partially hydrogenated pyridinyl derivatives may be further substituted with substituents such as, for example, methyl, to yield moieties such as, for example, 1,6-dihydro-1-methyl-6-oxo-3-pyridinyl and 1,2-dihydro-1-methyl-2-oxo-3-pyridinyl.

When $L^a$, $L^b$ or $L^c$ is defined as for instance $NR^9$—$C_{1-4}$alkanediyl, this means that the nitrogen of $NR^9$ is linked to the heterocyclic ring (a), (b) or (c) respectively, and $C_{1-4}$alkanediyl is linked to the $R^{5a}$, $R^{5b}$ or $R^{5c}$ moiety respectively.

When $L^a$, $L^b$ or $L^c$ is defined as for instance $NR^{12}$—(C=O), this means that the nitrogen of $NR^{12}$ is linked to the heterocyclic ring (a), (b) or (c) respectively, and (C=O) is linked to the $R^{5a}$, $R^{5b}$ or $R^{5c}$ moiety respectively.

The chemical names of the compounds of the present invention were generated according to the nomenclature rules agreed upon by the Chemical Abstracts Service, using Advanced Chemical Development, Inc., nomenclature software (ACD/Name product version 10.01; Build 15494, 1 Dec. 2006).

In case of tautomeric forms, it should be clear that the other non-depicted tautomeric form is also included within the scope of the present invention.

When any variable occurs more than one time in any constituent, each definition is independent.

It will be appreciated that some of the compounds of Formula (I) and their pharmaceutically acceptable addition salts and stereoisomeric forms may contain one or more centers of chirality and exist as stereoisomeric forms.

The term "stereoisomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereoisomeric forms of the compounds of Formula (I) are embraced within the scope of this invention.

When a specific stereoisomeric form is indicated, this means that said form is substantially free, i.e. associated with less than 50%, preferably less than 20%, more preferably less than 10%, even more preferably less than 5%, further preferably less than 2% and most preferably less than 1% of the other isomer(s).

For therapeutic use, salts of the compounds of Formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds of Formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the hydrates and solvent addition forms which the compounds of formula (I) are able to form, as well as the salts thereof. Examples of such forms are e.g. hydrates, alcoholates and the like.

The compounds of Formula (I) as prepared in the processes described below may be synthesized in the form of racemic mixtures of enantiomers that can be separated from one another following art-known resolution procedures. An manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In the framework of this application, a compound according to the invention is inherently intended to comprise all isotopic combinations of its chemical elements. In the framework of this application, a chemical element, in particular when mentioned in relation to a compound according to formula (I), comprises all isotopes and isotopic mixtures of this element. For example, when hydrogen is mentioned, it is understood to refer to $^1H$, $^2H$, $^3H$ and mixtures thereof.

A compound according to the invention therefore inherently comprises a compound with one or more isotopes of one or more element, and mixtures thereof, including a radioactive compound, also called radiolabelled compound, wherein one or more non-radioactive atoms has been replaced by one of its radioactive isotopes. By the term "radiolabelled compound" is meant any compound according to formula (I), or a pharmaceutically acceptable salt thereof, which contains at least one radioactive atom. For example, a compound can be labelled with positron or with gamma emitting radioactive isotopes. For radioligand-binding techniques, the $^3H$-atom or the $^{125}I$-atom is the atom of choice to be replaced. For imaging, the most commonly used positron emitting (PET) radioactive isotopes are $^{11}C$, $^{18}F$, $^{15}O$ and $^{13}N$, all of which are accelerator produced and have half-lives of 20, 100, 2 and 10 minutes (min) respectively. Since the half-lives of these radioactive isotopes are so short, it is only feasible to use them at institutions which have an accelerator on site for their production, thus limiting their use. The most widely used of these are $^{18}F$, $^{99m}Tc$, $^{201}Tl$ and $^{123}I$. The handling of these radioactive isotopes, their production, isolation and incorporation in a molecule are known to the skilled person.

In particular, the radioactive atom is selected from the group of hydrogen, carbon, nitrogen, sulfur, oxygen and halogen. In particular, the radioactive isotope is selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$.

As used in the specification and the appended claims, the singular forms "a", "an", and "the" also include plural referents unless the context clearly dictates otherwise. For example, "a compound" means 1 compound or more than 1 compound.

The terms described above and others used in the specification are well understood to those in the art.

Preferred features of the compounds of this invention are now set forth.

In an embodiment, the present invention concerns novel compounds of Formula (I) and stereoisomeric forms thereof, wherein $R^1$ is hydrogen or $C_{1-4}$alkyl;

$R^2$ is hydrogen or $C_{1-4}$alkyl;

X is CH or N;

$A^1$ is $CR^{3a}$ or N; wherein $R^{3a}$ is hydrogen; halo; or $C_{1-4}$alkyloxy;

$A^2$ is $CR^{3b}$ or N; wherein $R^{3b}$ is hydrogen or $C_{1-4}$alkyloxy;

$A^3$ and $A^4$ each independently are CH or N;

provided that no more than two of $A^1$, $A^2$, $A^3$ and $A^4$ are N;

$Het^1$ is a heterocycle, having formula (a), (b) or (c)

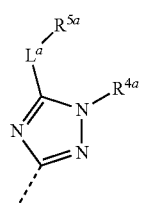

(a)

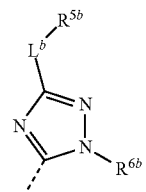

(b)

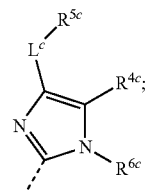

(c)

$R^{4a}$ is hydrogen; tetrahydropyranyl; tetrahydrofuranyl; piperidinyl; morpholinyl; pyrrolidinyl; cyclo$C_{3-7}$alkyl; $Ar^1$; or $C_{1-6}$alkyl optionally substituted with one or more substituents each independently selected from the group consisting of halo, $Ar^1$, tetrahydropyranyl, tetrahydrofuranyl, piperidinyl, morpholinyl, pyrrolidinyl, cyclo$C_{3-7}$alkyl, $C_{1-6}$alkyloxy, $C_{1-6}$alkylthio, and O—$Ar^1$;

$R^{4c}$ is hydrogen; tetrahydropyranyl; tetrahydrofuranyl; piperidinyl; morpholinyl; pyrrolidinyl; cyclo$C_{3-7}$alkyl; $C_{1-6}$alkyloxy; $C_{1-6}$alkylthio; $Ar^1$; or $C_{1-6}$alkyl optionally substituted with one or more substituents each independently selected from the group consisting of halo, $Ar^1$, tetrahydropyranyl, tetrahydrofuranyl, piperidinyl, morpholinyl, pyrrolidinyl, cyclo$C_{3-7}$alkyl, $C_{1-6}$alkyloxy, $C_{1-6}$alkylthio, and O—$Ar^1$;

wherein in the definitions of $R^{4a}$ and $R^{4c}$ piperidinyl, morpholinyl and pyrrolidinyl may be substituted with one or more substituents each independently selected from the group consisting of $C_{1-4}$alkyl, $C_{2-6}$alkenyl, $C_{1-4}$acyl, halo and $C_{1-4}$alkyloxycarbonyl;

wherein in the definitions of $R^{4a}$ and $R^{4c}$ each $Ar^1$ independently is phenyl optionally substituted with one or more substituents each independently selected from the group consisting of halo, $C_{1-4}$alkyloxy, cyano, $NR^7R^8$, morpholinyl, and $C_{1-4}$alkyl optionally substituted with one or more halo substituents; or each $Ar^1$ independently is a 5- or 6-membered heteroaryl selected from the group consisting of furanyl, thiophenyl, pyrazolyl, oxazolyl, isoxazolyl, thiazolyl, isothiazolyl, thiadiazolyl, oxadiazolyl, pyridinyl, pyrimidinyl, pyridazinyl, and pyrazinyl, wherein said 5- or 6-membered heteroaryl is optionally substituted with one or more substituents each independently selected from the group consisting of halo, $C_{1-4}$alkyloxy, cyano, $NR^7R^8$, morpholinyl, and $C_{1-4}$alkyl optionally substituted with one or more halo substituents;

wherein in the definitions of $R^{4a}$ and $R^{4c}$ each cyclo$C_{3-7}$alkyl, tetrahydropyranyl or tetrahydrofuranyl may be substituted with one or more substituents each independently selected from the group consisting of halo, $C_{1-4}$alkyloxy, cyano, and $C_{1-4}$alkyl optionally substituted with one or more halo substituents;

$R^{5a}$, $R^{5b}$ and $R^{5c}$ are hydrogen; tetrahydropyranyl; tetrahydrofuranyl; piperidinyl; morpholinyl; pyrrolidinyl; 1,6-dihydro-1-methyl-6-oxo-3-pyridinyl; 1,2-dihydro-1-methyl-2-oxo-3-pyridinyl; cyclo$C_{3-7}$alkyl; $Ar^2$; or $C_{1-6}$alkyl optionally substituted with one or more substituents each independently selected from the group consisting of halo, $C_{1-4}$alkyloxy, $C_{1-4}$acyl, and $C_{1-4}$alkyloxycarbonyl; in particular hydrogen; tetrahydropyranyl; tetrahydrofuranyl; piperidinyl; morpholinyl; pyrrolidinyl; cycloC$_{3-7}$alkyl; Ar$^2$; or C$_{1-6}$alkyl optionally substituted with one or more substituents each independently selected from the group consisting of halo, C$_{1-4}$alkyloxy, C$_{1-4}$acyl, and C$_{1-4}$alkyloxycarbonyl;

wherein in the definitions of R$^{5a}$, R$^{5b}$ and R$^{5c}$ tetrahydrofuranyl, tetrahydropyranyl, piperidinyl, morpholinyl, pyrrolidinyl and cycloC$_{3-7}$alkyl may be substituted with one or more substituents each independently selected from the group consisting of C$_{1-4}$alkyl, C$_{2-6}$alkenyl, C$_{1-4}$acyl, halo and C$_{1-4}$alkyloxycarbonyl;

wherein in the definitions of R$^{5a}$, R$^{5b}$ and R$^{5c}$, Ar$^2$ is phenyl optionally substituted with one or more substituents each independently selected from the group consisting of halo, C$_{1-4}$alkyloxy, cyano, NR$^7$R$^8$, morpholinyl, and C$_{1-4}$alkyl optionally substituted with one or more halo substituents; or Ar$^2$ is a 5- or 6-membered heteroaryl selected from the group consisting of furanyl, thiophenyl, pyrazolyl, oxazolyl, isoxazolyl, thiazolyl, isothiazolyl, thiadiazolyl, oxadiazolyl, pyridinyl, pyrimidinyl, pyridazinyl, and pyrazinyl, wherein said 5- or 6-membered heteroaryl is optionally substituted with one or more substituents each independently selected from the group consisting of halo, C$_{1-4}$alkyloxy, cyano, NR$^7$R$^8$, morpholinyl, and C$_{1-4}$alkyl optionally substituted with one or more halo substituents;

L$^a$, L$^b$ and L$^c$ represent a direct bond; C$_{2-6}$alkenediyl; carbonyl; O; S; S(=O)$_p$; NR$^9$; NR$^9$—C$_{1-4}$alkanediyl; or C$_{1-6}$alkanediyl optionally substituted with one or more halo substituents; or two geminal hydrogen atoms in said C$_{1-6}$alkanediyl may be replaced by C$_{1-6}$alkanediyl, in particular two geminal hydrogen atoms in said C$_{1-6}$alkanediyl may be replaced by C$_{2-6}$alkanediyl;

p represents 1 or 2;

or -L$^a$-R$^{5a}$ and R$^{4a}$; or -L$^c$-R$^{5c}$ and R$^{4c}$; can be taken together to form a bivalent radical -L$^a$-R$^{5a}$—R$^{4a}$— or -L$^c$-R$^{5c}$—R$^{4c}$— having formula

—(CH$_2$)$_{m-n}$—Y—(CH$_2$)$_n$—                    (d-1);

—(CH$_2$)$_n$—Y—(CH$_2$)$_{m-n}$—                    (d-2);

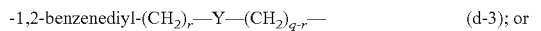

-1,2-benzenediyl-(CH$_2$)$_r$—Y—(CH$_2$)$_{q-r}$—      (d-3); or

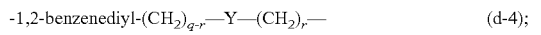

-1,2-benzenediyl-(CH$_2$)$_{q-r}$—Y—(CH$_2$)$_r$—      (d-4);

wherein (d-1), (d-2), (d-3) or (d-4) may be substituted on a CH$_2$ group with one or two substituents each independently selected from the group consisting of Ar$^3$, C$_{1-4}$acyl, and C$_{1-4}$alkyl optionally substituted with one or more halo substituents;

wherein (d-3) or (d-4) may be substituted on the 1,2-benzenediyl-moiety with one or more substituents each independently selected from the group consisting of halo, C$_{1-4}$alkyloxy, cyano, NR$^7$R$^8$, morpholinyl, and C$_{1-4}$alkyl optionally substituted with one or more halo substituents;

Y represents a direct bond, NR$^{10}$ or O; wherein R$^{10}$ is hydrogen, Ar$^3$, C$_{1-4}$acyl, or C$_{1-4}$alkyl optionally substituted with one or more halo substituents;

m represents 3, 4, 5, 6 or 7;

n represents 0, 1, 2 or 3;

q represents 3, 4, 5 or 6;

r represents 0, 1, 2 or 3;

each Ar$^3$ independently represents phenyl optionally substituted with one or more substituents each independently selected from the group consisting of halo, C$_{1-4}$alkyloxy, cyano, NR$^7$R$^8$, morpholinyl, and C$_{1-4}$alkyl optionally substituted with one or more halo substituents;

or a 5- or 6-membered heteroaryl selected from the group consisting of furanyl, thiophenyl, pyrazolyl, oxazolyl, isoxazolyl, thiazolyl, isothiazolyl, thiadiazolyl, oxadiazolyl, pyridinyl, pyrimidinyl, pyridazinyl, and pyrazinyl, wherein said 5- or 6-membered heteroaryl is optionally substituted with one or more substituents each independently selected from the group consisting of halo, C$_{1-4}$alkyloxy, cyano, NR$^7$R$^8$, morpholinyl, and C$_{1-4}$alkyl optionally substituted with one or more halo substituents;

or 1,6-dihydro-1-methyl-6-oxo-3-pyridinyl or 1,2-dihydro-1-methyl-2-oxo-3-pyridinyl;

R$^{6b}$ and R$^{6c}$ represent hydrogen or methyl;

each R$^7$ independently is hydrogen or C$_{1-4}$alkyl;

each R$^8$ independently is hydrogen or C$_{1-4}$alkyl;

R$^9$ is hydrogen or C$_{1-4}$alkyl optionally substituted with one or more substituents each independently selected from the group consisting of halo and cycloC$_{3-7}$alkyl;

and the pharmaceutically acceptable addition salts, and the solvates thereof;

provided that the compound is not 2-[4-(1H-imidazol-1-yl) phenyl]-4-(trifluoromethyl)-1H-Imidazole.

In another embodiment, the present invention concerns compounds of Formula (I)

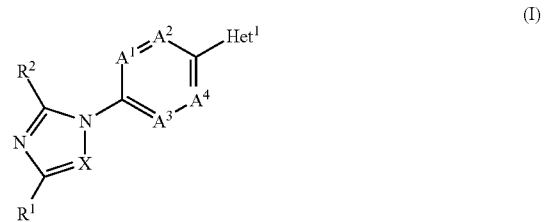

(I)

and stereoisomeric forms thereof, wherein

R$^1$ is hydrogen or C$_{1-4}$alkyl;

R$^2$ is hydrogen or C$_{1-4}$alkyl;

X is CH or N;

A$^1$ is CR$^{3a}$ or N; wherein R$^{3a}$ is hydrogen; halo; or C$_{1-4}$alkyloxy;

A$^2$ is CR$^{3b}$ or N; wherein R$^{3b}$ is hydrogen or C$_{1-4}$alkyloxy;

A$^3$ and A$^4$ each independently are CH or N;

provided that no more than two of A$^1$, A$^2$, A$^3$ and A$^4$ are N;

Het$^1$ is an heterocycle, having formula (a), (b) or (c)

(a)

(b)

-continued

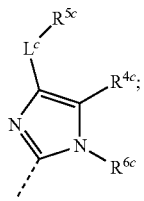
(c)

$R^{4a}$ is hydrogen; tetrahydropyranyl; tetrahydrofuranyl; piperidinyl; morpholinyl; pyrrolidinyl; cycloC$_{3-7}$alkyl; Ar$^1$; or C$_{1-6}$alkyl optionally substituted with one or more substituents selected from the group consisting of halo, Ar$^1$, tetrahydropyranyl, tetrahydrofuranyl, piperidinyl, morpholinyl, pyrrolidinyl, cycloC$_{3-7}$alkyl, C$_{1-6}$alkyloxy, C$_{1-6}$alkylthio, and O—Ar$^1$;

$R^{4c}$ is hydrogen; tetrahydropyranyl; tetrahydrofuranyl; piperidinyl; morpholinyl; pyrrolidinyl; cycloC$_{3-7}$alkyl; C$_{1-6}$alkyloxy; C$_{1-6}$alkylthio; Ar$^1$; or C$_{1-6}$alkyl optionally substituted with one or more substituents selected from the group consisting of halo, Ar$^1$, tetrahydropyranyl, tetrahydrofuranyl, piperidinyl, morpholinyl, pyrrolidinyl, cycloC$_{3-7}$alkyl, C$_{1-6}$alkyloxy, C$_{1-6}$alkylthio, and O—Ar$^1$;

wherein in the definitions of $R^{4a}$ and $R^{4c}$ each piperidinyl, morpholinyl and pyrrolidinyl independently may optionally be substituted with one or more substituents selected from the group consisting of C$_{1-4}$alkyl, C$_{2-6}$alkenyl, C$_{1-4}$acyl, halo and C$_{1-4}$alkyloxycarbonyl;

wherein in the definitions of $R^{4a}$ and $R^{4c}$ each Ar$^1$ independently is phenyl optionally substituted with one or more substituents each independently selected from the group consisting of halo, C$_{1-4}$alkyloxy, cyano, NR$^7$R$^8$, morpholinyl, and C$_{1-4}$alkyl optionally substituted with one or more substituents selected from halo; or each Ar$^1$ independently is a 5- or 6-membered heteroaryl selected from the group consisting of pyridinyl, oxopyridinyl, pyrimidinyl, oxazolyl, furanyl, thiophenyl, pyrazolyl, isoxazolyl, thiazolyl, isothiazolyl, thiadiazolyl, oxadiazolyl, pyridazinyl, and pyrazinyl, wherein said 5- or 6-membered heteroaryl is optionally substituted with 1 or more substituents each independently selected from the group consisting of halo, C$_{1-4}$alkyloxy, cyano, NR$^7$R$^8$, morpholinyl, and C$_{1-4}$alkyl optionally substituted with one or more substituents selected from halo;

wherein in the definitions of $R^{4a}$ and $R^{4c}$ each cycloC$_{3-7}$alkyl, tetrahydropyranyl or tetrahydrofuranyl may optionally be substituted with one or more substituents selected from the group consisting of halo, C$_{1-4}$alkyloxy, cyano, and C$_{1-4}$alkyl optionally substituted with one or more substituents selected from halo;

$R^{5a}$, $R^{5b}$, or $R^{5c}$ each independently is hydrogen; C$_{1-6}$alkyl optionally substituted with one or more substituents each independently selected from the group consisting of halo, C$_{1-4}$alkyloxy, C$_{1-4}$acyl, and C$_{1-4}$alkyloxycarbonyl; tetrahydropyranyl; tetrahydrofuranyl; piperidinyl; morpholinyl; pyrrolidinyl; cycloC$_{3-7}$alkyl; Ar$^2$;

wherein in the definitions of $R^{5a}$, $R^{5b}$ and $R^{5c}$ each piperidinyl, morpholinyl, pyrrolidinyl, cycloC$_{3-7}$alkyl, tetrahydrofuranyl and tetrahydropyranyl independently may optionally be substituted with one or more substituents selected from the group consisting of C$_{1-4}$alkyl, C$_{2-6}$alkenyl, C$_{1-4}$acyl, halo and C$_{1-4}$alkyloxycarbonyl;

wherein in the definitions of $R^{5a}$, $R^{5b}$ and $R^{5c}$ each Ar$^2$ independently is phenyl optionally substituted with one or more substituents each independently selected from the group consisting of halo, C$_{1-4}$alkyloxy, cyano, NR$^7$R$^8$, morpholinyl, and C$_{1-4}$alkyl optionally substituted with one or more substituents selected from halo; or a 5- or 6-membered heteroaryl selected from the group consisting of pyridinyl, oxopyridinyl, pyrimidinyl, oxazolyl, furanyl, thiophenyl, pyrazolyl, isoxazolyl, thiazolyl, isothiazolyl, thiadiazolyl, oxadiazolyl, pyridazinyl, and pyrazinyl, wherein said 5- or 6-membered heteroaryl is optionally substituted with one or more substituents each independently selected from the group consisting of halo, C$_{1-4}$alkyloxy, cyano, NR$^7$R$^8$, morpholinyl, and C$_{1-4}$alkyl optionally substituted with one or more substituents selected from halo;

or -L$^a$-R$^{5a}$ and $R^{4a}$; or -L$^c$-R$^{5c}$ and $R^{4c}$, can be taken together to form a bivalent radical of formula —(CH$_2$)$_{m-n}$—Y—(CH$_2$)$_n$—, —(CH$_2$)$_n$—Y—(CH$_2$)$_{m-n}$—, -1,2-benzenediyl-(CH$_2$)$_r$—Y—(CH$_2$)$_{q-r}$—, -1,2-benzenediyl-(CH$_2$)$_{q-r}$-Y—(CH$_2$)$_r$—, wherein said bivalent radical may optionally be substituted on a methylene group or where possible on the Y-moiety with one or two substituents each independently selected from Ar$^3$, C$_{1-4}$acyl, or C$_{1-4}$alkyl optionally substituted with one or more substituents selected from halo; and wherein said bivalent radical may optionally be substituted on the 1,2-benzenediyl-moiety with one or more substituents each independently selected from the group consisting of halo, C$_{1-4}$alkyloxy, cyano, NR$^7$R$^8$, morpholinyl, and C$_{1-4}$alkyl optionally substituted with one or more substituents selected from halo;

Y represents a direct bond, NH or O;

m represents 3, 4, 5, 6 or 7;

n represents 0, 1, 2 or 3;

q represents 3, 4, 5 or 6;

r represents 0, 1, 2 or 3;

Ar$^3$ represents phenyl optionally substituted with one or more substituents each independently selected from the group consisting of halo, C$_{1-4}$alkyloxy, cyano, NR$^7$R$^8$, morpholinyl, and C$_{1-4}$alkyl optionally substituted with one or more substituents selected from halo; or a 5- or 6-membered heteroaryl selected from the group consisting of pyridinyl, oxopyridinyl, pyrimidinyl, oxazolyl, furanyl, thiophenyl, pyrazolyl, isoxazolyl, thiazolyl, isothiazolyl, thiadiazolyl, oxadiazolyl, pyridazinyl, and pyrazinyl, wherein said 5- or 6-membered heteroaryl is optionally substituted with one or more substituents each independently selected from the group consisting of halo, C$_{1-4}$alkyloxy, cyano, NR$^7$R$^8$, morpholinyl, and C$_{1-4}$alkyl optionally substituted with one or more substituents selected from halo;

each R$^7$ independently is hydrogen or C$_{1-4}$alkyl;

each R$^8$ independently is hydrogen or C$_{1-4}$alkyl;

$R^{6b}$ or $R^{6c}$ each independently represents hydrogen or methyl;

L$^a$, L$^b$ or L$^c$ each independently represents a direct bond; C$_{2-6}$alkenediyl; carbonyl; P; S; S(=O)$_p$; NR$^9$; NR$^9$—C$_{1-4}$alkanediyl; or C$_{1-6}$alkanediyl optionally substituted with one or more substituents selected from halo; or two geminal hydrogen atoms attached to a carbon atom in said C$_{1-6}$alkanediyl may optionally be replaced by C$_{1-6}$alkanediyl;

p represents 1 or 2;

R$^9$ is hydrogen or C$_{1-4}$alkyl optionally substituted with one or more substituents selected from the group consisting of halo and cycloC$_{3-7}$alkyl;

and the pharmaceutically acceptable addition salts, and the solvates thereof;
provided that the compound is not 2-[4-(1H-imidazol-1-yl)phenyl]-4-(trifluoromethyl)-1H-imidazole.

An embodiment of the present invention relates to those compounds of Formula (I) and stereoisomeric forms thereof, wherein
$R^1$ is hydrogen or $C_{1-4}$alkyl;
$R^2$ is hydrogen or $C_{1-4}$alkyl;
X is CH or N;
$A^1$ is $CR^{3a}$ or N; wherein $R^{3a}$ is hydrogen; halo; cyano; $C_{1-4}$alkyl; or $C_{1-4}$alkyloxy optionally substituted with one or more halo substituents;
$A^2$ is $CR^{3b}$ or N; wherein $R^{3b}$ is hydrogen; fluoro; or $C_{1-4}$alkyloxy;
$A^3$ and $A^4$ each independently are CH; CF; or N;
provided that no more than two of $A^1$, $A^2$, $A^3$ and $A^4$ are N;
$Het^1$ is a heterocycle, having formula (a), (b) or (c);
$R^{4a}$ is hydrogen; tetrahydropyranyl; tetrahydrofuranyl; piperidinyl; morpholinyl; pyrrolidinyl; cyclo$C_{3-7}$alkyl; $Ar^1$; or $C_{1-6}$alkyl optionally substituted with one or more substituents each independently selected from the group consisting of halo, hydroxyl, cyano, $Ar^1$, tetrahydropyranyl, tetrahydrofuranyl, piperidinyl, morpholinyl, pyrrolidinyl, cyclo$C_{3-7}$alkyl, $C_{1-6}$alkyloxy, $C_{1-6}$alkylthio, and O—$Ar^1$;
$R^{4c}$ is hydrogen; tetrahydropyranyl; tetrahydrofuranyl; piperidinyl; morpholinyl; pyrrolidinyl; cyclo$C_{3-7}$alkyl; $C_{1-6}$alkyloxy; $C_{1-6}$alkylthio; $Ar^1$; or $C_{1-6}$alkyl optionally substituted with one or more substituents each independently selected from the group consisting of halo, $Ar^1$, tetrahydropyranyl, tetrahydrofuranyl, piperidinyl, morpholinyl, pyrrolidinyl, cyclo$C_{3-7}$alkyl, $C_{1-6}$alkyloxy, $C_{1-6}$alkylthio, and O—$Ar^1$;
wherein in the definitions of $R^{4a}$ and $R^{4c}$ piperidinyl, morpholinyl and pyrrolidinyl may be substituted with one or more substituents each independently selected from the group consisting of $C_{2-6}$alkenyl, $C_{1-4}$acyl, halo, $C_{1-4}$alkyloxycarbonyl, and $C_{1-4}$alkyl optionally substituted with one or more halo substituents;
wherein in the definitions of $R^{4a}$ and $R^{4c}$ each $Ar^1$ independently is phenyl optionally substituted with one or more substituents each independently selected from the group consisting of halo, $C_{1-4}$alkyloxy, cyano, $NR^7R^8$, morpholinyl, and $C_{1-4}$alkyl optionally substituted with one or more halo substituents; or each $Ar^1$ independently is a 5- or 6-membered heteroaryl selected from the group consisting of furanyl, thiophenyl, pyrazolyl, oxazolyl, isoxazolyl, thiazolyl, isothiazolyl, thiadiazolyl, oxadiazolyl, pyridinyl, pyrimidinyl, pyridazinyl, and pyrazinyl, wherein said 5- or 6-membered heteroaryl is optionally substituted with one or more substituents each independently selected from the group consisting of halo, $C_{1-4}$alkyloxy, cyano, $NR^7R^8$, morpholinyl, and $C_{1-4}$alkyl optionally substituted with one or more halo substituents;
wherein in the definitions of $R^{4a}$ and $R^{4c}$ each cyclo$C_{3-7}$alkyl, tetrahydropyranyl or tetrahydrofuranyl may be substituted with one or more substituents each independently selected from the group consisting of halo, $C_{1-4}$alkyloxy, cyano, and $C_{1-4}$alkyl optionally substituted with one or more halo substituents;
$R^{5a}$, $R^{5b}$ and $R^{5c}$ are hydrogen; tetrahydropyranyl; tetrahydrofuranyl; piperidinyl; morpholinyl; pyrrolidinyl; piperazinyl; hexahydro-1H-1,4-diazepin-1-yl; 1,2,3,4-tetrahydro-2-quinolinyl; 3,4-dihydro-2(1H)-isoquinolinyl; 3,4-dihydro-1(2H)-quinolinyl; 2,2-difluoro-1,3-benzodioxol-5-yl; 2,2-difluoro-1,3-benzodioxol-4-yl; 1,6-dihydro-1-methyl-6-oxo-3-pyridinyl; 1,2-dihydro-1-methyl-2-oxo-3-pyridinyl; 2,3-dihydro-4H-1,4-benzoxazin-4-yl; 3,4-dihydro-1,5-benzoxazepin-5(2H)-yl; cyclo$C_{3-7}$alkyl; $Ar^2$; or $C_{1-6}$alkyl optionally substituted with one or more substituents each independently selected from the group consisting of halo, $C_{1-4}$alkyloxy, $C_{1-4}$acyl, and $C_{1-4}$alkyloxycarbonyl;
wherein in the definitions of $R^{5a}$, $R^{5b}$ and $R^{5c}$ tetrahydrofuranyl, tetrahydropyranyl, piperidinyl, morpholinyl, pyrrolidinyl, piperazinyl, hexahydro-1H-1,4-diazepin-1-yl, 1,2,3,4-tetrahydro-2-quinolinyl, 3,4-dihydro-2(1H)-isoquinolinyl, 3,4-dihydro-1(2H)-quinolinyl and cyclo$C_{3-7}$alkyl may be substituted with one or more substituents each independently selected from the group consisting of $C_{2-6}$alkenyl, $C_{1-4}$acyl, halo, $C_{1-4}$alkyloxycarbonyl, $C_{1-4}$alkyl optionally substituted with one or more halo substituents, and
phenyl optionally substituted with one or more substituents each independently selected from the group consisting of $C_{1-4}$alkyl and trifluoromethyl;
wherein in the definitions of $R^{5a}$, $R^{5b}$ and $R^{5c}$,
$Ar^2$ is phenyl optionally substituted with one or more substituents each independently selected from the group consisting of halo, cyano, $NR^7R^8$, (C=O)—$NR^7R^8$, morpholinyl, $C_{1-4}$acyl, $C_{1-4}$alkylsulfonyl, $C_{1-4}$alkylsulfinyl, cyclo$C_{3-7}$alkyl, cyclo$C_{3-7}$alkyloxy, tetrahydropyranyloxy, tetrahydrofuranyloxy, $C_{1-4}$alkyloxy optionally substituted with one or more substituents each independently selected from the group consisting of halo, hydroxyl, $C_{1-4}$alkyloxy, and cyclopropyl,
and $C_{1-4}$alkyl optionally substituted with one or more substituents each independently selected from the group consisting of halo, hydroxyl and $C_{1-4}$alkyloxy optionally substituted with one or more halo substituents;
or $Ar^2$ is a 5- or 6-membered heteroaryl selected from the group consisting of furanyl, thiophenyl, pyrazolyl, oxazolyl, isoxazolyl, thiazolyl, isothiazolyl, thiadiazolyl, oxadiazolyl, pyridinyl, pyrimidinyl, pyridazinyl, and pyrazinyl, wherein said 5- or 6-membered heteroaryl is optionally substituted with one or more substituents each independently selected from the group consisting of halo, $C_{1-4}$alkyloxy, cyano, $NR^7R^8$, morpholinyl, and $C_{1-4}$alkyl optionally substituted with one or more halo substituents;
or $Ar^2$ is quinolinyl;
$L^a$, $L^b$ and $L^c$ represent a direct bond; $C_{2-6}$alkenediyl; carbonyl; O; S; S(=O)$_p$; $NR^9$; $NR^9$—$C_{1-4}$alkanediyl; $C_{1-4}$alkanediyl-$NR^9$; $NR^{12}$—(C=O); (C=O)—$NR^{12}$; or $C_{1-6}$alkanediyl optionally substituted with one or more substituents each independently selected from the group consisting of halo and hydroxy; two geminal hydrogen atoms in said $C_{1-6}$alkanediyl may be replaced by $C_{1-6}$alkanediyl, in particular two geminal hydrogen atoms may be replaced by $C_{2-6}$alkanediyl;
p represents 1 or 2;
$R^{6b}$ and $R^{6c}$ represent hydrogen or methyl;
each $R^7$ independently is hydrogen, $C_{1-4}$acyl, or $C_{1-4}$alkyl;
each $R^8$ independently is hydrogen or $C_{1-4}$alkyl;
$R^9$ is hydrogen, $C_{1-4}$acyl, or $C_{1-4}$alkyl optionally substituted with one or more substituents each independently selected from the group consisting of halo and cyclo$C_{3-7}$alkyl;
$R^{12}$ is hydrogen or methyl;
and the pharmaceutically acceptable addition salts, and the solvates thereof;
provided that the compound is not 2-[4-(1H-imidazol-1-yl)phenyl]-4-(trifluoromethyl)-1H-Imidazole.

An embodiment of the present invention relates to those compounds of Formula (I) and stereoisomeric forms thereof, wherein $R^1$ is hydrogen or $C_{1-4}$alkyl;
$R^2$ is hydrogen or $C_{1-4}$alkyl;
X is CH or N;
$A^1$ is $CR^{3a}$ or N; wherein $R^{3a}$ is hydrogen; halo; cyano; $C_{1-4}$alkyl; or $C_{1-4}$alkyloxy optionally substituted with one or more halo substituents;
$A^2$ is $CR^{3b}$ or N; wherein $R^{3b}$ is hydrogen; fluoro; or $C_{1-4}$alkyloxy;
$A^3$ and $A^4$ each independently are CH; CF; or N;
provided that no more than two of $A^1$, $A^2$, $A^3$ and $A^4$ are N;
$Het^1$ is a heterocycle, having formula (a) or (c);
-$L^a$-$R^{5a}$ and $R^{4a}$; or -$L^c$-$R^{5c}$ and $R^{4c}$; can be taken together to form a bivalent radical -$L^a$-$R^{5a}$—$R^{4a}$— or -$L^c$-$R^{5c}$—$R^{4c}$—, having formula $$—(CH_2)_{m-n}—Y—(CH_2)_n— \quad (d-1)$$

$$—(CH_2)_n—Y—(CH_2)_{m-n}— \quad (d-2)$$

$$\text{-1,2-benzenediyl-}(CH_2)_r—Y—(CH_2)_{q-r}— \quad (d-3)$$

$$\text{-1,2-benzenediyl-}(CH_2)_{q-r}—Y—(CH_2)_r— \quad (d-4)$$

$$—CH=CH—CH=CH— \quad (d-5)$$

$$—CH=CH—N=CH— \quad (d-6)$$

$$—CH=N—CH=CH— \quad (d-7)$$

$$—N=CH—CH=CH— \quad (d-8); \text{ or}$$

$$—CH=CH—CH=N— \quad (d-9)$$

wherein (d-1), (d-2), (d-3) or (d-4) may be substituted on one or more, in particular on one or two, $CH_2$ groups with one or two substituents each independently selected from the group consisting of hydroxyl, cyano, $Ar^3$, $C_{1-4}$acyl, and $C_{1-4}$alkyl optionally substituted with one or more substituents selected from the group consisting of halo and hydroxyl;
wherein two geminal hydrogen atoms in (d-1) or (d-2) may be replaced by $C_{2-6}$alkanediyl;
wherein (d-3) or (d-4) may be substituted on the 1,2-benzenediyl-moiety with one or more substituents each independently selected from the group consisting of halo, $C_{1-4}$alkyloxy, cyano, $NR^7R^8$, morpholinyl, and $C_{1-4}$alkyl optionally substituted with one or more halo substituents;
wherein (d-5), (d-6), (d-7), (d-8) or (d-9) may be substituted where possible with one or more substituents each independently selected from the group consisting of $Ar^3$, (C=O)—$Ar^3$, O—$Ar^3$, $NR^{11}$—$Ar^3$, $C_{1-4}$acyl, and $C_{1-4}$alkyl optionally substituted with one or more halo substituents;
Y represents a direct bond, $NR^{10}$ or O; wherein $R^{10}$ is hydrogen, $Ar^3$, $C_{1-4}$acyl, or $C_{1-4}$alkyl optionally substituted with one or more halo substituents;
m represents 3, 4, 5, 6 or 7;
n represents 0, 1, 2 or 3;
q represents 3, 4, 5 or 6;
r represents 0, 1, 2 or 3;
each $Ar^3$ independently represents phenyl optionally substituted with one or more substituents each independently selected from the group consisting of halo, cyano, $NR^7R^8$, morpholinyl, cyclo$C_{3-7}$alkyl, $C_{1-4}$alkyloxy optionally substituted with one or more halo substituents, and $C_{1-4}$alkyl optionally substituted with one or more halo substituents;
or a 5- or 6-membered heteroaryl selected from the group consisting of furanyl, thiophenyl, pyrazolyl, oxazolyl, isoxazolyl, thiazolyl, isothiazolyl, thiadiazolyl, oxadiazolyl, pyridinyl, pyrimidinyl, pyridazinyl, and pyrazinyl, wherein said 5- or 6-membered heteroaryl is optionally substituted with one or more substituents each independently selected from the group consisting of halo, $C_{1-4}$alkyloxy, cyano, $NR^7R^8$, morpholinyl, and $C_{1-4}$alkyl optionally substituted with one or more halo substituents;
or 1,6-dihydro-1-methyl-6-oxo-3-pyridinyl or 1,2-dihydro-1-methyl-2-oxo-3-pyridinyl;
$R^{6b}$ and $R^{6c}$ represent hydrogen or methyl;
each $R^7$ independently is hydrogen, $C_{1-4}$acyl, or $C_{1-4}$alkyl;
each $R^8$ independently is hydrogen or $C_{1-4}$alkyl;
$R^{11}$ is hydrogen or $C_{1-4}$alkyl;
and the pharmaceutically acceptable addition salts, and the solvates thereof.

An embodiment of the present invention relates to those compounds of Formula (I) and stereoisomeric forms thereof, wherein $R^1$ is hydrogen or $C_{1-4}$alkyl;
$R^2$ is hydrogen or $C_{1-4}$alkyl;
X is CH or N;
$A^1$ is $CR^{3a}$ or N; wherein $R^{3a}$ is hydrogen; halo; or $C_{1-4}$alkyloxy;
$A^2$ is $CR^{3b}$ or N; wherein $R^{3b}$ is hydrogen or $C_{1-4}$alkyloxy;
$A^3$ and $A^4$ each independently are CH or N;
provided that no more than two of $A^1$, $A^2$, $A^3$ and $A^4$ are N;
$Het^1$ is a heterocycle, having formula (a), (b) or (c);
$R^{4a}$ is hydrogen; tetrahydropyranyl; tetrahydrofuranyl; piperidinyl; morpholinyl; pyrrolidinyl; cyclo$C_{3-7}$alkyl; $Ar^1$; or $C_{1-6}$alkyl optionally substituted with one or more substituents each independently selected from the group consisting of halo, $Ar^1$, tetrahydropyranyl, tetrahydrofuranyl, piperidinyl, morpholinyl, pyrrolidinyl, cyclo$C_{3-7}$alkyl, $C_{1-6}$alkyloxy, $C_{1-6}$alkylthio, and O—$Ar^1$;
$R^{4c}$ is hydrogen; tetrahydropyranyl; tetrahydrofuranyl; piperidinyl; morpholinyl; pyrrolidinyl; cyclo$C_{3-7}$alkyl; $C_{1-6}$alkyloxy; $C_{1-6}$alkylthio; $Ar^1$; or $C_{1-6}$alkyl optionally substituted with one or more substituents each independently selected from the group consisting of halo, $Ar^1$, tetrahydropyranyl, tetrahydrofuranyl, piperidinyl, morpholinyl, pyrrolidinyl, cyclo$C_{3-7}$alkyl, $C_{1-6}$alkyloxy, $C_{1-6}$alkylthio, and O—$Ar^1$;
wherein in the definitions of $R^{4a}$ and $R^{4c}$ piperidinyl, morpholinyl and pyrrolidinyl may be substituted with one or more substituents each independently selected from the group consisting of $C_{1-4}$alkyl, $C_{2-6}$alkenyl, $C_{1-4}$acyl, halo and $C_{1-4}$alkyloxycarbonyl;
wherein in the definitions of $R^{4a}$ and $R^{4c}$ each $Ar^1$ independently is phenyl optionally substituted with one or more substituents each independently selected from the group consisting of halo, $C_{1-4}$alkyloxy, cyano, $NR^7R^8$, morpholinyl, and $C_{1-4}$alkyl optionally substituted with one or more halo substituents; or each $Ar^1$ independently is a 5- or 6-membered heteroaryl selected from the group consisting of furanyl, thiophenyl, pyrazolyl, oxazolyl, isoxazolyl, thiazolyl, isothiazolyl, thiadiazolyl, oxadiazolyl, pyridinyl, pyrimidinyl, pyridazinyl, and pyrazinyl, wherein said 5- or 6-membered heteroaryl is optionally substituted with one or more substituents each independently selected from the group consisting of halo, $C_{1-4}$alkyloxy, cyano, $NR^7R^8$, morpholinyl, and $C_{1-4}$alkyl optionally substituted with one or more halo substituents;

wherein in the definitions of $R^{4a}$ and $R^{4c}$ each cycloC$_{3-7}$alkyl, tetrahydropyranyl or tetrahydrofuranyl may be substituted with one or more substituents each independently selected from the group consisting of halo, C$_{1-4}$alkyloxy, cyano, and C$_{1-4}$alkyl optionally substituted with one or more halo substituents;

$R^{5a}$, $R^{5b}$ and $R^{5c}$ are hydrogen; C$_{1-6}$alkyl optionally substituted with one or more substituents each independently selected from the group consisting of halo, C$_{1-4}$alkyloxy, C$_{1-4}$acyl, and C$_{1-4}$alkyloxycarbonyl;

tetrahydropyranyl; tetrahydrofuranyl; piperidinyl; morpholinyl; pyrrolidinyl; 1,6-dihydro-1-methyl-6-oxo-3-pyridinyl; 1,2-dihydro-1-methyl-2-oxo-3-pyridinyl; cycloC$_{3-7}$alkyl; Ar$^2$;

wherein in the definitions of $R^{5a}$, $R^{5b}$ and $R^{5c}$ tetrahydrofuranyl, tetrahydropyranyl, piperidinyl, morpholinyl, pyrrolidinyl and cycloC$_{3-7}$alkyl may be substituted with one or more substituents selected from the group consisting of C$_{1-4}$alkyl, C$_{2-6}$alkenyl, C$_{1-4}$acyl, halo and C$_{1-4}$alkyloxycarbonyl;

wherein in the definitions of $R^{5a}$, $R^{5b}$ and $R^{5c}$, Ar$^2$ is phenyl optionally substituted with one or more substituents each independently selected from the group consisting of halo, C$_{1-4}$alkyloxy, cyano, NR$^7$R$^8$, morpholinyl, and C$_{1-4}$alkyl optionally substituted with one or more halo substituents; or Ar$^2$ is a 5- or 6-membered heteroaryl selected from the group consisting of furanyl, thiophenyl, pyrazolyl, oxazolyl, isoxazolyl, thiazolyl, isothiazolyl, thiadiazolyl, oxadiazolyl, pyridinyl, pyrimidinyl, pyridazinyl, and pyrazinyl, wherein said 5- or 6-membered heteroaryl is optionally substituted with one or more substituents each independently selected from the group consisting of halo, C$_{1-4}$alkyloxy, cyano, NR$^7$R$^8$, morpholinyl, and C$_{1-4}$alkyl optionally substituted with one or more halo substituents;

L$^a$, L$^b$ and L$^c$ represent a direct bond; C$_{2-6}$alkenediyl; carbonyl; O; S; S($=$O)$_p$; NR$^9$; NR$^9$—C$_{1-4}$alkanediyl; or C$_{1-6}$alkanediyl optionally substituted with one or more halo substituents; or two geminal hydrogen atoms in said C$_{1-6}$alkanediyl may be replaced by C$_{1-6}$alkanediyl, in particular two geminal hydrogen atoms may be replaced by C$_{2-6}$alkanediyl;

p represents 1 or 2;
$R^{6b}$ and $R^{6c}$ represent hydrogen or methyl;
each R$^7$ independently is hydrogen or C$_{1-4}$alkyl;
each R$^8$ independently is hydrogen or C$_{1-4}$alkyl;
R$^9$ is hydrogen or C$_{1-4}$alkyl optionally substituted with one or more substituents each independently selected from the group consisting of halo and cycloC$_{3-7}$alkyl;

and the pharmaceutically acceptable addition salts, and the solvates thereof;

provided that the compound is not 2-[4-(1H-imidazol-1-yl)phenyl]-4-(trifluoromethyl)-1H-imidazole.

An embodiment of the present invention relates to those compounds of Formula (I) and stereoisomeric forms thereof, wherein R$^1$ is hydrogen or C$_{1-4}$alkyl;
R$^2$ is hydrogen or C$_{1-4}$alkyl;
X is CH or N;
A$^1$ is CR$^{3a}$ or N; wherein R$^{3a}$ is hydrogen; halo; or C$_{1-4}$alkyloxy;
A$^2$ is CR$^{3b}$ or N; wherein R$^{3b}$ is hydrogen or C$_{1-4}$alkyloxy;
A$^3$ and A$^4$ each independently are CH or N;
provided that no more than two of A$^1$, A$^2$, A$^3$ and A$^4$ are N;
Het$^1$ is a heterocycle, having formula (a), (b) or (c);
-L$^a$-R$^{5a}$ and R$^{4a}$; or -L$^c$-R$^{5c}$ and R$^{4c}$; can be taken together to form a bivalent radical -L$^a$-R$^{5a}$—R$^{4a}$— or -L$^c$-R$^{5c}$—R$^{4c}$—, having formula $$—(CH_2)_{m-n}—Y—(CH_2)_n— \qquad (d\text{-}1);$$

$$—(CH_2)_n—Y—(CH_2)_{m-n}— \qquad (d\text{-}2);$$

$$\text{-1,2-benzenediyl-}(CH_2)_r—Y—(CH_2)_{q-r}— \qquad (d\text{-}3); \text{ or}$$

$$\text{-1,2-benzenediyl-}(CH_2)_{q-r}—Y—(CH_2)_r— \qquad (d\text{-}4);$$

wherein (d-1), (d-2), (d-3) or (d-4) may be substituted on a CH$_2$ group with one or two substituents each independently selected from the group consisting of Ar$^3$, C$_{1-4}$acyl, and C$_{1-4}$alkyl optionally substituted with one or more halo substituents;

wherein (d-3) or (d-4) may be substituted on the 1,2-benzenediyl-moiety with one or more substituents each independently selected from the group consisting of halo, C$_{1-4}$alkyloxy, cyano, NR$^7$R$^8$, morpholinyl, and C$_{1-4}$alkyl optionally substituted with one or more halo substituents;

Y represents a direct bond, NR$^{10}$ or O; wherein R$^{10}$ is hydrogen, Ar$^3$, C$_{1-4}$acyl, or C$_{1-4}$alkyl optionally substituted with one or more halo substituents;

m represents 3, 4, 5, 6 or 7;
n represents 0, 1, 2 or 3;
q represents 3, 4, 5 or 6;
r represents 0, 1, 2 or 3;
each Ar$^3$ independently represents phenyl optionally substituted with one or more substituents each independently selected from the group consisting of halo, C$_{1-4}$alkyloxy, cyano, NR$^7$R$^8$, morpholinyl, and C$_{1-4}$alkyl optionally substituted with one or more halo substituents;

or a 5- or 6-membered heteroaryl selected from the group consisting of furanyl, thiophenyl, pyrazolyl, oxazolyl, isoxazolyl, thiazolyl, isothiazolyl, thiadiazolyl, oxadiazolyl, pyridinyl, pyrimidinyl, pyridazinyl, and pyrazinyl, wherein said 5- or 6-membered heteroaryl is optionally substituted with one or more substituents each independently selected from the group consisting of halo, C$_{1-4}$alkyloxy, cyano, NR$^7$R$^8$, morpholinyl, and C$_{1-4}$alkyl optionally substituted with one or more halo substituents;

or 1,6-dihydro-1-methyl-6-oxo-3-pyridinyl or 1,2-dihydro-1-methyl-2-oxo-3-pyridinyl;

$R^{6b}$ and $R^{6c}$ represent hydrogen or methyl;
each R$^7$ independently is hydrogen or C$_{1-4}$alkyl;
each R$^8$ independently is hydrogen or C$_{1-4}$alkyl;
R$^9$ is hydrogen or C$_{1-4}$alkyl optionally substituted with one or more substituents each independently selected from the group consisting of halo and cycloC$_{3-7}$alkyl;

and the pharmaceutically acceptable addition salts, and the solvates thereof.

An embodiment of the present invention relates to those compounds of Formula (I) and stereoisomeric forms thereof, wherein R$^1$ is hydrogen or C$_{1-4}$alkyl;
R$^2$ is hydrogen or C$_{1-4}$alkyl;
X is CH or N;
A$^1$ is CR$^{3a}$ or N; wherein R$^{3a}$ is hydrogen; halo; cyano; C$_{1-4}$alkyl; or C$_{1-4}$alkyloxy optionally substituted with one or more halo substituents;
A$^2$ is CR$^{3b}$ or N; wherein R$^{3b}$ is hydrogen; fluoro; or C$_{1-4}$alkyloxy;
A$^3$ and A$^4$ each independently are CH; CF; or N;
provided that no more than two of A$^1$, A$^2$, A$^3$ and A$^4$ are N;
Het$^1$ is a heterocycle, having formula (a), (b) or (c);
R$^{4a}$ is hydrogen; cycloC$_{3-7}$alkyl; Ar$^1$; or C$_{1-6}$alkyl optionally substituted with one or more substituents each independently selected from the group consisting of halo, hydroxyl, cyano, Ar$^1$, cycloC$_{3-7}$alkyl, and C$_{1-6}$alkyloxy;
R$^{4c}$ is cycloC$_{3-7}$alkyl; C$_{1-6}$alkyloxy; C$_{1-6}$alkylthio; Ar$^1$; or C$_{1-6}$alkyl;

wherein in the definitions of $R^{4a}$ and $R^{4c}$ each $Ar^1$ independently is phenyl optionally substituted with one or more substituents each independently selected from the group consisting of halo, $C_{1-4}$alkyloxy, cyano, $NR^7R^8$, and $C_{1-4}$alkyl optionally substituted with one or more halo substituents;

$R^{5a}$, $R^{5b}$ and $R^{5c}$ are hydrogen; tetrahydropyranyl; tetrahydrofuranyl; piperidinyl; morpholinyl; pyrrolidinyl; piperazinyl; hexahydro-1H-1,4-diazepin-1-yl; 1,2,3,4-tetrahydro-2-quinolinyl; 3,4-dihydro-2(1H)-isoquinolinyl; 3,4-dihydro-1(2H)-quinolinyl; 2,2-difluoro-1,3-benzodioxol-5-yl; 2,2-difluoro-1,3-benzodioxol-4-yl; 1,6-dihydro-1-methyl-6-oxo-3-pyridinyl; 1,2-dihydro-1-methyl-2-oxo-3-pyridinyl; 2,3-dihydro-4H-1,4-benzoxazin-4-yl; 3,4-dihydro-1,5-benzoxazepin-5(2H)-yl; cyclo$C_{3-7}$alkyl; $Ar^2$; or $C_{1-6}$alkyl;

wherein in the definitions of $R^{5a}$, $R^{5b}$ and $R^{5c}$ tetrahydrofuranyl, tetrahydropyranyl, piperidinyl, morpholinyl, pyrrolidinyl, piperazinyl, hexahydro-1H-1,4-diazepin-1-yl, 1,2,3,4-tetrahydro-2-quinolinyl, 3,4-dihydro-2(1H)-isoquinolinyl, 3,4-dihydro-1(2H)-quinolinyl and cyclo$C_{3-7}$alkyl may be substituted with one or more substituents each independently selected from the group consisting of $C_{2-6}$alkenyl, $C_{1-4}$acyl, halo, $C_{1-4}$alkyloxycarbonyl, $C_{1-4}$alkyl optionally substituted with one or more halo substituents, and phenyl optionally substituted with one or more substituents each independently selected from the group consisting of $C_{1-4}$alkyl and trifluoromethyl;

wherein in the definitions of $R^{5a}$, $R^{5b}$ and $R^{5c}$, $Ar^2$ is phenyl optionally substituted with one or more substituents each independently selected from the group consisting of halo, cyano, $NR^7R^8$, (C=O)—$NR^7R^8$, morpholinyl, $C_{1-4}$acyl, $C_{1-4}$alkylsulfonyl, $C_{1-4}$alkylsulfinyl, cyclo$C_{3-7}$alkyl, cyclo$C_{3-7}$alkyloxy, tetrahydropyranyloxy, tetrahydrofuranyloxy, $C_{1-4}$alkyloxy optionally substituted with one or more substituents each independently selected from the group consisting of halo, hydroxyl, $C_{1-4}$alkyloxy, and cyclopropyl, and $C_{1-4}$alkyl optionally substituted with one or more substituents each independently selected from the group consisting of halo, hydroxyl and $C_{1-4}$alkyloxy optionally substituted with one or more halo substituents;

or $Ar^2$ is a 5- or 6-membered heteroaryl selected from the group consisting of furanyl, thiophenyl, pyrazolyl, oxazolyl, isoxazolyl, thiazolyl, isothiazolyl, thiadiazolyl, oxadiazolyl, pyridinyl, pyrimidinyl, pyridazinyl, and pyrazinyl, wherein said 5- or 6-membered heteroaryl is optionally substituted with one or more substituents each independently selected from the group consisting of halo, $C_{1-4}$alkyloxy, cyano, $NR^7R^8$, morpholinyl, and $C_{1-4}$alkyl optionally substituted with one or more halo substituents;

or $Ar^2$ is quinolinyl;

$L^a$, $L^b$ and $L^c$ represent a direct bond; $C_{2-6}$alkenediyl; carbonyl; O; S; S(=O)$_p$; $NR^9$; $NR^9$—$C_{1-4}$alkanediyl; $C_{1-4}$alkanediyl-$NR^9$; $NR^{12}$—(C=O); (C=O)—$NR^{12}$; or $C_{1-6}$alkanediyl optionally substituted with one or more substituents each independently selected from the group consisting of halo and hydroxy; two geminal hydrogen atoms in said $C_{1-6}$alkanediyl may be replaced by $C_{1-6}$alkanediyl;

p represents 1 or 2;

or -$L^a$-$R^{5a}$ and $R^{4a}$; or -$L^c$-$R^{5c}$ and $R^{4c}$; can be taken together to form a bivalent radical -$L^a$-$R^{5a}$—$R^{4a}$— or -$L^c$-$R^{5c}$—$R^{4c}$—, having formula —(CH$_2$)$_{m-n}$—Y—(CH$_2$)$_n$— (d-1);

—(CH$_2$)$_n$—Y—(CH$_2$)$_{m-n}$— (d-2);

-1,2-benzenediyl-(CH$_2$)$_r$—Y—(CH$_2$)$_{q-r}$— (d-3);

-1,2-benzenediyl-(CH$_2$)$_{q-r}$—Y—(CH$_2$)$_r$— (d-4);

—CH=CH—CH=CH— (d-5);

—CH=CH—N=CH— (d-6);

—CH=N—CH=CH— (d-7);

—N=CH—CH=CH— (d-8); or

—CH=CH—CH=N— (d-9);

wherein (d-1) or (d-2) may be substituted on one or two CH$_2$ groups with one or two substituents each independently selected from the group consisting of hydroxyl, cyano, $Ar^3$, $C_{1-4}$acyl, and $C_{1-4}$alkyl optionally substituted with one or more substituents selected from the group consisting of halo and hydroxyl;

wherein two geminal hydrogen atoms in (d-1) or (d-2) may be replaced by $C_{2-6}$alkanediyl;

wherein (d-5), (d-6), (d-7), (d-8) or (d-9) may be substituted where possible with one substituent selected from the group consisting of $Ar^3$ and $NR^{11}$—$Ar^3$;

in particular wherein (d-1) or (d-2) may be substituted on one CH$_2$ group with an $Ar^3$ substituent and optionally (d-1) or (d-2) is substituted on the same or a different CH$_2$ group with one substituent selected from the group consisting of hydroxyl and $C_{1-4}$alkyl optionally substituted with one or more hydroxyl substituents; wherein two geminal hydrogen atoms in (d-1) or (d-2) may be replaced by 1,5-pentanediyl;

wherein (d-5), (d-6), (d-7), (d-8) or (d-9) is substituted where possible with one substituent selected from the group consisting of $Ar^3$ and $NR^{11}$—$Ar^3$;

or more in particular wherein the bivalent radical -$L^a$-$R^{5a}$—$R^{4a}$— or -$L^c$-$R^{5c}$—$R^{4c}$— is selected from the group consisting of —CH($Ar^3$)—(CH$_2$)$_2$—, —CH($Ar^3$)—(CH$_2$)$_3$—, —CH($Ar^3$)—(CH$_2$)$_4$—, —N($Ar^3$)—(CH$_2$)$_3$—, —CH($Ar^3$)—N(CH$_3$)—(CH$_2$)$_2$—, —CH($Ar^3$)—N(acetyl)-(CH$_2$)$_2$—, —CH($Ar^3$)—NH—(CH$_2$)$_2$—, —CH($Ar^3$)—O—(CH$_2$)$_2$—, —CH($Ar^3$)—O—(CH$_2$)$_3$—, —C($Ar^3$)=CH—CH=CH—, —C($NR^{11}$—$Ar^3$)=CH—CH=CH—, —N=CH—CH=C($Ar^3$)—, —N=C($Ar^3$)—CH=CH—, —CH=N—CH=C($Ar^3$)—, —(CH$_2$)$_3$—CH($Ar^3$)—, —CH($Ar^3$)—(CH$_2$)$_2$—CH(CH$_3$)—, —CH($Ar^3$)—CH(CH$_3$)—(CH$_2$)$_2$— or —C($Ar^3$)=N—CH=CH—;

Y represents a direct bond, $NR^{10}$ or O; wherein $R^{10}$ is hydrogen, $Ar^3$, $C_{1-4}$acyl, or $C_{1-4}$alkyl optionally substituted with one or more halo substituents;

m represents 3, 4, 5 or 6; in particular 3, 4 or 5;

n represents 0, 1, 2 or 3; in particular 0, 1 or 2; more in particular 0 or 1; also more in particular 0 or 2;

q represents 3, 4, 5 or 6; in particular 3;

r represents 0, 1, 2 or 3; in particular 3;

each $Ar^3$ independently represents phenyl optionally substituted with one or more substituents each independently selected from the group consisting of halo, cyano, $NR^7R^8$, morpholinyl, cyclo$C_{3-7}$alkyl, $C_{1-4}$alkyloxy optionally substituted with one or more halo substituents, and $C_{1-4}$alkyl optionally substituted with one or more halo substituents;

$R^{6b}$ and $R^{6c}$ represent hydrogen or methyl;

each $R^7$ independently is hydrogen, $C_{1-4}$acyl, or $C_{1-4}$alkyl;

each $R^8$ independently is hydrogen or $C_{1-4}$alkyl;

$R^9$ is hydrogen, $C_{1-4}$acyl, or $C_{1-4}$alkyl optionally substituted with one or more substituents each independently selected from the group consisting of halo and cyclo$C_{3-7}$alkyl;

$R^{11}$ is hydrogen or $C_{1-4}$alkyl;
$R^{12}$ is hydrogen or methyl;
and the pharmaceutically acceptable addition salts, and the solvates thereof.

An embodiment of the present invention relates to those compounds of Formula (I) and stereoisomeric forms thereof, wherein
$R^1$ is hydrogen or $C_{1-4}$alkyl;
$R^2$ is hydrogen or $C_{1-4}$alkyl;
X is CH or N;
$A^1$ is $CR^{3a}$ or N; wherein $R^{3a}$ is hydrogen; cyano; $C_{1-4}$alkyl; or $C_{1-4}$alkyloxy optionally substituted with one or more halo substituents;
$A^2$ is $CR^{3b}$ or N; wherein $R^{3b}$ is hydrogen; fluoro; or $C_{1-4}$alkyloxy;
$A^3$ is CH or CF;
$A^4$ is CH;
provided that when $A^1$ is N, then $A^2$ is $CR^{3b}$, and when $A^2$ is N, then $A^1$ is $CR^{3a}$;
$Het^1$ is a heterocycle, having formula (a), (b) or (c)
$R^{4a}$ is hydrogen; $cycloC_{3-7}$alkyl; $Ar^1$; or $C_{1-6}$alkyl optionally substituted with one or more substituents each independently selected from the group consisting of halo, hydroxyl, cyano, $Ar^1$, $cycloC_{3-7}$alkyl, $C_{1-6}$alkyloxy;
$R^{4c}$ is $Ar^1$ or $C_{1-6}$alkyl;
wherein in the definitions of $R^{4a}$ and $R^{4c}$ each $Ar^1$ independently is phenyl optionally substituted with one or more substituents each independently selected from the group consisting of halo and $C_{1-4}$alkyl optionally substituted with one or more halo substituents;
$R^{5a}$, $R^{5b}$ and $R^{5c}$ are hydrogen; piperidinyl; morpholinyl; pyrrolidinyl; hexahydro-1H-1,4-diazepin-1-yl; 1,2,3,4-tetrahydro-2-quinolinyl; 3,4-dihydro-2(1H)-isoquinolinyl; 3,4-dihydro-1(2H)-quinolinyl; 2,2-difluoro-1,3-benzodioxol-5-yl; 2,2-difluoro-1,3-benzodioxol-4-yl; 2,2-difluoro-1,3-benzodioxol-4-yl; 1,6-dihydro-1-methyl-6-oxo-3-pyridinyl; 1,2-dihydro-1-methyl-2-oxo-3-pyridinyl; 2,3-dihydro-4H-1,4-benzoxazin-4-yl; 3,4-dihydro-1,5-benzoxazepin-5(2H)-yl; $cycloC_{3-7}$alkyl; $Ar^2$; or $C_{1-6}$alkyl;
wherein in the definitions of $R^{5a}$, $R^{5b}$ and $R^{5c}$ piperidinyl, morpholinyl, pyrrolidinyl, hexahydro-1H-1,4-diazepin-1-yl, and $cycloC_{3-7}$alkyl may be substituted with one or more substituents each independently selected from the group consisting of $C_{1-4}$acyl, $C_{1-4}$alkyl optionally substituted with one or more halo substituents, and phenyl optionally substituted with one or more trifluoromethyl groups;
wherein in the definitions of $R^{5a}$, $R^{5b}$ and $R^{5c}$,
$Ar^2$ is phenyl optionally substituted with one or more substituents each independently selected from the group consisting of halo, cyano, $NR^7R^8$, (C=O)—$NR^7R^8$, $C_{1-4}$acyl, $C_{1-4}$alkylsulfonyl, $C_{1-4}$alkylsulfinyl, tetrahydrofuranyloxy,
$C_{1-4}$alkyloxy optionally substituted with one or more substituents each independently selected from the group consisting of halo, $C_{1-4}$alkyloxy, and cyclopropyl,
and $C_{1-4}$alkyl optionally substituted with one or more substituents each independently selected from the group consisting of halo, hydroxyl and $C_{1-4}$alkyloxy;
or $Ar^2$ is a 5- or 6-membered heteroaryl selected from the group consisting of pyridinyl and pyrazolyl, wherein said 5- or 6-membered heteroaryl is optionally substituted with one or more substituents each independently selected from the group consisting of halo, $C_{1-4}$alkyloxy, and $C_{1-4}$alkyl optionally substituted with one or more halo substituents;
or $Ar^2$ is quinolinyl;

$L^a$, $L^b$ and $L^c$ represent a direct bond; $C_{2-6}$alkenediyl; carbonyl; O; S; $NR^9$; $NR^9$—$C_{1-4}$alkanediyl; $C_{1-4}$alkanediyl-$NR^9$; (C=O)—$NR^{12}$; or $C_{1-6}$alkanediyl optionally substituted with one or more substituents each independently selected from the group consisting of halo and hydroxy; two geminal hydrogen atoms in said $C_{1-6}$alkanediyl may be replaced by $C_{1-6}$alkanediyl;
or -$L^a$-$R^{5a}$ and $R^{4a}$; or -$L^c$-$R^{5c}$ and $R^{4c}$; can be taken together to form a bivalent radical -$L^a$-$R^{5a}$—$R^{4a}$— or -$L^c$-$R^{5c}$—$R^{4c}$—, having formula —(CH$_2$)$_{m-n}$—Y—(CH$_2$)$_n$—  (d-1);

—(CH$_2$)$_n$—Y—(CH$_2$)$_{m-n}$—  (d-2);

-1,2-benzenediyl-(CH$_2$)$_r$—Y—(CH$_2$)$_{q-r}$—  (d-3);

—CH=CH—CH=CH—  (d-5);

—CH=N—CH=CH—  (d-7); or

—N=CH—CH=CH—  (d-8);

wherein (d-1) or (d-2) may be substituted on one $CH_2$ group with an $Ar^3$ substituent and optionally (d-1) or (d-2) is substituted on the same or a different $CH_2$ group with one substituent selected from the group consisting of hydroxyl and $C_{1-4}$alkyl optionally substituted with one or more hydroxyl substituents; wherein two geminal hydrogen atoms in (d-1) or (d-2) may be replaced by 1,5-pentanediyl;
in particular (d-1) or (d-2) is substituted on one $CH_2$ group with an $Ar^3$ substituent and optionally (d-1) or (d-2) is further substituted on the same or a different $CH_2$ group with one substituent selected from the group consisting of hydroxyl and $C_{1-4}$alkyl optionally substituted with one or more hydroxyl substituents; or two geminal hydrogen atoms in (d-1) or (d-2) without a substituent on a $CH_2$ group are replaced by 1,5-pentanediyl;
wherein (d-5), (d-7) or (d-8) is substituted where possible with one substituent selected from the group consisting of $Ar^3$ and $NR^{11}$—$Ar^3$;
Y represents a direct bond, $NR^{10}$ or O; wherein $R^{10}$ is hydrogen, $Ar^3$, $C_{1-4}$acyl, or $C_{1-4}$alkyl;
m represents 3, 4, 5 or 6; in particular 3, 4 or 5;
n represents 0, 1, 2 or 3; in particular 0, 1 or 2; also in particular 0 or 1; also in particular 0 or 2;
q represents 3, 4, 5 or 6; in particular 3;
r represents 0, 1, 2 or 3; in particular 3;
each $Ar^3$ independently represents phenyl optionally substituted with one or more substituents each independently selected from the group consisting of halo, $cycloC_{3-7}$alkyl, $C_{1-4}$alkyloxy optionally substituted with one or more halo substituents, and $C_{1-4}$alkyl optionally substituted with one or more halo substituents;
$R^{6b}$ and $R^{6c}$ represent hydrogen or methyl;
each $R^7$ independently is $C_{1-4}$acyl or $C_{1-4}$alkyl;
each $R^8$ independently is hydrogen or $C_{1-4}$alkyl;
$R^9$ is hydrogen, $C_{1-4}$acyl, or $C_{1-4}$alkyl;
$R^{11}$ is hydrogen;
$R^{12}$ is hydrogen;
and the pharmaceutically acceptable addition salts, and the solvates thereof.

An embodiment of the present invention relates to those compounds of Formula (I) and stereoisomeric forms thereof, wherein
$R^1$ is hydrogen or $C_{1-4}$alkyl;
$R^2$ is hydrogen or $C_{1-4}$alkyl;
X is CH or N;

$A^1$ is $CR^{3a}$ or N; wherein $R^{3a}$ is hydrogen; cyano; $C_{1-4}$alkyl; or $C_{1-4}$alkyloxy optionally substituted with one or more halo substituents;

$A^2$ is $CR^{3b}$ or N; wherein $R^{3b}$ is hydrogen; fluoro; or $C_{1-4}$alkyloxy;

$A^3$ is CH or CF;

$A^4$ is CH;

provided that when $A^1$ is N, then $A^2$ is $CR^{3b}$, and when $A^2$ is N, then $A^1$ is $CR^{3a}$;

$Het^1$ is a heterocycle, having formula (a), (b) or (c)

$R^{4a}$ is hydrogen; cyclo$C_{3-7}$alkyl; $Ar^1$; or $C_{1-6}$alkyl optionally substituted with one or more substituents each independently selected from the group consisting of halo, hydroxyl, cyano, $Ar^1$, cyclo$C_{3-7}$alkyl, $C_{1-6}$alkyloxy;

$R^{4c}$ is $Ar^1$ or $C_{1-6}$alkyl;

wherein in the definitions of $R^{4a}$ and $R^{4c}$ each $Ar^1$ independently is phenyl optionally substituted with one or more substituents each independently selected from the group consisting of halo and $C_{1-4}$alkyl optionally substituted with one or more halo substituents;

$R^{5a}$, $R^{5b}$ and $R^{5c}$ are hydrogen; piperidinyl; morpholinyl; pyrrolidinyl; hexahydro-1H-1,4-diazepin-1-yl; 1,2,3,4-tetrahydro-2-quinolinyl; 3,4-dihydro-2(1H)-isoquinolinyl; 3,4-dihydro-1(2H)-quinolinyl; 2,2-difluoro-1,3-benzodioxol-5-yl; 2,2-difluoro-1,3-benzodioxol-4-yl; 2,2-difluoro-1,3-benzodioxol-4-yl; 1,6-dihydro-1-methyl-6-oxo-3-pyridinyl; 1,2-dihydro-1-methyl-2-oxo-3-pyridinyl; 2,3-dihydro-4H-1,4-benzoxazin-4-yl; 3,4-dihydro-1,5-benzoxazepin-5(2H)-yl; cyclo$C_{3-7}$alkyl; $Ar^2$; or $C_{1-6}$alkyl;

wherein in the definitions of $R^{5a}$, $R^{5b}$ and $R^{5c}$ piperidinyl, morpholinyl, pyrrolidinyl, hexahydro-1H-1,4-diazepin-1-yl, and cyclo$C_{3-7}$alkyl may be substituted with one or more substituents each independently selected from the group consisting of $C_{1-4}$acyl, $C_{1-4}$alkyl optionally substituted with one or more halo substituents, and phenyl optionally substituted with one or more trifluoromethyl groups;

wherein in the definitions of $R^{5a}$, $R^{5b}$ and $R^{5c}$, $Ar^2$ is phenyl optionally substituted with one or more substituents each independently selected from the group consisting of halo, cyano, $NR^7R^8$, (C=O)—$NR^7R^8$, $C_{1-4}$acyl, $C_{1-4}$alkylsulfonyl, $C_{1-4}$alkylsulfinyl, tetrahydrofuranyloxy, $C_{1-4}$alkyloxy optionally substituted with one or more substituents each independently selected from the group consisting of halo, $C_{1-4}$alkyloxy, and cyclopropyl, and $C_{1-4}$alkyl optionally substituted with one or more substituents each independently selected from the group consisting of halo, hydroxyl and $C_{1-4}$alkyloxy;

or $Ar^2$ is a 5- or 6-membered heteroaryl selected from the group consisting of pyridinyl and pyrazolyl, wherein said 5- or 6-membered heteroaryl is optionally substituted with one or more substituents each independently selected from the group consisting of halo, $C_{1-4}$alkyloxy, and $C_{1-4}$alkyl optionally substituted with one or more halo substituents;

or $Ar^2$ is quinolinyl;

$L^a$, $L^b$ and $L^c$ represent a direct bond; $C_{2-6}$alkenediyl; carbonyl; O; S; $NR^9$; $NR^9$—$C_{1-4}$alkanediyl; $C_{1-4}$alkanediyl-$NR^9$; (C=O)—$NR^{12}$; or $C_{1-6}$alkanediyl optionally substituted with one or more substituents each independently selected from the group consisting of halo and hydroxy; two geminal hydrogen atoms in said $C_{1-6}$alkanediyl may be replaced by $C_{1-6}$alkanediyl;

$R^{6b}$ and $R^{6c}$ represent hydrogen or methyl;

each $R^7$ independently is $C_{1-4}$acyl or $C_{1-4}$alkyl;

each $R^8$ independently is hydrogen or $C_{1-4}$alkyl;

$R^9$ is hydrogen, $C_{1-4}$acyl, or $C_{1-4}$alkyl;

$R^{12}$ is hydrogen;

and the pharmaceutically acceptable addition salts, and the solvates thereof.

An embodiment of the present invention relates to those compounds of Formula (I) and stereoisomeric forms thereof, wherein $R^1$ is hydrogen or $C_{1-4}$alkyl;

$R^2$ is hydrogen or $C_{1-4}$alkyl;

X is CH or N;

$A^1$ is $CR^{3a}$ or N; wherein $R^{3a}$ is hydrogen; cyano; $C_{1-4}$alkyl; or $C_{1-4}$alkyloxy optionally substituted with one or more halo substituents;

$A^2$ is $CR^{3b}$ or N; wherein $R^{3b}$ is hydrogen; fluoro; or $C_{1-4}$alkyloxy;

$A^3$ is CH or CF;

$A^4$ is CH;

provided that when $A^1$ is N, then $A^2$ is $CR^{3b}$, and when $A^2$ is N, then $A^1$ is $CR^{3a}$;

$Het^1$ is a heterocycle, having formula (a), (b) or (c)

-$L^a$-$R^{5a}$ and $R^{4a}$; or -$L^c$-$R^{5c}$ and $R^{4c}$; can be taken together to form a bivalent radical -$L^a$-$R^{5a}$—$R^{4a}$— or -$L^c$-$R^{5c}$—$R^{4c}$—, having formula $$—(CH_2)_{m-n}—Y—(CH_2)_n— \qquad (d\text{-}1);$$

$$—(CH_2)_n—Y—(CH_2)_{m-n}— \qquad (d\text{-}2);$$

$$\text{-1,2-benzenediyl-}(CH_2)_r—Y—(CH_2)_{q-r}— \qquad (d\text{-}3);$$

$$—CH{=}CH—CH{=}CH— \qquad (d\text{-}5);$$

$$—CH{=}N—CH{=}CH— \qquad (d\text{-}7); \text{ or}$$

$$—N{=}CH—CH{=}CH— \qquad (d\text{-}8); \text{ or}$$

wherein (d-1) or (d-2) may be substituted on one $CH_2$ group with an $Ar^3$ substituent and optionally (d-1) or (d-2) is substituted on the same or a different $CH_2$ group with one substituent selected from the group consisting of hydroxyl and $C_{1-4}$alkyl optionally substituted with one or more hydroxyl substituents;

wherein two geminal hydrogen atoms in (d-1) or (d-2) may be replaced by 1,5-pentanediyl;

in particular (d-1) or (d-2) is substituted on one $CH_2$ group with an $Ar^3$ substituent and optionally (d-1) or (d-2) is further substituted on the same or a different $CH_2$ group with one substituent selected from the group consisting of hydroxyl and $C_{1-4}$alkyl optionally substituted with one or more hydroxyl substituents; or two geminal hydrogen atoms in (d-1) or (d-2) without a substituent on a $CH_2$ group are replaced by 1,5-pentanediyl;

wherein (d-5), (d-7) or (d-8) is substituted where possible with one substituent selected from the group consisting of $Ar^3$ and $NR^{11}$—$Ar^3$;

Y represents a direct bond, $NR^{10}$ or O; wherein $R^{10}$ is hydrogen, $Ar^3$, $C_{1-4}$acyl, or $C_{1-4}$alkyl;

m represents 3, 4, 5 or 6; in particular 3, 4 or 5; more in particular 3 or 4;

n represents 0, 1, 2 or 3; in particular 0, 1 or 2; also in particular 0 or 1; also in particular 0 or 2;

q represents 3, 4, 5 or 6; in particular 3;

r represents 0, 1, 2 or 3; in particular 3;

each $Ar^3$ independently represents phenyl optionally substituted with one or more substituents each independently selected from the group consisting of halo, cyclo$C_{3-7}$alkyl, $C_{1-4}$alkyloxy optionally substituted with one or more halo substituents, and $C_{1-4}$alkyl optionally substituted with one or more halo substituents;

$R^{6b}$ and $R^{6c}$ represent hydrogen or methyl;

$R^{11}$ is hydrogen;

and the pharmaceutically acceptable addition salts, and the solvates thereof.

An embodiment of the present invention relates to those compounds of formula (I) or any subgroup thereof as mentioned in any of the other embodiments wherein one or where possible more of the following restrictions apply:

(i) $A^1$ is $CR^{3a}$ or N; wherein $R^{3a}$ is hydrogen; cyano; $C_{1-4}$alkyl; or $C_{1-4}$alkyloxy optionally substituted with one or more halo substituents;
  in particular $R^{3a}$ is hydrogen; cyano; methyl; or methyl optionally substituted with one or more fluoro substituents;

(ii) $A^3$ is CH or CF;

(iii) $A^4$ is CH;

(iv) provided that when $A^1$ is N, then $A^2$ is $CR^{3b}$, and when $A^2$ is N, then $A^1$ is $CR^{3a}$;

(v) $R^{4a}$ is hydrogen; cyclo$C_{3-7}$alkyl; $Ar^1$; or $C_{1-6}$alkyl optionally substituted with one or more substituents each independently selected from the group consisting of halo, hydroxyl, cyano, $Ar^1$, cyclo$C_{3-7}$alkyl, $C_{1-6}$alkyloxy;

(vi) $R^{4c}$ is $Ar^1$ or $C_{1-6}$alkyl;

(vii) wherein in the definitions of $R^{4a}$ and $R^{4c}$ each $Ar^1$ independently is phenyl optionally substituted with one or more substituents each independently selected from the group consisting of halo and $C_{1-4}$alkyl optionally substituted with one or more halo substituents; in particular each $Ar^1$ independently is phenyl optionally substituted with one or more substituents each independently selected from the group consisting of fluoro, and $C_{1-4}$alkyl optionally substituted with one or more fluoro substituents;

(viii) $R^{5a}$, $R^{5b}$ and $R^{5c}$ are hydrogen; piperidinyl; morpholinyl; pyrrolidinyl; hexahydro-1H-1,4-diazepin-1-yl; 1,2,3,4-tetrahydro-2-quinolinyl; 3,4-dihydro-2(1H)-isoquinolinyl; 3,4-dihydro-1(2H)-quinolinyl; 2,2-difluoro-1,3-benzodioxol-5-yl; 2,2-difluoro-1,3-benzodioxol-4-yl; 2,2-difluoro-1,3-benzodioxol-4-yl; 1,6-dihydro-1-methyl-6-oxo-3-pyridinyl; 1,2-dihydro-1-methyl-2-oxo-3-pyridinyl; 2,3-dihydro-4H-1,4-benzoxazin-4-yl; 3,4-dihydro-1,5-benzoxazepin-5(2H)-yl; cyclo$C_{3-7}$alkyl; $Ar^2$; or $C_{1-6}$alkyl;

(ix) wherein in the definitions of $R^{5a}$, $R^{5b}$ and $R^{5c}$ each piperidinyl, morpholinyl, pyrrolidinyl, hexahydro-1H-1,4-diazepin-1-yl, and cyclo$C_{3-7}$alkyl independently may be substituted with one or more substituents each independently selected from the group consisting of $C_{1-4}$acyl, $C_{1-4}$alkyl optionally substituted with one or more halo substituents, and
phenyl optionally substituted with one or more trifluoromethyl groups;

(x) wherein in the definitions of $R^{5a}$, $R^{5b}$ and $R^{5c}$,
  $Ar^2$ is phenyl optionally substituted with one or more substituents each independently selected from the group consisting of halo, cyano, $NR^7R^8$, (C=O)—$NR^7R^8$, $C_{1-4}$acyl, $C_{1-4}$alkylsulfonyl, $C_{1-4}$alkylsulfinyl, tetrahydrofuranyloxy,
  $C_{1-4}$alkyloxy optionally substituted with one or more substituents each independently selected from the group consisting of halo, $C_{1-4}$alkyloxy, and cyclopropyl,
  and $C_{1-4}$alkyl optionally substituted with one or more substituents each independently selected from the group consisting of halo, hydroxyl and $C_{1-4}$alkyloxy;
  or $Ar^2$ is a 5- or 6-membered heteroaryl selected from the group consisting of pyridinyl and pyrazolyl, wherein said 5- or 6-membered heteroaryl is optionally substituted with one or more substituents each independently selected from the group consisting of halo, $C_{1-4}$alkyloxy, and $C_{1-4}$alkyl optionally substituted with one or more halo substituents;
  or $Ar^2$ is quinolinyl;

(xi) $L^a$, $L^b$ and $L^c$ represent a direct bond; $C_{2-6}$alkenediyl; carbonyl; O; S; $NR^9$;
  $NR^9$—$C_{1-4}$alkanediyl; $C_{1-4}$alkanediyl-$NR^9$; (C=O)—$NR^{12}$; or $C_{1-6}$alkanediyl optionally substituted with one or more substituents each independently selected from the group consisting of halo and hydroxy; two geminal hydrogen atoms in said $C_{1-6}$alkanediyl may be replaced by $C_{1-6}$alkanediyl, in particular two geminal hydrogen atoms may be replaced by $C_{2-6}$alkanediyl;
  in particular $L^a$, $L^b$ and $L^c$ represent a direct bond; 1,2-ethenediyl; carbonyl; O; S; $NR^9$; $NR^9$-methylene; $NR^9$-ethylidene; $C_{1-4}$alkanediyl-$NR^9$; (C=O)—$NR^{12}$; or methylene optionally substituted with one or more substituents each independently selected from the group consisting of Cl and hydroxy; two geminal hydrogen atoms in said methylene may be replaced by 1,2-ethanediyl;

(xii) or -$L^a$-$R^{5a}$ and $R^{4a}$; or -$L^c$-$R^{5c}$ and $R^{4c}$; can be taken together to form a bivalent radical -$L^a$-$R^{5a}$—$R^{4a}$— or -$L^c$-$R^{5c}$—$R^{4c}$—, having formula $$-(CH_2)_{m-n}-Y-(CH_2)_n- \quad (d\text{-}1);$$

$$-(CH_2)_n-Y-(CH_2)_{m-n}- \quad (d\text{-}2);$$

$$\text{-1,2-benzenediyl-}(CH_2)_r-Y-(CH_2)_{q-r}- \quad (d\text{-}3);$$

$$-CH=CH-CH=CH- \quad (d\text{-}5);$$

$$-CH=N-CH=CH- \quad (d\text{-}7); \text{ or}$$

$$-N=CH-CH=CH- \quad (d\text{-}8);$$

(xiii) (d-1) or (d-2) may be substituted on one or two $CH_2$ groups with one or two substituents each independently selected from the group consisting of hydroxyl, $Ar^3$, and $C_{1-4}$alkyl optionally substituted with one or more hydroxyl substituents; wherein two geminal hydrogen atoms in (d-1) or (d-2) may be replaced by 1,5-pentanediyl;
in particular (d-1) or (d-2) may be substituted on one $CH_2$ group with an $Ar^3$ substituent and optionally (d-1) or (d-2) is substituted on the same or a different $CH_2$ group with one substituent selected from the group consisting of hydroxyl and $C_{1-4}$alkyl optionally substituted with one or more hydroxyl substituents; wherein two geminal hydrogen atoms in (d-1) or (d-2) may be replaced by 1,5-pentanediyl;
more in particular (d-1) or (d-2) is substituted on one $CH_2$ group with an $Ar^3$ substituent and optionally (d-1) or (d-2) is substituted on the same or a different $CH_2$ group with one substituent selected from the group consisting of hydroxyl and $C_{1-4}$alkyl optionally substituted with one or more hydroxyl substituents; more in particular (d-1) or (d-2) is substituted on one $CH_2$ group with an $Ar^3$ substituent and optionally the same $CH_2$ group is substituted with one substituent selected from the group consisting of hydroxyl and $C_{1-4}$alkyl optionally substituted with one or more hydroxyl substituents; even more in particular (d-1) or (d-2) is substituted on one $CH_2$ group with an $Ar^3$ substituent;

(xiv) (d-5), (d-7) or (d-8) is substituted where possible with one or more, in particular one, substituents each independently selected from the group consisting of $Ar^3$ and $NR^{11}$—$Ar^3$;

(xv) Y represents a direct bond, $NR^{10}$ or O; wherein $R^{10}$ is hydrogen, $Ar^3$, $C_{1-4}$acyl, or $C_{1-4}$alkyl; in particular $R^{10}$ is hydrogen, $Ar^3$, acetyl, or methyl;

(xvi) m represents 3, 4, 5 or 6; in particular 3, 4 or 5;
(xvii) n represents 0, 1 or 2; in particular 0 or 2; also in particular 0 or 1; more in particular 0;
(xviii) q represents 3, 4, 5 or 6; in particular 3;
(ixx) r represents 3;
(xx) each $Ar^3$ independently represents phenyl optionally substituted with one or more substituents each independently selected from the group consisting of halo, cyano, $NR^7R^8$, morpholinyl, cyclo$C_{3-7}$alkyl, $C_{1-4}$alkyloxy optionally substituted with one or more halo substituents, and $C_{1-4}$alkyl optionally substituted with one or more halo substituents;
  in particular each $Ar^3$ independently represents phenyl optionally substituted with one or more substituents each independently selected from the group consisting of halo, cyclo$C_{3-7}$alkyl, $C_{1-4}$alkyloxy optionally substituted with one or more halo substituents, and $C_{1-4}$alkyl optionally substituted with one or more halo substituents;
  more in particular each $Ar^3$ independently represents phenyl optionally substituted with one or more substituents each independently selected from the group consisting of chloro, fluoro, cyclopropyl, methoxy optionally substituted with one or more fluoro substituents, and methyl optionally substituted with one or more fluoro substituents;
(xxi) each $R^7$ independently is $C_{1-4}$acyl or $C_{1-4}$alkyl; in particular acetyl or methyl;
(xxii) $R^{11}$ is hydrogen;
(xxiii) $R^9$ is hydrogen, $C_{1-4}$acyl, or $C_{1-4}$alkyl;
(xxiv) $R^{12}$ is hydrogen.

An embodiment of the present invention relates to those compounds of formula (I) or any subgroup thereof as mentioned in any of the other embodiments wherein one or more, preferably all, of the following restrictions apply:
(i) $R^1$ is $C_{1-4}$alkyl;
(ii) $R^2$ is hydrogen;
(iii) X is CH or N;
(iv) $A^1$ is $CR^{3a}$ or N; wherein $R^{3a}$ is hydrogen or $C_{1-4}$alkyloxy;
(v) $A^2$ is $CR^{3b}$ or N; wherein $R^{3b}$ is hydrogen or $C_{1-4}$alkyloxy;
(vi) $A^3$ and $A^4$ represent CH;
(vii) $Het^1$ is a heterocycle, having formula (a), (b) or (c);
(viii) $R^{4a}$ is hydrogen; cyclo$C_{3-7}$alkyl; $Ar^1$; or $C_{1-6}$alkyl;
(ix) $R^{4c}$ is $Ar^1$ or $C_{1-6}$alkyl;
(x) $Ar^1$ is phenyl optionally substituted with one or more substituents each independently selected from the group consisting of halo and $C_{1-4}$alkyl optionally substituted with one or more halo substituents;
(xi) $R^{5a}$ is hydrogen; $C_{1-6}$alkyl; cyclo$C_{3-7}$alkyl; morpholinyl optionally substituted with one or more $C_{1-4}$alkyl substituents; or $Ar^2$;
(xii) $R^{5b}$ is morpholinyl optionally substituted with one or more $C_{1-4}$alkyl substituents; or $Ar^2$;
(xiii) $R^{5c}$ is $C_{1-6}$alkyl; or $Ar^2$;
(xiv) $Ar^2$ is phenyl optionally substituted with one or more substituents each independently selected from the group consisting of halo, $C_{1-4}$alkyloxy, and $C_{1-4}$alkyl optionally substituted with one or more halo substituents;
(xv) $L^a$ represents a direct bond; $C_{2-6}$alkenediyl; carbonyl; $NR^9$; $NR^9$—$C_{1-4}$alkanediyl; or $C_{1-6}$alkanediyl wherein optionally two geminal hydrogen atoms may be replaced by $C_{1-6}$alkanediyl, in particular two geminal hydrogen atoms may be replaced by $C_{2-6}$alkanediyl;
(xvi) $L^b$ represents a direct bond; $C_{2-6}$alkenediyl; $NR^9$; $NR^9$—$C_{1-4}$alkanediyl; $C_{1-6}$alkanediyl wherein optionally two geminal hydrogen atoms may be replaced by $C_{1-6}$alkanediyl, in particular two geminal hydrogen atoms may be replaced by $C_{2-6}$alkanediyl;
(xvii) $L^c$ represents a direct bond;
(xviii) or -$L^a$-$R^{5a}$ and $R^{4a}$ can be taken together to form a bivalent radical -$L^a$-$R^{5a}$—$R^{4a}$—, having formula (d-2) or (d-3); wherein (d-2) or (d-3) may be substituted on a methylene group with one or two, in particular one, $Ar^3$ substituents;
(ixx) Y represents a direct bond, or $NR^{10}$; wherein $R^{16}$ is hydrogen or $Ar^3$;
(xx) m represents 3, 4, 5, or 6;
(xxi) n represents 0;
(xxii) q represents 3, 4, 5 or 6;
(xx) r represents 3;
(xxi) each $Ar^3$ independently represents phenyl optionally substituted with one or more substituents selected from $C_{1-4}$alkyl optionally substituted with one or more halo substituents;
(xxii) $R^{6b}$ and $R^{6c}$ represent hydrogen or methyl;
(xxiii) $R^9$ is hydrogen or $C_{1-4}$alkyl.

Another embodiment of the present invention relates to those compounds of formula (I) or any subgroup thereof as mentioned in any of the other embodiments wherein one or more, preferably all, of the following restrictions apply:
(i) $R^1$ is hydrogen or methyl; in particular methyl;
(ii) $R^2$ is hydrogen or methyl; in particular hydrogen;
(iii) X is CH or N;
(iv) $A^1$ is $CR^{3a}$ or N; wherein $R^{3a}$ is hydrogen or methoxy;
(v) $A^2$ is $CR^{3b}$ or N; wherein $R^{3b}$ is hydrogen, fluoro or methoxy; in particular hydrogen or methoxy;
(vi) $A^3$ and $A^4$ represent CH;
(vii) $R^{4a}$ is hydrogen; cyclopentyl; $Ar^1$; or $C_{1-6}$alkyl optionally substituted with one or more substituents each independently selected from the group consisting of fluoro, hydroxyl, cyano, $Ar^1$, cyclopropyl, and methoxy; in particular $R^{4a}$ is hydrogen; cyclopentyl; $Ar^1$; methyl, or isopropyl;
(viii) $R^{4c}$ is $Ar^1$; methyl, or n-propyl;
(ix) $Ar^1$ is phenyl optionally substituted with one or more substituents each independently selected from the group consisting of fluoro, and methyl optionally substituted with one or more substituents selected from fluoro;
(x) $R^{5a}$ is hydrogen; methyl; isopropyl; cyclohexyl; morpholinyl optionally substituted with one or more methyl groups; or $Ar^2$;
(xi) $R^{5b}$ is morpholinyl optionally substituted with one or more methyl groups; or $Ar^2$;
(xii) $R^{5c}$ is methyl; isobutyl; or $Ar^2$;
(xiii) wherein in the definitions of $R^{5a}$, $R^{5b}$ and $R^{5c}$, $Ar^2$ is phenyl optionally substituted with one or more substituents each independently selected from the group consisting of halo, cyano, $NR^7R^8$, (C=O)—$NR^7R^8$, acetyl, methylsulfonyl, methylsulfinyl, tetrahydrofuranyloxy, $C_{1-4}$alkyloxy optionally substituted with one or more substituents each independently selected from the group consisting of fluoro, methoxy, and cyclopropyl,
  and $C_{1-4}$alkyl optionally substituted with one or more substituents each independently selected from the group consisting of fluoro, hydroxyl and methoxy;
  or $Ar^2$ is a 5- or 6-membered heteroaryl selected from the group consisting of pyridinyl and pyrazolyl, wherein said 5- or 6-membered heteroaryl is optionally substituted with one or more substituents each independently selected from the group consisting of chloro, methoxy, and $C_{1-4}$alkyl optionally substituted with one or more fluoro substituents;

or Ar² is 2-quinolinyl;
in particular Ar² is phenyl optionally substituted with one or more substituents each independently selected from the group consisting of fluoro, chloro, methoxy, methyl, and trifluoromethyl; more in particular phenyl optionally substituted with one or more substituents each independently selected from the group consisting of fluoro, chloro, methoxy, and trifluoromethyl;

(xiv) $L^a$ represents a direct bond; 1,2-ethenediyl; carbonyl; $NR^9$; $NR^9$—$C_{1-4}$alkanediyl; or methanediyl wherein optionally two geminal hydrogen atoms may be replaced by 1,2-ethanediyl or methanediyl, in particular two geminal hydrogen atoms may be replaced by 1,2-ethanediyl, or also in particular two geminal hydrogen atoms may be replaced by methanediyl;

(xv) $L^b$ represents a direct bond; 1,2-ethenediyl; $NR^9$; $NR^9$-methanediyl; methanediyl wherein optionally two geminal hydrogen atoms may be replaced by 1,2-ethanediyl or methanediyl, in particular two geminal hydrogen atoms may be replaced by 1,2-ethanediyl, or also in particular two geminal hydrogen atoms may be replaced by methanediyl;

(xvi) $L^c$ represents a direct bond;

(xvii) or -$L^a$-$R^{5a}$ and $R^{4a}$ can be taken together to form a bivalent radical -$L^a$-$R^{5a}$—$R^{4a}$—, having formula (d-2) or (d-3); wherein (d-2) or (d-3) may be substituted on a methylene group with one or two, in particular one, $Ar^3$ substituents;

(xviii) Y represents a direct bond, or $NR^{10}$; wherein $R^{10}$ is hydrogen or $Ar^3$;

(ixx) m represents 3 or 4;

(xx) n represents 0;

(xxi) q represents 3;

(xxii) r represents 3;

(xxiii) $Ar^3$ represents phenyl optionally substituted with one or more trifluoromethyl groups;

(xxiv) each $R^8$ independently is hydrogen or methyl;

(xxv) $R^9$ is hydrogen, acetyl or methyl; in particular hydrogen or methyl.

Another embodiment of the present invention relates to those compounds of formula (I) or any subgroup thereof as mentioned in any of the other embodiments wherein one or more, of the following restrictions apply:

(i) $R^{4a}$ is hydrogen; tetrahydropyranyl; tetrahydrofuranyl; piperidinyl; morpholinyl; pyrrolidinyl; cyclo$C_{3-7}$alkyl; $Ar^1$; or $C_{1-6}$alkyl optionally substituted with one or more substituents each independently selected from the group consisting of halo, tetrahydropyranyl, tetrahydrofuranyl, piperidinyl, morpholinyl, pyrrolidinyl, cyclo$C_{3-7}$alkyl, $C_{1-6}$alkyloxy, $C_{1-6}$alkylthio, and O—$Ar^1$; in particular $R^{4a}$ is hydrogen; tetrahydropyranyl; tetrahydrofuranyl; piperidinyl; morpholinyl; pyrrolidinyl; cyclo$C_{3-7}$alkyl; $Ar^1$; or $C_{1-6}$alkyl optionally substituted with one or more substituents each independently selected from the group consisting of halo, tetrahydropyranyl, tetrahydrofuranyl, piperidinyl, morpholinyl, pyrrolidinyl, cyclo$C_{3-7}$alkyl, $C_{1-6}$alkyloxy, and $C_{1-6}$alkylthio;

more in particular $R^{4a}$ is hydrogen; tetrahydropyranyl; tetrahydrofuranyl; piperidinyl; morpholinyl; pyrrolidinyl; cyclo$C_{3-7}$alkyl; $Ar^1$; or $C_{1-6}$alkyl optionally substituted with one or more substituents each independently selected from the group consisting of halo, tetrahydropyranyl, tetrahydrofuranyl, piperidinyl, morpholinyl, pyrrolidinyl, $C_{1-6}$alkyloxy, and $C_{1-6}$alkylthio;

even more in particular $R^{4a}$ is hydrogen; tetrahydropyranyl; tetrahydrofuranyl; piperidinyl; morpholinyl; pyrrolidinyl; cyclo$C_{3-7}$alkyl; or $C_{1-6}$alkyl optionally substituted with one or more substituents each independently selected from the group consisting of halo, tetrahydropyranyl, tetrahydrofuranyl, piperidinyl, morpholinyl, pyrrolidinyl, $C_{1-6}$alkyloxy, and $C_{1-6}$alkylthio;

(ii) $R^{4c}$ is hydrogen; tetrahydropyranyl; tetrahydrofuranyl; piperidinyl; morpholinyl; pyrrolidinyl; cyclo$C_{3-7}$alkyl; $Ar^1$; $C_{1-6}$alkyloxy; $C_{1-6}$alkylthio; or $C_{1-6}$alkyl optionally substituted with one or more substituents each independently selected from the group consisting of halo, tetrahydropyranyl, tetrahydrofuranyl, piperidinyl, morpholinyl, pyrrolidinyl, cyclo$C_{3-7}$alkyl, $C_{1-6}$alkyloxy, $C_{1-6}$alkylthio, and —O—$Ar^1$; in particular $R^{4c}$ is hydrogen; tetrahydropyranyl; tetrahydrofuranyl; piperidinyl; morpholinyl; pyrrolidinyl; cyclo$C_{3-7}$alkyl; $Ar^1$; $C_{1-6}$alkyloxy; $C_{1-6}$alkylthio; or $C_{1-6}$alkyl optionally substituted with one or more substituents each independently selected from the group consisting of halo, tetrahydropyranyl, tetrahydrofuranyl, piperidinyl, morpholinyl, pyrrolidinyl, cyclo$C_{3-7}$alkyl, $C_{1-6}$alkyloxy, and $C_{1-6}$alkylthio;

more in particular $R^{4c}$ is hydrogen; tetrahydropyranyl; tetrahydrofuranyl; piperidinyl; morpholinyl; pyrrolidinyl; cyclo$C_{3-7}$alkyl; $Ar^1$; $C_{1-6}$alkyloxy; $C_{1-6}$alkylthio; or $C_{1-6}$alkyl optionally substituted with one or more substituents each independently selected from the group consisting of halo, tetrahydropyranyl, tetrahydrofuranyl, piperidinyl, morpholinyl, pyrrolidinyl, $C_{1-6}$alkyloxy, and $C_{1-6}$alkylthio;

even more in particular $R^{4c}$ is hydrogen; tetrahydropyranyl; tetrahydrofuranyl; piperidinyl; morpholinyl; pyrrolidinyl; cyclo$C_{3-7}$alkyl; $C_{1-6}$alkyloxy; $C_{1-6}$alkylthio; or $C_{1-6}$alkyl optionally substituted with one or more substituents each independently selected from the group consisting of halo, tetrahydropyranyl, tetrahydrofuranyl, piperidinyl, morpholinyl, pyrrolidinyl, $C_{1-6}$alkyloxy, and $C_{1-6}$alkylthio;

(iii) $R^{5a}$, $R^{5b}$ and $R^{5c}$ are hydrogen; $C_{1-6}$alkyl optionally substituted with one or more substituents each independently selected from the group consisting of halo, $C_{1-4}$alkyloxy, $C_{1-4}$acyl, and $C_{1-4}$alkyloxycarbonyl; tetrahydropyranyl; tetrahydrofuranyl; piperidinyl; morpholinyl; pyrrolidinyl; cyclo$C_{3-7}$alkyl;

in particular $R^{5a}$, $R^{5b}$ and $R^{5c}$ are hydrogen; $C_{1-6}$alkyl optionally substituted with one or more substituents each independently selected from the group consisting of halo, $C_{1-4}$alkyloxy, $C_{1-4}$acyl, and $C_{1-4}$alkyloxycarbonyl; tetrahydropyranyl; tetrahydrofuranyl; piperidinyl; morpholiny; pyrrolidinyl;

more in particular $R^{5a}$, $R^{5b}$ and $R^{5c}$ are hydrogen; $C_{1-6}$alkyl; tetrahydropyranyl; tetrahydrofuranyl; piperidinyl; morpholinyl; pyrrolidinyl; cyclo$C_{3-7}$alkyl;

even more in particular $R^{5a}$, $R^{5b}$ and $R^{5c}$ are hydrogen; $C_{1-6}$alkyl; tetrahydropyranyl; tetrahydrofuranyl; piperidinyl; morpholinyl; pyrrolidinyl;

(iv) $L^a$, $L^b$ and $L^c$ represent a direct bond; $C_{2-6}$alkenediyl; $NR^9$—$C_{1-4}$alkanediyl; or $C_{1-6}$alkanediyl substituted with one or more halo substituents; or two geminal hydrogen atoms in said $C_{1-6}$alkanediyl may be replaced by $C_{1-6}$alkanediyl, in particular two geminal hydrogen atoms may be replaced by $C_{2-6}$alkanediyl;

in a particular embodiment $L^a$, $L^b$ and $L^c$ represent a direct bond; $C_{2-6}$alkenediyl; or $NR^9$—$C_{1-4}$alkanediyl;

in another particular embodiment $L^a$, $L^b$ and $L^c$ represent a direct bond or $C_{2-6}$alkenediyl;

more in particular $La^a$, $L^b$ and $L^c$ represent a direct bond or $NR^9$—$C_{1-4}$alkanediyl;

even more in particular $L^a$, $L^b$ and $L^c$ represent a direct bond.

Another embodiment of the present invention relates to those compounds of formula (I) or any subgroup thereof as mentioned in any of the other embodiments wherein the following restriction applies:

Het$^1$ is an heterocycle, having formula (a) or (c);
-L$^a$-R$^{5a}$ and R$^{4a}$; or -L$^c$-R$^{5c}$ and R$^{4c}$; can be taken together to form a bivalent radical -L$^a$-R$^{5a}$—R$^{4a}$— or -L$^c$-R$^{5c}$—R$^{4c}$—, having formula

—(CH$_2$)$_{m-n}$—Y—(CH$_2$)$_n$—                (d-1);

—(CH$_2$)$_n$—Y—(CH$_2$)$_{m-n}$—                (d-2);

-1,2-benzenediyl-(CH$_2$)$_r$—Y—(CH$_2$)$_{q-r}$—        (d-3); or

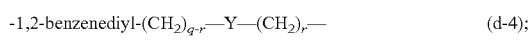

-1,2-benzenediyl-(CH$_2$)$_{q-r}$—Y—(CH$_2$)$_r$—        (d-4);

wherein (d-1), (d-2), (d-3) or (d-4) may be substituted on a CH$_2$ group with one or two substituents each independently selected from the group consisting of Ar$^3$, C$_{1-4}$acyl, and C$_{1-4}$alkyl optionally substituted with one or more halo substituents.

Another embodiment of the present invention relates to those compounds of formula (I) or any subgroup thereof as mentioned in any of the other embodiments wherein one or more of the following restriction applies:

(i) L$^a$, L$^b$ and L$^c$ represent C$_{2-6}$alkenediyl; carbonyl; O; S; S(=O)$_p$; NR$^9$; NR$^9$—C$_{1-4}$alkanediyl; or C$_{1-6}$alkanediyl optionally substituted with one or more halo substituents; or two geminal hydrogen atoms in said C$_{1-6}$alkanediyl may be replaced by C$_{1-6}$alkanediyl, in particular two geminal hydrogen atoms may be replaced by C$_{2-6}$alkanediyl;
in particular L$^a$, L$^b$ and L$^c$ represent carbonyl; O; S; S(=O)$_p$; NR$^9$; or C$_{1-6}$alkanediyl;

(ii) -L$^a$-R$^{5a}$ and R$^{4a}$; or -L$^c$-R$^{5c}$ and R$^{4c}$, are not taken together to form a bivalent radical;

(iii) R$^{4a}$ represents Ar$^1$ or C$_{1-6}$alkyl optionally substituted with one or more substituents each independently selected from the group consisting of Ar$^1$, cycloC$_{3-7}$alkyl and OAr$^1$; in particular R$^{4a}$ represents C$_{1-6}$alkyl optionally substituted with one or more substituents each independently selected from the group consisting of Ar$^1$, cycloC$_{3-7}$alkyl and OAr$^1$; more in particular R$^{4a}$ represents C$_{1-6}$alkyl optionally substituted with one or more Ar$^1$ substituents;

(iv) R$^{4c}$ represents Ar$^1$ or C$_{1-6}$alkyl optionally substituted with one or more substituents each independently selected from the group consisting of Ar$^1$, cycloC$_{3-7}$alkyl and OAr$^1$; in particular R$^{4a}$ represents C$_{1-6}$alkyl optionally substituted with one or more substituents selected from the group consisting of Ar$^1$, cycloC$_{3-7}$alkyl and OAr$^1$; more in particular R$^{4a}$ represents C$_{1-6}$alkyl optionally substituted with one or more Ar$^1$ substituents;

(v) R$^{5a}$, R$^{5b}$ and R$^{5c}$ are Ar$^2$.

Another embodiment of the present invention relates to those compounds of formula (I) or any subgroup thereof as mentioned in any of the other embodiments wherein one or more, of the following restrictions apply:

(i) R$^1$ represents hydrogen or methyl;
(ii) R$^2$ represents hydrogen or methyl;
(iii) X represents CH
(iv) A$^1$ represents C—O—CH$_3$;
(v) A$^2$ represents CH or N;
(vi) Het$^1$ is a heterocycle having formula (a);
(vii) Y represents a direct bond;
(viii) Ar$^3$ represents phenyl optionally substituted with one or more substituents each independently selected from the group consisting of halo, C$_{1-4}$alkyloxy, cyano, NR$^7$R$^8$, morpholinyl, and C$_{1-4}$alkyl optionally substituted with one or more halo substituents.

Another embodiment of the present invention relates to those compounds of formula (I) or any subgroup thereof as mentioned in any of the other embodiments wherein one or more of the following provisions apply:

(i) provided that if L$^a$, L$^b$ and L$^c$ represent carbonyl; O; S; S(=O)$_p$; NR$^9$; or C$_{1-6}$alkanediyl, then
R$^{4a}$ is hydrogen; tetrahydropyranyl; tetrahydrofuranyl; piperidinyl; morpholinyl; pyrrolidinyl; cycloC$_{3-7}$alkyl; Ar$^1$; or C$_{1-6}$alkyl optionally substituted with one or more substituents each independently selected from the group consisting of halo, tetrahydropyranyl, tetrahydrofuranyl, piperidinyl, morpholinyl, pyrrolidinyl, cycloC$_{3-7}$alkyl, C$_{1-6}$alkyloxy, C$_{1-6}$alkylthio, and O—Ar$^1$; R$^{4c}$ is hydrogen; tetrahydropyranyl; tetrahydrofuranyl; piperidinyl; morpholinyl; pyrrolidinyl; cycloC$_{3-7}$alkyl; Ar$^1$; C$_{1-6}$alkyloxy; C$_{1-6}$alkylthio; or C$_{1-6}$alkyl optionally substituted with one or more substituents each independently selected from the group consisting of halo, tetrahydropyranyl, tetrahydrofuranyl, piperidinyl, morpholinyl, pyrrolidinyl, cycloC$_{3-7}$alkyl, C$_{1-6}$alkyloxy, C$_{1-6}$alkylthio, and —O—Ar$^1$; R$^{5a}$, R$^{5b}$ and R$^{5c}$ are hydrogen; C$_{1-6}$alkyl optionally substituted with one or more substituents each independently selected from the group consisting of halo, C$_{1-4}$alkyloxy, C$_{1-4}$acyl, and C$_{1-4}$alkyloxycarbonyl; tetrahydropyranyl; tetrahydrofuranyl; piperidinyl; morpholinyl; pyrrolidinyl; cycloC$_{3-7}$alkyl;

(ii) provided that if R$^{4a}$ is C$_{1-6}$alkyl optionally substituted with Ar$^1$, then L$^a$, L$^b$ and L$^c$ represent a direct bond; C$_{2-6}$alkenediyl; NR$^9$—C$_{1-4}$alkanediyl; or C$_{1-6}$alkanediyl substituted with one or more halo substituents; or two geminal hydrogen atoms in said C$_{1-6}$alkanediyl may be replaced by C$_{1-6}$alkanediyl, in particular two geminal hydrogen atoms may be replaced by C$_{2-6}$alkanediyl;

(iii) provided that if R$^{4c}$ is C$_{1-6}$alkyl optionally substituted with Ar$^1$, then L$^a$, L$^b$ and L$^c$ represent a direct bond; C$_{2-6}$alkenediyl; NR$^9$—C$_{1-4}$alkanediyl; or C$_{1-6}$alkanediyl substituted with one or more halo substituents; or two geminal hydrogen atoms in said C$_{1-6}$alkanediyl may be replaced by C$_{1-6}$alkanediyl, in particular two geminal hydrogen atoms may be replaced by C$_{2-6}$alkanediyl;

(iv) provided that if R$^{5a}$, R$^{5b}$ or R$^{5c}$ is Ar$^2$, then L$^a$, L$^b$ and L$^c$ represent a direct bond; C$_{2-6}$alkenediyl; NR$^9$—C$_{1-4}$alkanediyl; or C$_{1-6}$alkanediyl substituted with one or more halo substituents;
or two geminal hydrogen atoms in said C$_{1-6}$alkanediyl may be replaced by C$_{1-6}$alkanediyl, in particular two geminal hydrogen atoms may be replaced by C$_{2-6}$alkanediyl.

Another embodiment of the present invention relates to those compounds of formula (I) or any subgroup thereof as mentioned in any of the other embodiments wherein one or more, preferably all, of the following restrictions apply:
(i) R$^1$ is C$_{1-4}$alkyl, in particular methyl;
(ii) R$^2$ is hydrogen;
(iii) X is CH;
(iv) A$^1$ is CR$^{3a}$; wherein R$^{3a}$ is C$_{1-4}$alkyloxy, in particular methoxy;
(v) A$^2$ is CH or N; in particular N;
(vi) A$^3$ and A$^4$ are CH;
(vii) Het$^1$ is a heterocycle having formula (a); wherein
R$^{4a}$ is C$_{1-6}$alkyl, in particular methyl;
R$^{5a}$ is phenyl substituted with one, two or three substituents each independently selected from the group consisting of halo, C$_{1-4}$alkyl optionally substituted with one or more halo substituents, and C$_{1-4}$alkyloxy optionally substituted with one or more halo substituents;
in particular R$^{5a}$ is phenyl substituted with one, two or three substituents each independently selected from the group consisting of halo, and $C_{1-4}$alkyl optionally substituted with one or more halo substituents;
in another particular embodiment $R^{5a}$ is phenyl substituted with one, two or three substituents each independently selected from the group consisting of fluoro, trifluoromethyl, trifluoromethoxy, methyl and methoxy;
in a further particular embodiment $R^{5a}$ is phenyl substituted with one or two substituents each independently selected from the group consisting of fluoro, methyl and trifluoromethyl;
$L^a$ represents NH;
or -$L^a$-$R^{5a}$ and $R^{4a}$ can be taken together to form a bivalent radical -$L^a$-$R^{5a}$—$R^{4a}$—, having formula (d-1) or (d-2); in particular (d-1); wherein (d-1) or (d-2) may be substituted on one $CH_2$ group with one $Ar^3$ substituent;
wherein Y is a bond or O;
wherein m represents 3, 4, 5 or 6; in particular 3, 4 or 5, more in particular 3 or 4;
wherein n represents 0, 1, 2 or 3; in particular 0, 1 or 2; more in particular 0 or 2;
also more in particular 0 or 1;
wherein $Ar^3$ is phenyl optionally substituted with one, two or three substituents selected from the group consisting of trifluoromethyl, halo, $C_{1-4}$alkyl, and $C_{1-4}$alkyloxy optionally substituted with halo; in particular $Ar^3$ is phenyl optionally substituted with one, two or three substituents selected from the group consisting of trifluoromethyl, fluoro, methyl, trifluoromethoxy and methoxy.

Another embodiment of the present invention relates to those compounds of formula (I) or any subgroup thereof as mentioned in any of the other embodiments wherein
$R^1$ is $C_{1-4}$alkyl, in particular methyl;
$R^2$ is hydrogen;
X is CH;
$A^1$ is $CR^{3a}$; wherein $R^{3a}$ is $C_{1-4}$alkyloxy, in particular methoxy;
$A^2$ is CH or N; in particular N;
$A^3$ and $A^4$ are CH;
$Het^1$ is a heterocycle having formula (a); wherein
$R^{4a}$ is $C_{1-6}$alkyl, in particular methyl;
$R^{5a}$ is phenyl substituted with one, two or three substituents each independently selected from the group consisting of halo, $C_{1-4}$alkyl optionally substituted with one or more halo substituents, and $C_{1-4}$alkyloxy optionally substituted with one or more halo substituents;
in particular $R^{5a}$ is phenyl substituted with one, two or three substituents each independently selected from the group consisting of halo, and $C_{1-4}$alkyl optionally substituted with one or more halo substituents;
in another particular embodiment $R^{5a}$ is phenyl substituted with one, two or three substituents each independently selected from the group consisting of fluoro, trifluoromethyl, trifluoromethoxy, methyl and methoxy;
in a further particular embodiment $R^{5a}$ is phenyl substituted with one or two substituents each independently selected from the group consisting of fluoro, methyl and trifluoromethyl;
$L^a$ represents NH.

Another embodiment of the present invention relates to those compounds of formula (I) or any subgroup thereof as mentioned in any of the other embodiments wherein $Het^1$ is a heterocycle having formula (a); wherein -$L^a$-$R^{5a}$ and $R^{4a}$ are taken together to form a bivalent radical -$L^a$-$R^{5a}$—$R^{4a}$—, having formula (d-1) or (d-2); in particular (d-1);
wherein (d-1) or (d-2) may be substituted on one $CH_2$ group with one $Ar^3$ substituent;
wherein Y is a bond or O;
wherein m represents 3, 4, 5 or 6; in particular 3, 4 or 5, more in particular 3 or 4;
wherein n represents 0, 1, 2 or 3; in particular 0, 1 or 2; more in particular 0 or 2; also more in particular 0 or 1;
wherein $Ar^3$ is phenyl optionally substituted with one, two or three substituents selected from the group consisting of trifluoromethyl, halo, $C_{1-4}$alkyl, and $C_{1-4}$alkyloxy optionally substituted with halo; in particular $Ar^3$ is phenyl optionally substituted with one, two or three substituents selected from the group consisting of trifluoromethyl, fluoro, methyl, trifluoromethoxy and methoxy.

Another embodiment of the present invention relates to those compounds of formula (I) or any subgroup thereof as mentioned in any of the other embodiments wherein in the definitions of $R^{4a}$ and $R^{4c}$ each $Ar^1$ independently is phenyl optionally substituted with one or more substituents each independently selected from the group consisting of halo, $C_{1-4}$alkyloxy, cyano, $NR^7R^8$, morpholinyl, and $C_{1-4}$alkyl optionally substituted with one or more halo substituents; or each $Ar^1$ independently is a 5- or 6-membered heteroaryl selected from the group consisting of furanyl, thiophenyl, pyrazolyl, oxazolyl, isoxazolyl, thiazolyl, isothiazolyl, thiadiazolyl, oxadiazolyl, pyridinyl, pyrimidinyl, pyridazinyl, and pyrazinyl, wherein said 5- or 6-membered heteroaryl is optionally substituted with one or more substituents each independently selected from the group consisting of halo, $C_{1-4}$alkyloxy, cyano, $NR^7R^8$, morpholinyl, and $C_{1-4}$alkyl optionally substituted with one or more halo substituents.

Another embodiment of the present invention relates to those compounds of formula (I) or any subgroup thereof as mentioned in any of the other embodiments wherein in the definitions of $R^{5a}$, $R^{5b}$ and $R^{5c}$, $Ar^2$ is phenyl optionally substituted with one or more substituents each independently selected from the group consisting of halo, $C_{1-4}$alkyloxy, cyano, $NR^7R^8$, morpholinyl, and $C_{1-4}$alkyl optionally substituted with one or more halo substituents; or a 5- or 6-membered heteroaryl selected from the group consisting of furanyl, thiophenyl, pyrazolyl, oxazolyl, isoxazolyl, thiazolyl, isothiazolyl, thiadiazolyl, oxadiazolyl, pyridinyl, pyrimidinyl, pyridazinyl, and pyrazinyl, wherein said 5- or 6-membered heteroaryl is optionally substituted with one or more substituents each independently selected from the group consisting of halo, $C_{1-4}$alkyloxy, cyano, $NR^7R^8$, morpholinyl, and $C_{1-4}$alkyl optionally substituted with one or more halo substituents.

Another embodiment of the present invention relates to those compounds of formula (I) or any subgroup thereof as mentioned in any of the other embodiments wherein in the definitions of $R^{5a}$, $R^{5b}$ and $R^{5c}$, $Ar^2$ is phenyl optionally substituted with one or more substituents each independently selected from the group consisting of halo, cyano, $NR^7R^8$, (C=O)—$NR^7R^8$, morpholinyl, $C_{1-4}$acyl, $C_{1-4}$alkylsulfonyl, $C_{1-4}$alkylsulfinyl, cyclo$C_{3-7}$alkyloxy, tetrahydropyranyloxy, tetrahydrofuranyloxy,
$C_{1-4}$alkyloxy optionally substituted with one or more substituents each independently selected from the group consisting of halo, hydroxyl, $C_{1-4}$alkyloxy, and cyclopropyl, and
$C_{1-4}$alkyl optionally substituted with one or more substituents each independently selected from the group consisting of halo, hydroxyl and
$C_{1-4}$alkyloxy optionally substituted with one or more halo substituents; in particular $Ar^2$ is phenyl optionally substituted with one or more $C_{1-4}$alkyl substituents optionally substituted with one or more substituents each independently selected from the group consisting of halo, hydroxyl and $C_{1-4}$alkyloxy optionally substituted with one or more halo substituents.

Another embodiment of the present invention relates to those compounds of formula (I) or any subgroup thereof as mentioned in any of the other embodiments wherein $A^1$ is $CR^{3a}$ or N; wherein $R^{3a}$ is hydrogen; halo; cyano; $C_{1-4}$alkyl; or $C_{1-4}$alkyloxy optionally substituted with one or more halo substituents;

$A^2$ is $CR^{3b}$ or N; wherein $R^{3b}$ is hydrogen; fluoro; or $C_{1-4}$alkyloxy;

$A^3$ and $A^4$ each independently are CH; CF; or N;

provided that no more than two of $A^1$, $A^2$, $A^3$ and $A^4$ are N; and provided that at least one of $A^1$, $A^2$, $A^3$ and $A^4$ is other than CH.

Another embodiment of the present invention relates to those compounds of formula (I) or any subgroup thereof as mentioned in any of the other embodiments wherein $A^1$ is $CR^{3a}$ or N, in particular $CR^{3a}$; wherein $R^{3a}$ is $C_{1-4}$alkyloxy, in particular $R^{3a}$ is methoxy.

Another embodiment of the present invention relates to those compounds of formula (I) or any subgroup thereof as mentioned in any of the other embodiments wherein each $Ar^3$ independently represents phenyl optionally substituted with one or more substituents each independently selected from the group consisting of halo, $C_{1-4}$alkyloxy, cyano, $NR^7R^8$, morpholinyl, and $C_{1-4}$alkyl optionally substituted with one or more halo substituents; or a 5- or 6-membered heteroaryl selected from the group consisting of furanyl, thiophenyl, pyrazolyl, oxazolyl, isoxazolyl, thiazolyl, isothiazolyl, thiadiazolyl, oxadiazolyl, pyridinyl, pyrimidinyl, pyridazinyl, and pyrazinyl, wherein said 5- or 6-membered heteroaryl is optionally substituted with one or more substituents each independently selected from the group consisting of halo, $C_{1-4}$alkyloxy, cyano, $NR^7R^8$, morpholinyl, and $C_{1-4}$alkyl optionally substituted with one or more halo substituents.

Another embodiment of the present invention relates to those compounds of formula (I) or any subgroup thereof as mentioned in any of the other embodiments wherein each $Ar^3$ independently represents phenyl optionally substituted with one or more substituents each independently selected from the group consisting of halo, cyano, $NR^7R^8$, morpholinyl, $C_{1-4}$alkyloxy optionally substituted with one or more halo substituents, and $C_{1-4}$alkyl optionally substituted with one or more halo substituents; or a 5- or 6-membered heteroaryl selected from the group consisting of furanyl, thiophenyl, pyrazolyl, oxazolyl, isoxazolyl, thiazolyl, isothiazolyl, thiadiazolyl, oxadiazolyl, pyridinyl, pyrimidinyl, pyridazinyl, and pyrazinyl, wherein said 5- or 6-membered heteroaryl is optionally substituted with one or more substituents each independently selected from the group consisting of halo, $C_{1-4}$alkyloxy, cyano, $NR^7R^8$, morpholinyl, and $C_{1-4}$alkyl optionally substituted with one or more halo substituents.

Another embodiment of the present invention relates to those compounds of formula (I) or any subgroup thereof as mentioned in any of the other embodiments wherein $R^{5a}$, $R^{5b}$ and $R^{5c}$ are hydrogen; tetrahydropyranyl; tetrahydrofuranyl; piperidinyl; morpholinyl; pyrrolidinyl; $cycloC_{3-7}$alkyl; $Ar^2$; or $C_{1-6}$alkyl optionally substituted with one or more substituents each independently selected from the group consisting of halo, $C_{1-4}$alkyloxy, $C_{1-4}$acyl, and $C_{1-4}$alkyloxycarbonyl.

Another embodiment of the present invention relates to those compounds of formula (I) or any subgroup thereof as mentioned in any of the other embodiments wherein $R^{5a}$, $R^{5b}$ and $R^{5c}$ are hydrogen; tetrahydropyranyl; tetrahydrofuranyl; piperidinyl; morpholinyl; pyrrolidinyl; $cycloC_{3-7}$alkyl; $Ar^2$; or $C_{1-6}$alkyl optionally substituted with one or more substituents each independently selected from the group consisting of halo, $C_{1-4}$alkyloxy, $C_{1-4}$acyl, and $C_{1-4}$alkyloxycarbonyl;

or $-L^a-R^{5a}$ and $R^{4a}$; or $-L^c-R^{5c}$ and $R^{4c}$; can be taken together to form a bivalent radical as defined in any of the other embodiments.

Another embodiment of the present invention relates to those compounds of formula (I) or any subgroup thereof as mentioned in any of the other embodiments wherein $R^{5a}$, $R^{5b}$ and $R^{5c}$ are hydrogen; tetrahydropyranyl; tetrahydrofuranyl; piperidinyl; morpholinyl; pyrrolidinyl; $cycloC_{3-7}$alkyl; $Ar^2$; or $C_{1-6}$alkyl optionally substituted with one or more substituents each independently selected from the group consisting of halo, $C_{1-4}$alkyloxy, $C_{1-4}$acyl, and $C_{1-4}$alkyloxycarbonyl;

wherein in the definitions of $R^{5a}$, $R^{5b}$ and $R^{5c}$ tetrahydrofuranyl, tetrahydropyranyl, piperidinyl, morpholinyl, pyrrolidinyl and $cycloC_{3-7}$alkyl may be substituted with one or more substituents each independently selected from the group consisting of $C_{1-4}$alkyl, $C_{2-6}$alkenyl, $C_{1-4}$acyl, halo and $C_{1-4}$alkyloxycarbonyl;

or $-L^a-R^{5a}$ and $R^{4a}$; or $-L^c-R^{5c}$ and $R^{4c}$; can be taken together to form a bivalent radical $-L^a-R^{5a}-R^{4a}-$ or $-L^c-R^{5c}-R^{4c}-$, having formula

$$-(CH_2)_{m-n}-Y-(CH_2)_n- \quad (d\text{-}1);$$

$$-(CH_2)_n-Y-(CH_2)_{m-n}- \quad (d\text{-}2);$$

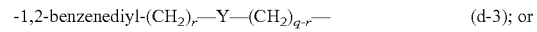

$$-1,2\text{-benzenediyl-}(CH_2)_r-Y-(CH_2)_{q-r}- \quad (d\text{-}3); \text{ or}$$

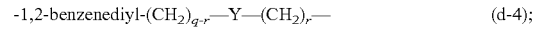

$$-1,2\text{-benzenediyl-}(CH_2)_{q-r}-Y-(CH_2)_r- \quad (d\text{-}4);$$

wherein (d-1), (d-2), (d-3) or (d-4) may be substituted on a $CH_2$ group with one or two substituents each independently selected from the group consisting of $Ar^3$, $C_{1-4}$acyl, and $C_{1-4}$alkyl optionally substituted with one or more halo substituents;

wherein (d-3) or (d-4) may be substituted on the 1,2-benzenediyl-moiety with one or more substituents each independently selected from the group consisting of halo, $C_{1-4}$alkyloxy, cyano, $NR^7R^8$, morpholinyl, and $C_{1-4}$alkyl optionally substituted with one or more halo substituents; in particular wherein (d-3) or (d-4) is not substituted on the 1,2-benzenediyl-moiety;

wherein each $Ar^3$ independently represents phenyl optionally substituted with one or more substituents each independently selected from the group consisting of halo, cyano, $NR^7R^8$, morpholinyl, $C_{1-4}$alkyloxy optionally substituted with one or more halo substituents, and $C_{1-4}$alkyl optionally substituted with one or more halo substituents;

or a 5- or 6-membered heteroaryl selected from the group consisting of furanyl, thiophenyl, pyrazolyl, oxazolyl, isoxazolyl, thiazolyl, isothiazolyl, thiadiazolyl, oxadiazolyl, pyridinyl, pyrimidinyl, pyridazinyl, and pyrazinyl, wherein said 5- or 6-membered heteroaryl is optionally substituted with one or more substituents each independently selected from the group consisting of halo, $C_{1-4}$alkyloxy, cyano, $NR^7R^8$, morpholinyl, and $C_{1-4}$alkyl optionally substituted with one or more halo substituents.

Another embodiment of the present invention relates to those compounds of formula (I) or any subgroup thereof as mentioned in any of the other embodiments wherein $L^a$, $L^b$ and $L^c$ represent a direct bond.

Another embodiment of the present invention relates to those compounds of formula (I) or any subgroup thereof as mentioned in any of the other embodiments wherein $L^a$, $L^b$ and $L^c$ represent NH.

Another embodiment of the present invention relates to those compounds of formula (I) or any subgroup thereof as mentioned in any of the other embodiments wherein $L^a$, $L^b$ and $L^c$ represent NH;

or -L$^a$-R$^{5a}$ and R$^{4a}$; or -L$^c$-R$^{5c}$ and R$^{4c}$; can be taken together to form a bivalent radical as defined in any of the other embodiments.

Another embodiment of the present invention relates to those compounds of formula (I) or any subgroup thereof as mentioned in any of the other embodiments wherein in the definition of L$^a$, L$^b$ and L$^c$, two geminal hydrogen atoms in the C$_{1-6}$alkanediyl moiety may be replaced by C$_{2-6}$alkanediyl, in particular 1,2-ethanediyl.

Another embodiment of the present invention relates to those compounds of formula (I) or any subgroup thereof as mentioned in any of the other embodiments wherein L$^a$, L$^b$ and L$^c$ represent a direct bond; C$_{2-6}$alkenediyl; carbonyl; O; S; S(=O)$_p$; NR$^9$; NR$^9$—C$_{1-4}$alkanediyl; C$_{1-4}$alkanediyl-NR$^9$; NR$^{12}$—(C=O); (C=O)—NR$^{12}$; or C$_{1-6}$alkanediyl optionally substituted with one or more substituents each independently selected from the group consisting of halo and hydroxy; two geminal hydrogen atoms in said C$_{1-6}$alkanediyl may be replaced by C$_{2-6}$alkanediyl, in particular 1,2-ethanediyl; or -L$^a$-R$^{5a}$ and R$^{4a}$; or -L$^c$R$^{5c}$ and R$^{4c}$; can be taken together to form a bivalent radical as defined in any of the other embodiments.

Another embodiment of the present invention relates to those compounds of formula (I) or any subgroup thereof as mentioned in any of the other embodiments wherein -L$^a$-R$^{5a}$ and R$^{4a}$; or -L$^c$-R$^{5c}$ and R$^{4c}$; can be taken together to form a bivalent radical as defined in any of the other embodiments.

Another embodiment of the present invention relates to those compounds of formula (I) or any subgroup thereof as mentioned in any of the other embodiments wherein -L$^a$-R$^{5a}$ and R$^{4a}$; or -L$^c$R$^{5c}$ and R$^{4c}$; are always taken together to form a bivalent radical.

It should be understood that any bivalent radical, in particular the bivalent radical -L$^a$-R$^{5a}$—R$^{4a}$— or -L$^c$-R$^{5c}$—R$^{4c}$—, in any of the embodiments hereabove may be substituted with substituents as listed in any of the other embodiments.

Another embodiment of the present invention relates to those compounds of formula (I) or any subgroup thereof as mentioned in any of the other embodiments wherein -L$^a$-R$^{5a}$ and R$^{4a}$; or -L$^c$R$^{5c}$ and R$^{4c}$; are not taken together to form a bivalent radical.

Another embodiment of the present invention relates to those compounds of formula (I) or any subgroup thereof as mentioned in any of the other embodiments wherein L$^a$, L$^b$ and L$^c$ represent NH;
or -L$^a$-R$^{5a}$ and R$^{4a}$; or -L$^c$-R$^{5c}$ and R$^{4c}$; can be taken together to form a bivalent radical -L$^a$-R$^{5a}$—R$^{4a}$— or -L$^c$-R$^{5c}$—R$^{4c}$—, having formula —(CH$_2$)$_{m-n}$—Y—(CH$_2$)$_n$—      (d-1);

—(CH$_2$)$_n$—Y—(CH$_2$)$_{m-n}$—      (d-2);

-1,2-benzenediyl-(CH$_2$)$_r$—Y—(CH$_2$)$_{q-r}$—      (d-3);

-1,2-benzenediyl-(CH$_2$)$_{q-r}$—Y—(CH$_2$)$_r$—      (d-4);

—CH=CH—CH=CH—      (d-5);

—CH=CH—N=CH—      (d-6);

—CH=N—CH=CH—      (d-7);

—N=CH—CH=CH—      (d-8); or

—CH=CH—CH=N—      (d-9);

wherein (d-1), (d-2), (d-3) or (d-4) may be substituted on one or more, in particular on one or two, CH$_2$ groups with one or two substituents each independently selected from the group consisting of hydroxyl, cyano, Ar$^3$, C$_{1-4}$acyl, and C$_{1-4}$alkyl optionally substituted with one or more substituents selected from the group consisting of halo and hydroxyl;
wherein two geminal hydrogen atoms in (d-1) or (d-2) may be replaced by C$_{2-6}$alkanediyl;
wherein (d-3) or (d-4) may be substituted on the 1,2-benzenediyl-moiety with one or more substituents each independently selected from the group consisting of halo, C$_{1-4}$alkyloxy, cyano, NR$^7$R$^8$, morpholinyl, and C$_{1-4}$alkyl optionally substituted with one or more halo substituents;
wherein (d-5), (d-6), (d-7), (d-8) or (d-9) may be substituted where possible with one or more substituents each independently selected from the group consisting of Ar$^3$, (C=O)—Ar$^3$, O—Ar$^3$, NR$^{11}$—Ar$^3$, C$_{1-4}$acyl, and C$_{1-4}$alkyl optionally substituted with one or more halo substituents.

Another embodiment of the present invention relates to those compounds of formula (I) or any subgroup thereof as mentioned in any of the other embodiments wherein -L$^a$-R$^{5a}$ and R$^{4a}$; or -L$^c$R$^{5c}$ and R$^{4c}$; when taken together form a bivalent radical -L$^a$-R$^{5a}$—R$^{4a}$— or -L$^c$-R$^{5c}$—R$^{4c}$—, having formula (d-1), (d-2), (d-5), (d-6), (d-7), (d-8) or (d-9); in particular (d-1), (d-2), (d-5), (d-7) or (d-8); more in particular (d-1) or (d-2);
wherein said bivalent radicals may be substituted with substituents listed in any of the other embodiments.

Another embodiment of the present invention relates to those compounds of formula (I) or any subgroup thereof as mentioned in any of the other embodiments wherein -L$^a$-R$^{5a}$ and R$^{4a}$; or -L$^c$R$^{5c}$ and R$^{4c}$; when taken together form a bivalent radical -L$^a$-R$^{5a}$—R$^{4a}$— or -L$^c$-R$^{5c}$—R$^{4c}$—, having formula (d-1), (d-2), (d-5), (d-6), (d-7), (d-8) or (d-9); in particular (d-1), (d-2), (d-5), (d-7) or (d-8); more in particular (d-1) or (d-2);
wherein (d-1) or (d-2) may be substituted on one or more, in particular on one or two, CH$_2$ groups with one or two substituents each independently selected from the group consisting of hydroxyl, cyano, Ar$^3$, C$_{1-4}$acyl, and C$_{1-4}$alkyl optionally substituted with one or more substituents selected from the group consisting of halo and hydroxyl;
in particular wherein (d-1) or (d-2) may be substituted on one CH$_2$ group with an Ar$^3$ substituent and optionally (d-1) or (d-2) is substituted on the same or a different CH$_2$ group with one substituent selected from the group consisting of hydroxyl and C$_{1-4}$alkyl optionally substituted with one or more hydroxyl substituents;
wherein two geminal hydrogen atoms in (d-1) or (d-2) may be replaced by C$_{2-6}$alkanediyl, in particular 1,5-pentanediyl;
wherein (d-5), (d-6), (d-7), (d-8) or (d-9) may be substituted where possible with one or more substituents each independently selected from the group consisting of Ar$^3$, (C=O)—Ar$^3$, O—Ar$^3$, NR$^{11}$—Ar$^3$, C$_{1-4}$acyl, and C$_{1-4}$alkyl optionally substituted with one or more halo substituents; in particular wherein (d-5), (d-6), (d-7), (d-8) or (d-9) is substituted where possible with one substituent selected from the group consisting of Ar$^3$ and NR$^{11}$—Ar$^3$.

Another embodiment of the present invention relates to those compounds of formula (I) or any subgroup thereof as mentioned in any of the other embodiments wherein -L$^a$-R$^{5a}$ and R$^{4a}$; or -L$^c$R$^{5c}$ and R$^{4c}$; when taken together form a bivalent radical -L$^a$-R$^{5a}$—R$^{4a}$— or -L$^c$-R$^{5c}$—R$^{4c}$—, having formula $$-(CH_2)_{m-n}-Y-(CH_2)_n- \qquad (d\text{-}1);$$

$$-(CH_2)_n-Y-(CH_2)_{m-n}- \qquad (d\text{-}2);$$

$$\text{-}1,2\text{-benzenediyl-}(CH_2)_r-Y-(CH_2)_{q-r}- \qquad (d\text{-}3);$$

$$\text{-}1,2\text{-benzenediyl-}(CH_2)_{q-r}-Y-(CH_2)_r- \qquad (d\text{-}4);$$

$$-CH=CH-CH=CH- \qquad (d\text{-}5);$$

$$-CH=CH-N=CH- \qquad (d\text{-}6);$$

$$-CH=N-CH=CH- \qquad (d\text{-}7);$$

$$-N=CH-CH=CH- \qquad (d\text{-}8); \text{ or}$$

$$-CH=CH-CH=N- \qquad (d\text{-}9);$$

wherein (d-1), (d-2), (d-3) or (d-4) may be substituted on one or more, in particular on one or two, $CH_2$ groups with one or two substituents each independently selected from the group consisting of hydroxyl, cyano, $Ar^3$, $C_{1-4}$acyl, and $C_{1-4}$alkyl optionally substituted with one or more substituents selected from the group consisting of halo and hydroxyl;

wherein two geminal hydrogen atoms in (d-1) or (d-2) may be replaced by $C_{2-6}$alkanediyl;

wherein (d-3) or (d-4) may be substituted on the 1,2-benzenediyl-moiety with one or two substituents each independently selected from the group consisting of halo, $C_{1-4}$alkyloxy, cyano, $NR^7R^8$, morpholinyl, and $C_{1-4}$alkyl optionally substituted with one or more halo substituents;

wherein (d-5), (d-6), (d-7), (d-8) or (d-9) may be substituted where possible with one or two substituents each independently selected from the group consisting of $Ar^3$, (C=O)—$Ar^3$, O—$Ar^3$, $NR^{11}$—$Ar^3$, $C_{1-4}$acyl, and $C_{1-4}$alkyl optionally substituted with one or more halo substituents.

Another embodiment of the present invention relates to those compounds of formula (I) or any subgroup thereof as mentioned in any of the other embodiments wherein -$L^a$-$R^{5a}$ and $R^{4a}$; or -$L^c$-$R^{5c}$ and $R^{4c}$; when taken together form a bivalent radical -$L^a$-$R^{5a}$—$R^{4a}$— or -$L^c$-$R^{5c}$—$R^{4c}$—, having formula $$-(CH_2)_{m-n}-Y-(CH_2)_n- \qquad (d\text{-}1);$$

$$-(CH_2)_n-Y-(CH_2)_{m-n}- \qquad (d\text{-}2);$$

$$\text{-}1,2\text{-benzenediyl-}(CH_2)_r-Y-(CH_2)_{q-r}- \qquad (d\text{-}3);$$

$$\text{-}1,2\text{-benzenediyl-}(CH_2)_{q-r}-Y-(CH_2)_r- \qquad (d\text{-}4);$$

$$-CH=CH-CH=CH- \qquad (d\text{-}5);$$

$$-CH=CH-N=CH- \qquad (d\text{-}6);$$

$$-CH=N-CH=CH- \qquad (d\text{-}7);$$

$$-N=CH-CH=CH- \qquad (d\text{-}8); \text{ or}$$

$$-CH=CH-CH=N- \qquad (d\text{-}9);$$

wherein (d-1) or (d-2) may be substituted on one $CH_2$ group with an $Ar^3$ substituent and optionally (d-1) or (d-2) is substituted on the same or a different $CH_2$ group with one substituent selected from the group consisting of hydroxyl, cyano, $Ar^3$, $C_{1-4}$acyl, and $C_{1-4}$alkyl optionally substituted with one or more substituents selected from the group consisting of halo and hydroxyl;

wherein two geminal hydrogen atoms in (d-1) or (d-2) may be replaced by $C_{2-6}$alkanediyl;

wherein (d-3) or (d-4) may be substituted on the 1,2-benzenediyl-moiety with one or two substituents each independently selected from the group consisting of halo, $C_{1-4}$alkyloxy, cyano, $NR^7R^8$, morpholinyl, and $C_{1-4}$alkyl optionally substituted with one or more halo substituents;

wherein (d-5), (d-6), (d-7), (d-8) or (d-9) may be substituted where possible with one substituent selected from the group consisting of $Ar^3$, (C=O)—$Ar^3$, O—$Ar^3$, and $NR^{11}$—$Ar^3$.

Another embodiment of the present invention relates to those compounds of formula (I) or any subgroup thereof as mentioned in any of the other embodiments wherein -$L^a$-$R^{5a}$ and $R^{4a}$; or -$L^c$-$R^{5c}$ and $R^{4c}$; when taken together form a bivalent radical -$L^a$-$R^{5a}$—$R^{4a}$— or -$L^c$-$R^{5c}$—$R^{4c}$—, having formula $$-(CH_2)_{m-n}-Y-(CH_2)_n- \qquad (d\text{-}1);$$

$$-(CH_2)_n-Y-(CH_2)_{m-n}- \qquad (d\text{-}2);$$

$$\text{-}1,2\text{-benzenediyl-}(CH_2)_r-Y-(CH_2)_{q-r}- \qquad (d\text{-}3);$$

$$-CH=CH-CH=CH- \qquad (d\text{-}5);$$

$$-CH=N-CH=CH- \qquad (d\text{-}7); \text{ or}$$

$$-N=CH-CH=CH- \qquad (d\text{-}8);$$

wherein (d-1) or (d-2) may be substituted on one $CH_2$ group with an $Ar^3$ substituent and optionally (d-1) or (d-2) is substituted on the same or a different $CH_2$ group with one substituent selected from the group consisting of hydroxyl and $C_{1-4}$alkyl optionally substituted with one or more hydroxyl substituents;
in particular (d-1) or (d-2) is substituted on one $CH_2$ group with an $Ar^3$ substituent and optionally (d-1) or (d-2) is further substituted on the same or a different $CH_2$ group with one substituent selected from the group consisting of hydroxyl and $C_{1-4}$alkyl optionally substituted with one or more hydroxyl substituents;
wherein (d-5), (d-7) or (d-8) is substituted where possible with one substituent selected from the group consisting of $Ar^3$ and $NR^{11}$—$Ar^3$.

Another embodiment of the present invention relates to those compounds of formula (I) or any subgroup thereof as mentioned in any of the other embodiments wherein -$L^a$-$R^{5a}$ and $R^{4a}$; or -$L^c R^{5c}$ and $R^{4c}$; when taken together form a bivalent radical -$L^a$-$R^{5a}$—$R^{4a}$— or -$L^c$-$R^{5c}$—$R^{4c}$—, having formula —$(CH_2)_5$—, —$(CH_2)_4$—, —$(CH_2)_3$—, -1,2-benzenediyl-$(CH_2)_3$—, —$NR^{10}$—$(CH_2)_3$—, —$(CH_2)$—$NR^{10}$—$(CH_2)_2$—, —$(CH_2)$—O—$(CH_2)_2$—, —$(CH_2)$—O—$(CH_2)_3$—, —CH=CH—CH=CH—, —N=CH—CH=CH—, or —CH=N—CH=CH—;
in particular —$(CH_2)_4$— or —$(CH_2)$—O—$(CH_2)_2$—;
wherein said bivalent radicals may be substituted with substituents listed in any of the other embodiments.

Another embodiment of the present invention relates to those compounds of formula (I) or any subgroup thereof as mentioned in any of the other embodiments wherein -$L^a$-$R^{5a}$ and $R^{4a}$; or -$L^c R^{5c}$ and $R^{4c}$; when taken together form a bivalent radical -$L^a$-$R^{5a}$—$R^{4a}$— or -$L^c$-$R^{5c}$—$R^{4c}$—, having formula —$(CH_2)_5$—, —$(CH_2)_4$—, —$(CH_2)_3$—, -1,2-benzenediyl-$(CH_2)_3$—, —$NR^{10}$—$(CH_2)_3$—, —$(CH_2)$—$NR^{10}$—$(CH_2)_2$—, —$(CH_2)$—O—$(CH_2)_2$—, —$(CH_2)$—O—$(CH_2)_3$—, —CH=CH—CH=CH—, —N=CH—CH=CH—, or —CH=N—CH=CH—;
in particular —$(CH_2)_4$— or —$(CH_2)$—O—$(CH_2)_2$—;
wherein —$(CH_2)_5$—, —$(CH_2)_4$—, —$(CH_2)_3$—, —$NR^{10}$—$(CH_2)^3$—, —$(CH_2)$—$NR^{10}$—$(CH_2)_2$—, —$(CH_2)$—O—$(CH_2)_2$—, —$(CH_2)$—O—$(CH_2)_3$— or -1,2-benzenediyl-$(CH_2)_3$—, may be substituted on one or more, in particular on one or two, $CH_2$ groups with one or two substituents each independently selected from the group consisting of hydroxyl, cyano, $Ar^3$, $C_{1-4}$acyl, and $C_{1-4}$alkyl optionally substituted with one or more substituents selected from the group consisting of halo and hydroxyl;
wherein two geminal hydrogen atoms in —$(CH_2)_5$—, —$(CH_2)_4$—, —$(CH_2)_3$—, —$NR^{10}$—$(CH_2)_3$—, —$(CH_2)$—$NR^{10}$—$(CH_2)_2$—, —$(CH_2)$—O—$(CH_2)_2$— or —$(CH_2)$—O—$(CH_2)_3$— may be replaced by $C_{2-6}$alkanediyl;
wherein -1,2-benzenediyl-$(CH_2)_3$— may be substituted on the 1,2-benzenediyl-moiety with one or more substituents each independently selected from the group consisting of halo, $C_{1-4}$alkyloxy, cyano, $NR^7R^8$, morpholinyl, and $C_{1-4}$alkyl optionally substituted with one or more halo substituents;
and wherein —CH=CH—CH=CH—, —N=CH—CH=CH—, or —CH=N—CH=CH— may be substituted where possible with one or more substituents each independently selected from the group consisting of $Ar^3$, (C=O)—$Ar^3$, O—$Ar^3$, $NR^{11}$—$Ar^3$, $C_{1-4}$acyl, and $C_{1-4}$alkyl optionally substituted with one or more halo substituents.

Another embodiment of the present invention relates to those compounds of formula (I) or any subgroup thereof as mentioned in any of the other embodiments wherein -$L^a$-$R^{5a}$ and $R^{4a}$; or -$L^c R^{5c}$ and $R^{4c}$; when taken together form a bivalent radical -$L^a$-$R^{5a}$—$R^{4a}$— or -$L^c$-$R^{5c}$—$R^{4c}$—, having formula —$(CH_2)_5$—, —$(CH_2)_4$—, —$(CH_2)_3$—, -1,2-benzenediyl-$(CH_2)_3$—, —$NR^{10}$—$(CH_2)_3$—, —$(CH_2)$—$NR^{10}$—$(CH_2)_2$—, —$(CH_2)$—O—$(CH_2)_2$—, —$(CH_2)$—O—$(CH_2)_3$—, —CH=CH—CH=CH—, —N=CH—CH=CH—, or —CH=N—CH=CH—;
in particular —$(CH_2)_4$— or —$(CH_2)$—O—$(CH_2)_2$—;
wherein —$(CH_2)_5$—, —$(CH_2)_4$—, —$(CH_2)_3$—, —$NR^{10}$—$(CH_2)_3$—, —$(CH_2)$—$NR^{10}$—$(CH_2)_2$—, —$(CH_2)$—O—$(CH_2)_2$— or —$(CH_2)$—O—$(CH_2)_3$—, is substituted on one $CH_2$ group with an $Ar^3$ substituent and optionally is substituted on the same or a different $CH_2$ group with one substituent selected from the group consisting of hydroxyl and $C_{1-4}$alkyl optionally substituted with one or more hydroxyl substituents;
or wherein two geminal hydrogen atoms in —$(CH_2)_5$—, —$(CH_2)_4$—, —$(CH_2)_3$—, —$NR^{10}$—$(CH_2)_3$—, —$(CH_2)$—$NR^{10}$—$(CH_2)_2$—, —$(CH_2)$—O—$(CH_2)_2$— or —$(CH_2)$—O—$(CH_2)_3$—, in particular in —$(CH_2)_5$—, —$(CH_2)_4$— or —$(CH_2)_3$—, may be replaced by 1,5-pentanediyl;
and wherein —CH=CH—CH=CH—, —N=CH—CH=CH—, or —CH=N—CH=CH— may be substituted where possible with one substituent selected from the group consisting of $Ar^3$ and $NR^{11}$—$Ar^3$.

Another embodiment of the present invention relates to those compounds of formula (I) or any subgroup thereof as mentioned in any of the other embodiments wherein -$L^a$-$R^{5a}$ and $R^{4a}$; or -$L^c R^{5c}$ and $R^{4c}$; are taken together to form a bivalent radical -$L^a$-$R^{5a}$—$R^{4a}$— or -$L^c$-$R^{5c}$—$R^{4c}$—, having formula $$—(CH_2)_{m-n}—Y—(CH_2)_n— \quad (d\text{-}1);$$

$$—(CH_2)_n—Y—(CH_2)_{m-n}— \quad (d\text{-}2);$$

$$\text{-1,2-benzenediyl-}(CH_2)_r—Y—(CH_2)_{q-r}— \quad (d\text{-}3);$$

$$—CH=CH—CH=CH— \quad (d\text{-}5);$$

$$—CH=N—CH=CH— \quad (d\text{-}7); \text{ or}$$

$$—N=CH—CH=CH— \quad (d\text{-}8);$$

wherein (d-1), (d-2) or (d-3) may be substituted on one or more, in particular on one or two, $CH_2$ groups with one or two substituents each independently selected from the group consisting of hydroxyl, $Ar^3$, and $C_{1-4}$alkyl optionally substituted with one or more hydroxyl substituents;
in particular (d-1), (d-2) or (d-3) may be substituted on one or two $CH_2$ groups with one or two substituents each independently selected from the group consisting of hydroxyl, $Ar^3$, and $C_{1-4}$alkyl optionally substituted with one or more hydroxyl substituents;
wherein (d-5), (d-7) or (d-8) may be substituted where possible with one or more substituents each independently selected from the group consisting of $Ar^3$ and $NR^{11}$—$Ar^3$.

Another embodiment of the present invention relates to those compounds of formula (I) or any subgroup thereof as mentioned in any of the other embodiments wherein -$L^a$-$R^{5a}$ and $R^{4a}$; or -$L^c R^{5c}$ and $R^{4c}$; when taken together form a bivalent radical -$L^a$-$R^{5a}$—$R^{4a}$— or -$L^c$-$R^{5c}$—$R^{4c}$—, having formula —CH($Ar^3$)—$(CH_2)_2$—, —CH($Ar^3$)—$(CH_2)_3$—, —CH($Ar^3$)—$(CH_2)_4$—, —N($Ar^3$)—$(CH_2)_3$—, —CH($Ar^3$)—N($CH_3$)—$(CH_2)_2$—, —CH($Ar^3$)—N(acetyl)-$(CH_2)_2$—, —CH($Ar^3$)—NH—$(CH_2)_2$—, —CH($Ar^3$)—O—$(CH_2)_2$—, —CH($Ar^3$)—O—$(CH_2)_3$, —C($Ar^3$)=CH—CH=CH—, —C($NR^{11}$—$Ar^3$)=CH—CH=CH—, —N=CH—CH=C($Ar^3$)—, —N=C($Ar^3$)—CH=CH—, —CH=N—CH=C($Ar^3$)—, —$(CH_2)_3$—CH($Ar^3$)—, —CH (Ar³)—(CH₂)₂—CH(CH₃)—, —CH(Ar³)—CH(CH₃)—(CH₂)₂— or —C(Ar³)=N—CH=CH—;
in particular —CH(Ar³)—(CH₂)₃— or —CH(Ar³)—O—(CH₂)₂—.

Another embodiment of the present invention relates to those compounds of formula (I) or any subgroup thereof as mentioned in any of the other embodiments wherein the bivalent radical -L$^a$-R$^{5a}$—R$^{4a}$— or -L$^c$-R$^{5c}$—R$^{4c}$— is further substituted with substituents according to any of the other embodiments.

Another embodiment of the present invention relates to those compounds of formula (I) or any subgroup thereof as mentioned in any of the other embodiments wherein the expression "on one or more CH₂ groups" is restricted to "on one or two CH₂ groups".

Another embodiment of the present invention relates to those compounds of formula (I) or any subgroup thereof as mentioned in any of the other embodiments wherein pyridinyl in particular is 2-pyridinyl, 3-pyridinyl or 4-pyridinyl.

Another embodiment of the present invention relates to those compounds of formula (I) or any subgroup thereof as mentioned in any of the other embodiments wherein quinolinyl in particular is 2-quinolinyl.

Another embodiment of the present invention relates to those compounds of formula (I) or any subgroup thereof as mentioned in any of the other embodiments wherein two geminal hydrogen atoms in (d-1) or (d-2) may be replaced by 1,5-pentanediyl.

Another embodiment of the present invention relates to those compounds of formula (I) or any subgroup thereof as mentioned in any of the other embodiments wherein Het¹ is a heterocycle having formula (a).

Another embodiment of the present invention relates to those compounds of formula (I) or any subgroup thereof as mentioned in any of the other embodiments wherein Het¹ is a heterocycle having formula (b).

Another embodiment of the present invention relates to those compounds of formula (I) or any subgroup thereof as mentioned in any of the other embodiments wherein Het¹ is a heterocycle having formula (c).

Another embodiment of the present invention relates to those compounds of formula (I) or any subgroup thereof as mentioned in any of the other embodiments wherein A¹ represents CR$^{3a}$.

Another embodiment of the present invention relates to those compounds of formula (I) or any subgroup thereof as mentioned in any of the other embodiments wherein A¹ represents N.

Another embodiment of the present invention relates to those compounds of formula (I) or any subgroup thereof as mentioned in any of the other embodiments wherein A² represents CR$^{3b}$.

Another embodiment of the present invention relates to those compounds of formula (I) or any subgroup thereof as mentioned in any of the other embodiments wherein A² represents N.

Another embodiment of the present invention relates to those compounds of formula (I) or any subgroup thereof as mentioned in any of the other embodiments wherein A³ represents CH.

Another embodiment of the present invention relates to those compounds of formula (I) or any subgroup thereof as mentioned in any of the other embodiments wherein A³ represents N.

Another embodiment of the present invention relates to those compounds of formula (I) or any subgroup thereof as mentioned in any of the other embodiments wherein A⁴ represents CH.

Another embodiment of the present invention relates to those compounds of formula (I) or any subgroup thereof as mentioned in any of the other embodiments wherein A⁴ represents N.

Another embodiment of the present invention relates to those compounds of formula (I) or any subgroup thereof as mentioned in any of the other embodiments wherein A³ and A⁴ each independently are CH or CF.

Another embodiment of the present invention relates to those compounds of formula (I) or any subgroup thereof as mentioned in any of the other embodiments, wherein at least one of A¹, A², A³ and A⁴ is other than CH.

Another embodiment of the present invention relates to those compounds of formula (I) or any subgroup thereof as mentioned in any of the other embodiments wherein R$^{3a}$ represents hydrogen or C$_{1-4}$alkyloxy.

Another embodiment of the present invention relates to those compounds of formula (I) or any subgroup thereof as mentioned in any of the other embodiments wherein Y represents NH.

Another embodiment of the present invention relates to those compounds of formula (I) or any subgroup thereof as mentioned in any of the other embodiments wherein one or more, preferably all, of the following restrictions apply: (i) R⁷ represents C$_{1-4}$alkyl; (ii) R⁸ represents C$_{1-4}$alkyl.

Another embodiment of the present invention relates to those compounds of Formula (I) or any subgroup thereof as mentioned in any of the other embodiments wherein R⁹ is hydrogen or C$_{1-4}$alkyl optionally substituted with one or more halo substituents.

Another embodiment of the present invention relates to those compounds of Formula (I) or any subgroup thereof as mentioned in any of the other embodiments wherein r is 0.

In an embodiment the compound of Formula (I) is selected from the group comprising:
5-[6-(4-methyl-1H-imidazol-1-yl)-3-pyridinyl]-N-[3-(trifluoromethyl)phenyl]-1H-1,2,4-triazol-3-amine.2HCl,
2-[3-methoxy-4-(4-methyl-1H-imidazol-1-yl)phenyl]-5-methyl-4-phenyl-1H-imidazole,
2-[3-methoxy-4-(4-methyl-1H-imidazol-1-yl)phenyl]-4,5-dimethyl-1H-imidazole,
2-[3-methoxy-4-(4-methyl-1H-imidazol-1-yl)phenyl]-5-methyl-4-(2-methylpropyl)-1H-imidazole,
2-[2-methoxy-4-(4-methyl-1H-imidazol-1-yl)phenyl]-5-methyl-4-phenyl-1H-imidazole,
2-[3-methoxy-4-(4-methyl-1H-imidazol-1-yl)phenyl]-5-methyl-4-[3-(trifluoromethyl)phenyl]-1H-imidazole,
1-[2-methoxy-4-(5-methyl-4-phenyl-1H-imidazol-2-yl)phenyl]-3-methyl-1H-1,2,4-triazole,
2-[3-methoxy-4-(4-methyl-1H-imidazol-1-yl)phenyl]-1,4-dimethyl-5-[3-(trifluoromethyl)phenyl]-1H-imidazole,
2-[3-methoxy-4-(4-methyl-1H-imidazol-1-yl)phenyl]-1,5-dimethyl-4-[3-(trifluoromethyl)phenyl]-1H-imidazole,
2-[3-methoxy-4-(4-methyl-1H-imidazol-1-yl)phenyl]-4-phenyl-5-propyl-1H-imidazole,
1-(4-fluorophenyl)-3-[3-methoxy-4-(4-methyl-1H-imidazol-1-yl)phenyl]-5-methyl-1H-1,2,4-triazole,
3-[3-methoxy-4-(4-methyl-1H-imidazol-1-yl)phenyl]-1-methyl-5-phenyl-1H-1,2,4-triazole,
5-[(4-fluorophenyl)methyl]-3-[3-methoxy-4-(4-methyl-1H-imidazol-1-yl)phenyl]-1H-1,2,4-triazole, N-[4-fluoro-2-(trifluoromethyl)phenyl]-3-[3-methoxy-4-(4-methyl-1H-imidazol-1-yl)phenyl]-1-methyl-1H-1,2,4-triazol-5-amine, N-[4-fluoro-2-(trifluoromethyl)phenyl]-5-[3-methoxy-4-(4-methyl-1H-imidazol-1-yl)phenyl]-1-methyl-1H-1,2,4-triazol-3-amine, 4-[5-[3-methoxy-4-(4-methyl-1H-imidazol-1-yl)phenyl]-1-methyl-1H-1,2,4-triazol-3-yl]-2,6-dimethyl-morpholine (CIS), 5-(4-fluorophenyl)-3-[3-methoxy-4-(4-methyl-1H-imidazol-1-yl)phenyl]-1-(1-methylethyl)-1H-1,2,4-triazole, 3-(4-fluorophenyl)-5-[3-methoxy-4-(4-methyl-1H-imidazol-1-yl)phenyl]-1H-1,2,4-triazole, 5-cyclohexyl-3-[3-methoxy-4-(4-methyl-1H-imidazol-1-yl)phenyl]-1H-1,2,4-triazole, 5-[3-methoxy-4-(4-methyl-1H-imidazol-1-yl)phenyl]-3-(3-methoxyphenyl)-1H-1,2,4-triazole, 4-[3-[3-methoxy-4-(4-methyl-1H-imidazol-1-yl)phenyl]-1-methyl-1H-1,2,4-triazol-5-yl]-2,6-dimethyl-morpholine (CIS), 3-[3-methoxy-4-(4-methyl-1H-imidazol-1-yl)phenyl]-5-(3-methoxyphenyl)-1-(1-methylethyl)-1H-1,2,4-triazole, 5-cyclohexyl-3-[3-methoxy-4-(4-methyl-1H-imidazol-1-yl)phenyl]-1-methyl-1H-1,2,4-triazole, 3-(4-fluorophenyl)-5-[3-methoxy-4-(4-methyl-1H-imidazol-1-yl)phenyl]-1-methyl-1H-1,2,4-triazole, 5-(4-fluorophenyl)-3-[3-methoxy-4-(4-methyl-1H-imidazol-1-yl)phenyl]-1-methyl-1H-1,2,4-triazole, 3-[3-methoxy-4-(4-methyl-1H-imidazol-1-yl)phenyl]-1-methyl-5-[3-(trifluoromethyl)phenyl]-1H-1,2,4-triazole, 5-[3-methoxy-4-(4-methyl-1H-imidazol-1-yl)phenyl]-1-methyl-3-[3-(trifluoromethyl)phenyl]-1H-1,2,4-triazole, 3-[3-methoxy-4-(4-methyl-1H-imidazol-1-yl)phenyl]-1-(1-methylethyl)-5-[3-(trifluoromethyl)phenyl]-1H-1,2,4-triazole, 5-[3-methoxy-4-(4-methyl-1H-imidazol-1-yl)phenyl]-3-[3-(trifluoromethyl)phenyl]-1H-1,2,4-triazole, N-[(1S)-1-(4-fluorophenyl)ethyl]-5-[3-methoxy-4-(4-methyl-1H-imidazol-1-yl)phenyl]-1-methyl-1H-1,2,4-triazol-3-amine N-[(1S)-1-(4-fluorophenyl)ethyl]-3-[3-methoxy-4-(4-methyl-1H-imidazol-1-yl)phenyl]-1-methyl-1H-1,2,4-triazol-5-amine, 5-[(4-fluorophenyl)methyl]-3-[3-methoxy-4-(4-methyl-1H-imidazol-1-yl)phenyl]-1-methyl-1H-1,2,4-triazole, 5,6,7,8-tetrahydro-2-[3-methoxy-4-(4-methyl-1H-imidazol-1-yl)phenyl]-8-[2-(trifluoromethyl)phenyl]-[1,2,4]triazolo[1,5-a]pyridine, 5-[3-methoxy-4-(4-methyl-1H-imidazol-1-yl)phenyl]-3-(3-methoxyphenyl)-1-methyl-1H-1,2,4-triazole, 3-[3-methoxy-4-(4-methyl-1H-imidazol-1-yl)phenyl]-5-(3-methoxyphenyl)-1-methyl-1H-1,2,4-triazole, 6-[3-(4-fluorophenyl)-1H-1,2,4-triazol-5-yl]-2-methoxy-3-(4-methyl-1H-imidazol-1-yl)-pyridine, 3-[3-methoxy-4-(4-methyl-1H-imidazol-1-yl)phenyl]-1-methyl-5-[2-(trifluoromethyl)phenyl]-1H-1,2,4-triazole, 5-[3-methoxy-4-(4-methyl-1H-imidazol-1-yl)phenyl]-1-methyl-3-[2-(trifluoromethyl)phenyl]-1H-1,2,4-triazole, 3-(2-chlorophenyl)-5-[3-methoxy-4-(4-methyl-1H-imidazol-1-yl)phenyl]-1-methyl-1H-1,2,4-triazole, 5-(2-chlorophenyl)-3-[3-methoxy-4-(4-methyl-1H-imidazol-1-yl)phenyl]-1-methyl-1H-1,2,4-triazole, N-[4-fluoro-2-(trifluoromethyl)phenyl]-5-[3-methoxy-4-(4-methyl-1H-imidazol-1-yl)phenyl]-N,1-dimethyl-1H-1,2,4-triazol-3-amine, N-[4-fluoro-2-(trifluoromethyl)phenyl]-3-[3-methoxy-4-(4-methyl-1H-imidazol-1-yl)phenyl]-N,1-dimethyl-1H-1,2,4-triazol-5-amine, 4,5,6,7-tetrahydro-2-[3-methoxy-4-(4-methyl-1H-imidazol-1-yl)phenyl]-4-[2-(trifluoromethyl)phenyl]-[1,2,4]triazolo[1,5-a]pyrimidine, 3-[(E)-2-(4-fluorophenyl)ethenyl]-5-[3-methoxy-4-(4-methyl-1H-imidazol-1-yl)phenyl]-1-methyl-1H-1,2,4-triazole, 5-[(E)-2-(4-fluorophenyl)ethenyl]-3-[3-methoxy-4-(4-methyl-1H-imidazol-1-yl)phenyl]-1-methyl-1H-1,2,4-triazole, 3-[[4-fluoro-2-(trifluoromethyl)phenyl]methyl]-5-[3-methoxy-4-(4-methyl-1H-imidazol-1-yl)phenyl]-1-methyl-1H-1,2,4-triazole, 5-[[4-fluoro-2-(trifluoromethyl)phenyl]methyl]-3-[3-methoxy-4-(4-methyl-1H-imidazol-1-yl)phenyl]-1-methyl-1H-1,2,4-triazole, 5-[1-(4-fluorophenyl)cyclopropyl]-3-[3-methoxy-4-(4-methyl-1H-imidazol-1-yl)phenyl]-1-methyl-1H-1,2,4-triazole, 3-[1-(4-fluorophenyl)cyclopropyl]-5-[3-methoxy-4-(4-methyl-1H-imidazol-1-yl)phenyl]-1-methyl-1H-1,2,4-triazole, 6,7-dihydro-2-[3-methoxy-4-(4-methyl-1H-imidazol-1-yl)phenyl]-5H-[1,2,4]triazolo[5,1-a][2]benzazepine, 3-[3-methoxy-4-(4-methyl-1H-imidazol-1-yl)phenyl]-5-methyl-1-[3-(trifluoromethyl)phenyl]-1H-1,2,4-triazole.2HCl, 3-[3-methoxy-4-(4-methyl-1H-imidazol-1-yl)phenyl]-5-methyl-1-[2-(trifluoromethyl)phenyl]-1H-1,2,4-triazole.2HCl, 1-(4-fluorophenyl)-3-[3-methoxy-4-(4-methyl-1H-imidazol-1-yl)phenyl]-5-(1-methylethyl)-1H-1,2,4-triazole.HCl, 3-[3-methoxy-4-(4-methyl-1H-imidazol-1-yl)phenyl]-5-(1-methylethyl)-1-[3-(trifluoromethyl)phenyl]-1H-1,2,4-triazole.HCl, (4-fluorophenyl) [3-[3-methoxy-4-(4-methyl-1H-imidazol-1-yl)phenyl]-1-methyl-1H-1,2,4-triazol-5-yl]-methanone, 1-cyclopentyl-5-(4-fluorophenyl)-3-[3-methoxy-4-(4-methyl-1H-imidazol-1-yl)phenyl]-1H-1,2,4-triazole, 3-(4-chloro-3-methoxyphenyl)-5-[3-methoxy-4-(4-methyl-1H-imidazol-1-yl)phenyl]-1H-1,2,4-triazole, N-[4-fluoro-2-(trifluoromethyl)phenyl]-3-[3-methoxy-4-(4-methyl-1H-imidazol-1-yl)phenyl]-1-(1-methylethyl)-1H-1,2,4-triazol-5-amine, 3-[3-methoxy-4-(4-methyl-1H-imidazol-1-yl)phenyl]-1-methyl-N-(3,4,5-trifluorophenyl)-1H-1,2,4-triazol-5-amine, 5-[3-methoxy-4-(4-methyl-1H-imidazol-1-yl)phenyl]-1-methyl-N-(3,4,5-trifluorophenyl)-1H-1,2,4-triazol-3-amine, 5-(4-chloro-3-methoxyphenyl)-3-[3-methoxy-4-(4-methyl-1H-imidazol-1-yl)phenyl]-1-methyl-1H-1,2,4-triazole, 3-(4-chloro-3-methoxyphenyl)-5-[3-methoxy-4-(4-methyl-1H-imidazol-1-yl)phenyl]-1-methyl-1H-1,2,4-triazole, 5-(2-chlorophenyl)-3-[3-methoxy-4-(4-methyl-1H-imidazol-1-yl)phenyl]-1H-1,2,4-triazole, 3-[3-methoxy-4-(4-methyl-1H-imidazol-1-yl)phenyl]-1-[3-(trifluoromethyl)phenyl]-1H-1,2,4-triazole, 5-(2-chlorophenyl)-3-[3-methoxy-4-(4-methyl-1H-imidazol-1-yl)phenyl]-1-(1-methylethyl)-1H-1,2,4-triazole, 3-[3-methoxy-4-(4-methyl-1H-imidazol-1-yl)phenyl]-1-(1-methylethyl)-5-[2-(trifluoromethyl)phenyl]-1H-1,2,4-triazole.2HCl, 2-methoxy-6-[1-(1-methylethyl)-5-[3-(trifluoromethyl)phenyl]-1H-1,2,4-triazol-3-yl]-3-(4-methyl-1H-imidazol-1-yl)-pyridine.2HCl,
1-[2-methoxy-4-(5-methyl-4-phenyl-1H-imidazol-2-yl)phenyl]-5-methyl-1H-1,2,4-triazole,
5-(4-fluorophenyl)-3-[3-methoxy-4-(4-methyl-1H-imidazol-1-yl)phenyl]-1-(1-methylethyl)-1H-1,2,4-triazole.1.3HCl.H₂O,
6',7'-dihydro-2'-[3-methoxy-4-(4-methyl-1H-imidazol-1-yl)phenyl]-spiro[cyclohexane-1,8'(5'H)-[1,2,4]triazolo[1,5-a]pyridine],
3-[3-methoxy-4-(4-methyl-1H-imidazol-1-yl)phenyl]-1-(1-methylethyl)-5-(3,4,5-trifluorophenyl)-1H-1,2,4-triazole,
3-[3-methoxy-4-(4-methyl-1H-imidazol-1-yl)phenyl]-1-[2-(trifluoromethyl)phenyl]-1H-1,2,4-triazole.2HCl,
3-[3-methoxy-4-(4-methyl-1H-imidazol-1-yl)phenyl]-1-methyl-5-[3-(trifluoromethyl)phenoxy]-1H-1,2,4-triazole,
5-(2-chlorophenyl)-1-(cyclopropylmethyl)-3-[3-methoxy-4-(4-methyl-1H-imidazol-1-yl)phenyl]-1H-1,2,4-triazole.2H₂O.0.8HCl,
3-(5-chloro-2-methylphenyl)-5-[3-methoxy-4-(4-methyl-1H-imidazol-1-yl)phenyl]-1H-1,2,4-triazole,
5-(2-chlorophenoxy)-3-[3-methoxy-4-(4-methyl-1H-imidazol-1-yl)phenyl]-1-(1-methylethyl)-1H-1,2,4-triazole,
5-(2-chlorophenoxy)-3-[3-methoxy-4-(4-methyl-1H-imidazol-1-yl)phenyl]-1-methyl-1H-1,2,4-triazole,
5-(2-chlorophenyl)-3-[3-methoxy-4-(4-methyl-1H-imidazol-1-yl)phenyl]-1-(2,2,2-trifluoroethyl)-1H-1,2,4-triazole.1.2HCl.1.6H₂O,
5',6'-dihydro-2'-[3-methoxy-4-(4-methyl-1H-imidazol-1-yl)phenyl]-spiro[cyclohexane-1,7'(8'H)-[1,2,4]triazolo[1,5-a]pyridine].1.8HCl.2.2H₂O,
5-(2-chlorophenyl)-1-(2-methoxyethyl)-3-[3-methoxy-4-(4-methyl-1H-imidazol-1-yl)phenyl]-1H-1,2,4-triazole,
5-(5-chloro-2-methylphenyl)-3-[3-methoxy-4-(4-methyl-1H-imidazol-1-yl)phenyl]-1-methyl-1H-1,2,4-triazole,
3-(5-chloro-2-methylphenyl)-5-[3-methoxy-4-(4-methyl-1H-imidazol-1-yl)phenyl]-1-methyl-1H-1,2,4-triazole,
5-(2-chlorophenoxy)-3-[3-methoxy-4-(3-methyl-1H-1,2,4-triazol-1-yl)phenyl]-1-methyl-1H-1,2,4-triazole,
5-(4-fluoro-2-methylphenyl)-2-[3-methoxy-4-(4-methyl-1H-imidazol-1-yl)phenyl]-[1,2,4]triazolo[1,5-a]pyrazine,
8-(2-chlorophenyl)-2-[3-methoxy-4-(4-methyl-1H-imidazol-1-yl)phenyl]-[1,2,4]triazolo[1,5-a]pyridine,
4-[1-(4-fluorophenyl)-3-[3-methoxy-4-(4-methyl-1H-imidazol-1-yl)phenyl]-1H-1,2,4-triazol-5-yl]-morpholine,
3-[3-methoxy-4-(4-methyl-1H-imidazol-1-yl)phenyl]-1-methyl-N-[3-(trifluoromethyl)phenyl]-1H-1,2,4-triazol-5-amine,
9-(4-fluorophenyl)-6,7-dihydro-2-[3-methoxy-4-(4-methyl-1H-imidazol-1-yl)phenyl]-5H,9H-[1,2,4]triazolo[5,1-c][1,4]oxazepine,
6,7-dihydro-2-[3-methoxy-4-(4-methyl-1H-imidazol-1-yl)phenyl]-9-[2-(trifluoromethyl)phenyl]-5H,9H-[1,2,4]triazolo[5,1-c][1,4]oxazepine,
8-(4-fluorophenyl)-5,6,7,8-tetrahydro-2-[6-methoxy-5-(4-methyl-1H-imidazol-1-yl)-2-pyridinyl]-[1,2,4]triazolo[1,5-a]pyridine,
2-[3-methoxy-4-(4-methyl-1H-imidazol-1-yl)phenyl]-7-[2-(trifluoromethyl)phenyl]-[1,2,4]triazolo[1,5-a]pyrimidine,
2-[3-methoxy-4-(4-methyl-1H-imidazol-1-yl)phenyl]-5-[2-(trifluoromethyl)phenyl]-[1,2,4]triazolo[1,5-a]pyrimidine,
3-[3-methoxy-4-(4-methyl-1H-imidazol-1-yl)phenyl]-1-methyl-5-[2-methyl-5-(trifluoromethyl)phenyl]-1H-1,2,4-triazole,
5-[3-methoxy-4-(4-methyl-1H-imidazol-1-yl)phenyl]-1-methyl-3-[2-methyl-5-(trifluoromethyl)phenyl]-1H-1,2,4-triazole,
2-[3-methoxy-4-(4-methyl-1H-imidazol-1-yl)phenyl]-8-phenyl-[1,2,4]triazolo[1,5-a]pyrazine,
3-[3-methoxy-4-(4-methyl-1H-imidazol-1-yl)phenyl]-1-(1-methylethyl)-5-[2-methyl-5-(trifluoromethyl)phenyl]-1H-1,2,4-triazole,
1-[3-[3-methoxy-4-(4-methyl-1H-imidazol-1-yl)phenyl]-1-(1-methylethyl)-1H-1,2,4-triazol-5-yl]-3-phenyl-piperidine.HCl,
3-[3-methoxy-4-(3-methyl-1H-1,2,4-triazol-1-yl)phenyl]-1-methyl-N-[3-(trifluoromethyl)phenyl]-1H-1,2,4-triazol-5-amine,
1,2,3,4-tetrahydro-2-[3-[3-methoxy-4-(4-methyl-1H-imidazol-1-yl)phenyl]-1-methyl-1H-1,2,4-triazol-5-yl]-isoquinoline,
1-[3-[3-methoxy-4-(4-methyl-1H-imidazol-1-yl)phenyl]-1-methyl-1H-1,2,4-triazol-5-yl]-4-phenyl-piperidine,
1-[3-[3-methoxy-4-(4-methyl-1H-imidazol-1-yl)phenyl]-1-methyl-1H-1,2,4-triazol-5-yl]-3-phenyl-piperidine.2.5H₂O.1.5HCl,
N-[4-fluoro-3-(trifluoromethyl)phenyl]-3-[3-methoxy-4-(4-methyl-1H-imidazol-1-yl)phenyl]-1-methyl-1H-1,2,4-triazol-5-amine,
3-[3-methoxy-4-(4-methyl-1H-imidazol-1-yl)phenyl]-1-methyl-N-[4-(trifluoromethyl)phenyl]-1H-1,2,4-triazol-5-amine,
5,6-dihydro-2-[3-methoxy-4-(4-methyl-1H-imidazol-1-yl)phenyl]-8-[2-(trifluoromethyl)phenyl]-8H-[1,2,4]triazolo[5,1-c][1,4]oxazine,
N-[4-fluoro-2-(trifluoromethyl)phenyl]-3-[6-methoxy-5-(4-methyl-1H-imidazol-1-yl)-2-pyridinyl]-1-methyl-1H-1,2,4-triazol-5-amine,
3-[3-methoxy-4-(4-methyl-1H-imidazol-1-yl)phenyl]-1-methyl-N-(phenylmethyl)-1H-1,2,4-triazol-5-amine,
N-[3-[3-methoxy-4-(4-methyl-1H-imidazol-1-yl)phenyl]-1-methyl-1H-1,2,4-triazol-5-yl]-2-(trifluoromethyl)-4-pyridinamine,
2-methoxy-6-[1-(1-methylethyl)-5-(3-phenyl-1-piperidinyl)-1H-1,2,4-triazol-3-yl]-3-(4-methyl-1H-imidazol-1-yl)-pyridine.HCl,
8-(2-chlorophenyl)-5,6,7,8-tetrahydro-2-[3-methoxy-4-(4-methyl-1H-imidazol-1-yl)phenyl]-[1,2,4]triazolo[1,5-a]pyridine,
3-[6-methoxy-5-(4-methyl-1H-imidazol-1-yl)-2-pyridinyl]-1-methyl-N-[3-(trifluoromethyl)phenyl]-1H-1,2,4-triazol-5-amine,
N-[3,5-bis(trifluoromethyl)phenyl]-3-[3-methoxy-4-(4-methyl-1H-imidazol-1-yl)phenyl]-1-methyl-1H-1,2,4-triazol-5-amine,
3-[3-methoxy-4-(4-methyl-1H-imidazol-1-yl)phenyl]-N-[3-methoxy-5-(trifluoromethyl)phenyl]-1-methyl-1H-1,2,4-triazol-5-amine,
N-[2-fluoro-5-(trifluoromethyl)phenyl]-3-[3-methoxy-4-(4-methyl-1H-imidazol-1-yl)phenyl]-1-methyl-1H-1,2,4-triazol-5-amine,
N-(3,4-difluorophenyl)-3-[3-methoxy-4-(4-methyl-1H-imidazol-1-yl)phenyl]-1-methyl-1H-1,2,4-triazol-5-amine,
N-(3-chlorophenyl)-3-[6-methoxy-5-(4-methyl-1H-imidazol-1-yl)-2-pyridinyl]-1-methyl-1H-1,2,4-triazol-5-amine, N-[2-fluoro-3-(trifluoromethyl)phenyl]-3-[3-methoxy-4-(4-methyl-1H-imidazol-1-yl)phenyl]-1-methyl-1H-1,2,4-triazol-5-amine,
N-(4-chloro-3-methoxyphenyl)-3-[3-methoxy-4-(4-methyl-1H-imidazol-1-yl)phenyl]-1-methyl-1H-1,2,4-triazol-5-amine,
N-(4-fluorophenyl)-3-[3-methoxy-4-(4-methyl-1H-imidazol-1-yl)phenyl]-1-methyl-1H-1,2,4-triazol-5-amine,
N-[3-fluoro-5-(trifluoromethyl)phenyl]-3-[3-methoxy-4-(4-methyl-1H-imidazol-1-yl)phenyl]-1-methyl-1H-1,2,4-triazol-5-amine,
2-[3-methoxy-4-(4-methyl-1H-imidazol-1-yl)phenyl]-8-[2-(trifluoromethyl)phenyl]-[1,2,4]triazolo[1,5-a]pyrazine,
N-(2,2-difluoro-1,3-benzodioxol-5-yl)-3-[3-methoxy-4-(4-methyl-1H-imidazol-1-yl)phenyl]-1-methyl-1H-1,2,4-triazol-5-amine,
2-[3-methoxy-4-(4-methyl-1H-imidazol-1-yl)phenyl]-N-[3-(trifluoromethyl)phenyl]-[1,2,4]triazolo[1,5-a]pyridin-8-amine,
N-(3-chlorophenyl)-3-[3-methoxy-4-(4-methyl-1H-imidazol-1-yl)phenyl]-1-methyl-1H-1,2,4-triazol-5-amine,
4,5,6,7-tetrahydro-2-[3-methoxy-4-(4-methyl-1H-imidazol-1-yl)phenyl]-5-[2-(trifluoromethyl)phenyl]-[1,2,4]triazolo[1,5-a]pyrimidine,
N-(4-fluoro-3-methoxyphenyl)-3-[3-methoxy-4-(4-methyl-1H-imidazol-1-yl)phenyl]-1-methyl-1H-1,2,4-triazol-5-amine,
N-(2-chlorophenyl)-3-[3-methoxy-4-(4-methyl-1H-imidazol-1-yl)phenyl]-1-methyl-1H-1,2,4-triazol-5-amine,
3-[3-methoxy-4-(4-methyl-1H-imidazol-1-yl)phenyl]-1-(1-methylethyl)-5-[3-[3-(trifluoromethyl)phenyl]-1-pyrrolidinyl]-1H-1,2,4-triazole.2HCl.2.5H$_2$O,
5,6,7,8-tetrahydro-2-[3-methoxy-4-(4-methyl-1H-imidazol-1-yl)phenyl]-8-[2-(trifluoromethyl)phenyl]-[1,2,4]triazolo[1,5-a]pyrazine,
N-(4-fluoro-2-methylphenyl)-3-[3-methoxy-4-(4-methyl-1H-imidazol-1-yl)phenyl]-1-methyl-1H-1,2,4-triazol-5-amine,
N-[2-fluoro-5-(trifluoromethyl)phenyl]-3-[6-methoxy-5-(4-methyl-1H-imidazol-1-yl)-2-pyridinyl]-1-methyl-1H-1,2,4-triazol-5-amine,
3-[3-methoxy-4-(4-methyl-1H-imidazol-1-yl)phenyl]-N-(5-methoxy-2-methylphenyl)-1-methyl-1H-1,2,4-triazol-5-amine,
3-[3-methoxy-4-(4-methyl-1H-imidazol-1-yl)phenyl]-1-methyl-N-[2-(trifluoromethyl)phenyl]-1H-1,2,4-triazol-5-amine,
N-(2-fluorophenyl)-3-[3-methoxy-4-(4-methyl-1H-imidazol-1-yl)phenyl]-1-methyl-1H-1,2,4-triazol-5-amine,
N-(3-fluorophenyl)-3-[3-methoxy-4-(4-methyl-1H-imidazol-1-yl)phenyl]-1-methyl-1H-1,2,4-triazol-5-amine,
1,2,3,4-tetrahydro-2-[3-[3-methoxy-4-(4-methyl-1H-imidazol-1-yl)phenyl]-1-(1-methylethyl)-1H-1,2,4-triazol-5-yl]-isoquinoline.HCl,
(8R)-8-(2-chlorophenyl)-5,6,7,8-tetrahydro-2-[3-methoxy-4-(4-methyl-1H-imidazol-1-yl)phenyl]-[1,2,4]triazolo[1,5-a]pyridine,
(8S)-8-(2-chlorophenyl)-5,6,7,8-tetrahydro-2-[3-methoxy-4-(4-methyl-1H-imidazol-1-yl)phenyl]-[1,2,4]triazolo[1,5-a]pyridine,
1-[3-[3-methoxy-4-(4-methyl-1H-imidazol-1-yl)phenyl]-1-(1-methylethyl)-1H-1,2,4-triazol-5-yl]-3-(trifluoromethyl)-piperidine.1.8HCl.1.5H$_2$O,
5,6,7,8-tetrahydro-2-[3-methoxy-4-(4-methyl-1H-imidazol-1-yl)phenyl]-7-methyl-8-[2-(trifluoromethyl)phenyl]-[1,2,4]triazolo[1,5-a]pyrazine,
7-acetyl-5,6,7,8-tetrahydro-2-[3-methoxy-4-(4-methyl-1H-imidazol-1-yl)phenyl]-8-[2-(trifluoromethyl)phenyl]-[1,2,4]triazolo[1,5-a]pyrazine,
3-[[3-[3-methoxy-4-(4-methyl-1H-imidazol-1-yl)phenyl]-1-methyl-1H-1,2,4-triazol-5-yl]amino]-benzonitrile,
3-[3-methoxy-4-(4-methyl-1H-imidazol-1-yl)phenyl]-N-(3-methoxyphenyl)-1-methyl-1H-1,2,4-triazol-5-amine,
2-[3-methoxy-4-(4-methyl-1H-imidazol-1-yl)phenyl]-8-[3-(trifluoromethyl)phenyl]-[1,2,4]triazolo[1,5-a]pyrazine,
3-[3-methoxy-4-(4-methyl-1H-imidazol-1-yl)phenyl]-1-(2,2,2-trifluoroethyl)-N-[3-(trifluoromethyl)phenyl]-1H-1,2,4-triazol-5-amine,
N-(2,5-dichlorophenyl)-3-[3-methoxy-4-(4-methyl-1H-imidazol-1-yl)phenyl]-1-methyl-1H-1,2,4-triazol-5-amine,
3-[3-methoxy-4-(4-methyl-1H-imidazol-1-yl)phenyl]-1-methyl-N-[3-(trifluoromethoxy)phenyl]-1H-1,2,4-triazol-5-amine,
3-[3-methoxy-4-(4-methyl-1H-imidazol-1-yl)phenyl]-N-[2-methoxy-5-(trifluoromethyl)phenyl]-1-methyl-1H-1,2,4-triazol-5-amine,
N-(3-chloro-2-methylphenyl)-3-[3-methoxy-4-(4-methyl-1H-imidazol-1-yl)phenyl]-1-methyl-1H-1,2,4-triazol-5-amine,
N-(5-chloro-2-fluorophenyl)-3-[3-methoxy-4-(4-methyl-1H-imidazol-1-yl)phenyl]-1-methyl-1H-1,2,4-triazol-5-amine,
1-methyl-3-[4-(4-methyl-1H-imidazol-1-yl)phenyl]-N-[3-(trifluoromethyl)phenyl]-1H-1,2,4-triazol-5-amine,
N-[2-fluoro-5-(trifluoromethyl)phenyl]-1-methyl-3-[4-(4-methyl-1H-imidazol-1-yl)phenyl]-1H-1,2,4-triazol-5-amine,
8-(3-fluorophenyl)-5,6,7,8-tetrahydro-2-[3-methoxy-4-(4-methyl-1H-imidazol-1-yl)phenyl]-[1,2,4]triazolo[1,5-a]pyridine,
7-acetyl-5,6,7,8-tetrahydro-2-[3-methoxy-4-(4-methyl-1H-imidazol-1-yl)phenyl]-8-[3-(trifluoromethyl)phenyl]-[1,2,4]triazolo[1,5-a]pyrazine,
N-(2-chloro-5-methoxyphenyl)-3-[3-methoxy-4-(4-methyl-1H-imidazol-1-yl)phenyl]-1-methyl-1H-1,2,4-triazol-5-amine,
N-[4-fluoro-2-(trifluoromethyl)phenyl]-1-methyl-3-[4-(4-methyl-1H-imidazol-1-yl)phenyl]-1H-1,2,4-triazol-5-amine,
1,3-benzenediamine, 4-fluoro-N$^3$-[3-[3-methoxy-4-(4-methyl-1H-imidazol-1-yl)phenyl]-1-methyl-1H-1,2,4-triazol-5-yl]-N$^1$,N$^1$-dimethyl-N-[2-chloro-5-(trifluoromethyl)phenyl]-3-[3-methoxy-4-(4-methyl-1H-imidazol-1-yl)phenyl]-1-methyl-1H-1,2,4-triazol-5-amine,
N-(5-fluoro-2-methylphenyl)-3-[3-methoxy-4-(4-methyl-1H-imidazol-1-yl)phenyl]-1-methyl-1H-1,2,4-triazol-5-amine.2HCl,
N-(5-chloro-2-methylphenyl)-3-[3-methoxy-4-(4-methyl-1H-imidazol-1-yl)phenyl]-1-methyl-1H-1,2,4-triazol-5-amine,
N-[5-fluoro-2-(trifluoromethyl)phenyl]-3-[3-methoxy-4-(4-methyl-1H-imidazol-1-yl)phenyl]-1-methyl-1H-1,2,4-triazol-5-amine,
5,6,7,8-tetrahydro-2-[3-methoxy-4-(4-methyl-1H-imidazol-1-yl)phenyl]-8-[4-(trifluoromethyl)phenyl]-[1,2,4]triazolo[1,5-a]pyridine,
8-(2-fluorophenyl)-5,6,7,8-tetrahydro-2-[3-methoxy-4-(4-methyl-1H-imidazol-1-yl)phenyl]-[1,2,4]triazolo[1,5-a]pyridine,
N-[3-fluoro-2-(trifluoromethyl)phenyl]-3-[3-methoxy-4-(4-methyl-1H-imidazol-1-yl)phenyl]-1-methyl-1H-1,2,4-triazol-5-amine, 3-[3-methoxy-4-(4-methyl-1H-imidazol-1-yl)phenyl]-1-methyl-N-[2-methyl-5-(trifluoromethyl)phenyl]-1H-1,2,4-triazol-5-amine, 3-[6-methoxy-5-(4-methyl-1H-imidazol-1-yl)-2-pyridinyl]-1-methyl-N-[2-(trifluoromethyl)phenyl]-1H-1,2,4-triazol-5-amine, 3-[3-methoxy-4-(4-methyl-1H-imidazol-1-yl)phenyl]-1-(1-methylethyl)-N-[3-(trifluoromethyl)phenyl]-1H-1,2,4-triazol-5-amine, N-[2,5-bis(trifluoromethyl)phenyl]-3-[3-methoxy-4-(4-methyl-1H-imidazol-1-yl)phenyl]-1-methyl-1H-1,2,4-triazol-5-amine, N-(2-fluoro-5-methoxyphenyl)-3-[3-methoxy-4-(4-methyl-1H-imidazol-1-yl)phenyl]-1-methyl-1H-1,2,4-triazol-5-amine, 2-[3-methoxy-4-(4-methyl-1H-imidazol-1-yl)phenyl]-8-[3-(trifluoromethoxy)phenyl]-[1,2,4]triazolo[1,5-a]pyridine, N-cyclohexyl-3-[3-methoxy-4-(4-methyl-1H-imidazol-1-yl)phenyl]-1-methyl-1H-1,2,4-triazol-5-amine, 7-(2-chlorophenyl)-6,7-dihydro-2-[3-methoxy-4-(4-methyl-1H-imidazol-1-yl)phenyl]-5H-pyrrolo[1,2-b][1,2,4]triazole, N-(2-chloro-6-fluorophenyl)-3-[3-methoxy-4-(4-methyl-1H-imidazol-1-yl)phenyl]-1-methyl-1H-1,2,4-triazol-5-amine, 5-[5-chloro-1-[2-(trifluoromethyl)phenyl]pentyl]-3-[3-methoxy-4-(4-methyl-1H-imidazol-1-yl)phenyl]-1H-1,2,4-triazole, 8-(4-fluorophenyl)-5,6,7,8-tetrahydro-2-[3-methoxy-4-(4-methyl-1H-imidazol-1-yl)phenyl]-[1,2,4]triazolo[1,5-a]pyridine, N-[2-fluoro-4-(trifluoromethyl)phenyl]-3-[3-methoxy-4-(4-methyl-1H-imidazol-1-yl)phenyl]-1-methyl-1H-1,2,4-triazol-5-amine, N-[5-chloro-2-(trifluoromethyl)phenyl]-3-[3-methoxy-4-(4-methyl-1H-imidazol-1-yl)phenyl]-1-methyl-1H-1,2,4-triazol-5-amine, N-[3-[3-methoxy-4-(4-methyl-1H-imidazol-1-yl)phenyl]-1-methyl-1H-1,2,4-triazol-5-yl]-6-(trifluoromethyl)-2-pyridinamine, N-[2-fluoro-6-(trifluoromethyl)phenyl]-3-[3-methoxy-4-(4-methyl-1H-imidazol-1-yl)phenyl]-1-methyl-1H-1,2,4-triazol-5-amine, N-[4-fluoro-2-(trifluoromethyl)phenyl]-1-methyl-3-[5-(4-methyl-1H-imidazol-1-yl)-2-pyridinyl]-1H-1,2,4-triazol-5-amine, N-[3-chloro-2-(trifluoromethyl)phenyl]-3-[3-methoxy-4-(4-methyl-1H-imidazol-1-yl)phenyl]-1-methyl-1H-1,2,4-triazol-5-amine, 5,6,7,8-tetrahydro-2-[3-methoxy-4-(4-methyl-1H-imidazol-1-yl)phenyl]-8-[3-(trifluoromethoxy)phenyl]-[1,2,4]triazolo[1,5-a]pyridine, 3-[3-methoxy-4-(4-methyl-1H-imidazol-1-yl)phenyl]-1-methyl-5-[[3-(trifluoromethyl)phenyl]thio]-1H-1,2,4-triazole.2HCl.H$_2$O, 2-[3-methoxy-4-(4-methyl-1H-imidazol-1-yl)phenyl]-8-[2-(trifluoromethoxy)phenyl]-[1,2,4]triazolo[1,5-a]pyridine, N-(4,5-difluoro-2-iodophenyl)-3-[3-methoxy-4-(4-methyl-1H-imidazol-1-yl)phenyl]-1-methyl-1H-1,2,4-triazol-5-amine, N-(2-chloro-4,5-difluorophenyl)-3-[3-methoxy-4-(4-methyl-1H-imidazol-1-yl)phenyl]-1-methyl-1H-1,2,4-triazol-5-amine, N-[2-fluoro-5-(trifluoromethoxy)phenyl]-3-[3-methoxy-4-(4-methyl-1H-imidazol-1-yl)phenyl]-1-methyl-1H-1,2,4-triazol-5-amine, 4-[[3-[3-methoxy-4-(4-methyl-1H-imidazol-1-yl)phenyl]-1-methyl-1H-1,2,4-triazol-5-yl]amino]-benzonitrile, N-(4-chlorophenyl)-3-[3-methoxy-4-(4-methyl-1H-imidazol-1-yl)phenyl]-1-methyl-1H-1,2,4-triazol-5-amine, N-(2-chloro-5-fluorophenyl)-3-[3-methoxy-4-(4-methyl-1H-imidazol-1-yl)phenyl]-1-methyl-1H-1,2,4-triazol-5-amine, N-(3,5-dichlorophenyl)-3-[3-methoxy-4-(4-methyl-1H-imidazol-1-yl)phenyl]-1-methyl-1H-1,2,4-triazol-5-amine, N-(4,5-difluoro-2-iodophenyl)-N-[3-[3-methoxy-4-(4-methyl-1H-imidazol-1-yl)phenyl]-1-methyl-1H-1,2,4-triazol-5-yl]-acetamide, N-(5-chloro-2-fluorophenyl)-3-[6-methoxy-5-(4-methyl-1H-imidazol-1-yl)-2-pyridinyl]-1-methyl-1H-1,2,4-triazol-5-amine, N-[2-chloro-5-(trifluoromethyl)phenyl]-3-[6-methoxy-5-(4-methyl-1H-imidazol-1-yl)-2-pyridinyl]-1-methyl-1H-1,2,4-triazol-5-amine, 5,6,7,8-tetrahydro-2-[3-methoxy-4-(4-methyl-1H-imidazol-1-yl)phenyl]-8-[2-(trifluoromethoxy)phenyl]-[1,2,4]triazolo[1,5-a]pyridine, 8-(4-fluoro-2-methylphenyl)-5,6,7,8-tetrahydro-2-[3-methoxy-4-(4-methyl-1H-imidazol-1-yl)phenyl]-[1,2,4]triazolo[1,5-a]pyridine, 8-(2,4-difluorophenyl)-5,6,7,8-tetrahydro-2-[3-methoxy-4-(4-methyl-1H-imidazol-1-yl)phenyl]-[1,2,4]triazolo[1,5-a]pyridine, 1-[1-(4-fluorophenyl)ethyl]-3-[3-methoxy-4-(4-methyl-1H-imidazol-1-yl)phenyl]-5-(1-pyrrolidinyl)-1H-1,2,4-triazole, N-[5-chloro-2-(trifluoromethoxy)phenyl]-3-[3-methoxy-4-(4-methyl-1H-imidazol-1-yl)phenyl]-1-methyl-1H-1,2,4-triazol-5-amine, N-[2-fluoro-5-(trifluoromethoxy)phenyl]-3-[6-methoxy-5-(4-methyl-1H-imidazol-1-yl)-2-pyridinyl]-1-methyl-1H-1,2,4-triazol-5-amine, N-[3-[3-methoxy-4-(4-methyl-1H-imidazol-1-yl)phenyl]-1-methyl-1H-1,2,4-triazol-5-yl]-3-pyridinamine, N-(2-chloro-4-fluorophenyl)-3-[3-methoxy-4-(4-methyl-1H-imidazol-1-yl)phenyl]-1-methyl-1H-1,2,4-triazol-5-amine, N-[4-chloro-2-(trifluoromethyl)phenyl]-3-[3-methoxy-4-(4-methyl-1H-imidazol-1-yl)phenyl]-1-methyl-1H-1,2,4-triazol-5-amine, 4-fluoro-3-[[3-[3-methoxy-4-(4-methyl-1H-imidazol-1-yl)phenyl]-1-methyl-1H-1,2,4-triazol-5-yl]amino]-benzonitrile, N-(2,3-dichlorophenyl)-3-[3-methoxy-4-(4-methyl-1H-imidazol-1-yl)phenyl]-1-methyl-1H-1,2,4-triazol-5-amine, N-[3-[3-methoxy-4-(4-methyl-1H-imidazol-1-yl)phenyl]-1-methyl-1H-1,2,4-triazol-5-yl]-6-methyl 3-pyridinamine, —N-(4-chloro-2-fluorophenyl)-3-[3-methoxy-4-(4-methyl-1H-imidazol-1-yl)phenyl]-1-methyl-1H-1,2,4-triazol-5-amine, 3-fluoro-4-[[3-[3-methoxy-4-(4-methyl-1H-imidazol-1-yl)phenyl]-1-methyl-1H-1,2,4-triazol-5-yl]amino]-benzonitrile, N-(3-chloro-2-fluorophenyl)-3-[3-methoxy-4-(4-methyl-1H-imidazol-1-yl)phenyl]-1-methyl-1H-1,2,4-triazol-5-amine, 4-[[3-[3-methoxy-4-(4-methyl-1H-imidazol-1-yl)phenyl]-1-methyl-1H-1,2,4-triazol-5-yl]amino]-3-(trifluoromethyl)-benzonitrile, 5-fluoro-2-[[3-[3-methoxy-4-(4-methyl-1H-imidazol-1-yl)phenyl]-1-methyl-1H-1,2,4-triazol-5-yl]amino]-benzonitrile, 5-[[3-[3-methoxy-4-(4-methyl-1H-imidazol-1-yl)phenyl]-1-methyl-1H-1,2,4-triazol-5-yl]amino]-1-methyl-2(1H)-pyridinone, N-[3-[3-methoxy-4-(4-methyl-1H-imidazol-1-yl)phenyl]-1-methyl-1H-1,2,4-triazol-5-yl]-2-methyl-4-pyridinamine, N-(5-chloro-2-methoxyphenyl)-3-[3-methoxy-4-(4-methyl-1H-imidazol-1-yl)phenyl]-1-methyl-1H-1,2,4-triazol-5-amine, N-(5-fluoro-2-methoxyphenyl)-3-[3-methoxy-4-(4-methyl-1H-imidazol-1-yl)phenyl]-1-methyl-1H-1,2,4-triazol-5-amine, (8R)-5,6,7,8-tetrahydro-2-[3-methoxy-4-(4-methyl-1H-imidazol-1-yl)phenyl]-8-[2-(trifluoromethyl)phenyl]-[1,2,4]triazolo[1,5-a]pyridine, (8S)-5,6,7,8-tetrahydro-2-[3-methoxy-4-(4-methyl-1H-imidazol-1-yl)phenyl]-8-[2-(trifluoromethyl)phenyl]-[1,2,4]triazolo[1,5-a]pyridine, 3-[3-methoxy-4-(4-methyl-1H-imidazol-1-yl)phenyl]-1-methyl-N-[2-(trifluoromethoxy)phenyl]-1H-1,2,4-triazol-5-amine.2HCl.1.4H₂O, N-(3-chloro-2,6-difluorophenyl)-3-[3-methoxy-4-(4-methyl-1H-imidazol-1-yl)phenyl]-1-methyl-1H-1,2,4-triazol-5-amine, 5-[5-[[2-fluoro-5-(trifluoromethyl)phenyl]amino]-1-methyl-1H-1,2,4-triazol-3-yl]-2-(4-methyl-1H-imidazol-1-yl)-benzonitrile, N-[4-fluoro-3-(trifluoromethyl)phenyl]-3-[6-methoxy-5-(4-methyl-1H-imidazol-1-yl)-2-pyridinyl]-1-methyl-1H-1,2,4-triazol-5-amine, 3-[6-methoxy-5-(4-methyl-1H-imidazol-1-yl)-2-pyridinyl]-N-[2-methoxy-5-(trifluoromethyl)phenyl]-1-methyl-1H-1,2,4-triazol-5-amine, 2-(4-methyl-1H-imidazol-1-yl)-5-[1-methyl-5-[[2-(trifluoromethyl)phenyl]amino]-1H-1,2,4-triazol-3-yl]-benzonitrile, N-[2-fluoro-3-(trifluoromethyl)phenyl]-3-[6-methoxy-5-(4-methyl-1H-imidazol-1-yl)-2-pyridinyl]-1-methyl-1H-1,2,4-triazol-5-amine, N-(2-bromophenyl)-3-[3-methoxy-4-(4-methyl-1H-imidazol-1-yl)phenyl]-1-methyl-1H-1,2,4-triazol-5-amine.2HCl.H₂O, N-[3-[3-methoxy-4-(4-methyl-1H-imidazol-1-yl)phenyl]-1-methyl-1H-1,2,4-triazol-5-yl]-2-(trifluoromethyl)-3-pyridinamine, 2-chloro-N-[3-[3-methoxy-4-(4-methyl-1H-imidazol-1-yl)phenyl]-1-methyl-1H-1,2,4-triazol-5-yl]-4-pyridinamine, 3-[[3-[3-methoxy-4-(4-methyl-1H-imidazol-1-yl)phenyl]-1-methyl-1H-1,2,4-triazol-5-yl]amino]-1-methyl-2(1H)-pyridinone, N-(3-chloro-2-methoxyphenyl)-3-[3-methoxy-4-(4-methyl-1H-imidazol-1-yl)phenyl]-1-methyl-1H-1,2,4-triazol-5-amine, N-(2,5-difluorophenyl)-3-[3-methoxy-4-(4-methyl-1H-imidazol-1-yl)phenyl]-1-methyl-1H-1,2,4-triazol-5-amine, 3-[3-methoxy-4-(4-methyl-1H-imidazol-1-yl)phenyl]-N-[5-methoxy-2-(trifluoromethyl)phenyl]-1-methyl-1H-1,2,4-triazol-5-amine, N-[4-fluoro-2-methoxy-5-(trifluoromethyl)phenyl]-3-[3-methoxy-4-(4-methyl-1H-imidazol-1-yl)phenyl]-1-methyl-1H-1,2,4-triazol-5-amine, N-(2,3-difluoro-5-methoxyphenyl)-3-[3-methoxy-4-(4-methyl-1H-imidazol-1-yl)phenyl]-1-methyl-1H-1,2,4-triazol-5-amine, N-(2-fluoro-6-methoxyphenyl)-3-[3-methoxy-4-(4-methyl-1H-imidazol-1-yl)phenyl]-1-methyl-1H-1,2,4-triazol-5-amine, N-[2,3-difluoro-5-(trifluoromethyl)phenyl]-3-[3-methoxy-4-(4-methyl-1H-imidazol-1-yl)phenyl]-1-methyl-1H-1,2,4-triazol-5-amine, N-[4,5-difluoro-2-(trifluoromethyl)phenyl]-3-[3-methoxy-4-(4-methyl-1H-imidazol-1-yl)phenyl]-1-methyl-1H-1,2,4-triazol-5-amine, N-[3-fluoro-2-(trifluoromethyl)phenyl]-3-[6-methoxy-5-(4-methyl-1H-imidazol-1-yl)-2-pyridinyl]-1-methyl-1H-1,2,4-triazol-5-amine, 6,7,8,9-tetrahydro-2-[3-methoxy-4-(4-methyl-1H-imidazol-1-yl)phenyl]-9-[2-(trifluoromethyl)phenyl]-5H-[1,2,4]triazolo[1,5-a]azepine, 3-[3-methoxy-4-(4-methyl-1H-imidazol-1-yl)phenyl]-1-methyl-N-(2-methylphenyl)-1H-1,2,4-triazol-5-amine, N-(4-fluoro-2-methoxyphenyl)-3-[3-methoxy-4-(4-methyl-1H-imidazol-1-yl)phenyl]-1-methyl-1H-1,2,4-triazol-5-amine, 2-methoxy-N-[3-[3-methoxy-4-(4-methyl-1H-imidazol-1-yl)phenyl]-1-methyl-1H-1,2,4-triazol-5-yl]-3-pyridinamine, N-(2-chloro-3-fluorophenyl)-3-[3-methoxy-4-(4-methyl-1H-imidazol-1-yl)phenyl]-1-methyl-1H-1,2,4-triazol-5-amine, 2-fluoro-3-[[3-[3-methoxy-4-(4-methyl-1H-imidazol-1-yl)phenyl]-1-methyl-1H-1,2,4-triazol-5-yl]amino]-benzonitrile, N-[4-fluoro-3-[[3-[3-methoxy-4-(4-methyl-1H-imidazol-1-yl)phenyl]-1-methyl-1H-1,2,4-triazol-5-yl]amino]phenyl]-acetamide, N-(3-fluoro-2-methoxyphenyl)-3-[3-methoxy-4-(4-methyl-1H-imidazol-1-yl)phenyl]-1-methyl-1H-1,2,4-triazol-5-amine, N-[2-fluoro-5-(trifluoromethyl)phenyl]-1-(2-methoxyethyl)-3-[3-methoxy-4-(4-methyl-1H-imidazol-1-yl)phenyl]-1H-1,2,4-triazol-5-amine, N-(2-fluoro-3-methylphenyl)-3-[3-methoxy-4-(4-methyl-1H-imidazol-1-yl)phenyl]-1-methyl-1H-1,2,4-triazol-5-amine, N-[2-chloro-3-(trifluoromethyl)phenyl]-3-[3-methoxy-4-(4-methyl-1H-imidazol-1-yl)phenyl]-1-methyl-1H-1,2,4-triazol-5-amine, 3-[3-methoxy-4-(4-methyl-1H-imidazol-1-yl)phenyl]-1-methyl-N-[2-methyl-3-(trifluoromethyl)phenyl]-1H-1,2,4-triazol-5-amine, N-[3-[[3-[3-methoxy-4-(4-methyl-1H-imidazol-1-yl)phenyl]-1-methyl-1H-1,2,4-triazol-5-yl]amino]phenyl]-acetamide, 3-[3-methoxy-4-(4-methyl-1H-imidazol-1-yl)phenyl]-N-(2-methoxyphenyl)-1-methyl-1H-1,2,4-triazol-5-amine, N-(2,6-difluorophenyl)-3-[3-methoxy-4-(4-methyl-1H-imidazol-1-yl)phenyl]-1-methyl-1H-1,2,4-triazol-5-amine, N-[3-(1,1-dimethylethyl)-1-methyl-1H-pyrazol-5-yl]-3-[3-methoxy-4-(4-methyl-1H-imidazol-1-yl)phenyl]-1-methyl-1H-1,2,4-triazol-5-amine, N-[3-[3-methoxy-4-(4-methyl-1H-imidazol-1-yl)phenyl]-1-methyl-1H-1,2,4-triazol-5-yl]-3-(trifluoromethyl)-2-pyridinamine, N-(2-fluorophenyl)-3-[6-methoxy-5-(4-methyl-1H-imidazol-1-yl)-2-pyridinyl]-1-methyl-1H-1,2,4-triazol-5-amine, N-(2,6-difluoro-3-methoxyphenyl)-3-[3-methoxy-4-(4-methyl-1H-imidazol-1-yl)phenyl]-1-methyl-1H-1,2,4-triazol-5-amine, 3-[3-methoxy-4-(4-methyl-1H-imidazol-1-yl)phenyl]-N-methyl-1-[3-(trifluoromethyl)phenyl]-1H-1,2,4-triazol-5-amine HCl,

[3-[3-methoxy-4-(4-methyl-1H-imidazol-1-yl)phenyl]-1-(1-methylethyl)-1H-1,2,4-triazol-5-yl][3-(trifluoromethyl)phenyl]-methanone,
6-[1-[1-(4-fluorophenyl)ethyl]-5-methyl-1H-1,2,4-triazol-3-yl]-2-methoxy-3-(4-methyl-1H-imidazol-1-yl)-pyridine,
3-[6-methoxy-5-(4-methyl-1H-imidazol-1-yl)-2-pyridinyl]-N-methyl-1-[3-(trifluoromethyl)phenyl]-1H-1,2,4-triazol-5-amine HCl,
N-(2,2-difluoro-1,3-benzodioxol-4-yl)-3-[3-methoxy-4-(4-methyl-1H-imidazol-1-yl)phenyl]-1-methyl-1H-1,2,4-triazol-5-amine,
5-[1-[2-fluoro-5-(trifluoromethyl)phenyl]cyclopropyl]-3-[3-methoxy-4-(4-methyl-1H-imidazol-1-yl)phenyl]-1-methyl-1H-1,2,4-triazole,
(8R)-5,6,7,8-tetrahydro-2-[6-methoxy-5-(4-methyl-1H-imidazol-1-yl)-2-pyridinyl]-8-[2-(trifluoromethyl)phenyl]-[1,2,4]triazolo[1,5-a]pyridine,
(8S)-5,6,7,8-tetrahydro-2-[6-methoxy-5-(4-methyl-1H-imidazol-1-yl)-2-pyridinyl]-8-[2-(trifluoromethyl)phenyl]-[1,2,4]triazolo[1,5-a]pyridine,
3-[3-methoxy-4-(4-methyl-1H-imidazol-1-yl)phenyl]-1-methyl-N-[3-(trifluoromethyl)cyclohexyl]-1H-1,2,4-triazol-5-amine (CIS),
N-(3-bromo-2,6-difluorophenyl)-3-[3-methoxy-4-(4-methyl-1H-imidazol-1-yl)phenyl]-1-methyl-1H-1,2,4-triazol-5-amine,
3-[3-methoxy-4-(4-methyl-1H-imidazol-1-yl)phenyl]-alpha-methyl-1-(1-methylethyl)-alpha-[3-(trifluoromethyl)phenyl]-1H-1,2,4-triazole-5-methanol,
3-[3-methoxy-4-(4-methyl-1H-imidazol-1-yl)phenyl]-N-[2-(methoxymethyl)phenyl]-1-methyl-1H-1,2,4-triazol-5-amine HCl.0.12H$_2$O,
1-ethyl-N-[2-fluoro-5-(trifluoromethyl)phenyl]-3-[3-methoxy-4-(4-methyl-1H-imidazol-1-yl)phenyl]-1H-1,2,4-triazol-5-amine,
5-[[2-fluoro-5-(trifluoromethyl)phenyl]amino]-3-[3-methoxy-4-(4-methyl-1H-imidazol-1-yl)phenyl]-alpha,alpha-dimethyl-1H-1,2,4-triazole-1-ethanol,
5-[[2-fluoro-5-(trifluoromethyl)phenyl]amino]-3-[3-methoxy-4-(4-methyl-1H-imidazol-1-yl)phenyl]-1H-1,2,4-triazole-1-propanenitrile,
N-[2,5-difluoro-4-(trifluoromethyl)phenyl]-3-[3-methoxy-4-(4-methyl-1H-imidazol-1-yl)phenyl]-1-methyl-1H-1,2,4-triazol-5-amine,
3-[3-methoxy-4-(4-methyl-1H-imidazol-1-yl)phenyl]-1-methyl-N-[3-(trifluoromethyl)cyclohexyl]-1H-1,2,4-triazol-5-amine (TRANS),
N-(4-chloro-2-methoxyphenyl)-3-[3-methoxy-4-(4-methyl-1H-imidazol-1-yl)phenyl]-1-methyl-1H-1,2,4-triazol-5-amine,
N-[2-fluoro-5-(trifluoromethyl)phenyl]-3-[3-methoxy-4-(4-methyl-1H-imidazol-1-yl)phenyl]-1-(1-methylethyl)-1H-1,2,4-triazol-5-amine,
N-(2-ethoxyphenyl)-3-[3-methoxy-4-(4-methyl-1H-imidazol-1-yl)phenyl]-1-methyl-1H-1,2,4-triazol-5-amine,
N-(3-chloro-2-fluoro-5-(trifluoromethyl)phenyl]-3-[3-methoxy-4-(4-methyl-1H-imidazol-1-yl)phenyl]-1-methyl-1H-1,2,4-triazol-5-amine,
N-(2-fluoro-4-methoxyphenyl)-3-[3-methoxy-4-(4-methyl-1H-imidazol-1-yl)phenyl]-1-methyl-1H-1,2,4-triazol-5-amine,
N-[2-fluoro-5-(trifluoromethyl)phenyl]-3-[3-methoxy-4-(4-methyl-1H-imidazol-1-yl)phenyl]-1-(1-methylpropyl)-1H-1,2,4-triazol-5-amine,
3-[3-methoxy-4-(4-methyl-1H-imidazol-1-yl)phenyl]-1-(1-methylethyl)-N-[2-(trifluoromethyl)phenyl]-1H-1,2,4-triazol-5-amine,
N-(2,3-difluorophenyl)-3-[3-methoxy-4-(4-methyl-1H-imidazol-1-yl)phenyl]-1-methyl-1H-1,2,4-triazol-5-amine,
N-[2-fluoro-5-methoxy-3-(trifluoromethyl)phenyl]-3-[3-methoxy-4-(4-methyl-1H-imidazol-1-yl)phenyl]-1-methyl-1H-1,2,4-triazol-5-amine,
N-[2,4-difluoro-5-(trifluoromethyl)phenyl]-3-[3-methoxy-4-(4-methyl-1H-imidazol-1-yl)phenyl]-1-methyl-1H-1,2,4-triazol-5-amine,
4-methoxy-2-[[3-[3-methoxy-4-(4-methyl-1H-imidazol-1-yl)phenyl]-1-methyl-1H-1,2,4-triazol-5-yl]amino]-benzenemethanol,
8-(4-fluoro-2-methylphenyl)-5,6-dihydro-2-[3-methoxy-4-(4-methyl-1H-imidazol-1-yl)phenyl]-8H-[1,2,4]triazolo[5,1-c][1,4]oxazine,
8-[2-fluoro-5-(trifluoromethoxy)phenyl]-5,6-dihydro-2-[3-methoxy-4-(4-methyl-1H-imidazol-1-yl)phenyl]-8H-[1,2,4]triazolo[5,1-c][1,4]oxazine,
8-(2,4-difluorophenyl)-5,6-dihydro-2-[3-methoxy-4-(4-methyl-1H-imidazol-1-yl)phenyl]-8H-[1,2,4]triazolo[5,1-c][1,4]oxazine,
5,6,7,8-tetrahydro-2-[3-methoxy-4-(4-methyl-1H-imidazol-1-yl)phenyl]-8-[2-methyl-5-(trifluoromethyl)phenyl]-[1,2,4]triazolo[1,5-a]pyridine,
1-[4-fluoro-3-[[3-[3-methoxy-4-(4-methyl-1H-imidazol-1-yl)phenyl]-1-methyl-1H-1,2,4-triazol-5-yl]amino]phenyl]-ethanone,
N-(2,5-dimethylphenyl)-3-[3-methoxy-4-(4-methyl-1H-imidazol-1-yl)phenyl]-1-methyl-1H-1,2,4-triazol-5-amine,
8-[2-fluoro-5-(trifluoromethoxy)phenyl]-5,6,7,8-tetrahydro-2-[3-methoxy-4-(4-methyl-1H-imidazol-1-yl)phenyl]-[1,2,4]triazolo[1,5-a]pyridine,
N-[4-chloro-2-fluoro-5-(trifluoromethyl)phenyl]-3-[3-methoxy-4-(4-methyl-1H-imidazol-1-yl)phenyl]-1-methyl-1H-1,2,4-triazol-5-amine,
N-[2-fluoro-3-methoxy-5-(trifluoromethyl)phenyl]-3-[3-methoxy-4-(4-methyl-1H-imidazol-1-yl)phenyl]-1-methyl-1H-1,2,4-triazol-5-amine,
1-ethyl-3-[3-methoxy-4-(4-methyl-1H-imidazol-1-yl)phenyl]-N-[2-(trifluoromethyl)phenyl]-1H-1,2,4-triazol-5-amine,
3-[3-methoxy-4-(4-methyl-1H-imidazol-1-yl)phenyl]-1-methyl-N-[2-(1-methylethyl)phenyl]-1H-1,2,4-triazol-5-amine,
8-(4-fluoro-2-methylphenyl)-5,6,7,8-tetrahydro-2-[3-methoxy-4-(4-methyl-1H-imidazol-1-yl)phenyl]-[1,2,4]triazolo[1,5-a]pyridin-8-ol,
N-[2,6-difluoro-3-(trifluoromethyl)phenyl]-3-[3-methoxy-4-(4-methyl-1H-imidazol-1-yl)phenyl]-1-methyl-1H-1,2,4-triazol-5-amine,
3-[2-fluoro-3-methoxy-4-(4-methyl-1H-imidazol-1-yl)phenyl]-1-methyl-N-(2-methylphenyl)-1H-1,2,4-triazol-5-amine,
1-methyl-3-[4-(4-methyl-1H-imidazol-1-yl)-3-(trifluoromethoxy)phenyl]-N-(2-methylphenyl)-1H-1,2,4-triazol-5-amine,
4-fluoro-3-[[3-[3-methoxy-4-(4-methyl-1H-imidazol-1-yl)phenyl]-1-methyl-1H-1,2,4-triazol-5-yl]amino]-alpha,alpha-dimethyl-benzenemethanol,
N-[2-fluoro-5-(trifluoromethyl)phenyl]-1-methyl-3-[4-(4-methyl-1H-imidazol-1-yl)-3-(trifluoromethoxy)phenyl]-1H-1,2,4-triazol-5-amine, 3-[2-fluoro-3-methoxy-4-(4-methyl-1H-imidazol-1-yl)phenyl]-N-[2-fluoro-5-(trifluoromethyl)phenyl]-1-methyl-1H-1,2,4-triazol-5-amine, N-(3-fluoro-2-methylphenyl)-3-[3-methoxy-4-(4-methyl-1H-imidazol-1-yl)phenyl]-1-methyl-1H-1,2,4-triazol-5-amine, 1-[1-(4-fluorophenyl)ethyl]-3-[3-methoxy-4-(4-methyl-1H-imidazol-1-yl)phenyl]-alpha,alpha-dimethyl-1H-1,2,4-triazole-5-methanol, N-[2-fluoro-5-(1-methylethoxy)phenyl]-3-[3-methoxy-4-(4-methyl-1H-imidazol-1-yl)phenyl]-1-methyl-1H-1,2,4-triazol-5-amine, (8R)-5,6-dihydro-2-[3-methoxy-4-(4-methyl-1H-imidazol-1-yl)phenyl]-8-[2-(trifluoromethyl)phenyl]-8H-[1,2,4]triazolo[5,1-c][1,4]oxazine, (8S)-5,6-dihydro-2-[3-methoxy-4-(4-methyl-1H-imidazol-1-yl)phenyl]-8-[2-(trifluoromethyl)phenyl]-8H-[1,2,4]triazolo[5,1-c][1,4]oxazine, (8R)-8-(4-fluoro-2-methylphenyl)-5,6,7,8-tetrahydro-2-[3-methoxy-4-(4-methyl-1H-imidazol-1-yl)phenyl]-[1,2,4]triazolo[1,5-a]pyridine, (8R)-8-(4-fluoro-2-methylphenyl)-5,6,7,8-tetrahydro-2-[3-methoxy-4-(4-methyl-1H-imidazol-1-yl)phenyl]-[1,2,4]triazolo[1,5-a]pyridine.HCl, (8S)-8-(4-fluoro-2-methylphenyl)-5,6,7,8-tetrahydro-2-[3-methoxy-4-(4-methyl-1H-imidazol-1-yl)phenyl]-[1,2,4]triazolo[1,5-a]pyridine, (8S)-8-(4-fluoro-2-methylphenyl)-5,6,7,8-tetrahydro-2-[3-methoxy-4-(4-methyl-1H-imidazol-1-yl)phenyl]-[1,2,4]triazolo[1,5-a]pyridine.HCl, N-(2-chloro-3-fluorophenyl)-3-[6-methoxy-5-(4-methyl-1H-imidazol-1-yl)-2-pyridinyl]-1-methyl-1H-1,2,4-triazol-5-amine, N-[2-fluoro-5-(methylsulfonyl)phenyl]-3-[3-methoxy-4-(4-methyl-1H-imidazol-1-yl)phenyl]-1-methyl-1H-1,2,4-triazol-5-amine, 4-fluoro-3-[[3-[3-methoxy-4-(4-methyl-1H-imidazol-1-yl)phenyl]-1-methyl-1H-1,2,4-triazol-5-yl]amino]-N,N-dimethyl-benzamide, N-(5-bromo-2-fluorophenyl)-3-[3-methoxy-4-(4-methyl-1H-imidazol-1-yl)phenyl]-1-methyl-1H-1,2,4-triazol-5-amine, 3-[3-methoxy-4-(4-methyl-1H-imidazol-1-yl)phenyl]-1-methyl-N-[3-(trifluoromethyl)phenyl]-1H-1,2,4-triazole-5-methanamine, 5,6,7,8-tetrahydro-2-[3-methoxy-4-(4-methyl-1H-imidazol-1-yl)phenyl]-8-(2,4,6-trifluorophenyl)-[1,2,4]triazolo[1,5-a]pyridine, N-[2-(difluoromethoxy)phenyl]-3-[3-methoxy-4-(4-methyl-1H-imidazol-1-yl)phenyl]-1-methyl-1H-1,2,4-triazol-5-amine, 1-acetylhexahydro-4-[3-[3-methoxy-4-(4-methyl-1H-imidazol-1-yl)phenyl]-1-(1-methylethyl)-1H-1,2,4-triazol-5-yl]-1H-1,4-diazepine.HCl.H$_2$O, N-[2-fluoro-5-(trifluoromethyl)phenyl]-1-methyl-3-[6-methyl-5-(4-methyl-1H-imidazol-1-yl)-2-pyridinyl]-1H-1,2,4-triazol-5-amine, (8R)-8-(4-fluoro-2-methylphenyl)-5,6-dihydro-2-[3-methoxy-4-(4-methyl-1H-imidazol-1-yl)phenyl]-8H-[1,2,4]triazolo[5,1-c][1,4]oxazine, (8S)-8-(4-fluoro-2-methylphenyl)-5,6-dihydro-2-[3-methoxy-4-(4-methyl-1H-imidazol-1-yl)phenyl]-8H-[1,2,4]triazolo[5,1-c][1,4]oxazine, (8R)-8-[2-fluoro-5-(trifluoromethoxy)phenyl]-5,6-dihydro-2-[3-methoxy-4-(4-methyl-1H-imidazol-1-yl)phenyl]-8H-[1,2,4]triazolo[5,1-c][1,4]oxazine, (8S)-8-[2-fluoro-5-(trifluoromethoxy)phenyl]-5,6-dihydro-2-[3-methoxy-4-(4-methyl-1H-imidazol-1-yl)phenyl]-8H-[1,2,4]triazolo[5,1-c][1,4]oxazine, 8-(4-fluoro-2-methylphenyl)-5,6,7,8-tetrahydro-2-[6-methoxy-5-(4-methyl-1H-imidazol-1-yl)-2-pyridinyl]-[1,2,4]triazolo[1,5-a]pyridine, N-(2-fluoro-6-methylphenyl)-3-[3-methoxy-4-(4-methyl-1H-imidazol-1-yl)phenyl]-1-methyl-1H-1,2,4-triazol-5-amine, 1-[2-[[3-[3-methoxy-4-(4-methyl-1H-imidazol-1-yl)phenyl]-1-methyl-1H-1,2,4-triazol-5-yl]amino]phenyl]-ethanone.HCl, 3,4-dihydro-4-[3-[3-methoxy-4-(4-methyl-1H-imidazol-1-yl)phenyl]-1-methyl-1H-1,2,4-triazol-5-yl]-2H-1,4-benzoxazine.2HCl.H$_2$O, 2-[3-[3-methoxy-4-(4-methyl-1H-imidazol-1-yl)phenyl]-1-methyl-1H-1,2,4-triazol-5-yl]-quinoline, 2,3,4,5-tetrahydro-5-[3-[3-methoxy-4-(4-methyl-1H-imidazol-1-yl)phenyl]-1-methyl-1H-1,2,4-triazol-5-yl]-1,5-benzoxazepine, N-[4-ethoxy-2-methyl-5-(1-methylethyl)phenyl]-3-[3-methoxy-4-(4-methyl-1H-imidazol-1-yl)phenyl]-1-methyl-1H-1,2,4-triazol-5-amine, 8-(4-fluoro-2-methylphenyl)-5,6,7,8-tetrahydro-2-[3-methoxy-4-(4-methyl-1H-imidazol-1-yl)phenyl]-[1,2,4]triazolo[1,5-a]pyridine-8-methanol, 3-[3-methoxy-4-(4-methyl-1H-imidazol-1-yl)phenyl]-1-methyl-N-[3-(trifluoromethyl)phenyl]-1H-1,2,4-triazole-5-carboxamide, N-[2-fluoro-5-(methylsulfinyl)phenyl]-3-[3-methoxy-4-(4-methyl-1H-imidazol-1-yl)phenyl]-1-methyl-1H-1,2,4-triazol-5-amine, N-[2-fluoro-5-(methoxymethyl)phenyl]-3-[3-methoxy-4-(4-methyl-1H-imidazol-1-yl)phenyl]-1-methyl-1H-1,2,4-triazol-5-amine, 3-[3-methoxy-4-(4-methyl-1H-imidazol-1-yl)phenyl]-1-methyl-N-phenyl-1H-1,2,4-triazol-5-amine, 5,6,7,8-tetrahydro-2-[3-methoxy-4-(4-methyl-1H-imidazol-1-yl)phenyl]-5-[2-(trifluoromethyl)phenyl]-[1,2,4]triazolo[1,5-a]pyridine, N-[2-fluoro-5-(trifluoromethyl)phenyl]-3-[6-methoxy-5-(4-methyl-1H-imidazol-1-yl)-2-pyridinyl]-N,1-dimethyl-1H-1,2,4-triazol-5-amine, (8R)-5,6,7,8-tetrahydro-2-[3-methoxy-4-(4-methyl-1H-imidazol-1-yl)phenyl]-8-[2-methyl-5-(trifluoromethyl)phenyl]-[1,2,4]triazolo[1,5-a]pyridine, (8R)-5,6,7,8-tetrahydro-2-[3-methoxy-4-(4-methyl-1H-imidazol-1-yl)phenyl]-8-[2-methyl-5-(trifluoromethyl)phenyl]-[1,2,4]triazolo[1,5-a]pyridine.HCl, (8S)-5,6,7,8-tetrahydro-2-[3-methoxy-4-(4-methyl-1H-imidazol-1-yl)phenyl]-8-[2-methyl-5-(trifluoromethyl)phenyl]-[1,2,4]triazolo[1,5-a]pyridine, (8S)-5,6,7,8-tetrahydro-2-[3-methoxy-4-(4-methyl-1H-imidazol-1-yl)phenyl]-8-[2-methyl-5-(trifluoromethyl)phenyl]-[1,2,4]triazolo[1,5-a]pyridine.HCl, (8R)-5,6,7,8-tetrahydro-2-[6-methoxy-5-(4-methyl-1H-imidazol-1-yl)-2-pyridinyl]-8-[2-methyl-5-(trifluoromethyl)phenyl]-[1,2,4]triazolo[1,5-a]pyridine, (8S)-5,6,7,8-tetrahydro-2-[6-methoxy-5-(4-methyl-1H-imidazol-1-yl)-2-pyridinyl]-8-[2-methyl-5-(trifluoromethyl)phenyl]-[1,2,4]triazolo[1,5-a]pyridine, 5,6,7,8-tetrahydro-2-[3-methoxy-4-(4-methyl-1H-imidazol-1-yl)phenyl]-8-(2-methylphenyl)-[1,2,4]triazolo[1,5-a]pyridine, 8-(3-fluoro-2-methylphenyl)-5,6-dihydro-2-[3-methoxy-4-(4-methyl-1H-imidazol-1-yl)phenyl]-8H-[1,2,4]triazolo[5,1-c][1,4]oxazine, 5,6-dihydro-2-[3-methoxy-4-(4-methyl-1H-imidazol-1-yl)
phenyl]-8-[2-(trifluoromethoxy)phenyl]-8H-[1,2,4]tria-
zolo[5,1-c][1,4]oxazine,
1,2,3,4-tetrahydro-1-[3-[3-methoxy-4-(4-methyl-1H-imida-
zol-1-yl)phenyl]-1-methyl-1H-1,2,4-triazol-5-yl]-
quinoline.2HCl.H₂O,
8-(3-fluoro-2-methylphenyl)-5,6-dihydro-2-[6-methoxy-5-
(4-methyl-1H-imidazol-1-yl)-2-pyridinyl]-8H-[1,2,4]tria-
zolo[5,1-c][1,4]oxazine,
5,6-dihydro-2-[6-methoxy-5-(4-methyl-1H-imidazol-1-yl)-
2-pyridinyl]-8-[2-(trifluoromethoxy)phenyl]-8H-[1,2,4]
triazolo[5,1-c][1,4]oxazine,
N-(2-fluoro-5-methylphenyl)-3-[3-methoxy-4-(4-methyl-
1H-imidazol-1-yl)phenyl]-1-methyl-1H-1,2,4-triazol-5-
amine,
3-[3-methoxy-4-(4-methyl-1H-imidazol-1-yl)phenyl]-1-
methyl-N-[5-methyl-2-(trifluoromethyl)phenyl]-1H-1,2,
4-triazol-5-amine,
N-(2-fluoro-4-methylphenyl)-3-[3-methoxy-4-(4-methyl-
1H-imidazol-1-yl)phenyl]-1-methyl-1H-1,2,4-triazol-5-
amine,
N-[2-fluoro-3-methoxy-5-(trifluoromethyl)phenyl]-3-[6-
methoxy-5-(4-methyl-1H-imidazol-1-yl)-2-pyridinyl]-1-
methyl-1H-1,2,4-triazol-5-amine,
N-(5-ethoxy-2-fluorophenyl)-3-[3-methoxy-4-(4-methyl-
1H-imidazol-1-yl)phenyl]-1-methyl-1H-1,2,4-triazol-5-
amine,
N-[2-fluoro-5-(2-methoxyethoxy)phenyl]-3-[3-methoxy-4-
(4-methyl-1H-imidazol-1-yl)phenyl]-1-methyl-1H-1,2,4-
triazol-5-amine,
N-[5-(cyclopropylmethoxy)-2-fluorophenyl]-3-[3-methoxy-
4-(4-methyl-1H-imidazol-1-yl)phenyl]-1-methyl-1H-1,2,
4-triazol-5-amine,
N-[5-(1,1-dimethylethyl)-2-fluorophenyl]-3-[3-methoxy-4-
(4-methyl-1H-imidazol-1-yl)phenyl]-1-methyl-1H-1,2,4-
triazol-5-amine,
N-[2-fluoro-5-[(tetrahydro-3-furanyl)oxy]phenyl]-3-[3-
methoxy-4-(4-methyl-1H-imidazol-1-yl)phenyl]-1-me-
thyl-1H-1,2,4-triazol-5-amine,
N-[2-fluoro-5-(trifluoromethyl)phenyl]-3-[4-(1H-imidazol-
1-yl)-3-methoxyphenyl]-1-methyl-1H-1,2,4-triazol-5-
amine,
(8R)-8-(4-fluoro-2-methylphenyl)-5,6,7,8-tetrahydro-2-[6-
methoxy-5-(4-methyl-1H-imidazol-1-yl)-2-pyridinyl]-[1,
2,4]triazolo[1,5-a]pyridine,
(8S)-8-(4-fluoro-2-methylphenyl)-5,6,7,8-tetrahydro-2-[6-
methoxy-5-(4-methyl-1H-imidazol-1-yl)-2-pyridinyl]-[1,
2,4]triazolo[1,5-a]pyridine,
8-(4-fluoro-2-methylphenyl)-5,6,7,8-tetrahydro-2-[6-meth-
oxy-5-(4-methyl-1H-imidazol-1-yl)-2-pyridinyl]-5-me-
thyl-[1,2,4]triazolo[1,5-a]pyridine (CIS),
8-(4-fluoro-2-methylphenyl)-5,6,7,8-tetrahydro-2-[3-meth-
oxy-4-(4-methyl-1H-imidazol-1-yl)phenyl]-5-methyl-[1,
2,4]triazolo[1,5-a]pyridine (CIS),
8-(2-fluoro-5-methoxyphenyl)-5,6,7,8-tetrahydro-2-[3-
methoxy-4-(4-methyl-1H-imidazol-1-yl)phenyl]-[1,2,4]
triazolo[1,5-a]pyridine,
1,2,3,4-tetrahydro-2-[3-[3-methoxy-4-(4-methyl-1H-imida-
zol-1-yl)phenyl]-1-methyl-1H-1,2,4-triazol-5-yl]-quino-
line,
1,2,3,4-tetrahydro-2-[3-[3-methoxy-4-(4-methyl-1H-imida-
zol-1-yl)phenyl]-1-methyl-1H-1,2,4-triazol-5-yl]-1-me-
thyl-quinoline,
3-[3-methoxy-4-(4-methyl-1H-imidazol-1-yl)phenyl]-1-
methyl-N-[2-(1-methylethoxy)phenyl]-1H-1,2,4-triazol-
5-amine,
8-(4-fluorophenyl)-5,6,7,8-tetrahydro-2-[6-methoxy-5-(4-
methyl-1H-imidazol-1-yl)-2-pyridinyl]-7-methyl-[1,2,4]
triazolo[1,5-a]pyridine (CIS),
8-(4-fluorophenyl)-5,6,7,8-tetrahydro-2-[3-methoxy-4-(4-
methyl-1H-imidazol-1-yl)phenyl]-7-methyl-[1,2,4]tria-
zolo[1,5-a]pyridine (CIS),
5,6-dihydro-2-[6-methoxy-5-(4-methyl-1H-imidazol-1-yl)-
2-pyridinyl]-8-[2-methyl-5-(trifluoromethyl)phenyl]-8H-
[1,2,4]triazolo[5,1-c][1,4]oxazine,
5,6-dihydro-2-[3-methoxy-4-(4-methyl-1H-imidazol-1-yl)
phenyl]-8-[2-methyl-5-(trifluoromethyl)phenyl]-8H-[1,2,
4]triazolo[5,1-c][1,4]oxazine,
5,6,7,8-tetrahydro-2-[6-methoxy-5-(4-methyl-1H-imidazol-
1-yl)-2-pyridinyl]-8-[2-methyl-5-(trifluoromethyl)phe-
nyl]-[1,2,4]triazolo[1,5-a]pyridine,
including any stereochemically isomeric form thereof, the
free bases thereof,
and the pharmaceutically acceptable addition salts and the
solvates thereof.

In an embodiment, the compound of Formula (I) is:
N-[2-fluoro-3-methoxy-5-(trifluoromethyl)phenyl]-3-[6-
methoxy-5-(4-methyl-1H-imidazol-1-yl)-2-pyridinyl]-1-
methyl-1H-1,2,4-triazol-5-amine,
(8S)-5,6,7,8-tetrahydro-2-[6-methoxy-5-(4-methyl-1H-imi-
dazol-1-yl)-2-pyridinyl]-8-[2-methyl-5-(trifluoromethyl)
phenyl]-[1,2,4]triazolo[1,5-a]pyridine,
(8S)-8-[2-fluoro-5-(trifluoromethoxy)phenyl]-5,6-dihydro-
2-[3-methoxy-4-(4-methyl-1H-imidazol-1-yl)phenyl]-
8H-[1,2,4]triazolo[5,1-c][1,4]oxazine,
(8S)-8-(4-fluoro-2-methylphenyl)-5,6,7,8-tetrahydro-2-[3-
methoxy-4-(4-methyl-1H-imidazol-1-yl)phenyl]-[1,2,4]
triazolo[1,5-a]pyridine,
(8S)-8-(4-fluoro-2-methylphenyl)-5,6,7,8-tetrahydro-2-[3-
methoxy-4-(4-methyl-1H-imidazol-1-yl)phenyl]-[1,2,4]
triazolo[1,5-a]pyridine.HCl,
N-[2-fluoro-3-methoxy-5-(trifluoromethyl)phenyl]-3-[3-
methoxy-4-(4-methyl-1H-imidazol-1-yl)phenyl]-1-me-
thyl-1H-1,2,4-triazol-5-amine,
(8S)-5,6,7,8-tetrahydro-2-[6-methoxy-5-(4-methyl-1H-imi-
dazol-1-yl)-2-pyridinyl]-8-[2-(trifluoromethyl)phenyl]-
[1,2,4]triazolo[1,5-a]pyridine,
3-[3-methoxy-4-(4-methyl-1H-imidazol-1-yl)phenyl]-1-
methyl-N-(2-methylphenyl)-1H-1,2,4-triazol-5-amine,
N-[3-fluoro-2-(trifluoromethyl)phenyl]-3-[6-methoxy-5-(4-
methyl-1H-imidazol-1-yl)-2-pyridinyl]-1-methyl-1H-1,2,
4-triazol-5-amine,
N-[2-fluoro-3-(trifluoromethyl)phenyl]-3-[6-methoxy-5-(4-
methyl-1H-imidazol-1-yl)-2-pyridinyl]-1-methyl-1H-1,2,
4-triazol-5-amine,
N-[2-fluoro-5-(trifluoromethoxy)phenyl]-3-[6-methoxy-5-
(4-methyl-1H-imidazol-1-yl)-2-pyridinyl]-1-methyl-1H-
1,2,4-triazol-5-amine,
3-[3-methoxy-4-(4-methyl-1H-imidazol-1-yl)phenyl]-1-
methyl-N-[2-(trifluoromethyl)phenyl]-1H-1,2,4-triazol-
5-amine, or
N-[2-fluoro-5-(trifluoromethyl)phenyl]-3-[6-methoxy-5-(4-
methyl-1H-imidazol-1-yl)-2-pyridinyl]-1-methyl-1H-1,2,
4-triazol-5-amine,
including the pharmaceutically acceptable addition salts and
the solvates thereof.

All possible combinations of the above-indicated interesting embodiments are considered to be embraced within the scope of this invention.

The present invention also encompasses processes for the preparation of compounds of Formula (I) and subgroups thereof. In the reactions described, it can be necessary to protect reactive functional groups, for example hydroxy, amino, or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1999.

The compounds of Formula (I) and the subgroups thereof can be prepared by a succession of steps as described hereunder. They are generally prepared from starting materials which are either commercially available or prepared by standard means obvious to those skilled in the art. The compounds of the present invention can be also prepared using standard synthetic processes commonly used by those skilled in the art of organic chemistry.

The general preparation of some typical examples is shown below. All variables are defined as mentioned hereabove unless otherwise is indicated. LG is defined as a leaving group such as, for example, Cl, Br, I, tosylate, mesylate or triflate, in particular F, Cl, Br or I, more in particular Cl, Br or I, unless otherwise is indicated.

Experimental Procedure 1

In general, compounds of formula (I), wherein

Het$^1$ is restricted to (a);

$L^a$ is defined as hereabove provided however that La is not $NR^9$, $NR^9$—$C_{1-4}$alkanediyl, carbonyl, O, S or $S(=O)_p$;

$R^{4a}$ is other than hydrogen;

all other variables are defined as hereabove;

hereby named compounds of formula (III), can be prepared by substitution of a compound of formula (II), with a compound of formula $R^{4a}$-LG such as, for example, aryl halide or alkyl halide (halide is defined as I, Cl, Br or F), according to Scheme 1. The reaction can be performed in the presence of a base such as, for example, NaH, in the presence of reaction inert solvents such as N,N-dimethylformamide (DMF) or tetrahydrofuran (THF). The reaction may be optionally performed in the presence of a copper catalyst and/or a ligand such as N,N'-dimethylethylenediamine (DMEN), (1R,2R)-(–)-1,2-diaminocyclohexane, or 1,10-phenanthroline. Copper salts such as, for example, copper(I)oxide, copper(I)iodide, or copper(I)bromide can be used in catalytic or stoichiometric amounts. Elevated temperatures and/or pressure may enhance the rate of the reaction. In general, mixtures are obtained of compounds of formula (III) and regioisomeric compounds of formula (IV). When the alkylating reagent $R^{6b}$-LG is defined as $CH_3$-LG, such as in $CH_3I$, regioisomeric compounds of formula (IV) are obtained which are the compounds of formula (I) wherein Het$^1$ is restricted to (b), and wherein $R^{6b}$ is methyl.

Scheme 1

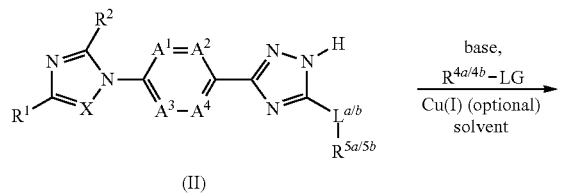

(II)

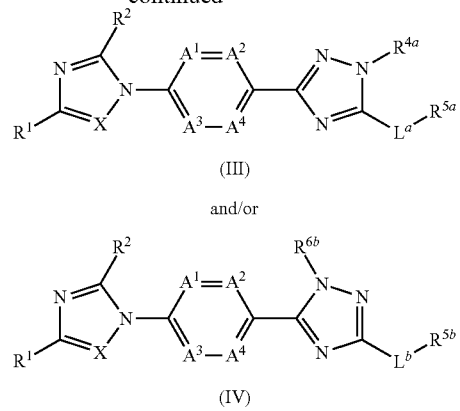

Experimental Procedure 2

Compounds of formula (III), wherein $R^{4a}$ is other than hydrogen, and wherein all other variables are defined as in experimental procedure 1, can also be prepared via a condensation reaction between an intermediate of formula (V-a) and an intermediate of formula (VI), or via a condensation reaction between an intermediate of formula (V-b) and an intermediate of formula (VI) according to Scheme 2.

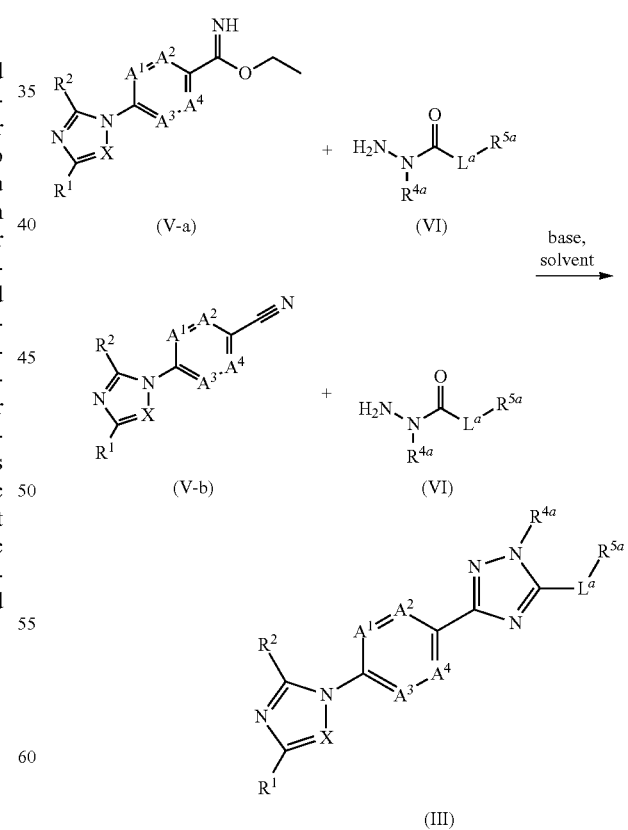

The reaction between intermediates of formula (V-a) and (VI) can be performed in the presence of an ammonium source such as ammonium acetate ($NH_4^+$ $^-OAc$) in solvents such as, for example, acetic acid (AcOH) or in the presence of a base such as, for example, sodium acetate (NaOAc) and in a solvent such as, for example, dioxane. The reaction between intermediates of formula (V-b) and (VI) is performed in the presence of a suitable base such as, for example, $K_2CO_3$ and in a solvent such as n-butanol. Stirring, elevated temperatures and/or pressure may enhance the rate of the reactions, which can be carried out in the microwave or by conventional oil-bath heating.

In the particular case wherein $R^{4a}$ is H, compounds are obtained wherein Het$^1$ has formula (b) and wherein $R^{6b}$ is H.

Experimental Procedure 3

Compounds of formula (II), wherein all variables are defined as mentioned before, can also be prepared via a condensation reaction between an intermediate of formula (VII) and an intermediate of formula (VIII) or via a condensation reaction between an intermediate of formula (VII) and an intermediate of formula (VIIIa), according to Scheme 3:

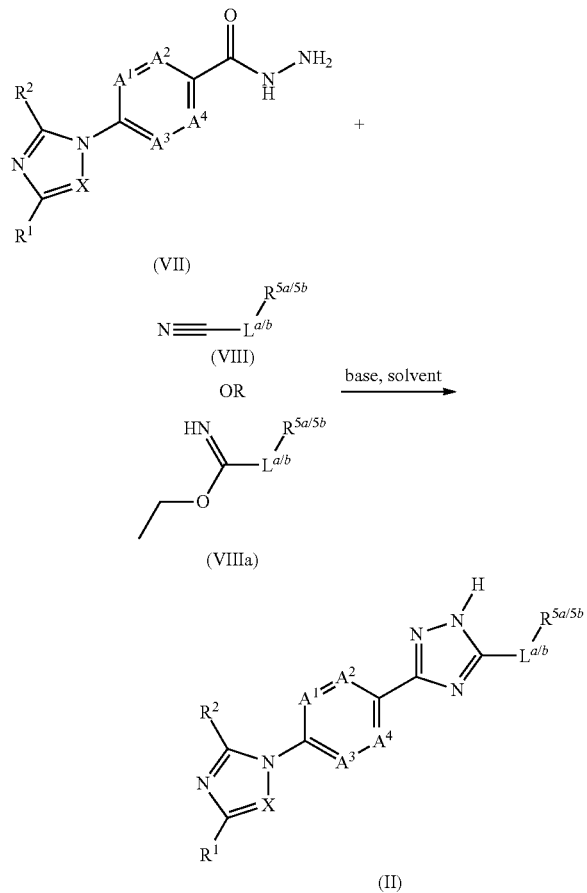

The reaction in Scheme 3 may be performed in the presence of an ammonium source such as NH$_4$OAc in solvents such as AcOH or in the presence of a base such as $K_2CO_3$ or NaOAc and in a solvent such as n-butanol (n-BuOH) or dioxane. Stirring, elevated temperatures and/or pressure may enhance the rate of reaction, which can be carried out in the microwave or by conventional heating. Intermediates of formula (VIIIa) can be prepared from an intermediate of formula (VIII), by using a similar procedure as described in experimental procedure 6.

Experimental Procedure 4

Compounds of formula (I), can be prepared via a coupling reaction between an intermediate of formula (IX) and formula (X), according to Scheme 4:

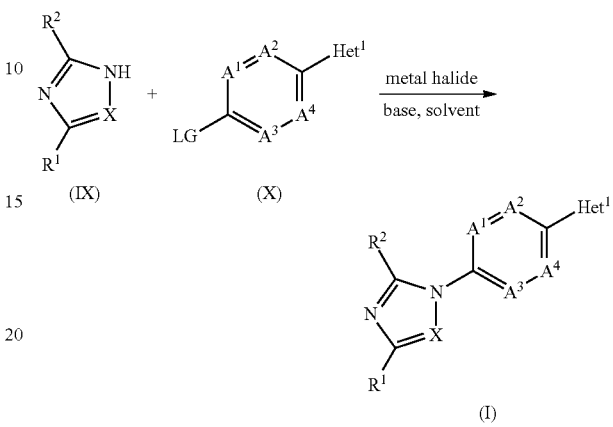

In Scheme 4, LG is preferably Cl, Br or I. The reaction may be performed in the presence of a metal halide such as CM, and in the presence of a base such as $Cs_2CO_3$. The reaction may be performed in a reaction-inert solvent (e.g. DMF). A ligand such as DMEN, (1R,2R)-(−)-1,2-diaminocyclohexane or 1,10-phenanthroline may be present.

Experimental Procedure 5

A compound of formula (I) may be prepared by a Suzuki-Miyaura cross-coupling reaction between an intermediate of formula (XI) and formula (XII) according to Scheme 5. In formula (XII), LG is preferably Cl or Br, and in formula (XI) B(OR)$_2$ refers to the boronic acid B(OH)$_2$ or its corresponding boronate ester, such as a pinacol ester. The reaction can be catalysed by a Pd catalyst such as Pd(PPh$_3$)$_4$ or PdCl$_2$(dppf). The reaction is performed in the presence of a base such as $K_2CO_3$ or $K_3PO_4$ and in a reaction-inert solvent such as toluene, DMF or CH$_3$CN and may include H$_2$O, Stirring, elevated temperatures (e.g. between 50-120° C.) and/or pressure may enhance the rate of reaction which can be carried out in the microwave or conventional heating.

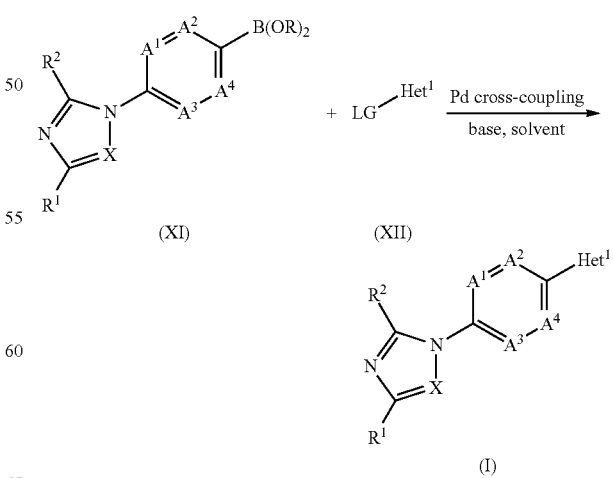

Alternatively the boronic acid intermediate or boronate ester intermediate can also be replaced by the corresponding potassium trifluoroborate derivative which can be easily prepared by using typical reaction conditions known to those skilled in the art.

Experimental Procedure 6

An intermediate of formula (V-a), wherein all variables are defined as mentioned before, can be prepared by reaction of a nitrile (V-b) with ethanol (EtOH) under acidic conditions such as, for example, HCl, according to Scheme 6. This reaction may be performed in solvents such as, for example, diethyl ether (Et$_2$O).

Scheme 6

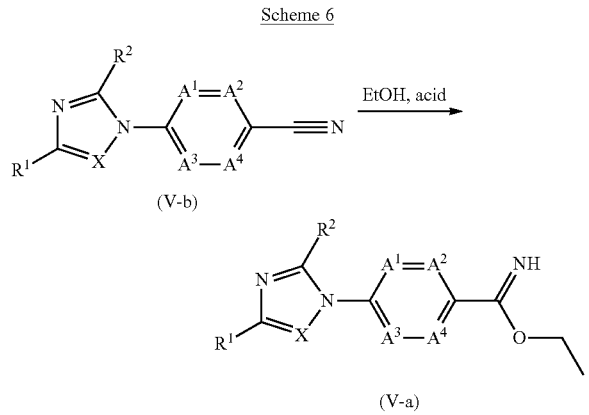

Experimental Procedure 7

An intermediate of formula (V-b), wherein all variables are defined as mentioned before, can be prepared via a nucleophilic aromatic substitution of an intermediate of formula (XIII) with a (un)substituted imidazole or triazole of formula (IX) according to Scheme 7, wherein halo is defined as F, Cl, or Br and wherein all other variables are defined as mentioned hereabove. The reaction may be performed under a protecting atmosphere such as, for example, N$_2$ atmosphere. Stirring, elevated temperatures (for example between 70-170° C.) and/or pressure may enhance the rate of the reaction. The reaction typically is performed in an organic solvent such as, for example, DMSO, DMF, or N-methylpyrrolidinone (NMP) in the presence of a base such as, for example K$_2$CO$_3$, Cs$_2$CO$_3$, or Et$_3$N.

According to Scheme 7, the reaction may be performed in the presence of a copper catalyst. Copper salts such as, for example, copper(I)oxide, copper(I)iodide, or copper(I)bromide can be used in catalytic or stoichiometric amounts.

Scheme 7

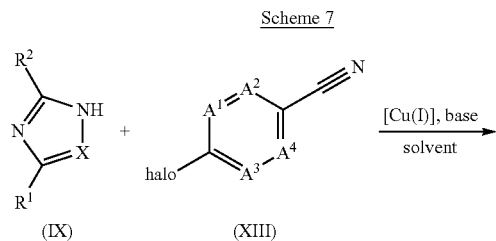

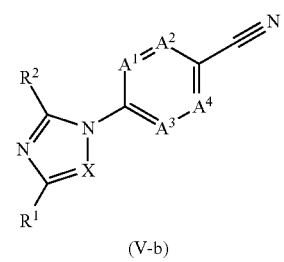

Experimental Procedure 8

An intermediate of formula (VII), wherein all variables are defined as mentioned before, can be prepared by treatment of an intermediate with formula (XIV-a), with hydrazine hydrate in solvents such as EtOH, according to Scheme 8. This reaction may be performed under a protecting atmosphere such as, for example, N$_2$ atmosphere. This reaction typically can be performed in an autoclave at elevated temperatures (for example between 120-130° C.). An intermediate of formula (VII) can also be prepared by standard amide bond formation reaction, using hydrazine as the amine source and an intermediate of formula (XIV-b) as the carboxylic acid source. As an alternative for hydrazine, Boc-protected hydrazine can be used for the amide bond formation, after which the obtained Boc protected hydrazide amide can be deprotected via standard Boc deprotecting methods (such as treatment with TFA of HCl). Intermediates of formula (XIV-a) can be obtained from an intermediate of formula (XIV-b) via an esterification reaction using typical reaction conditions known to those skilled in the art reaction, for example, by treatment of an intermediate with formula (XIV-b) with an alcoholic solvent such as, for example, MeOH or EtOH under acidic conditions.

In experimental procedure 8, hydrazine can also be replaced by a substituted hydrazine of formula H$_2$N—NH—R$^{4a}$, wherein R$^{4a}$ is defined as before.

Scheme 8

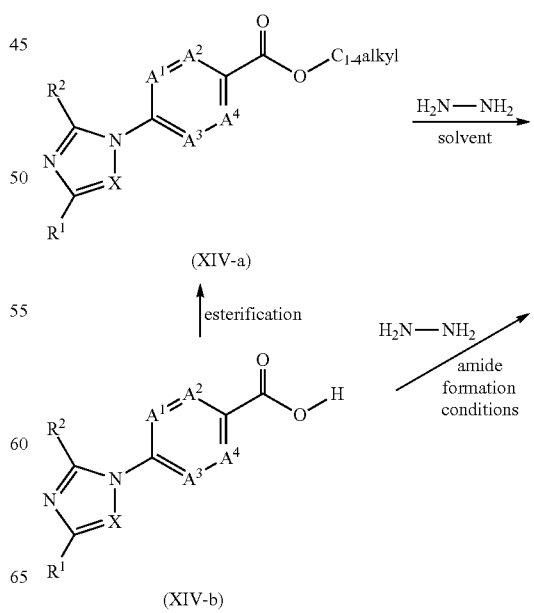

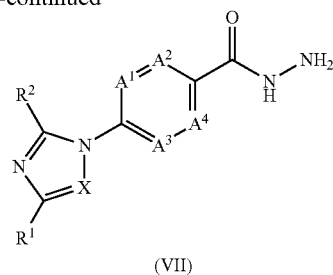

(VII)

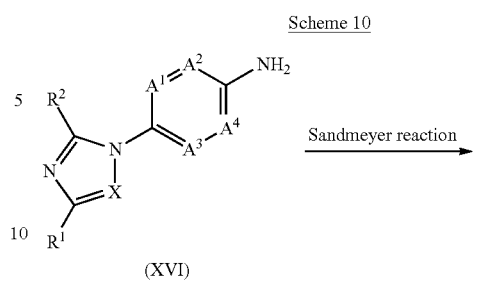

(XVI)

Experimental Procedure 9

An intermediate of formula (XIV-a or XIV-b), wherein all variables are defined as mentioned before, can be prepared by a Pd-catalysed CO-insertion reaction of intermediate (XV) according to Scheme 9, wherein halo is defined as Br, Cl or I and wherein all other variables are defined as mentioned hereabove. Stirring, elevated temperatures (for example 150° C.) and/or pressure may enhance the rate of the reaction. The reaction is charged with CO gas and is typically performed in an organic solvent such as for example THF. In the presence of alcoholic solvents such as methanol (MeOH), intermediates of formula (XIV-a) are obtained. The reaction is catalysed by a Pd source such as, for example, $Pd(OAc)_2$, $Pd_2(dba)_3$ or $Pd(PPh_3)_4$, and in conjunction with an appropriate ligand if required.

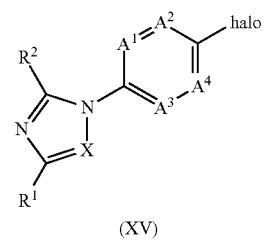

(XV)

Experimental Procedure 11

An intermediate of formula (XVI), wherein all variables are defined as mentioned before, can be prepared by reduction of an intermediate of formula (XVII), according to Scheme 11. The reduction of intermediate (XVII) to intermediate (XVI) can be conducted by a conventional method such as, for example, reductive hydrogenation or reduction with a metal or a metal salt and an acid [for example a metal such as Fe, or a metal salt such as $SnCl_2$ and an acid such as an inorganic acid (HCl, $H_2SO_4$ or the like) or an organic acid (AcOH or the like)]. Alternatively, other well-known methods for converting a nitro-group to its corresponding amine may be used.

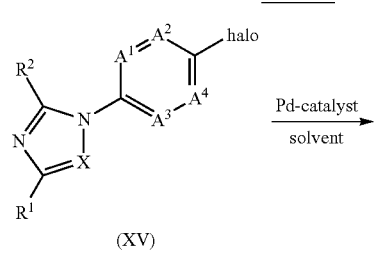

(XV)

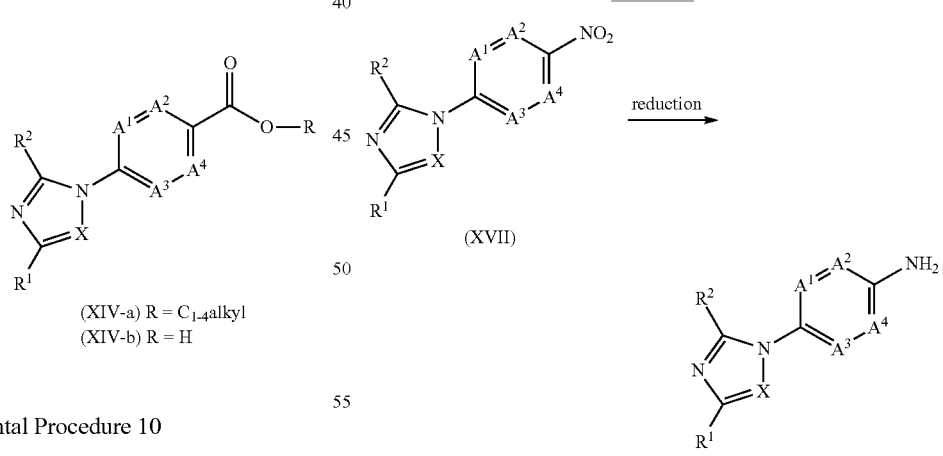

(XIV-a) R = $C_{1-4}$alkyl
(XIV-b) R = H

Experimental Procedure 10

An intermediate of formula (XV), wherein all variables are defined as mentioned before, can be prepared by conversion of the amino-moiety in intermediate (XVI) into a halo-group, known as the Sandmeyer reaction. In Scheme 10, halo is defined as I, Br or Cl, and all other variables are defined as mentioned hereabove. Intermediate (XVI) is first converted to the corresponding diazonium salt by treatment with $NaNO_2$ under acidic conditions, then treated with a halide source such as, for example, KI, CuBr or CuCl. Typical reaction conditions known to those skilled in the art can be used.

Experimental Procedure 12

An intermediate of formula (XVII), wherein all variables are defined as mentioned before, can be prepared via a nucleophilic aromatic substitution of an intermediate (XVIII) with a (un)substituted imidazole or triazole of formula (IX), according to Scheme 12, wherein LG is preferably F, Cl, or Br and wherein all other variables are defined as mentioned hereabove. The reaction may be performed under a protecting atmosphere such as, for example, $N_2$ atmosphere. Stirring, elevated temperatures (for example between 70-170° C.) and/or pressure may enhance the rate of the reaction. The reaction typically is performed in an organic solvent such as, for example, DMSO, DMF, or N-methylpyrrolidinone (NMP) in the presence of a base such as, for example $K_2CO_3$, $Cs_2CO_3$, or $Et_3N$. The reaction may be performed in the presence of a copper catalyst. Copper salts such as, for example, copper(I) oxide, copper(I)iodide, or copper(I)bromide can be used in catalytic or stoichiometric amounts.

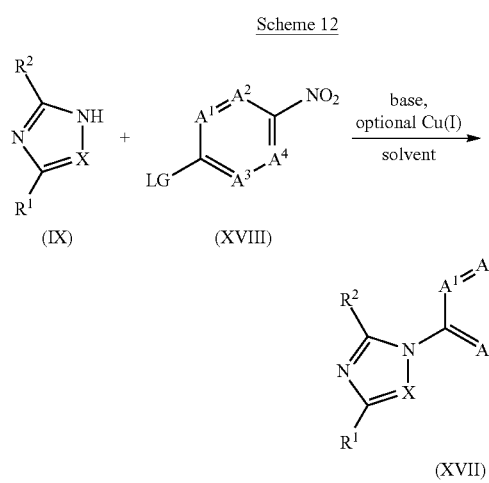

Experimental Procedure 13

An intermediate of formula (XV) wherein at least one of $A^1$ or $A^3$ represents N, and, wherein all other variables are defined as mentioned before, hereby named an intermediate of formula (XV-a), can be prepared via a nucleophilic aromatic substitution of an intermediate of formula (XIX), wherein at least one of $A^1$ or $A^3$ represents N, with an optionally substituted imidazole or triazole of formula (IX) according to Scheme 13, wherein LG preferably is F, Cl or Br, wherein halo is defined as Br or I, and wherein all other substituents are defined as mentioned before. The reaction may be performed under similar conditions as described for Experimental procedure 12.

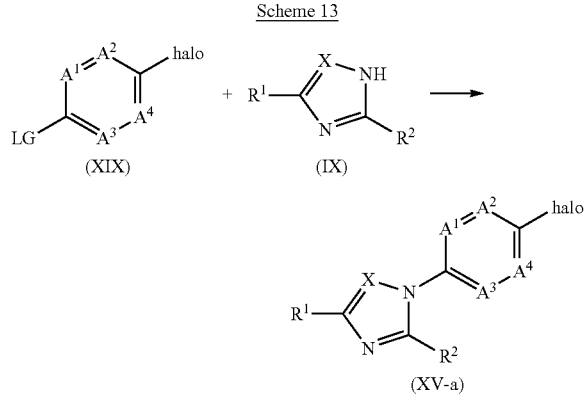

Experimental Procedure 14

An intermediate of formula (XV) wherein X represents CH, and wherein all other variables are defined as mentioned before, hereby named an intermediate of formula (XV-b), can also be prepared via acylation of intermediate (XX) to yield intermediate (XXI) in the presence of a reaction inert solvent, such as, for example, THF, and optionally a suitable base, such as $Et_3N$, according to Scheme 14. An intermediate of formula (XXIII) can subsequently be prepared via alkylation of an intermediate of formula (XXI) with an intermediate of formula (XXII), in the presence of a reaction inert solvent such as, for example, DMF, and a suitable base such as, for example, $Cs_2CO_3$ or $K_2CO_3$, and optionally in the presence of a catalytic amount of a iodide salt such as, for example, KI or NaI. A condensation reaction of intermediate (XXIII) with an ammonia source such as, for example, $NH_4(OAc)$ subsequently yields a compound of formula (XV-b). In Scheme 14, halo is defined as Cl, Br, or I, LG is preferably Cl or Br, and all other variables are defined as mentioned hereinbefore.

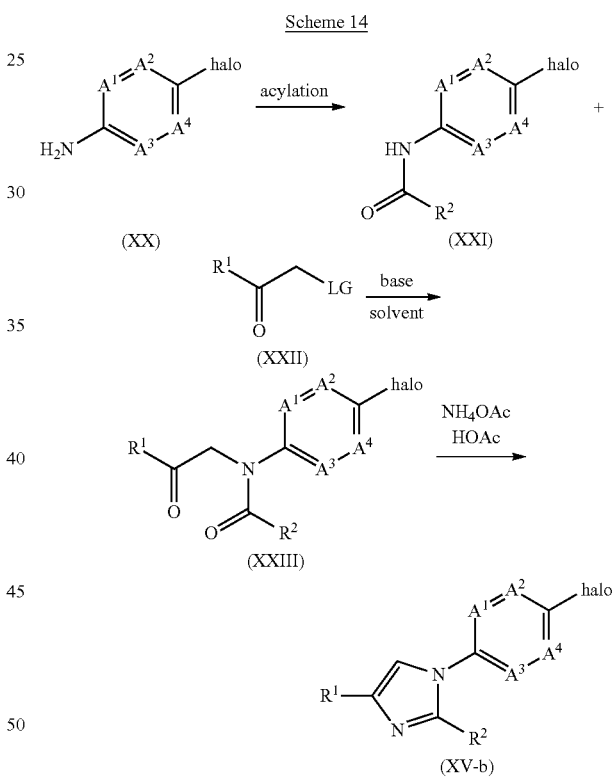

Experimental Procedure 15

An intermediate of formula (X), wherein $Het^1$ is restricted to heterocycles of formula (a), wherein $L^a$ is defined as in experimental procedure 1, and wherein all other variables are defined as in compounds of formula (I), hereby named intermediates of formula (X-a), can be prepared via a 2-step reaction sequence starting with a condensation reaction between an intermediate of formula (XXIV) and an intermediate of formula (VIII) to yield an intermediate of formula (XXV), according to Scheme 15. This reaction is performed in the presence of a suitable base such as, for example, $K_2CO_3$ and in a solvent such as n-butanol. The reaction may be performed in the microwave or by conventional oil-bath heating. In the second step, an intermediate of formula (XXV) can be substituted with $R^4$-LG such as, for example, an aryl halide or alkyl halide (halide is I, Cl Br or F), to yield an intermediate of formula (X-a). The reaction can be performed in the presence of a base such as, for example, NaH in reaction inert solvents such as DMF or THF.

Scheme 15

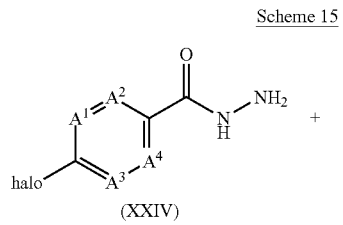

(XXIV)

$$N\!\!\equiv\!\!\!=\!\!\!-\!\!L^a\!\!-\!\!R^{5a}$$

(VIII)

base / solvent →

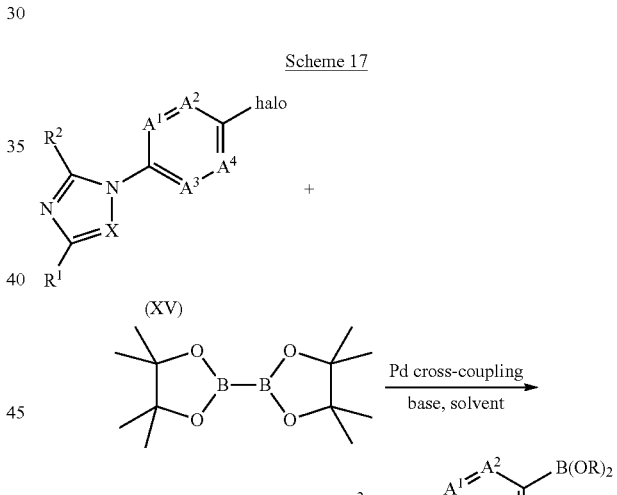

Experimental Procedure 16

An intermediate of formula (XXIV) wherein all variables are defined as mentioned before can be prepared by treatment of an intermediate of formula (XXVI), with hydrazine hydrate in a solvent such as, for example, EtOH, according to Scheme 16. This reaction may be performed under a protecting atmosphere such as, for example, $N_2$ atmosphere. This reaction is typically performed in an autoclave at elevated temperatures (for example between 120-130° C.).

Scheme 16

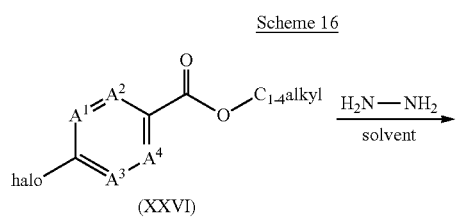

(XXVI)

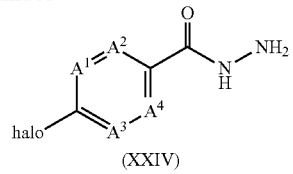

(XXIV)

Similarly hydrazides of formula (VI) can be prepared from the corresponding carboxylic acid alkylesters and the required hydrazines.

Experimental Procedure 17

An intermediate of formula (XI) wherein all variables are defined as mentioned before may be prepared by Suzuki-Miyaura cross-coupling reaction between an intermediate of formula (XV) and a boron species such as pinacolatodiboron, according to Scheme 17. In Scheme 17, halo is defined as I, Br, or Cl and $B(OR)_2$ refers to the boronate ester or it's corresponding acid $B(OH)_2$. This reaction is catalysed by a Pd catalyst, such as, for example $Pd(PPh_3)_4$ or $PdCl_2(dppf)$. The reaction is performed in the presence of a suitable base, such as, for example $K_2CO_3$, or $K_3PO_4$ and in a reaction-inert solvent such as DMF, MeCN, or dioxane and may also include $H_2O$, Stirring, elevated temperatures (for example, between 50-120° C.) and/or pressure may enhance the rate of the reaction, which can be carried out in the microwave or by conventional heating.

Scheme 17

An intermediate of formula (XI) can also be converted into the corresponding potassium trifluoroborate derivative by using typical reaction conditions known to those skilled in the art, which can subsequently be used as an alternative to (XI) in Suzuki coupling reactions such as described in Experimental procedure 5.

Experimental Procedure 18

An intermediate of formula (XII), wherein $Het^1$ is restricted to heterocycles of formula (a), wherein $L^a$ represents a direct bond, and wherein all other variables are defined as in compounds of formula (I), hereby named intermediates of formula (XII-a), may be prepared starting by substitution of an intermediate (XXVII) with $R^{4a}$, for example via alkylation with an alkylhalide, followed by a regioselective Suzuki-Miyaura cross-coupling reaction between the obtained intermediate of formula (XXVIII) and a boron species (XXIX), according to Scheme 18. In Scheme 18, LG is preferably Cl or Br, halo is defined as I, Br, or Cl and $B(OR)_2$ refers to the boronic acid, $B(OH)_2$ or it's corresponding boronate ester. The Suzuki-Miyaura cross-coupling reaction is catalysed by a Pd catalyst, such as, for example $Pd(PPh_3)_4$ or $PdCl_2(dppf)$. and is performed in the presence of a suitable base, such as, for example $K_2CO_3$, or $K_3PO_4$ and in a reaction-inert solvent such as DMF, MeCN and may also include $H_2O$. This reaction is typically performed at room temperature (r.t.), however elevated temperatures (for example 40-50° C.) and/or pressure may enhance the rate of the reaction.

Scheme 18

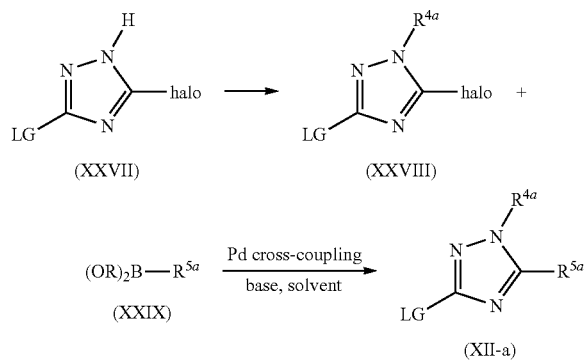

Experimental Procedure 19

In general, compounds of formula (I), wherein $Het^1$ is restricted to (c), and $R^{6c}$ is hydrogen, and wherein all other variables are defined as hereabove, hereby named compounds of formula (XXX), can be prepared by condensation of an intermediate of formula (XXXI), with an intermediate of formula (XXXII) in the presence of an ammonia source such as $NH_4OAc$, according to Scheme 19. The reaction can be carried out in an acidic solvent such as AcOH, using elevated temperatures (for example 100-180° C.), which can be carried out in the microwave or by conventional heating.

Scheme 19

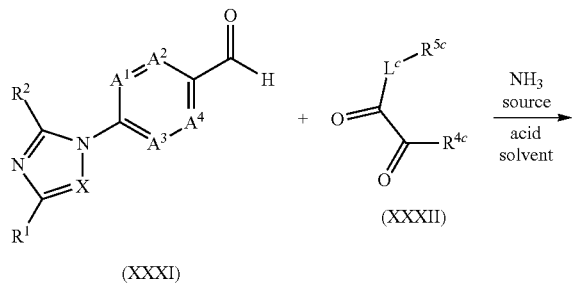

Experimental Procedure 20

Compounds of formula (I), wherein $Het^1$ is restricted to (c), and $R^{6c}$ is methyl, and wherein all other variables are defined as hereabove, hereby named compounds of formula (XXXIII), can be prepared via alkylation of compound (XXX) with $CH_3I$, according to Scheme 20. The reaction can be performed in the presence of a base such as, for example, NaH in reaction inert solvents such as DMF or THF.

Scheme 20

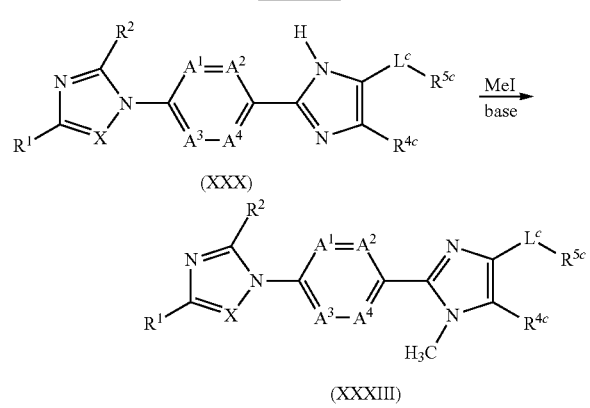

Experimental Procedure 21

An intermediate of formula (XXXI), wherein all variables are defined as mentioned before, can be prepared by via a nucleophilic aromatic substitution of an aldehyde intermediate (XXXIV) with a (un)substituted imidazole or triazole of formula (IX), according to Scheme 21, wherein LG is preferably defined as F, Cl, or Br and wherein all other variables are defined as mentioned hereabove. The reaction may be performed under a protecting atmosphere such as, for example, $N_2$ atmosphere. Stirring, elevated temperatures (for example between 70-170° C.) and/or pressure may enhance the rate of the reaction. The reaction typically is performed in an organic solvent such as, for example, DMSO, DMF, or N-methylpyrrolidinone (NMP) in the presence of a base such as, for example $K_2CO_3$, $Cs_2CO_3$, or $Et_3N$. The reaction may be performed in the presence of a copper catalyst. Copper salts such as, for example, copper(I)oxide, copper(I)iodide, or copper(I)bromide can be used in catalytic or stoichiometric amounts.

Scheme 21

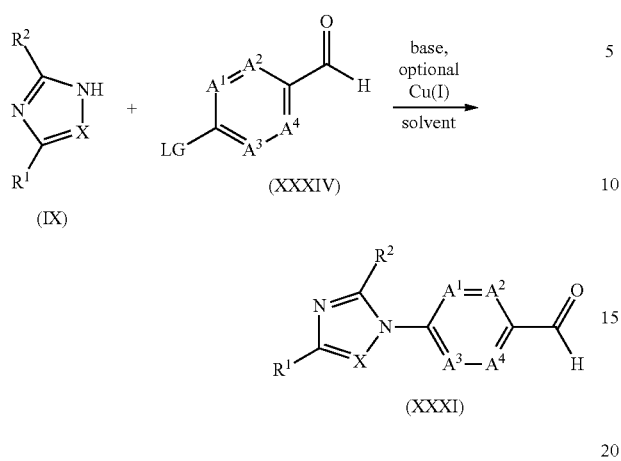

Experimental Procedure 22

In general, compounds of formula (I), wherein Het$^1$ is restricted to (a), and wherein L$^a$ represents NR$^9$, and wherein all other variables are defined as hereabove, hereby named compounds of formula (III-a), can be prepared according to Scheme 22 by transforming an N-acyl carbomimidothioic acid, methyl ester derivative of general formula (XXXV) into a 1,2,4-triazoles of formula (III-a) using an appropriate hydrazine (XXXVI) under art known conditions. This transformation is typically performed in a protic solvent, such as MeOH or a higher alcohol and requires a temperature between r.t. and 150° C. In a particular embodiment the higher alcohol is tertiary butyl alcohol and the reaction temperature is between 70 and 120° C., most preferably 100° C. For those reactions wherein the hydrazine (XXXVI) is used as an HCl salt, the addition of a stoichiometric amount of a base is preferred. Said base can be an inorganic base, such as potassium acetate or potassium carbonate, more preferably, said base is a tertiary amine, such as diisopropyl ethyl amine or the like (Scheme 22).

In general, mixtures are obtained of compounds of formula (III-a) and regioisomeric compounds of formula (IV-a). The compounds of formula (IV-a), wherein R$^{6b}$ is defined as methyl are the compounds of formula (I) wherein Het$^1$ is restricted to (b), wherein L$^b$ represents NR$^9$, and wherein R$^{6b}$ is methyl.

Scheme 22

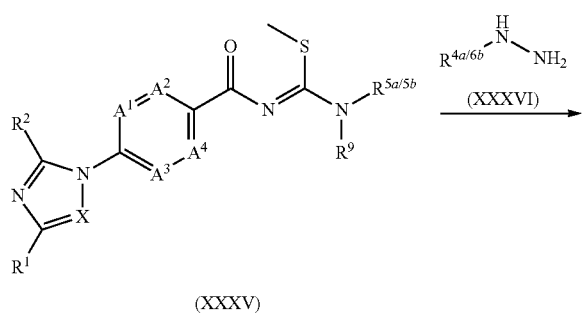

Compounds of formula (I), wherein Het$^1$ is restricted to (a), and wherein La represents NR$^9$—C$_{1-4}$alkanediyl, and wherein all other variables are defined as hereabove, can be prepared in analogy to Scheme 22.

Experimental Procedure 23

An intermediate of formula (XXXV) wherein all variables are defined as mentioned before, can be prepared by a protocol that consists of 3 synthetic transformations (Scheme 23), starting from an acyl chloride of formula (XXXVII), which can be obtained by treatment of the carboxylic acid (XIV-b) with an excess of oxalyl chloride or thionyl chloride, optionally in the presence of DMF as a catalyst, at elevated temperature, in particular at reflux temperature. Said transformation may also be effected in the presence of an organic solvent, such as dichloromethane or the like. In a first step the acylating agent, such as an acyl chloride (XXXVII), a mixed or symmetric anhydride, an acyl fluoride and the like; is reacted with a monovalent cation thiocyanate (MNCS in scheme 23), such as for example potassium thiocyanate or ammonium thiocyanate to yield the corresponding acyl isothiocyanate. This reaction is usually performed using acetone as a solvent and at a temperature between 0° C. and 70° C., preferably at r.t. The intermediate acyl isothiocyanate is not isolated but treated in the same reaction medium with an appropriate amine (XXXVIII) to yield the N-acyl thiourea of the general formula (XXXIX). This transformation reaction is usually performed at a temperature between 0° C. and 70° C., preferably at r.t. In a final step, S-methylation of the N-acyl thiourea (XXXIX) provides the N-acyl carbomimidothioic acid, methyl ester derivative of general formula (XXXV).

Scheme 23

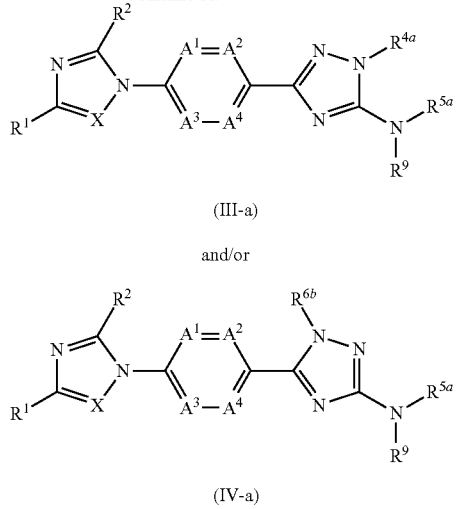

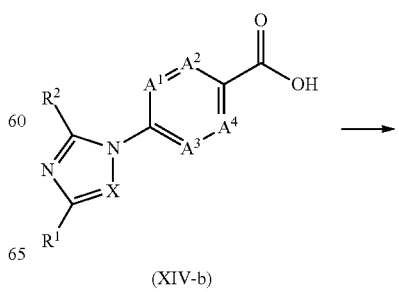

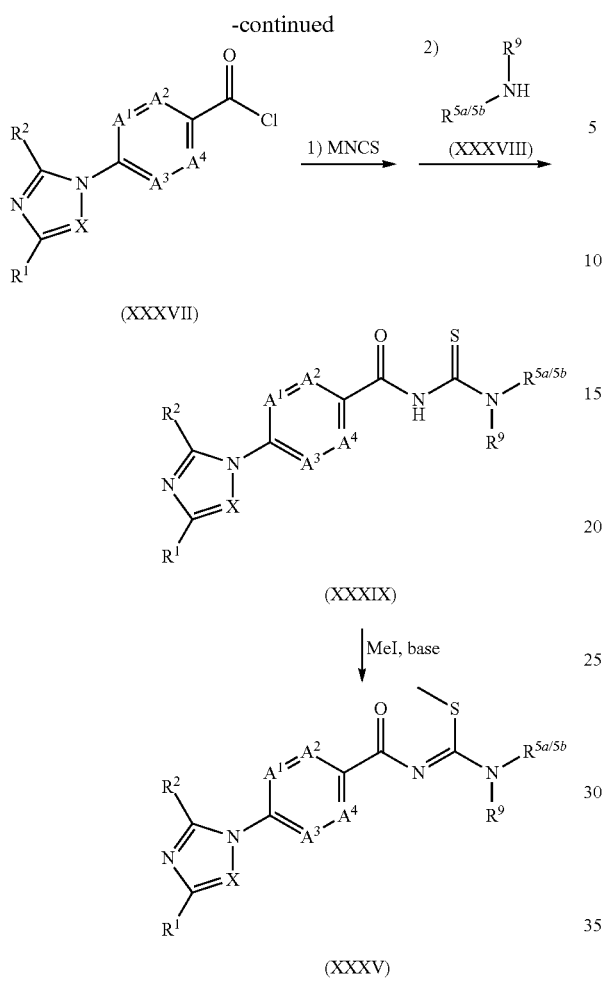

(XXXVII)

(XXXIX)

(XXXV)

Experimental Procedure 24

Compounds of formula (III) wherein $R^{4a}$ is not hydrogen, and wherein all other variables are defined as mentioned before (see experimental procedure 1), can also be prepared via an acylation of an intermediate of formula (V-a) with an acid chloride intermediate of formula (XL), followed by a condensation reaction with a hydrazine intermediate of formula (XXXVI), according to Scheme 24.

Scheme 24

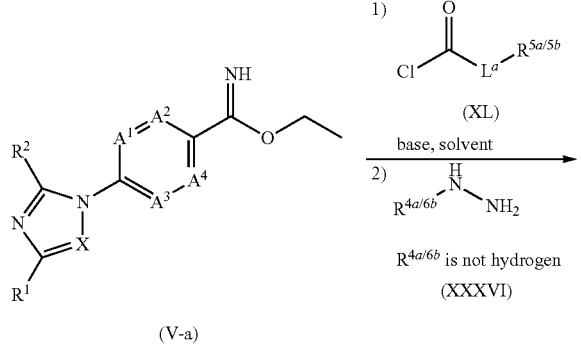

(V-a)

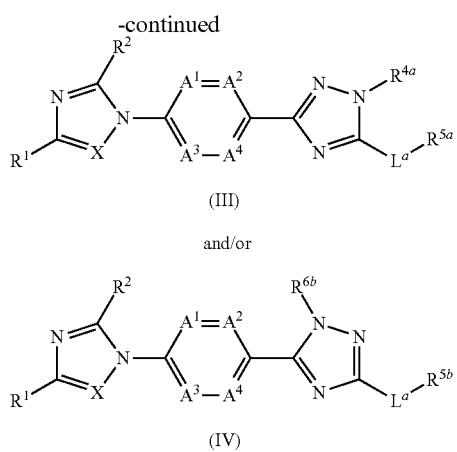

The reaction between intermediates of formula (V-a) and (XL) is performed in the presence of a suitable base such as, for example, pyridine or $Et_3N$, and in a solvent such as toluene, dichloroethane, DCM, chloroform. This reaction is typically performed at r.t., however elevated temperatures (for example 40-120° C.) may enhance the rate of the reaction. In general, (XXXVI) is added to the crude reaction mixture (r.m.) obtained after the acylation. The condensation step to (III) is performed at elevated temperatures ((for example 40-120° C.), and optionally in the presence of base, such as, for example, pyridine or $Et_3N$. Typically, also the regioisomeric compounds of formula (IV) are obtained which are the compounds of formula (I) wherein $Het^1$ is restricted to (b), and wherein $R^{6b}$ is methyl.

Experimental Procedure 25

Compounds of formula (III-a), wherein $R^9$ is restricted to hydrogen, and wherein all variables are defined as hereabove, hereby named compounds (XLI), can also be prepared, according to Scheme 25, via a condensation reaction between an intermediate of formula (XLIII) and an hydrazine derivative of formula (XXXVI) wherein $R^{4a/6b}$ is restricted to $R^{4a}$ and hereby named compounds of formula (XLII). This transformation is typically performed in a protic solvent, such as MeOH or a higher alcohol and requires a temperature between r.t. and 100° C.

Scheme 25

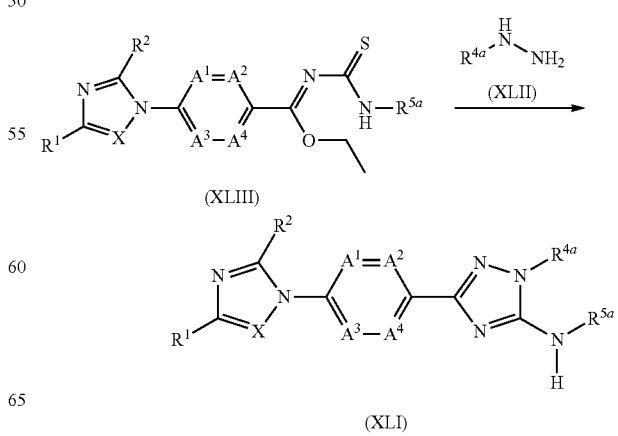

(XLI)

Experimental Procedure 26

An intermediate of formula (XLIII) wherein all variables are defined as mentioned before can be prepared by reaction of an intermediate of formula (V-a) with an arylisothiocyanate of formula (XLIV) according to Scheme 26. This reaction is typically performed in a reaction-inert solvent such as Et₂O, THF, acetone, or CH₃CN and at a temperature between r.t. and 70° C.

Scheme 26

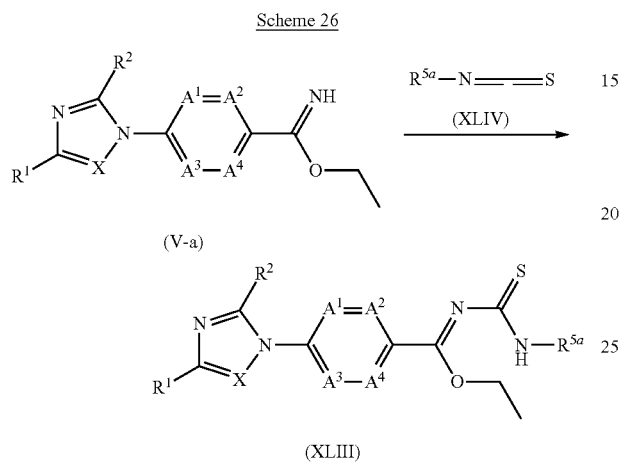

Experimental Procedure 27

An intermediate of formula (XII), can be prepared by conversion of the amino-moiety in intermediate (XLV) into a leaving group (LG) (Sandmeyer reaction). In Scheme 27, LG is preferably Cl, Br or I. Intermediate (XLV) is first converted to the corresponding diazonium salt by treatment with NaNO₂ or tert-Butyl nitrite in a reaction-inert solvent such as CH₃CN in neutral or acidic conditions, then treated with a halide source such as, for example, CuBr, CuBr₂, CuCl or 1,2-diiodoethane. This transformation requires a temperature between r.t. and 80° C.

Scheme 27

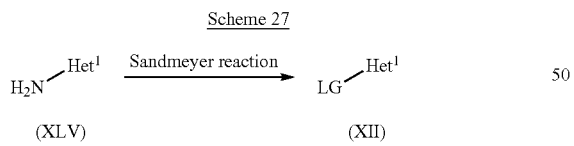

Experimental Procedure 28

An intermediate of formula (XLV) wherein Het¹ is restricted to heterocycles of formula (a), wherein $L^a$ is restricted to NH, and wherein all other variables are defined as in compounds of formula (I), hereby named intermediates of formula (XLV-b), can be prepared, according to Scheme 28, by condensation of an intermediate of formula (XLVI) and an hydrazine derivative of (XLII). This transformation is typically performed in a protic solvent, such as isopropanol, under reflux conditions.

Scheme 28

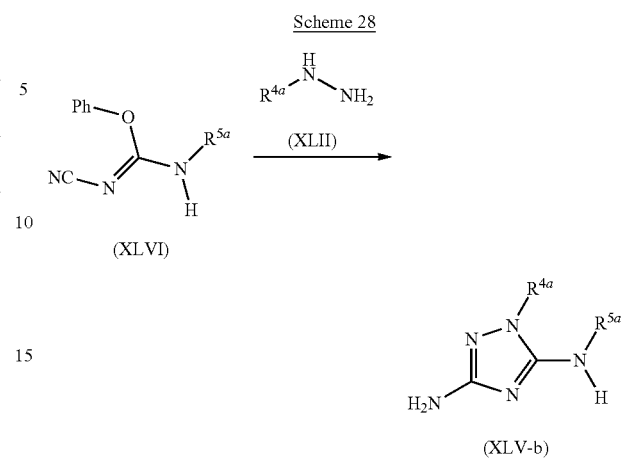

Experimental Procedure 29

An intermediate of formula (XLVI), wherein all variables are defined as mentioned before, can be prepared, according to Scheme 29, by reaction of an aniline of formula (XLVII) and diphenyl N-cyanocarboimidate (XLVIII). This reaction is typically performed either in the absence of a base, in a protic solvent such as isopropanol and under heating conditions or in the presence of a base, such as, for example, lithium hexamethyldisilazide, in a reaction-inert solvent such as THF and at r.t.

Scheme 29

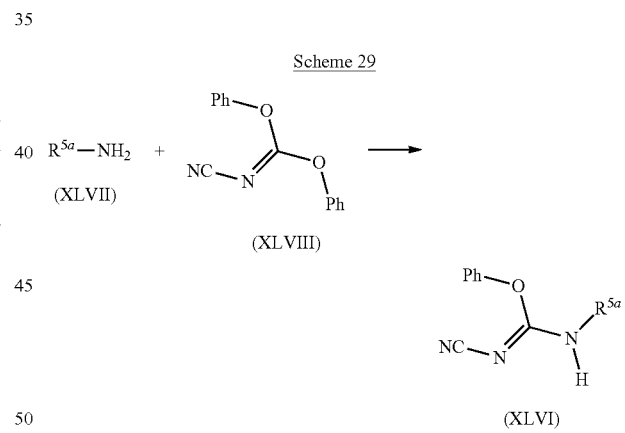

Experimental Procedure 30

An intermediate of formula (XII), wherein Het¹ is restricted to heterocycles of formula (a), wherein $L^a$ is restricted to NH, and wherein all other variables are defined as in compounds of formula (I), hereby named intermediates of formula (XII-b), can be prepared by reaction of an amino intermediate of formula (XLVII), with an intermediate of formula (XXVIII) wherein all variables are defined as mentioned before as in Scheme 30. This reaction is typically performed in the presence of a base, such as, for example, lithium hexamethyldisilazide, in a reaction-inert solvent such as THF and at a temperature between r.t. and 70° C.

Scheme 30

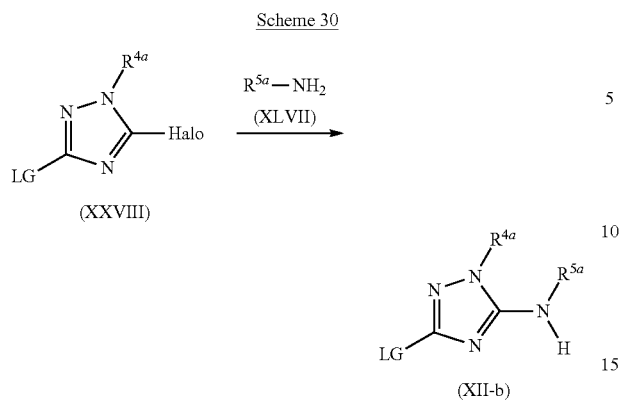

In the particular case wherein $R^{5a}$ is phenyl substituted with $CF_3$ ortho to the amino function, experimental procedure 30 is not applicable.

Experimental Procedure 31

An intermediate of formula (XLIX), wherein all variables are defined as mentioned before, can be prepared according to Scheme 31, by reaction between an amine of formula (L) and an intermediate of formula (XXVIII). This reaction is performed in the presence of a suitable base such as, for example, $Na_2CO_3$ or $K_2CO_3$, and in a solvent such as, for example, DMF, DMA or DMSO. This reaction is typically performed at elevated temperatures (e.g. 100-160° C.). Stirring and microwave conditions may enhance the rate of the reaction.

Scheme 31

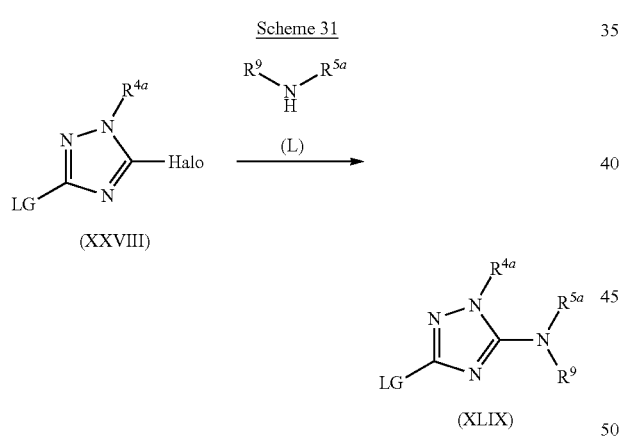

Experimental Procedure 32

A compound of formula (XLI), can also be prepared according to Scheme 32, by reaction between an intermediate of formula (LI) and an intermediate of formula (LII), wherein all variables are defined as mentioned before. This reaction is performed in the presence of a suitable base such as, for example, $Na_2CO_3$, $K_2CO_3$, or $Cs_2CO_3$ and in a solvent such as, for example, DMF, DMA or DMSO. This reaction may also typically be performed in the presence of a copper catalyst, such as copper(I)iodide, and in the presence of a ligand such as a diamino derivative, for instance DMEN, and at elevated temperatures, for example 100-200° C. Stirring and microwave assisted conditions may enhance the rate of the reaction.

Scheme 32

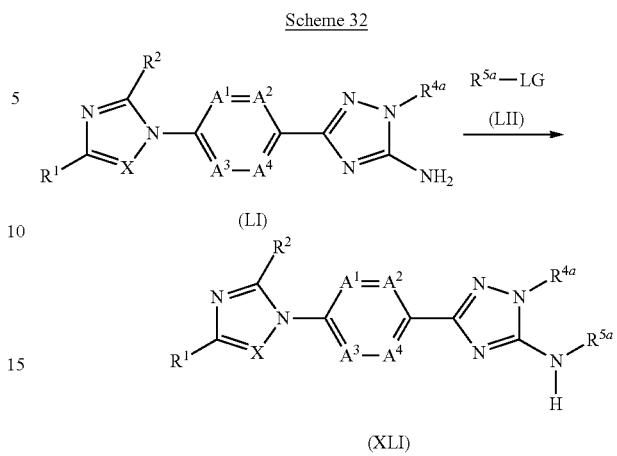

Experimental Procedure 33

An intermediate of formula (LI) can be prepared, according to Scheme 33, by selective removal of the protecting group (PG) of the intermediate of formula (LIII), wherein all variables are defined as mentioned before. In a typical example when PG is benzyl, the reaction can be performed under hydrogenolysis conditions well know by a person skilled in the art.

Scheme 33

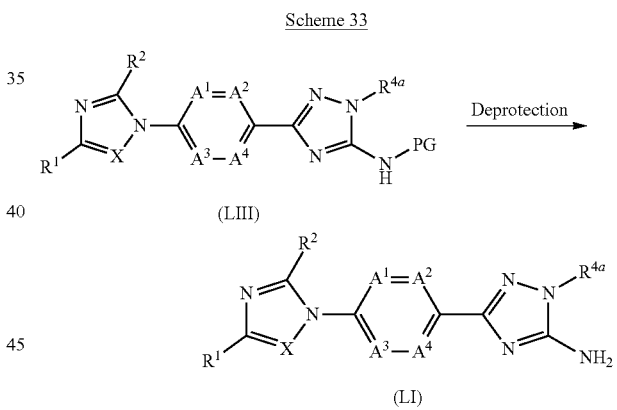

The preparation of an intermediate of formula (LIII) can be easily achieved by following experimental procedures similar to those of 31 and 5 successively.

Experimental Procedure 34

A compound of formula (I), wherein $Het^1$ is restricted to (a), and wherein $L^a$ represents S, and wherein all other variables are defined as hereabove, hereby named compounds of formula (LIV), wherein all variables are defined as mentioned before, can be prepared, according to Scheme 34, by reaction between an intermediate of formula (LV) and an intermediate of formula (LII). In formula (LII) LG is preferably Br or I. This reaction is performed in the presence of a suitable base such as, for example, $Na_2CO_3$, $K_2CO_3$, or $Cs_2CO_3$ and in a solvent such as, for example, DMF, DMA or Dioxane. This reaction is catalyzed by a Pd catalyst such as $Pd_2(dba)_3$ and in the presence of a ligand such as for example, 9,9-dimethyl- 4,5-bis(diphenylphosphino)-xanthene. This reaction may be performed at a temperature between 70° C. and 120° C.

Scheme 34

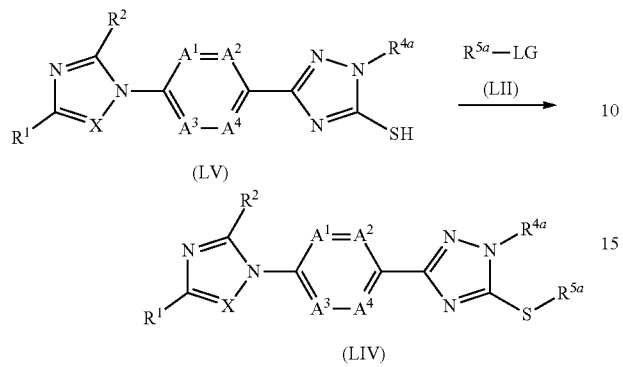

(LV)

(LIV)

Intermediate of formula (LV) can be obtained as a side product when experimental procedure 25 is performed.

Experimental Procedure 35

An intermediate of formula (XLIV), wherein $R^{5a}$ is restricted to $Ar^2$, hereby named compounds (XLIV-a), can be prepared as in Scheme 35, by the reaction of an intermediate of formula (LVI) with a thiocarbonyl transfer reagent such as, for example, 1,1'-thiocarbonyl-2,2'-pyridone or thiophosgene. This reaction is typically performed in an reaction-inert solvent such as, for example, DCM, at r.t.

Scheme 35

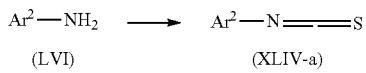

(LVI)            (XLIV-a)

Experimental Procedure 36

An intermediate of formula (V-b), wherein all variables are defined as mentioned before, can also be prepared by the cyanation of an intermediate of formula (XV) wherein halo is defined as Br, Cl or I as depicted in Scheme 36. This reaction is performed in the presence of a suitable base such as, for example, $Na_2CO_3$, $K_2CO_3$, and in a solvent such as, for example, DMF, DMA or DMSO. This reaction is typically performed in the presence of a source of cyanide, such as zinc cyanide, for instance and is catalyzed by a Pd catalyst such as, for example, $Pd(PPh_3)_4$. Stirring, elevated temperatures (for example, between 100-160° C.) and/or pressure may enhance the rate of the reaction, which can be carried out in the microwave or by conventional heating.

Scheme 36

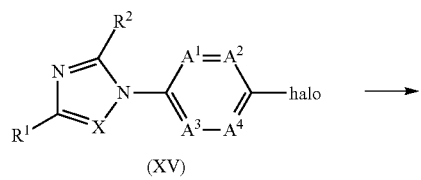

(XV)

-continued

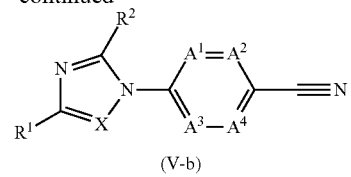

(V-b)

Experimental Procedure 37

An intermediate of formula (XLV), wherein $Het^1$ is restricted to heterocycles of formula (a), wherein $L^a$-$R^{5a}$ and $R^{4a}$ are taken together to form a bivalent radical as shown in Scheme 37, with n being 0, 1 or 2, and wherein all other variables are defined as in compounds of Formula (I), hereby named intermediates of formula (XLV-c), may be prepared by a condensation reaction between an intermediate of formula (LVII), wherein Halo is defined as Cl, Br, I, and an amino guanidine species (LVIII) according to Scheme 37. Stirring at elevated temperatures (e.g. 40-160° C.) and/or pressure may enhance the rate of the reaction, which can be carried out using microwave irradiation or by conventional heating. Typically an alcoholic solvent such as 2-propanol (iPrOH)

Scheme 37

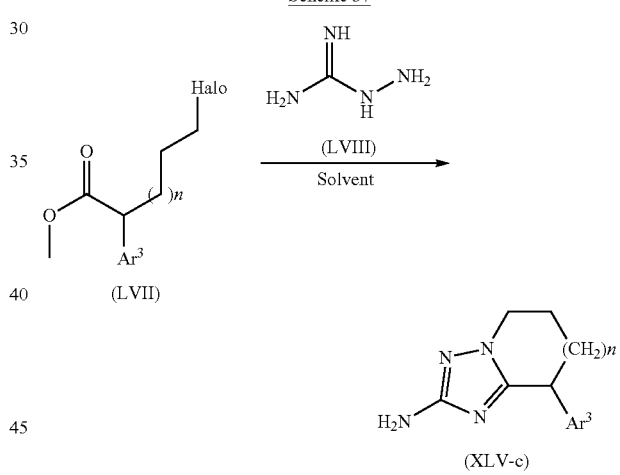

n = 0-2

Experimental Procedure 38

Alternatively, an intermediate of formula (XLV-c), can be prepared via an intermediate of formula (LIX) resulting from a substitution reaction of an intermediate of formula (LVII) with hydrazine (step a), followed by a condensation reaction with an amidine of formula (LX) bearing a leaving group LG such as a benzotriazole (step b, Scheme 38). The substitution reaction is performed in the presence of a suitable base, such as, for example, NaH, and in a reaction-inert solvent such as DMF. This reaction is typically performed at low temperature or at r.t., however elevated temperatures (for example 40-160° C.) and/or pressure may enhance the rate of the reaction, which can be carried out using microwave irradiation or conventional heating. This type of reaction typically may be performed in an alcoholic solvent such as iPrOH.

Scheme 38

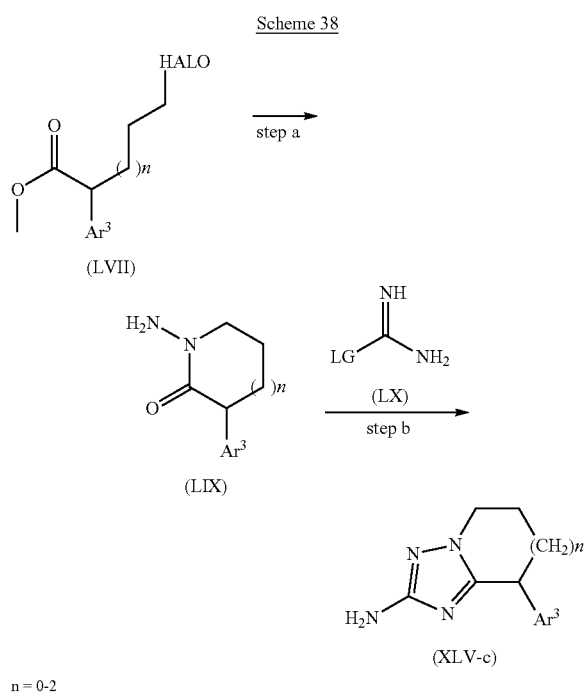

n = 0-2

Experimental Procedure 39

An intermediate of formula (XLV), wherein $Het^1$ is restricted to heterocycles of formula (a), wherein $L^a$-$R^{5a}$ and $R^{4a}$ are taken together to form a bivalent radical of formula —CH=CH—CH=CH— or —CH=CH—N=CH—, hereby named intermediates of formula (XLV-d) ($Z^a$ representing N, CH or C—$C_{1-4}$alkyl (e.g. C—$CH_3$)), may be prepared starting by a condensation reaction between an intermediate of formula (LXI) and an isothiocyanate species of formula (LXII) in a reaction inert solvent such as dioxane at r.t., according to scheme 39. This reaction is typically performed at low temperature or at r.t., however elevated temperatures (for example 40-160° C.) and/or pressure may enhance the rate of the reaction which can be carried out using microwave irradiation or conventional heating. The condensation reaction between an intermediate of formula (LXIII) and an amine source such as hydroxylamine to give intermediate (XLV-d) typically can be performed in an appropriate alcoholic solvent such EtOH or MeOH at r.t., however elevated temperatures (for example 40-160° C.) in microwave and/or pressure may enhance the rate of the reaction.

Scheme 39

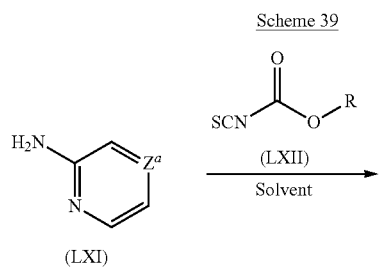

An analogous reaction procedure can be followed to prepare intermediates of formula (XLV-d) wherein the bivalent radical -$L^a$-$R^{5a}$-$L^{4a}$- of formula —CH=CH—CH=CH— or —CH=CH—N=CH— is further substituted with substituents as defined for compounds of Formula (I). In this case typically a Pd mediated coupling of an intermediate of formula (LXIV) with for example the corresponding amine, phenol, boronic acid or ester species is performed to obtain an intermediate of formula (LXI-a) which can be further reacted in Scheme 39. Halo is defined as Br, Cl or I; $Z^a$ is defined as mentioned hereabove. This is illustrated below in Scheme 39a.

Scheme 39a

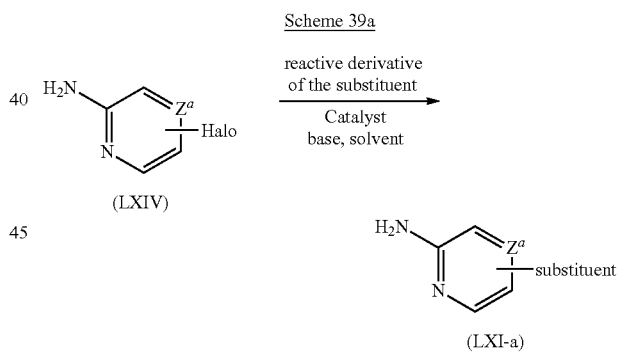

Alternatively, intermediates of formula (XLV-d) wherein the bivalent radical -$L^a$-$R^{5a}$-$L^{4a}$- of formula —CH=CH—CH=CH— or —CH=CH—N=CH— is further substituted with substituents as defined for compounds of Formula (I), hereby named intermediates of formula (XLV-e), can be obtained by converting an intermediate such as, for example, an intermediate of formula (LXIV) to an intermediate of formula (XLV-f) by following the reaction protocol described in Scheme 39. Subsequently, the intermediate of formula (XLV-f) can be converted to an intermediate of formula (XLV-e) in a Pd mediated coupling with for example the corresponding amine, phenol or boronic acid or ester species. This is illustrated below in Scheme 39b. All variables are defined as mentioned in Scheme 39a.

Scheme 39b

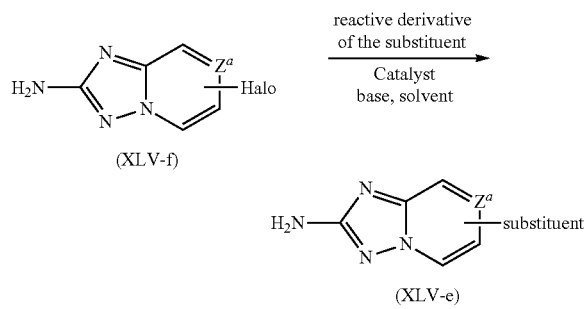

In case the substituent in formula (LXI-a) or (XLV-e) is Ar³, the intermediate of formula (LXIV) or (XLV-f) respectively, typically can be reacted with a boronic acid (Ar³—B(OH)$_2$) or ester derivative (Ar³—B(OR)$_2$) of Ar³. This coupling reaction may be performed in a suitable solvent such as, for example, dioxane, in the presence of a Pd catalyst such as Pd(PPh$_3$)$_4$, and a base such as NaHCO$_3$ in the presence of H$_2$O. The reaction can be carried out using microwave irradiation or conventional heating (e.g. 150° C.).

In case the substituent in formula (LXI-a) or (XLV-e) is NR¹¹—Ar³, the intermediate of formula (LXIV) or (XLV-f) respectively, typically can be reacted with an amine derivative (Ar³—NHR¹¹) of Ar³. This coupling reaction may be performed in a suitable solvent such as, for example, t-BuOH, in the presence of a Pd catalyst such as Pd$_2$(dba)$_3$, and a base such as Cs$_2$CO$_3$. The reaction can be carried out in the presence of a ligand such as, for example, X-Phos. Typically, the reaction can be carried out using conventional heating (e.g. 100° C.).

In case the substituent in formula (LXI-a) or (XLV-e) is O—Ar³, the intermediate of formula (LXIV) or (XLV-f) respectively, typically can be reacted with a phenol derivative (HO—Ar³) of Ar³. This coupling reaction may be performed in a suitable solvent such as N,N-dimethylacetamide (DMA), in the presence of a copper catalyst. Copper salts such as, for example, Cu$_2$O, CuI, or CuBr are used. Usually a base such as K$_2$CO$_3$ is added to the r.m. Typically, the reaction can be carried out using conventional heating (e.g. 150-175° C.).

In case the substituent in formula (LXI-a) or (XLV-e) is (C=O)—Ar³ or C$_{1-4}$alkyl-carbonyl, the intermediate of formula (LXIV) or (XLV-f) respectively, typically can be reacted with the corresponding aldehyde of Ar³ (Ar³—(C=O)H) or C$_{1-4}$alkyl (C$_{1-4}$alkyl-(C=O)H). This coupling reaction typically may be performed in the presence of an organometallic compound, in particular an organolithium reagent such as n-butyl lithium. Usually the reaction can be carried out in a suitable solvent such as, for example, THF. In a final step, the hydroxyl group can be oxidized to the corresponding ketone, using reaction conditions known to those skilled in the art.

In case the substituent in formula (LXI-a) or (XLV-e) is C$_{1-4}$alkyl, the intermediate of formula (LXIV) or (XLV-f) respectively, typically can be reacted with the corresponding aldehyde. This coupling reaction typically may be performed in the presence of an organometallic compound, in particular an organolithium reagent such as n-butyl lithium. Usually the reaction can be carried out in a suitable solvent such as, for example, THF. Subsequently, the hydroxyl group can be converted to the tosylate by reaction with a tosyl chloride in the presence of a base such as, for example, Et$_3$N, in a suitable solvent such as typically DCM. In final step, the tosylate group may be removed with a reducing agent such as, for example, NaBH$_4$, in the presence of an alcoholic solvent such as MeOH. The reaction can be performed at r.t. or at elevated temperatures.

Experimental Procedure 40

The aromatic intermediates of formula (XLV-d), (XLV-e) and (XLV-f) can be reduced to the corresponding reduced (tetrahydro) forms by conventional methods such as, for example, reductive hydrogenation or reduction with a metal or a metal salt and an acid [for example a metal such as Fe, or a metal salt such as SnCl$_2$ and an acid such as an inorganic acid (HCl, H$_2$SO$_4$ or the like) or an organic acid (AcOH or the like)]. Alternatively, other well-known methods for converting an aromatic to its corresponding reduced form may be used.

An analogous reaction protocol may be used to convert compounds of Formula (I) wherein R$^{4a}$ and -L$^a$-R$^{5a}$ are taken together to form a bivalent radical of formula —CH=CH—CH=CH— or —CH=CH—N=CH— to their corresponding reduced forms.

Experimental Procedure 41

An intermediate of Formula (XII), wherein Het¹ is restricted to heterocycles of formula (a), wherein LG being Br, wherein L$^a$-R$^{5a}$ and R$^{4a}$ are taken together to form a bivalent radical as shown in scheme 41, wherein n being 1 or 2, and wherein all other variables are defined as in compounds of Formula (I), hereby named intermediates of Formula (LXV), can be prepared starting from 3,5-dibromo-1H-1,2,4-triazole (LXVI) according to the reaction steps shown in Scheme 41. Alkylation of (LXVI) with a suitably O-protected hydroxyethylhalide (n=1) or hydroxyl-n-propylhalide (n=2) will give an intermediate of Formula (LXVII). Lithium-halogen exchange of (LXVII), for example via treatment of (LXVII) with n-BuLi at a temperature below −50° C., followed by addition of the required Ar³-aldehyde will give an intermediate of Formula (LXVIII). Deprotection of (LXVIII) to give (LXIX), followed by a dehydration/cyclization reaction, for example via treatment of (LXIX) with an acid, such as HCl, methylsulfonic acid, or p-toluenesulfonic acid, in a suitable solvent, such as toluene or xylene at refluxing temperatures (Dean-Stark conditions), will then give an intermediate of Formula (LXV). The protection group PG should be selected according to the known art to survive the reaction conditions of the steps leading to intermediate (LXVIII), for example a tetrahydropyranyl group. Deprotection conditions to give intermediate (LXIX) can be carried out according to procedures known in the art.

Scheme 41

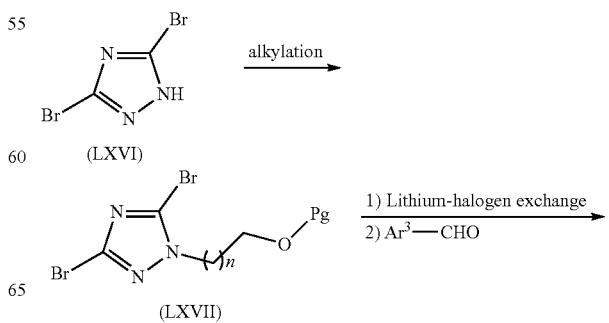

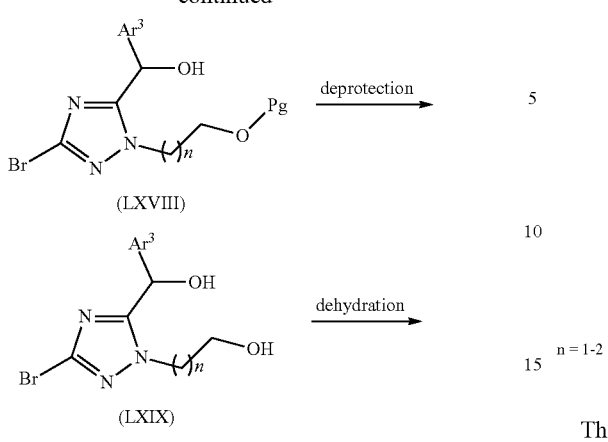

(LXVIII)

(LXIX)

(LXV)

Experimental Procedure 42

A compound of Formula (I), wherein $Het^1$ is restricted to heterocycles of formula (a), wherein $L^a$-$R^{5a}$ and $R^{4a}$ are taken together to form a bivalent radical as shown in scheme 42, wherein n being 1 or 2, and A being a direct bond, O or CR', wherein R' being H or $C_{1-4}$ alkyl, and wherein all other variables are defined as in compounds of Formula (I), hereby named compounds of Formula (I-b1), can be prepared via a condensation reaction of an intermediate of Formula (VII) with an intermediate of Formula (LXX). In Formula (LXX), HALO is defined as Cl, Br, I, preferably Cl, Br.

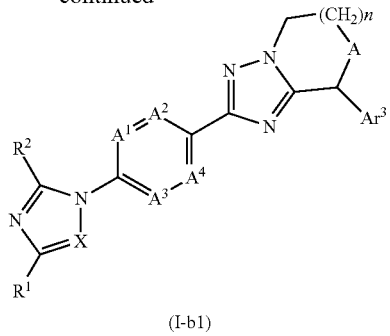

(I-b1)

n = 1-2

The reaction in Scheme 42 may be performed in the presence of a base such as imidazole, triethylamine ($Et_3N$), $K_2CO_3$ or NaOAc and in a solvent such as MeOH, EtOH, n-BuOH or dioxane. Stirring, elevated temperatures and/or pressure may enhance the rate of the reaction, which can be carried out in the microwave or by conventional oil-bath heating. Intermediates of formula (LXX) can be prepared starting from an intermediate of formula (LXXI), using procedures known in the art, for example as described in experimental procedure 6.

Experimental Procedure 43

Alternatively, a compound of Formula (I-b1), can be prepared via a condensation reaction of an intermediate of Formula (LXXII) with an intermediate of Formula (V-a). In Formula (LXXII), HALO is defined as Cl, Br, I, preferably Cl, Br.

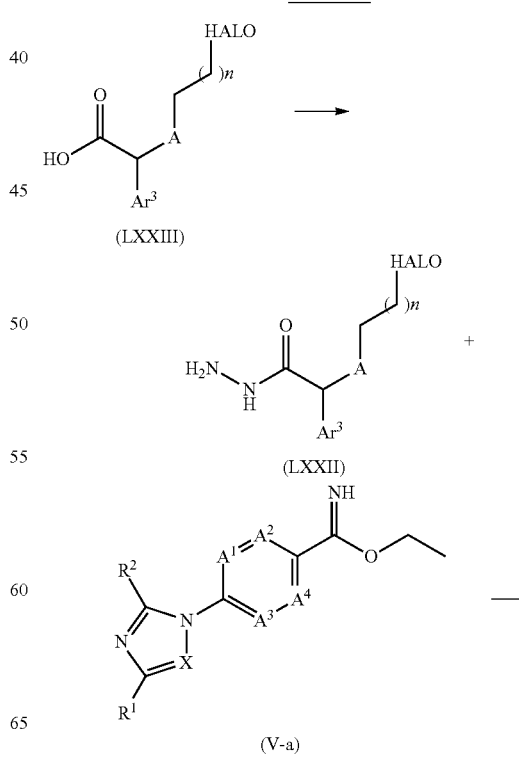

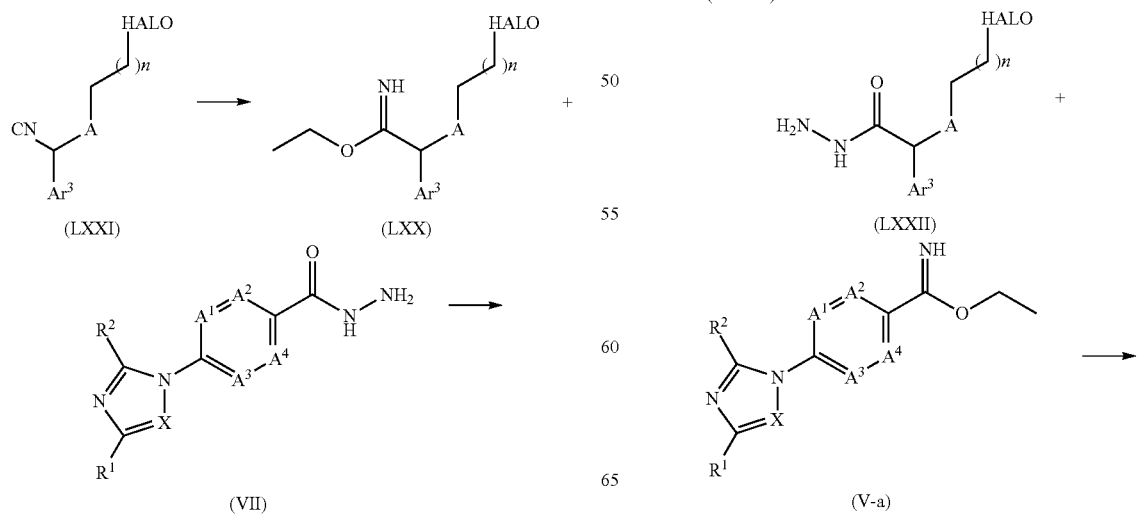

-continued

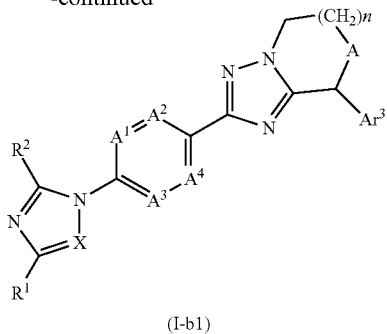

(I-b1)

n = 1-2

The reaction in Scheme 43 may be performed in the presence of a base such as imidazole, Et₃N, K₂CO₃ or NaOAc and in a solvent such as MeOH, EtOH, n-BuOH or dioxane. Stirring, elevated temperatures and/or pressure may enhance the rate of the reaction, which can be carried out in the microwave or by conventional oil-bath heating. Intermediates of formula (LXXII) can be prepared starting from an intermediate of formula (LXXIII), using procedures known in the art, for example as described in experimental procedure 8.

Experimental Procedure 44

A compound of Formula (I), wherein Het¹ is restricted to heterocycles of formula (a), wherein $L^a$-$R^{5a}$ and $R^{4a}$ are taken together to form a bivalent radical as shown in scheme 44, with n being 0, 1 or 2, and A being CH or N, and wherein all other variables are defined as in compounds of Formula (I), hereby named compounds of Formula (I-b2), can be prepared via a condensation reaction of an intermediate of Formula (LXXIV) with an intermediate of Formula (V-a).

Scheme 44

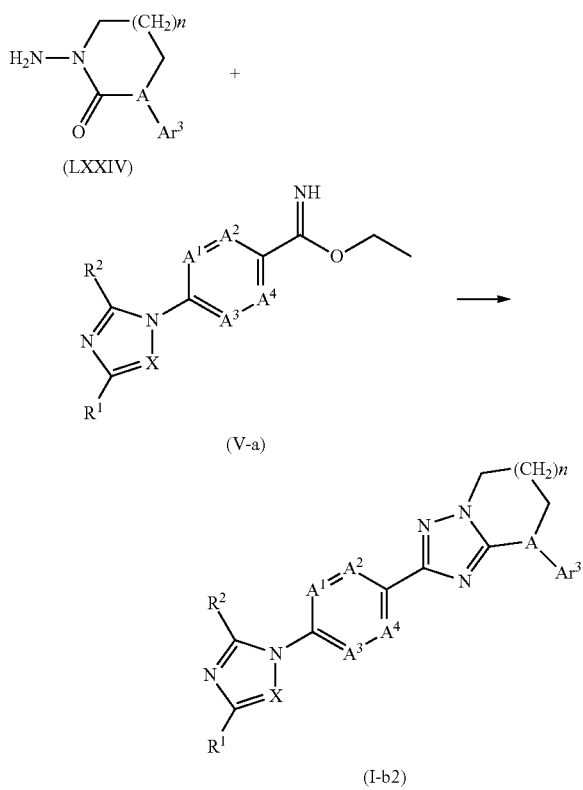

The reaction in Scheme 44 may be performed in the presence of a base such as K₂CO₃, imidazole, Et₃N or NaOAc and in a solvent such as MeOH, EtOH, n-BuOH or dioxane. Stirring, elevated temperatures and/or pressure may enhance the rate of the reaction, which can be carried out in the microwave or by conventional oil-bath heating.

Experimental Procedure 45

Alternatively, a compound of Formula (I-b2), can be prepared via an amide bond forming reaction between an intermediate of Formula (XIV-b) or (XXXVII) and an intermediate of Formula (LXXIV) to give an intermediate of Formula (LXXV), followed by treatment of (LXXV) with POCl₃ under elevated temperatures, ranging from 80° C. to reflux, and subsequent reaction in the presence of an ammonium source such as NH₄OAc in solvents such as AcOH. For the last reaction, typically elevated temperatures are used, for example 130-160° C., which can be carried out in the microwave or by conventional oil-bath heating.

Scheme 45

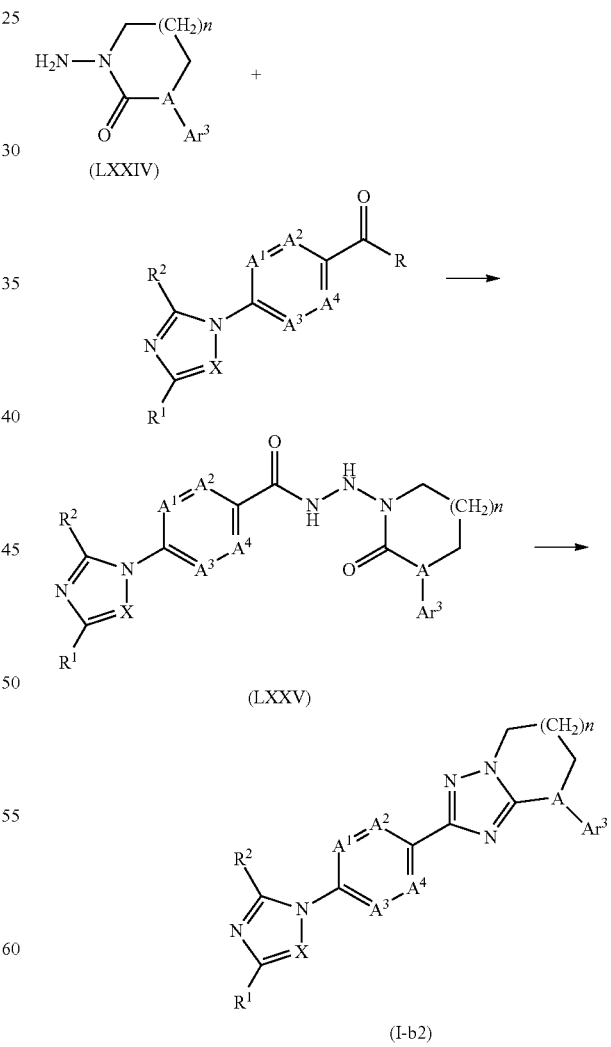

R = OH (XIV-b)
R = Cl (XXXVII)

Experimental Procedure 46

A compound of formula (I), wherein $Het^1$ is restricted to heterocycles of formula (a), wherein $L^a$-$R^{5a}$ and $R^{4a}$ are taken together to form a bivalent radical as shown in scheme 46, with n being 1 or 2, and A being a direct bond, O or CR', with R' being H or $C_{1-4}$ alkyl, wherein the stereochemistry of the indicated carbon atom has the S-configuration, and wherein all other variables are defined as in compounds of Formula (I), hereby named compounds of formula (I-b3), may be prepared via chiral separation of the corresponding racemic compound of formula (I-b1), using procedures known in the art. For example, preparative SFC can be used, using chiral columns such as Chiralpak Diacel OD or AD and mobile phases of $CO_2$, combined with $CH_3CN$ or MeOH with 0.2% 2-propylamine Evidently, also the corresponding R-enantiomers can be obtained via this procedure. The S-enantiomers are preferred.

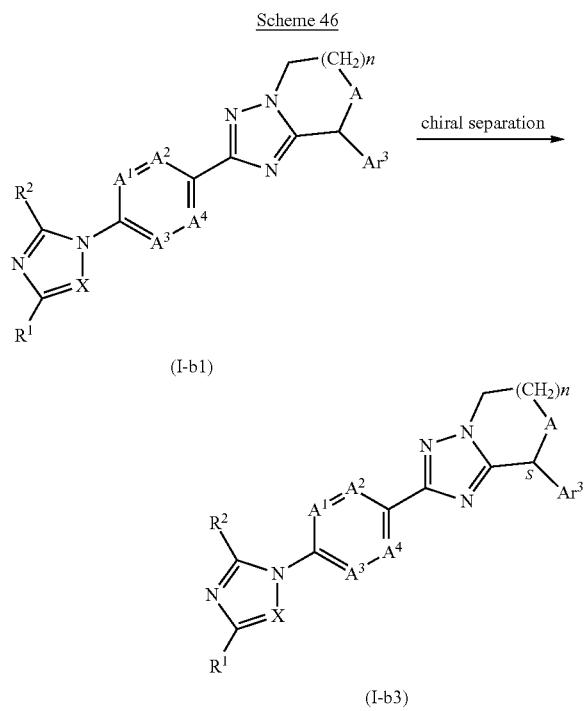

Scheme 46

Intermediates of formula (VI), (VIII), (IX), (XIII), (XVIII), (XIX), (XX), (XXII), (XXVI), (XXVIII), (XXXII), (XXXIV), (XXXVI), (XXXVIII), (XL), (XLII), (XLIV), (XLVII), (XLVIII), (L), (LII), (LVI), (LVII), (LIX), LX), (LXI), (LXII), (LXIV), (LXVI), LXXI), (LXXIII), (LXXIV) are commercially available or can be easily prepared by those skilled in the art.

Where necessary or desired, any one or more of the following further steps in any order may be performed:

Intermediates of formula (X), (XII), or (XLV) and compounds of formula (I), any subgroup thereof, addition salts, solvates, and stereochemical isomeric forms thereof can be converted into further intermediates and compounds according to the invention using procedures known in the art.

It will be appreciated by those skilled in the art that in the processes described above the functional groups of intermediate compounds may need to be blocked by protecting groups. In case the functional groups of intermediate compounds were blocked by protecting groups, they can be deprotected after a reaction step.

Pharmacology

It has been found that the compounds of the present invention modulate the γ-secretase activity. The compounds according to the invention and the pharmaceutically acceptable compositions thereof therefore may be useful in the treatment or prevention of AD, TBI, MCI, senility, dementia, dementia with Lewy bodies, cerebral amyloid angiopathy, multi-infarct dementia, Down's syndrome, dementia associated with Parkinson's disease, or dementia associated with beta-amyloid; preferably AD.

The compounds according to the present invention and the pharmaceutically acceptable compositions thereof may be useful in the treatment or prevention of a disease or condition selected from the group consisting of AD, TBI, MCI, senility, dementia, dementia with Lewy bodies, cerebral amyloid angiopathy, multi-infarct dementia, Down's syndrome, dementia associated with Parkinson's disease and dementia associated with beta-amyloid.

As used herein, the term "modulation of γ-secretase activity" refers to an effect on the processing of APP by the γ-secretase-complex. Preferably it refers to an effect in which the overall rate of processing of APP remains essentially as without the application of said compounds, but in which the relative quantities of the processed products are changed, more preferably in such a way that the amount of the Aβ42-peptide produced is reduced. For example a different Abeta species can be produced (e.g. Abeta-38 or other Abeta peptide species of shorter amino acid sequence instead of Abeta-42) or the relative quantities of the products are different (e.g. the ratio of Abeta-40 to Abeta-42 is changed, preferably increased).

It has been previously shown that the γ-secretase complex is also involved in the processing of the Notch-protein. Notch is a signaling protein which plays a crucial role in developmental processes (e.g. reviewed in Schweisguth F (2004) Curr. Biol. 14, R129). With respect to the use of γ-secretase modulators in therapy, it seems particularly advantageous not to interfere with the Notch-processing activity of the γ-secretase activity in order to avoid putative undesired side-effects. While γ-secretase inhibitors show side effects due to concomitant inhibition of Notch processing, γ-secretase modulators may have the advantage of selectively decreasing the production of highly aggregatable and neurotoxic forms of Aβ, i.e. Aβ42, without decreasing the production of smaller, less aggregatable forms of Aβ, i.e. Aβ38 and without concomitant inhibition of Notch processing. Thus, compounds are preferred which do not show an effect on the Notch-processing activity of the γ-secretase-complex.

As used herein, the term "treatment" is intended to refer to all processes, wherein there may be a slowing, interrupting, arresting, or stopping of the progression of a disease, but does not necessarily indicate a total elimination of all symptoms.

The invention relates to a compound according to the general Formula (I), the stereoisomeric forms thereof and the pharmaceutically acceptable acid or base addition salts and the solvates thereof, for use as a medicament.

The invention also relates to a compound according to the general Formula (I), the stereoisomeric forms thereof and the pharmaceutically acceptable acid or base addition salts and the solvates thereof, for use in the modulation of γ-secretase activity.

The invention also relates to a compound according to the general Formula (I), the stereoisomeric forms thereof and the pharmaceutically acceptable acid or base addition salts and the solvates thereof, for use in the treatment or prevention of diseases or conditions selected from the group consisting of AD, TBI, MCI, senility, dementia, dementia with Lewy bodies, cerebral amyloid angiopathy, multi-infarct dementia, Down's syndrome, dementia associated with Parkinson's disease and dementia associated with beta-amyloid.

In an embodiment, said disease or condition is preferably AD.

The invention also relates to a compound according to the general Formula (I), the stereoisomeric forms thereof and the pharmaceutically acceptable acid or base addition salts and the solvates thereof, for use in the treatment of said diseases.

The invention also relates to a compound according to the general Formula (I), the stereoisomeric forms thereof and the pharmaceutically acceptable acid or base addition salts and the solvates thereof, for the treatment or prevention of said diseases.

The invention also relates to a compound according to the general formula (I), the stereoisomeric forms thereof and the pharmaceutically acceptable acid or base addition salts and the solvates thereof, for the treatment or prevention, in particular treatment, of γ-secretase mediated diseases or conditions.

The invention also relates to the use of a compound according to the general Formula (I), the stereoisomeric forms thereof and the pharmaceutically acceptable acid or base addition salts and the solvates thereof, for the manufacture of a medicament.

The invention also relates to the use of a compound according to the general Formula (I), the stereoisomeric forms thereof and the pharmaceutically acceptable acid or base addition salts and the solvates thereof, for the manufacture of a medicament for the modulation of γ-secretase activity.

The invention also relates to the use of a compound according to the general Formula (I), the stereoisomeric forms thereof and the pharmaceutically acceptable acid or base addition salts and the solvates thereof, for the manufacture of a medicament for the treatment or prevention of any one of the disease conditions mentioned hereinbefore.

The invention also relates to the use of a compound according to the general Formula (I), the stereoisomeric forms thereof and the pharmaceutically acceptable acid or base addition salts and the solvates thereof, for the manufacture of a medicament for the treatment of any one of the disease conditions mentioned hereinbefore.

In the invention, particular preference is given to compounds of Formula (I), or any subgroup thereof with a $IC_{50}$ value for the inhibition of the production of Aβ42-peptide of less than 1000 nM, preferably less than 100 nM, more preferably less than 50 nM, even more preferably less than 20 nM as determined by a suitable assay, such as the assay used in the Examples below.

The compounds of the present invention can be administered to mammals, preferably humans for the treatment or prevention of any one of the diseases mentioned hereinbefore.

In view of the utility of the compound of Formula (I), there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I), a stereoisomeric form thereof and a pharmaceutically acceptable addition salt or solvate thereof, to warm-blooded animals, including humans.

The present invention also concerns to the use of a compound of Formula (I) for the modulation of γ-secretase activity resulting in a decrease in the relative amount of Aβ42-peptides produced.

An advantage of the compounds or a part of the compounds of the present invention may be their enhanced CNS-penetration.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent AD or the symptoms thereof, may be administered alone or in combination with one or more additional therapeutic agents. Combination therapy includes administration of a single pharmaceutical dosage formulation which contains a compound of Formula (I) and one or more additional therapeutic agents, as well as administration of the compound of Formula (I) and each additional therapeutic agents in its own separate pharmaceutical dosage formulation. For example, a compound of Formula (I) and a therapeutic agent may be administered to the patient together in a single oral dosage composition such as a tablet or capsule, or each agent may be administered in separate oral dosage formulations.

While it is possible for the active ingredient to be administered alone, it is preferable to present it as a pharmaceutical composition.

Accordingly, the present invention further provides a pharmaceutical composition comprising a pharmaceutically acceptable carrier and, as active ingredient, a therapeutically effective amount of a compound according to Formula (I).

The carrier or diluent must be "acceptable" in the sense of being compatible with the other ingredients of the composition and not deleterious to the recipients thereof.

For ease of administration, the subject compounds may be formulated into various pharmaceutical forms for administration purposes. The compounds according to the invention, in particular the compounds according to Formula (I), a pharmaceutically acceptable acid or base addition salt thereof, a stereochemically isomeric form thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing compounds of Formula (I) may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally administrable compounds, pharmaceutical compositions comprising said compounds for administration orally are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-3-cyclodextrin or sulfobutyl-3-cyclodextrin. Also co-solvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the compound of formula (I), and, from 1 to 99.95% by weight, more preferably from 30 to 99.9% by weight, even more preferably from 50 to 99.9% by weight of a pharmaceutically acceptable carrier, all percentages being based on the total weight of the composition.

The following examples illustrate the present invention.

EXAMPLES

Hereinafter, the term "DCM" means dichloromethane; "MeOH" means methanol; "EtOH" means ethanol; "n-BuOH" means N-butanol; "MeCN" means acetonitrile; "THF" means tetrahydrofuran; "HPLC" means high-performance liquid chromatography; "sol." means solution; "sat." means saturated; "aq." means aqueous; "r.t." means room temperature; "o.l." means organic layer(s); "AcOH" means acetic acid; "RP" means reversed phase; "NaBH(OAc)$_3$" means sodium triacetoxyborohydride; "SFC" means Supercritical Fluid Chromatography; "min" means minute(s); "conc." means concentrated; "h" means hour(s); "q.s." means quantum sufficit; "I.D." means internal diameter; "KOAc" means potassium acetate; "NH$_4$OAc" means ammonium acetate; "NH$_4$SCN" means ammonium thiocyanate; "Et$_2$O" means diethyl ether; "DCE" means 1,2-dichloroethane; "DMA" means N,N-dimethylacetamide; "LiHMDS" means lithium hexamethyldisilazane; "MeI" means methyl iodide; "EtOAc" means ethyl acetate; "NaOAc" means sodium acetate; "Et$_3$N" means triethylamine; "DIPEA" means diisopropylethylamine; "eq" means equivalent; "r.m." means reaction mixture(s); "DIPE" means diisopropyl ether; "DME" means dimethoxyethane; "DMSO" means dimethyl sulfoxide; "DMF" means N,N-dimethyl formamide; "Pd(OAc)" means palladium(II) acetate; "PdCl$_2$(dppf)" means [1,1'-bis(diphenyl-phosphino-κP)ferrocene]dichloropalladium(II); "Pd(PPh$_3$)$_4$" means tetrakis(triphenyl-phosphine)palladium; "Xantphos" means (9,9-dimethyl-9H-xanthene-4,5-diyl) bis [diphenylphosphine]. "X-Phos" means dicyclohexyl[2',4',6'-tris(1-methylethyl)[1,1'-biphenyl]-2-yl]-phosphine; "Pd$_2$(dba)$_3$" means tris(dibenzylideneacetone)dipalladium; "Grubbs second generation catalyst" means (1,3-dimesityl-imidazolidin-2-ylidene)(tricyclohexylphosphine)benzylidene ruthenium dichloride; "Tebbes reagent" means μ-chlorobis(η5-2,4-cyclopentadien-1-yl)(dimethylaluminum)-μ-methylene-titanium; "Dess-Martin periodinane" means 1,1,1-tris(acetyloxy)-1,1-dihydro-1,2-benziodoxol-3 (1H)-one; and "iPrOH" means 2-propanol.

In order to obtain the HCl salt forms of some of the final compounds, several procedures known to those skilled in the art were used. In a typical procedure, for example, the crude residue (free base) was dissolved in DIPE or Et$_2$O, and a 6 N HCl sol. in iPrOH or a 1 N HCl sol. in Et$_2$O was added dropwise. The mixture was stirred for 10 min and the product was filtered off. The HCl salt was dried in vacuo.

The absolute stereochemical configuration for some of the compounds was determined using vibrational circular dichroism (VCD). A description on the use of VCD for the determination of absolute configuration can be found in Dyatkin A. B. et. al, *Chirality*, 14:215-219 (2002).

A. Preparation of the Intermediates

Example A1 a) Preparation of Intermediate 1

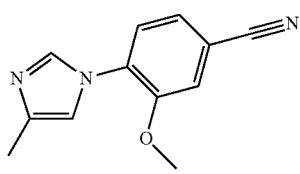

K₂CO₃ (112 g, 0.81 mol) was added to a stirred sol. of 4-methylimidazole (66.0 g, 0.804 mol) in DMSO (600 ml). The r.m. was heated at 120° C. Subsequently 4-fluoro-3-methoxybenzonitrile (60.0 g, 0.397 mol) was added portionwise (internal reaction temperature increased to 140° C.). The r.m. was maintained at 120° C. for 1 h, was cooled, and was then poured onto ice-water (3 l). This mixture was stirred for 30 min. The precipitated solid was collected by filtration and washed with H₂O. The off-white solid was recrystallised from MeCN to yield 30.0 g of intermediate 1. A second crop of product was obtained from the mother liquor. Yield: 12.3 g of intermediate 1 (combined yield; 49.9%).

b) Preparation of Intermediate 2 and 2a

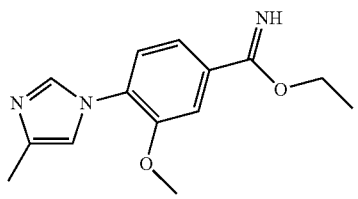

2: •2HCl salt
2a: free base

A stirred sol. of intermediate 1 (1.40 g, 6.57 mmol) in anhydrous EtOH (1.4 ml) and Et₂O (28 ml) was cooled at 0° C. HCl gas was bubbled through the contents for 20 min, then the ensuing r.m. left to stir overnight at r.t. The precipitated product was collected by filtration and dried to give the HCl salt of the desired product as an off-white solid. Yield: 1.72 g of intermediate 2 (78.9%). Intermediate 2 was used as such in the next reaction step, or was converted into the free base by dissolving it in water, basifying the solution via addition of Na₂CO₃, and extraction of the resulting suspension with DCM. The organic layer was dried (MgSO₄), filtered and conc. in vacuo to yield intermediate 2a (quantitative yield).

Example A2 a) Preparation of Intermediate 3

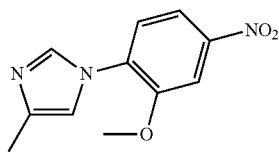

(NOTE: this reaction was carried out in 4 batches of 50 g of 2-fluoro-5-nitroanisole). A mixture of 2-fluoro-5-nitroanisole (200 g, 1.17 mol), 4-methyl-1H-imidazole (143.9 g, 1.75 mol) and K₂CO₃ (161.5 g, 1.17 mol) in DMSO (600 ml) was prepared in a stainless steel autoclave under a N₂ atmosphere. The vessel was closed and the r.m. heated at 125° C. for 16 h. The contents were allowed to cool and the solvent was evaporated under reduced pressure. H₂O (q.s.) was added to the residue and the precipitated product was collected by filtration. This solid was then triturated with DIPE and collected by filtration to yield a light-brown solid. Yield: 215 g of intermediate 3 (78.9%).

b) Preparation of Intermediate 4

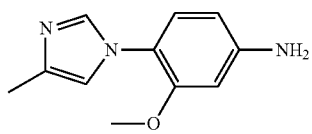

Intermediate 3 (215 g) was added to a stirred mixture of 10% Pd/C (10 g) and a 4% thiophene sol. in MeOH (700 ml). The ensuing r.m. was heated at 50° C. under a H₂ atmosphere. After 3 eq. of H₂ were absorbed, the catalyst was removed by filtration over diatomaceous earth. The filtrate was evaporated under reduced pressure and the crude product was purified by column chromatography on silica gel (eluent: 10:90 MeOH/DCM). The product fractions were combined and evaporated to yield a light-brown solid. Yield: 180 g of intermediate 4 (96.1%).

c) Preparation of Intermediate 5

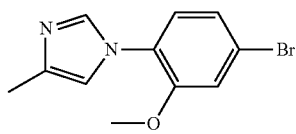

A stirred sol. of NaNO₂ (7.47 g, 108 mmol) in conc. H₂SO₄ (160 ml) was cooled to 10° C. A sol. of intermediate 4 (20.0 g, 98.4 mmol) in AcOH (200 ml) was added at such a rate that the temperature of the r.m. was maintained below 10° C. After addition was completed, the ensuing r.m. was stirred at r.t. for 30 min. This sol. was added, dropwise, to a stirred sol. of CuBr (28.2 g, 196.8 mmol) in 48% HBr (200 ml) at r.t. The ensuing r.m. was stirred for 1 h, then diluted with 1 l ice/H₂O. The resulting white precipitate was collected by filtration and washed with H₂O. (The mother liquor was treated as described below). The solid was then suspended in DCM/sat. aq. Na₂CO₃ sol. and the resulting slurry filtered over dicalite. The o.l. of the filtrate was washed with diluted NH₄OH until the disappearance of blue colour. The organic phase was dried (MgSO₄), filtered and evaporated to give a brown solid. The mother liquor was basified with solid Na₂CO₃, then extracted with DCM. The combined organic extracts were washed with diluted NH₄OH until the disappearance of blue colour. The organic phase was dried (MgSO₄), filtered and evaporated to give a brown solid which was combined with the previously obtained solid. Yield: 24.0 g of intermediate 5 (91.3%).

d) Preparation of Intermediate 6

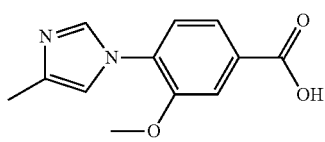

A mixture of intermediate 5 (24.0 g, 89.8 mmol), Pd(OAc)₂ (403 mg, 1.80 mmol) and 1,3-bis(diphenylphosphino)propane (1.48 g, 3.59 mmol) in THF/H₂O (300 ml/3 ml) was prepared in a stainless steel autoclave under a N₂ atmosphere. The vessel was closed and pressurized to 20 bar CO (gas). This r.m. was heated at 150° C. for 24 h. The cooled r.m. was evaporated under reduced pressure, then acidified with 30% aq. AcOH sol. Et₂O was added and the resulting mixture was evaporated until crystallization occurred. The light-brown crystals were collected by filtration. Yield: 18.1 g of intermediate 6 (86.7%).

e) Preparation of Intermediate 7

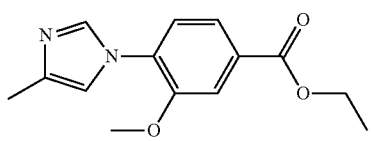

Intermediate 6 was converted to the corresponding HCl salt by addition of HCl in dioxane to a stirred sol. of intermediate 6 (5.00 g, 21.5 mmol) in 1,4-dioxane. The r.m. was stirred for 30 min at r.t. and was then evaporated under reduced pressure to yield the HCl salt. A stirred sol. of this salt in oxalyl chloride (5.47 g, 43.1 mmol), DMF (5 ml) and DCM (300 ml) was refluxed for 1 h (additional oxalyl chloride (q.s.) and DMF (q.s.) was required to complete reaction). The cooled r.m. was evaporated under reduced pressure and co-evaporated with toluene. The resulting solid was cooled on ice, EtOH (200 ml) was added and the ensuing mixture was left stirring overnight at r.t. The r.m. was evaporated under reduced pressure and the resulting residue taken up in DCM then washed with sat. aq. NaHCO₃. The organic extract was dried (MgSO₄), filtered and evaporated. The crude product was purified by column chromatography on silica gel (eluent: 98:2 to 92:8 DCM/EtOH, gradient elution). The product fractions were collected and evaporated and the resulting material crystallized in DIPE yielding the desired product. Yield: 5.00 g of intermediate 7 (89.2%).

f) Preparation of Intermediate 8

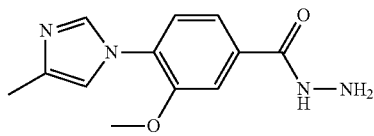

A mixture of intermediate 7 (6.35 g, 24.4 mmol) and hydrazine hydrate (4.88 g, 97.6 mmol) in EtOH (40 ml) was reacted in a stainless steel autoclave under an atmosphere of N₂. The vessel was closed and the r.m. was heated at 130° C. for 32 h. The cooled r.m. was evaporated under reduced pressure and co-evaporated with xylene. The resulting residue was crystallized from Et₂O and the crystals collected by filtration to yield the desired product. Yield: 5.97 g of intermediate 8 (99.4%).

Example A3 a) Preparation of Intermediate 9

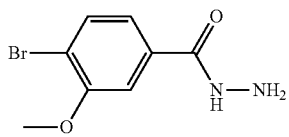

A mixture of methyl 4-bromo-3-methoxybenzoate (11.0 g, 44.9 mmol) and hydrazine hydrate (13.6 ml, 180 mmol) in EtOH (250 ml) was prepared in a stainless steel autoclave under an atmosphere of N₂. The vessel was closed and the r.m. was heated at 125° C. for 16 h. The cooled r.m. was conc. under reduced pressure and the precipitated product collected by filtration to yield the desired product as a dark-grey solid. Yield: 6.18 g of intermediate 9 (56.2%).

b) Preparation of Intermediate 10

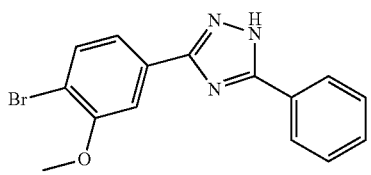

A mixture of intermediate 9 (1.23 g, 5.00 mmol), benzonitrile (1.55 g, 15.0 mmol) and K₂CO₃ (345 mg, 2.50 mmol) in n-BuOH (15 ml) was heated under microwave irradiation at 150° C. for 3 h. The solvent was removed under reduced pressure and the resulting residue partitioned between EtOAc/H₂O and the phases were separated. The aq. phase was extracted with EtOAc and the combined organic extracts washed with brine and then dried (MgSO$_4$). Filtration and concentration under reduced pressure yielded the desired product. Yield: 728 mg of intermediate 10 (44.1%).

c) Preparation of Intermediate 11 and Intermediate 11a

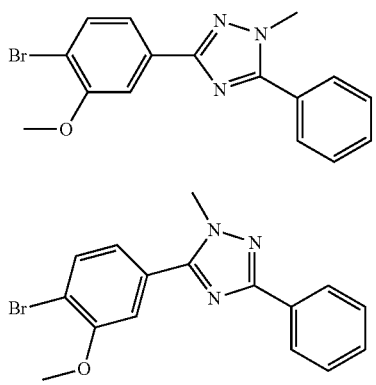

NaH (60% in mineral oil, 176 mg, 4.41 mmol) was added to an ice-cooled, stirred sol. of intermediate 10 (728 mg, 2.2 mmol) in anhydrous THF (10 ml) under an atmosphere of N$_2$. MeI (206 μl, 3.31 mmol) was then added, followed by DMF (15 ml). The r.m. was stirred at 60° C. for 0.5 h. The reaction was quenched by the addition of MeOH (20 ml), and then the solvents were removed under reduced pressure. The resulting residue was partitioned between EtOAc/H$_2$O and the phases were separated. The aq. phase was extracted with DCM, and the combined organic extracts were washed with brine and dried (MgSO$_4$). Filtration and concentration under reduced pressure gave a residue which was purified by flash chromatography over silica gel (eluent: 100:0 to 90:10 DCM/MeOH, gradient elution). The product fractions were collected and evaporated. Yield: 0.45 g as a mixture of intermediates 11 and 11a, which was used as such in the next reaction step.

Example A4 a) Preparation of Intermediate 12

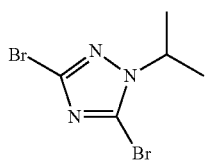

NaH (5.29 g, 132 mmol) was added to a stirred sol. of 3,5-dibromotriazole (20.0 g, 88.2 mmol) in DMF under an atmosphere of N$_2$ at r.t. After 30 min, 2-iodopropane (10.6 ml, 106 mmol) was added slowly and the r.m. was heated at 40° C. for 2-3 h. The mixture was carefully poured onto ice/H$_2$O (1 l) and extracted with DIPE. The combined organic extracts were washed with H$_2$O (4×200 ml), with brine and then dried (Na$_2$SO$_4$). Filtration and concentration under reduced pressure gave a yellow oil. Yield: 16.5 g of intermediate 12 (69.5%).

b) Preparation of Intermediate 13

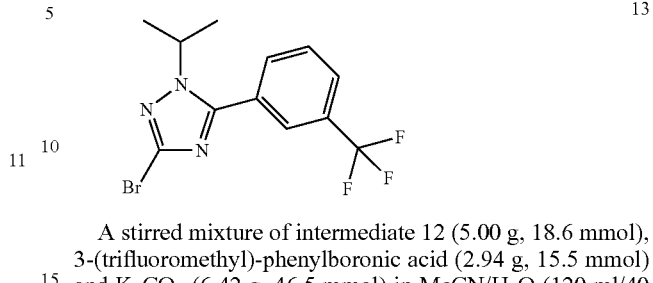

A stirred mixture of intermediate 12 (5.00 g, 18.6 mmol), 3-(trifluoromethyl)-phenylboronic acid (2.94 g, 15.5 mmol) and K$_2$CO$_3$ (6.42 g, 46.5 mmol) in MeCN/H$_2$O (120 ml/40 ml) was flushed with N$_2$ for 10 min. PdCl$_2$(dppf) (1.16 g, 1.55 mmol) was added and the vessel was sealed. The r.m. was stirred overnight at 40° C. The solvent was then evaporated and the residue partitioned between DCM/H$_2$O and the phases were separated. The aq. phase was extracted with DCM and the combined organic extracts were washed with brine and then dried (Na$_2$SO$_4$). Filtration and concentration gave the crude material as a dark-brown oil. This material was purified by flash chromatography over silicagel (eluent, 90:10 to 50:50 heptane/EtOAc, gradient elution). The product fractions were combined and evaporated. Yield: 1.59 g of intermediate 13 (30.7%).

Example A5

Preparation of Intermediate 14

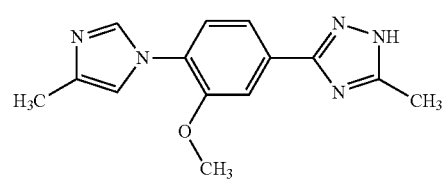

A mixture of intermediate 8 (246 mg, 1 mmol), K$_2$CO$_3$ (138 mg, 1 mmol) and CH$_3$CN (410 mg, 10 mmol) in n-BuOH (15 ml) was heated at 150° C. in a sealed tube for 3 h. The r.m. was cooled, and the mixture was partitioned between EtOAc and H$_2$O. The o.l. was washed with brine, dried (MgSO$_4$), filtered and then conc. under reduced pressure. The residue was triturated with DIPE and dried in vacuo. Yield: 150 mg of intermediate 14 (56%).

Example A6 a) Preparation of Intermediate 15

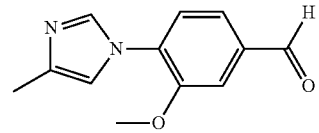

A mixture of K$_2$CO$_3$ (16.8 g, 122 mmol), 4-fluoro-3-methoxy-benzaldehyde (10 g, 65 mmol), and 4-methylimidazole (10.6 g, 129 mmol) in DMF (150 ml) was heated at 80° C. for 3 days. The r.m. was allowed to cool, the solids were filtered off, and the filtrate was partitioned between EtOAc and brine. The o.l. was separated, dried (MgSO$_4$), filtered and then conc.

The residue was purified by flash chromatography over silicagel (eluent: 99:1 to 96:4 DCM/MeOH, gradient elution). The product fractions were evaporated. Yield: 2.32 g of intermediate 15 (17%).

Example A1a a) Preparation of Intermediate 16

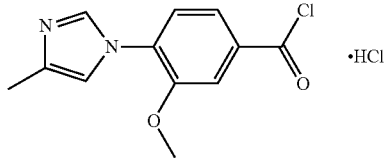

16

A mixture of intermediate 6 (3.24 g, 12 mmol), oxalyl chloride (1.68 g, 13 mmol) and DMF (5 ml) in DCM (300 ml) was stirred and heated at reflux temperature for 1 h. The r.m. was then conc., and co-evaporated with toluene. The residue was used as such in the next reaction step. Yield: 3.5 g (quantitative) of intermediate 16.

b) Preparation of Intermediate 17

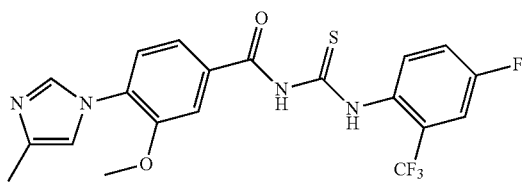

17

Intermediate 16 (3.5 g, 12 mmol) was added to a stirred mixture of NH$_4$SCN (1.06 g, 14 mmol) in acetone (300 ml). The r.m. was stirred at r.t. and another portion of NH$_4$SCN (3.18 g, 42 mmol) was added. The r.m. was stirred at r.t. for 2 h., and was then cooled to 0° C. 4-Fluoro-2-trifluoromethylaniline (2.18 g, 12 mmol) was added dropwise and the r.m. was then stirred overnight at r.t. The r.m. was poured on ice and an aq. sat. NaHCO$_3$ sol. was added until basic pH (~8). The resulting precipitate was filtered off and dried. Yield: 3.59 g of intermediate 17 (65%).

c) Preparation of Intermediate 18

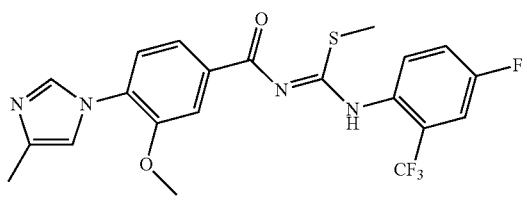

18

K$_2$CO$_3$ (1.1 g, 8 mmol) was added to a stirred sol. of intermediate 17 (3.59 g, 7.9 mmol) in acetone (100 ml). The r.m. was stirred at r.t. for 0.5 h., then CH$_3$I (1.13 g, 7.9 mmol) was added and the r.m. was stirred again at r.t. for 0.5 h. The r.m. was poured on ice. The resulting precipitate was filtered off and dried. Yield: 3.7 g of intermediate 18 (approximately 100%).

Example A7b

Preparation of Intermediate 19

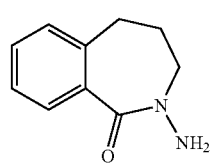

19

NaH (60% in mineral oil, 48 mg, 2.0 mmol) was added to a sol. of 2,3,4,5-tetrahydro-1H-2-benzazepin-1-one (161 mg, 1.0 mmol) in THF (10 ml) and DMF (10 ml). The mixture was stirred at r.t. for 15 min., and then a sol. of hydroxylamine-O-sulfonic acid (226 mg, 2.0 mmol) in DMF (10 ml) was added at r.t. The r.m. was stirred at r.t. for 1 h, and the mixture was partioned between THF and brine. The o.l. was dried (MgSO$_4$), filtered, and conc. under reduced pressure. The residue was used as such in the next reaction step. Yield: 440 mg of crude intermediate 19.

Example A8 a) Preparation of Intermediate 20

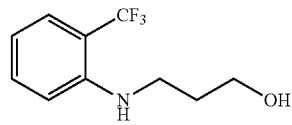

20

3-Bromo-1-propanol (12.9 g, 93 mmol), DIPEA (9.42 g, 93 mmol), and a catalytic amount of KI were added to a sol. of 2-trifluomethylaniline (15 g, 93 mmol) in isobutyronitrile (100 ml). The r.m. was heated at reflux for 16 h, then cooled, and the solvents removed under reduced pressure. The residue was partitioned between DCM and a sat. aq. NaHCO$_3$ sol. The o.l. was separated, dried (MgSO$_4$), filtered, and conc. under reduced pressure. The residue was purified by flash chromatography over silicagel (eluent heptanes/EtOAc 80/20 to 20/80). The product fractions were combined and evaporated. Yield: 11 g of intermediate 20 (54%).

b) Preparation of Intermediate 21

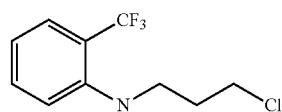

21

SOCl$_2$ (22.3 ml, 306 mmol) was added to a sol. of intermediate 20 (11 g, 50 mmol) in toluene (100 ml). The r.m. was heated at 60° C. for 5 h, then cooled, and the solvents removed under reduced pressure. The residue was partitioned between EtOAc (200 ml) and a sat. aq. NaHCO$_3$ sol. The o.l. was separated, dried (MgSO$_4$), and filtered. Heptane (100 ml) was added to the filtrate and the mixture was filtered over a silicagel pad (eluent heptanes/EtOAc 1/2). The product fractions were combined and evaporated. Yield: 11 g of intermediate 21 (92%).

c) Preparation of Intermediate 22

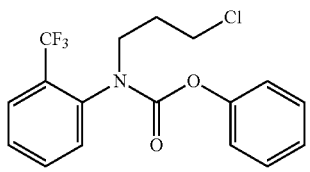

22

Phenyl chloroformate (7.9 g, 50 mmol) was added to a sol. of intermediate 21 (8 g, 33.7 mmol) in THF (160 ml). The r.m. was cooled to ~0° C., and then pyridine (8 g, 101 mmol) was added dropwise. The r.m. was allowed to warm to r.t., stirred at r.t. for 2 h, and then heated at reflux temperature for 16 h. The r.m. was cooled to r.t., and the mixture was partitioned between EtOAc and H$_2$O. The o.l. was separated, dried (MgSO$_4$), filtered, and conc. under reduced pressure. The residue was purified by flash chromatography over silicagel (eluent heptanes/EtOAc 90/10 to 33/67). The product fractions were combined and evaporated. Yield: 12 g of intermediate 22 (82%; crude used as such in the next reaction step).

d) Preparation of Intermediate 23

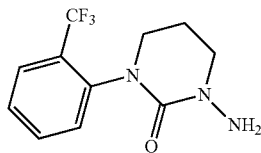

23

Hydrazine hydrate (20 ml, 415 mmol) was added dropwise to a sol. of intermediate 22 (12 g, approximately 28 mmol) in iPrOH (100 ml). The r.m. was heated at reflux temperature for 16 h, cooled and then conc. under reduced pressure. The residue was partitioned between DCM and a sat. aq. NaHCO$_3$ sol. The o.l. was separated, dried (MgSO$_4$), filtered and then conc. under reduced pressure. The residue was purified by flash chromatography over silicagel (eluent DCM/MeOH 95/5). The product fractions were combined and evaporated. Yield: 6.75 g of intermediate 23 (93%).

e) Preparation of Intermediate 24

24

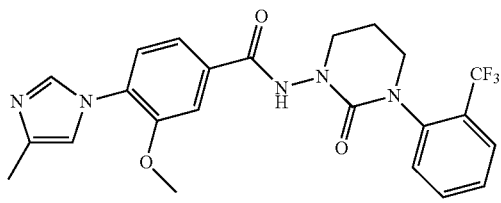

Bis(2-oxo-3-oxazolidinyl)phosphinic chloride (493 mg, 1.94 mmol) was added to a sol. of intermediate 23 (502 mg, 1.94 mmol), intermediate 6 (300 mg, 1.29 mmol), and Et$_3$N (359 µl, 2.58 mmol) in DMF (15 ml). The r.m. was stirred overnight at r.t., and then conc. under reduced pressure. The residue was partitioned between EtOAc and H$_2$O. The o.l. was washed with brine, dried (MgSO$_4$), filtered, and conc. under reduced pressure. The residue was purified by flash chromatography over silicagel (eluent DCM/MeOH(NH$_3$) 100/0 to 95/5). The product fractions were combined and evaporated. Yield: 582 mg of intermediate 24.

Example A9

Preparation of Intermediate 25

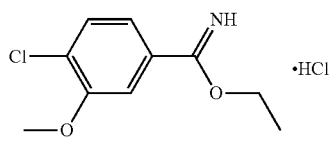

25

A stirred sol. of 4-chloro-3-methoxy-benzonitrile (0.9 g, 5.37 mmol) in anhydrous EtOH (0.8 ml) and Et$_2$O (25 ml) was cooled at ~0° C. HCl gas was bubbled through the sol. for 20 min., and then the r.m. was left stirring overnight at r.t. The precipitated product was collected by filtration and dried to Yield the HCl salt of the desired product as an off-white solid. Yield: 807 mg of intermediate 25 (60%).

Example A10 a) Preparation of Intermediate 26

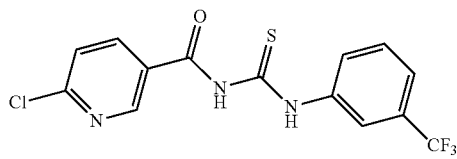

26

6-Chloro-3-pyridylcarbonyl chloride hydrochloride (17 g, 80 mmol) was added to a stirred mixture of NH$_4$SCN (6.64 g, 87.3 mmol) in acetone (150 ml). The r.m. was stirred at r.t. for 0.5 h. and then cooled to 0° C. 3-Trifluoromethyl-aniline (9 ml, 72.7 mmol) was added dropwise and the r.m. was stirred at r.t. for 1 h. Subsequently, 2 additional portions 3-trifluoromethyl-aniline (2×2 ml) were added and the mixture was stirred at r.t. An aq. sat. NaHCO$_3$ sol. was added followed by H$_2$O. The mixture was extracted with EtOAc and the o.l. was dried (MgSO$_4$), filtered and conc. under reduced pressure to form a precipitate which was collected by filtration. Yield: 12.8 g of intermediate 26. The filtrate was conc. further and the residue was recrystallized from iPrOH to provide another 8.96 g of intermediate 26. (combined yield 76%).

b) Preparation of Intermediate 27

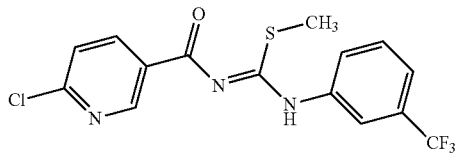

NaH (60% in mineral oil, 2.87 g, 71.7 mmol) was added to a stirred sol. of intermediate 26 (21.5 g, 59.8 mmol) in THF (500 ml). The r.m. was stirred at r.t. for 0.5 h, then MeI (8.5 g, 59.8 mmol) was added and the r.m. was stirred again at r.t. for 3 h. The r.m. was quenched with H$_2$O, and the THF was removed under reduced pressure. The resulting precipitate was filtered off and washed with H$_2$O. The filtrate was sat. with NH$_4$Cl and extracted with EtOAc. The o.l. was dried (MgSO$_4$), filtered and conc. under reduced pressure. The residue was combined with the first precipitate and recrystallized from DIPE. Yield: 16.6 g of intermediate 27 (74%).

c) Preparation of Intermediate 28

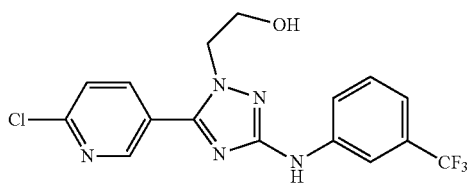

A mixture of intermediate 27 (5 g, 13.4 mmol), N-(2-hydroxyethyl)hydrazine (1.22 g, 16 mmol) in 2-methyl-2-propanol (100 ml) was stirred and heated at reflux for 2 h. The r.m. was slowly cooled to r.t. and the resulting precipitate was filtered off and dried. Yield: 2.58 g of intermediate 28 (50%).

Example A11

Preparation of Intermediates 29 and 30

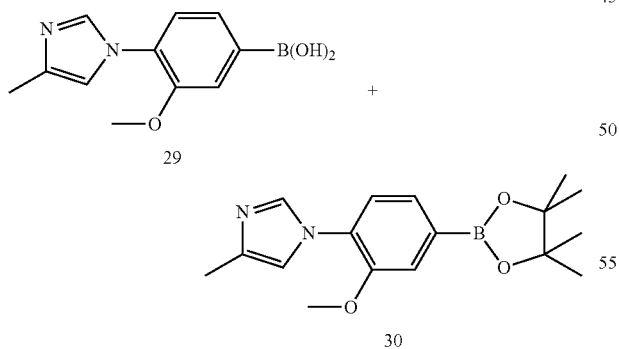

Bis(pinacolato)diboron (481 mg, 1.89 mmol), PdCl$_2$(dppf) (281 mg, 0.344 mmol), and KOAc (507 mg, 5.17 mmol) were added to a solution of intermediate 5 (460 mg, 1.72 mmol) in DMF (5 ml). The r.m. was heated at 120° C. for 30 min, and was then cooled to r.t. H$_2$O and EtOAc were added and the resulting mixture was filtered over diatomaceous earth. The layers were separated and the o.l. was dried (MgSO$_4$), filtered, and conc. under reduced pressure. The crude residue, mainly a mixture of intermediates 29 and 30 (660 mg) with intermediate 30 as the major component, was used as such in the subsequent reaction steps.

Example A12 a) Preparation of Intermediate 31

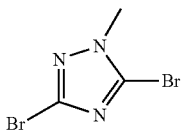

K$_2$CO$_3$ (182.5 g, 1322 mmol) was added to a stirred sol. of 3,5-dibromotriazole (150 g, 661.2 mmol) in DMF (1 l) under an atmosphere of N$_2$ at r.t. MeI (53.5 ml, 859.6 mmol) was added dropwise (slowly). The temperature was kept below 30° C. with an ice-bath. The r.m. was stirred ar r.t. for 2 h and then carefully poured onto ice/H$_2$O (5 l) and extracted with EtOAc (2×1.5 l). The combined o.l. were conc. under reduced pressure to complete dryness. The residue was suspended in H$_2$O and a white crystalline precipitate was formed, filtered off and dried under vacuum at 45° C. Yield: 130 g of intermediate 31 (81.6%).

b) Preparation of Intermediate 32

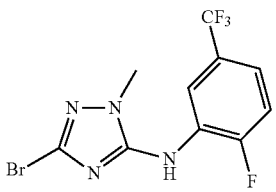

LiHMDS (1 M in THF, 420 ml, 420 mmol) was added dropwise to a cooled (ice-bath) sol. of 3-amino-4-fluorobenzotrifluoride (70 ml, 527.8 mmol) and intermediate 31 (50 g, 207.6 mmol) in dry THF (500 ml). The r.m. was stirred ar r.t. for 20 h. A sat. aq. NH$_4$Cl sol. was added slowly. The r.m. was extracted with DCM and the o.l. was washed with brine, dried (MgSO$_4$) and conc. under reduced pressure. The resulting slurry was triturated in heptane/DIPE and a solid was formed, filtered off and dried under vacuum at 60° C. Yield: 55 g of intermediate 32 (78.1%).

Example A13

Preparation of Intermediate 33

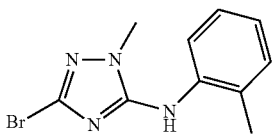

LiHMDS (1 M in THF, 421 ml, 421 mmol) was added dropwise to a cooled (ice bath) sol. of 2-methylaniline (47.3 ml, 437 mmol) and intermediate 31 (52.6 g, 218.4 mmol) in dry THF (526 ml). The r.m. was stirred at r.t. for 30 min. A sat. aq. NH$_4$Cl sol. was added slowly. The r.m. was extracted (DCM) and the o.l. was washed with brine, dried (MgSO$_4$)

and conc. The resulting slurry was triturated in DIPE and a solid was formed, filtered off and dried in vacuo at 60° C. Yield: 48 g of intermediate 33 (82.3%).

Example A14 a) Preparation of Intermediate 34

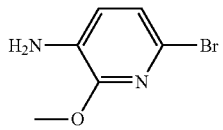

34

Sodium methoxide (176.2 g, 3.26 mol) was added in portions to a sol. of 3-amino-2,6-dibromopyridine (100 g, 939 mmol) in 1,4-dioxane (1 l) and the r.m. was stirred under reflux for 3 h. After cooling, the r.m. was poured onto a sat. aq. NH$_4$Cl aq. sol (1 l). Additional NH$_4$Cl (150 g) and H$_2$O (1 l) were added and the r.m. was stirred at r.t. for 30 min. Et$_2$O (2 l) was added and the r.m. was stirred for 30 min. The layers were separated and the aq. layer was diluted with H$_2$O (1.5 l) and further extracted with Et$_2$O (6×0.5 l). The combined o.l. were treated with brine (2×0.5 l), dried (MgSO$_4$) and conc. under reduced pressure to give a black residue. The residue was purified by flash chromatography over silicagel (glass filter, eluent DCM). The product fractions were combined and conc. under reduced pressure to afford an orange-brownish solid residue. Yield: 67.2 g of intermediate 34 (78.3%).

b) Preparation of Intermediate 35

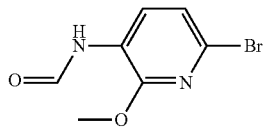

35

Acetic anhydride (110 ml, 1.16 mol) was added dropwise at r.t. to formic acid (170 ml) and this sol. was stirred at r.t. for 30 min. A sol. of intermediate 34 (67.2 g, 308 mmol) in THF (300 ml) was then added dropwise and the r.m. was stirred at 60° C. for 16 h. After cooling, the r.m. was poured onto ice/H$_2$O (1.5 l) and this resulting suspension was stirred for 30 min, and was then filtered off. Additional product was obtained by crystallization in the filtrate. Yield: 65 g of intermediate 35 (91.3%).

c) Preparation of Intermediate 36

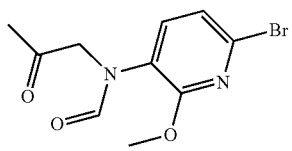

36

Chloroacetone (55.9 ml, 701 mmol) was added dropwise to a mechanically stirred suspension of intermediate 36 (65 g, 281 mmol), K$_2$CO$_3$ (135.6 g, 981 mmol), and KI (4.65 g, 28 mmol) in DMF (542 ml). The r.m. was stirred for 16 h at r.t. then poured onto ice/H$_2$O (2 l) and the resulting off white solid was collected by filtration and dried in vacuo at 60° C. Yield: 77.6 g of intermediate 36 (96.1%).

d) Preparation of Intermediate 37

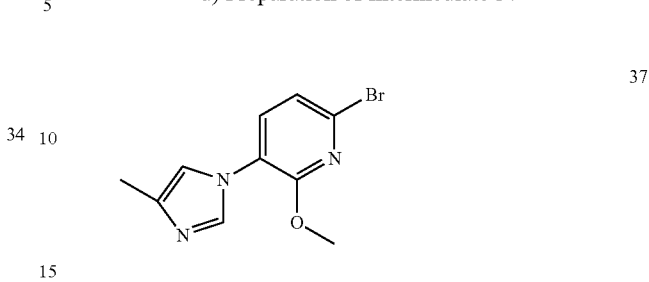

37

Intermediate 36 (77.6 g, 270 mmol) was added portionwise to a mechanically stirred sol. of NH$_4$OAc (105 g, 1.362 mol) in AcOH (500 ml). The r.m. was refluxed for 1 h, cooled and poured onto ice/H$_2$O (1 l), then diluted with toluene (1 l). This mixture was neutralized by addition of a 50% NaOH aq. sol. (590 ml). The layers were separated and the aq. layer was further extracted with toluene (4×0.3 l) and EtOAc (2×0.5 l). The combined o.l. were dried, filtered and conc. under reduced pressure. The residue was purified by column chromatography on silica gel (eluent: DCM/MeOH 99/1). The product fractions were collected and the solvent was removed under reduced pressure. The resulting white-brownish residue was triturated in DIPE to yield an off white solid which was filtered, washed with DIPE and dried under vacuum at 60° C. Yield: 40 g of intermediate 37 (55.2%).

e) Preparation of Intermediate 38

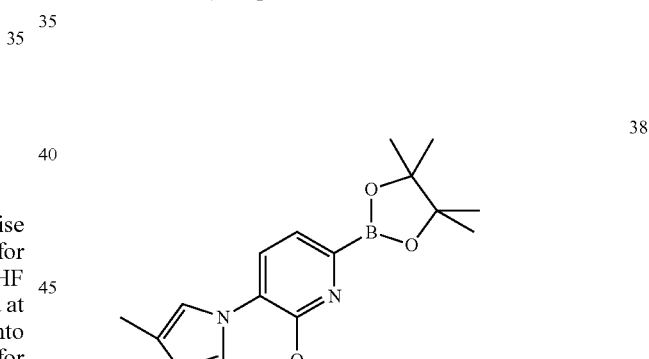

38

Bis(pinacolato)diborane (27.8 g, 109.6 mmol), KOAc (23.1 g, 235 mmol) and PdCl$_2$(dppf) (6.4 g, 7.8 mmol) were added to a solution of intermediate 37 (21 g, 78.3 mmol) in DMSO (140 ml). The r.m. was stirred at 90° C. for 2 h. After cooling, the r.m. was diluted with DCM. The o.l. was washed twice with H$_2$O and then extracted with 1000 ml of an 1 N aq. NaOH sol. The aq. layer was acidified with a conc. HCl sol. (pH 6) and some product precipitated and was filtered off, washed and dried in vacuo. The rest of the product, in the aq. layer, was extracted with DCM. The combined o.l. were dried (MgSO$_4$), filtered and conc. under reduced pressure. The residue was crystallized from DIPE, filtered, washed with DIPE and dried under vacuum at 60° C. to yield a second crop of the product. The 2 product fractions were combined. Yield: 14.4 g of intermediate 38 (58%).

Example A15

Preparation of Intermediate 39

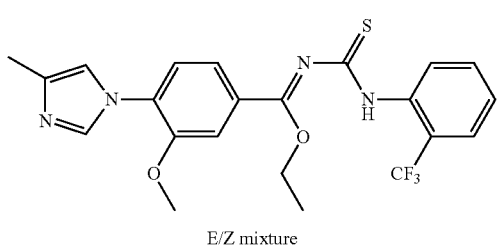

E/Z mixture 2-(Trifluoromethylphenyl)isothiocyanate (2.6 ml, 18.9 mmol) was added dropwise to a sol. of intermediate 2a (4.35 g, 16.8 mmol) in MeCN (44 ml). The r.m. was stirred at 50° C. for 32 h and then at r.t. for 16 h. A precipitate was formed which was filtered and dried in vacuo at 60° C. Yield: 5.1 g of intermediate 39 (65.5%; E/Z mixture).

Example A16

Preparation of Intermediate 40

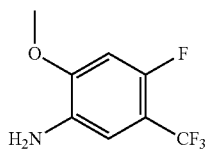

A suspension of 2-bromo-4-fluoro-5-trifluoromethylaniline (2.5 g, 9.7 mmol) and CuI (1.8 g, 9.7 mmol) in a 25% methanolic sol. of NaOMe (11 ml, 48 mmol) was heated under microwave irradiation at 90° C. for 75 min. The r.m. was filtered over diatomaceaous earth and washed with DCM. The filtrate was washed with a 1 M aq. NH$_4$OH sol., dried (MgSO$_4$) and the solvent was removed. The resulting oil was purified by column chromatography on silica gel (eluent: DCM). The product fractions were collected and evaporated. Yield: 0.52 g of intermediate 40 (25.7%).

Example A17 a) Preparation of Intermediate 41

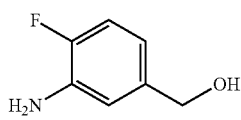

MeOH (150 ml) was added to Pd/C 10% (500 mg) under N$_2$ atmosphere. Subsequently, a 0.4% thiophene sol. in DIPE (1 ml) and 4-fluoro-3-nitrobenzyl alcohol (5 g, 28 mmol) were added. The r.m. was stirred at 25° C. under H$_2$ atmosphere until 3 eq of H$_2$ were absorbed. The catalyst was filtered off over diatomaceous earth. The filtrate was evaporated and the residue was purified by column chromatography on silica gel (eluent: DCM/MeOH(NH$_3$) from 100/0 to 95:5). The product fractions were collected and conc. in vacuo to yield a fluffy solid. Yield: 3.3 g of intermediate 41 (83.3%).

b) Preparation of Intermediate 42

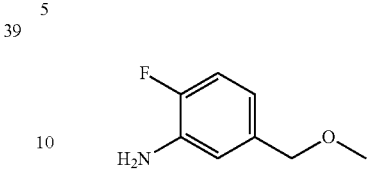

NaH (60% dispersion in mineral oil, 0.96 g, 24.2 mmol) was added portionwise to a solution of intermediate 41 (3.1 g, 22 mmol) in THF (62 ml) at 0° C. The r.m. was stirred at r.t. for 10 min and MeI (1.37 ml, 22 mmol) was added dropwise. The r.m. was stirred at r.t. for 16 h. The mixture was quenched with H$_2$O and conc. in vacuo. The residue was partitioned between H$_2$O and DCM. The o.l. was separated, dried (MgSO$_4$) and the solvent was removed under reduced pressure. The residue was purified by column chromatography on silica gel (eluent: Heptane/EtOAc from 100/0 to 50:50). The product fractions were collected and conc. in vacuo. Yield: 2.6 g of intermediate 42 (76.3%).

Example A18 a) Preparation of Intermediate 43

A mixture of 2,3-difluoro-5-hydroxy-benzoic acid (10 g, 57.4 mmol), MeI (40.7 g, 287 mmol) and K$_2$CO$_3$ (31.7 g, 230 mmol) in acetone (200 ml) was stirred at 65° C. for 16 h. After cooling the r.m. was filtered on a glass filter and the filtrate was evaporated. The residue was dissolved in DCM and the o.l. was washed with H$_2$O, dried (MgSO$_4$), filtered and the solvent was removed under reduced pressure to afford a light brown oil. Yield: 11.4 g of intermediate 43 (98.2%).

b) Preparation of Intermediate 44

A mixture of intermediate 43 (11.4 g, 56.4 mmol) and LiOH (2.7 g, 112.8 mmol) in MeOH (90 ml) and H$_2$O (10 ml) was stirred at r.t. for 16 h. MeOH was removed under reduced pressure and EtOAc (20 ml) was added. The aq. layer was isolated and acidified with an aq. 6 N HCl sol. The product was extracted with EtOAc. The o.l. was dried (MgSO$_4$), fil- c) Preparation of Intermediate 45

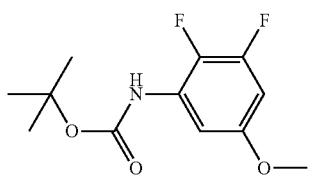

Et$_3$N (2.9 g, 29 mmol) and t-BuOH (26 ml) were added to a sol. of intermediate 44 (5.2 g, 27.6 mmol) and diphenylphosphoryl azide (8 g, 29 mmol) in 1,4-dioxane (78 ml) and the r.m. was refluxed for 16 h. The mixture was conc. and the residue was diluted with EtOAc and washed with H$_2$O. The organic layer was dried (MgSO4), filtered and the solvent was removed under reduced pressure. DCM was added to the residue, and insoluble material was removed via filtration. The filtrate was evaporated and the residue was purified by flash chromatography on silica gel (glass filter; eluent: heptane/DCM from 20/80 to 0/100). The purest fractions were collected and the solvent was removed under reduced pressure. Yield: 3.9 g of intermediate 45 (55.1%).

d) Preparation of Intermediate 46

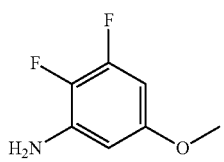

A mixture of intermediate 45 (4.5 g, 17.4 mmol) and trifluoroacetic acid (10 ml) in DCM (40 ml) was stirred at r.t. for 16 h. After evaporation the residue was dissolved in a mixture H$_2$O/DCM and the water layer was basified by addition of Na$_2$CO$_3$. The product was extracted with DCM. The o.l. was washed with H$_2$O, dried (MgSO4), filtered and the solvent was removed under reduced pressure to afford a light brown oil. Yield: 2.5 g of intermediate 45 (90.3%).

Example A19 a) Preparation of Intermediate 47

47

Et$_3$N (3.2 ml, 23 mmol) and t-BuOH (21 ml) were added to a solution of 2,6-difluoro-3-trifluoromethylbenzoic acid (5 g, 22.1 mmol) and diphenylphosphoryl azide (5 ml, 23 mmol) in 1,4-dioxane (62 ml) and the r.m. was refluxed for 16 h. The mixture was conc. and the residue was diluted with EtOAc and washed with H$_2$O. The organic layer was dried (MgSO4), filtered and the solvent was removed under reduced pressure. The residue was purified by chromatography on silica gel (eluent: Heptane/DCM from 40/60 up to 60/40). The purest fractions were collected and the solvent was removed under reduced pressure yielding a white solid. Yield: 4 g of intermediate 47 (60.8%).

b) Preparation of Intermediate 48

48

A mixture of intermediate 47 (4 g, 13.4 mmol) and trifluoroacetic acid (8 ml) in DCM (31 ml) was stirred at r.t. for 16 h. The solvent was evaporated under reduced pressure. The resulting oil was taken up in DCM, washed with a sat. NaHCO$_3$ sol., dried (MgSO4), filtered and evaporated under reduced pressure. The resulting oil which solidified on standing was purified by chromatography on silica gel (eluent: DCM). The product fractions were isolated an evaporated under reduced pressure, yielding a light yellow oil. Yield: 4 g of intermediate 48 (71.6%).

Example A20 a) Preparation of Intermediate 49

49

LiHMDS (2.0 M in THF, 13.5 ml, 27 mmol) was added dropwise to a solution of 4-fluoro-3-methoxybenzotrifluoride (5 g, 25.7 mmol) in THF at −78° C. The r.m. was stirred for an additional 5 min, after which freshly crushed CO$_2$ was added. The mixture was allowed to warm up to r.t. and diluted with Et$_2$O (100 ml). The mixture was washed with a 1 N HCl sol. and water. The o.l. was extracted with a 0.2 N NaOH sol. (3×). The combined aq. layers were washed with Et$_2$O, acidified with an aq. 1 N HCl sol. The aq. layer was extracted 3× with Et$_2$O. The combined o.l. were washed with brine, dried (MgSO$_4$), filtered and evaporated under reduced pressure, yielding a white solid. Yield: 4.1 g of intermediate 49 (67.3%).

b) Preparation of Intermediate 50

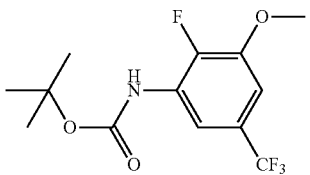

Et$_3$N (2.5 ml, 18 mmol) and t-BuOH (16 ml) were added to a solution of intermediate 49 (4.1 g, 17.2 mmol) and diphenylphosphoryl azide (3.9 ml, 18 mmol) in 1,4-dioxane (49 ml) and the r.m. was refluxed for 16 h. The mixture was conc. and the residue was diluted with EtOAc and washed with H$_2$O. The organic layer was dried (MgSO4), filtered and the solvent was removed under reduced pressure. The residue was purified by chromatography on silica gel (eluent: Heptane/DCM from 80/20 up to 50/50). The purest fractions were collected and the solvent was removed under reduced pressure. Yield: 3.3 g of intermediate 50 (61.9%).

c) Preparation of Intermediate 51

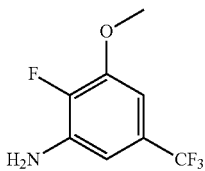

A mixture of intermediate 50 (3.3 g, 10.7 mmol) and trifluoroacetic acid (6.1 ml) in DCM (25 ml) was stirred at r.t. for 16 h. The solvent was evaporated under reduced pressure. The resulting oil was taken up in DCM, washed with a sat. NaHCO$_3$ sol., dried (MgSO$_4$), filtered and evaporated under reduced pressure. The residue was purified by chromatography on silica gel (eluent: DCM). The product fractions were evaporated, yielding a colourless oil. Yield: 1.6 g of intermediate 51 (71.7%).

Example A21

Preparation of Intermediate 52

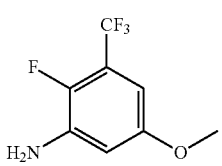

Intermediate 52 was obtained by the same sequence of 3 reactions as described in Example A20, but starting from 4-fluoro-3-trifluoromethylanisole.

Example A22

Preparation of Intermediate 53

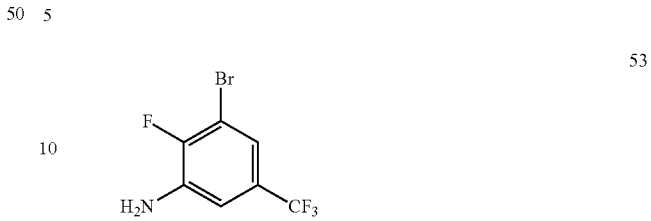

Intermediate 53 was obtained by the same sequence of 3 reactions as described in Example A20, but starting from 3-bromo-4-fluorobenzotrifluoride.

Example A23

Preparation of Intermediate 54

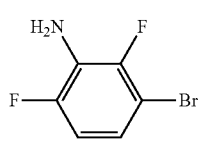

Intermediate 54 was obtained by the same sequence of 3 reactions as described in Example A20, but starting from 1-bromo-2,4-difluorobenzene.

Example A24 a) Preparation of Intermediate 55

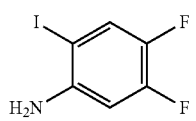

3,4-difluoroaniline (5 ml, 50 mmol) was suspended in H$_2$O (250 ml) and NaHCO$_3$ (6.3 g, 75 mmol) was added, followed by iodine (16.5 g, 65.1 mmol). The r.m. was stirred for 30 min at r.t. and poured out in a sat. aq. Na$_2$S$_2$O$_3$ sol. The aq. layer was extracted with EtOAc and the o.l. was dried (MgSO$_4$), filtered and evaporated under reduced pressure, yielding the product as a dark oil. Yield: 12.5 g of intermediate 55 (97.8%).

b) Preparation of Intermediate 56

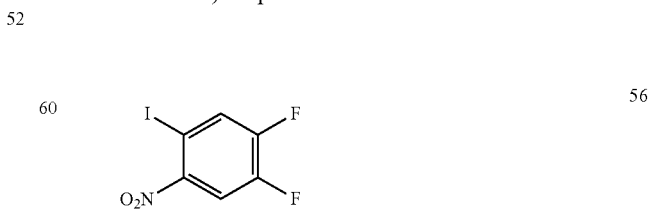

3-Chloroperbenzoic acid (9.6 g, 38.8 mmol) was added portionwise to a solution of intermediate 55 (3.3 g, 12.9 mmol) in DCE (130 ml) (exothermic reaction). The r.m. was stirred for 90 min at r.t. and was then poured out in a H₂O/DCM mixture. A sat. NaHCO₃ sol. was added until pH 8. The o.l. was isolated, dried (MgSO₄), filtered and evaporated under reduced pressure. The crude was purified by chromatography on silica gel (eluent: heptane/EtOAc from 100/0 to 99/1). The product fractions where collected and evaporated, yielding the product as a yellow oil. Yield: 0.62 g of intermediate 56 (16.8%).

c) Preparation of Intermediate 57

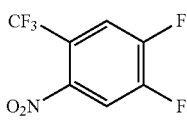

57

In a sealed tube, a sol. of intermediate 56 (1.7 g, 6.1 mmol) in DMF (14 ml) was flushed with N₂ for a few min. Then CuI (1.2 g, 6.2 mmol) was added, followed by methyl(fluorosulfonyl)difluoroacetate (1.6 ml, 12.3 mmol) and the r.m. was heated at 100° C. for 3 h. The r.m. was filtered over diatomaceous earth. To the filtrate was added H₂O and the mixture was extracted with EtOAc. The o.l. was washed with brine, dried (MgSO₄), filtered and evaporated under reduced pressure. The crude was purified by chromatography on silica gel (eluent: heptane/EtOAc from 100/0 to 95/5). The product fractions were collected and evaporated under reduced pressure. Yield: 1.35 g of intermediate 57 (82.2%).

d) Preparation of Intermediate 58

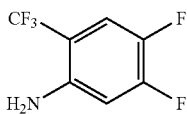

58

MeOH (150 ml) was added to Pd/C 10% (500 mg) under N₂ atmosphere. Subsequently, a 0.4% thiophene sol. in DIPE (1 ml) and intermediate 57 (1.35 g, 5 mmol) were added. The r.m. was stirred at 25° C. under H₂ atmosphere until 3 eq of H₂ were absorbed. The catalyst was filtered off over diatomaceous earth. The solvent was evaporated under reduced pressure to afford the product. Yield: 0.93 g of intermediate 58 (82%).

Example A25 a) Preparation of Intermediate 59

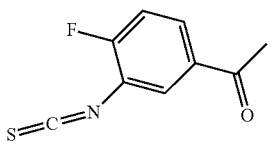

59

Under a N₂ atmosphere, 4-acetyl-2-aminofluorobenzene (1.6 g, 10.1 mmol) was dissolved in DCM (80 ml). 1,1'-Thiocarbonyl-2,2'-pyridone (2.7 g, 11.1 mmol) was added and the r.m. was stirred at r.t. for 16 h. The r.m. was washed twice with H₂O and with a 10% aq. sol. of Na₂CO₃. The o.l. was dried (MgSO₄), filtered and the solvent was removed by evaporation. The residue was purified by column chromatography over silica gel (eluent: heptane/DCM from 50/50 to 0/100). The best fractions were collected and conc. in vacuo to give the product as a colorless liquid. Yield: 1.67 g of intermediate 59 (84.4%).

b) Preparation of Intermediate 60

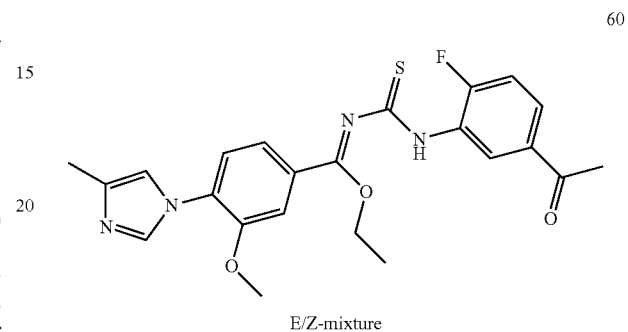

60

E/Z-mixture

Intermediate 59 (2.2 g, 8.5 mmol) was added dropwise to a sol. of intermediate 2a (2.21 g, 8.55 mmol) in MeCN (15 ml). The r.m. was stirred at 60° C. for 16 h. The mixture was cooled to r.t. and was conc. in vacuo. The residue was purified by column chromatography over silica gel (eluent DCM/MeOH from 100/0 to 98/2). The product fractions were collected, the solvent evaporated, and the residue triturated in DIPE/MeCN to afford product. Yield: 2.4 g of intermediate 60 (38%; E/Z mixture).

Example A26 a) Preparation of Intermediate 61

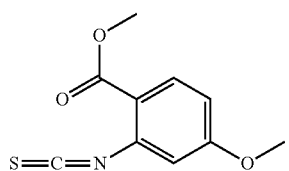

61

Under a N₂ atmosphere, methyl 2-amino-4-methoxybenzoate (1.1 g, 5.9 mmol) was dissolved in DCM (80 ml). 1,1'-Thiocarbonyl-2,2'-pyridone (1.5 g, 6.5 mmol) was added and the r.m. was stirred at r.t. for 2 h. The r.m. was washed twice with H₂O and with a 10% aq. sol. of Na₂CO₃. The o.l. was dried (MgSO₄), filtered and the solvent was removed by evaporation. The residue was purified by column chromatography over silica gel (eluent: heptane/DCM from 50/50 to 0/100). The best fractions were collected and conc. in vacuo to give the product as a white solid. Yield: 1.05 g of intermediate 61 (79. %).

b) Preparation of Intermediate 62

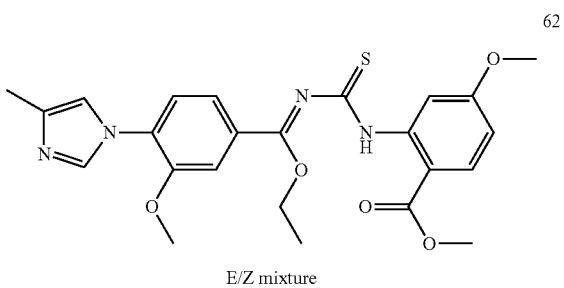

E/Z mixture

Intermediate 61 (1.05 g, 4.5 mmol) was added dropwise to a sol. of intermediate 2a (1.17 g, 4.5 mmol) in MeCN (10 ml). The r.m. was stirred at 60° C. for 16 h. The mixture was cooled to r.t. and was conc. in vacuo. The residue was purified by column chromatography over silica gel (eluent DCM/MeOH from 100/0 to 98/2). The product fractions were collected, the solvent evaporated to afford product. Yield: 1.2 g of intermediate 62 (42%).

c) Preparation of Intermediate 63

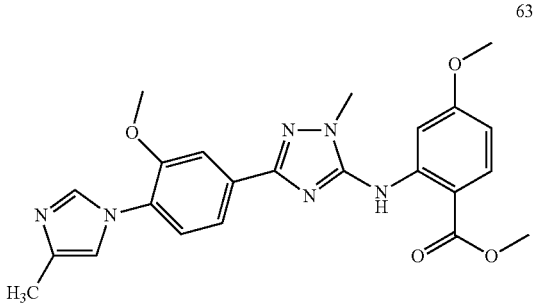

Methylhydrazine (0.10 ml, 1.9 mmol) was added to a solution of intermediate 62 (1.2 g, 1.9 mmol) in MeOH (30 ml). The r.m. was stirred at 50° C. for 40 min. After cooling, the r.m. was conc. in vacuo. The residue was triturated with DIPE. The major impurity precipitated and was filtered off. The filtrate was evaporated under reduced pressure. The resulting residue was purified by flash chromatography over silica gel (eluent: DCM/MeOH(NH$_3$) from 100/0 to 98/2). The product fractions were collected and the solvent was removed under reduced pressure. The residue was crystallized from DIPE, filtered off and dried in vacuo. Yield: 0.12 g of intermediate 63 (13.7%).

Example A27

Preparation of Intermediate 64

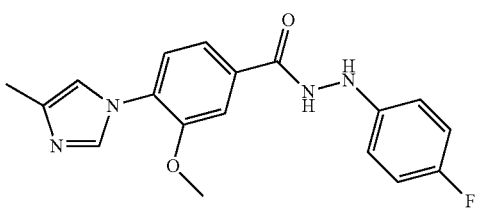

First DIPEA (11.8 ml, 68.9 mmol), and then bis(2-oxo-3-oxazolidinyl)phosphonic chloride (6.6 g, 25.8 mmol) were added to a cooled (ice-bath) solution of intermediate 6 (4 g, 17.2 mmol) and 4-fluorophenylhydrazine hydrochloride (4.0 g, 24.0 mmol) in DCM (42 ml). The r.m. was stirred at r.t. for 1 h. H$_2$O was added and the o.l. was separated, dried (MgSO4), filtered and conc. in vacuo. The product was purified chromatography over silica gel (DCM/MeOH(NH$_3$) from 100/0 to 97/3). The product fractions were collected and conc. in vacuo. The product was triturated in DIPE, filtered off and dried on air. Yield: 1.1 g of intermediate 64 (18.7%).

Example A28 a) Preparation of Intermediate 65

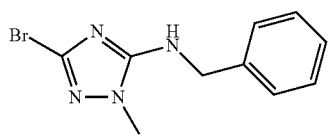

A mixture of intermediate 31 (1 g, 4.1 mmol), benzylamine (0.45 ml, 4.1 mmol), K$_2$CO$_3$ (1.15 g, 8.3 mmol) in DMF (0.5 ml) was heated at 160° C. under microwave irradiation for 1.5 h. The r.m. was poured out in H$_2$O. The H$_2$O layer was extracted with EtOAc and the o.l. was dried (MgSO$_4$), filtered and evaporated under reduced pressure. The resulting oil was purified by chromatography on silica gel (eluent: heptanes/EtOAc from 100/0 to 50/50). The product fractions were collected and evaporated under reduced pressure yielding the product as a white solid. Yield: 0.7 g of intermediate 65 (63.1%).

b) Preparation of Intermediate 66

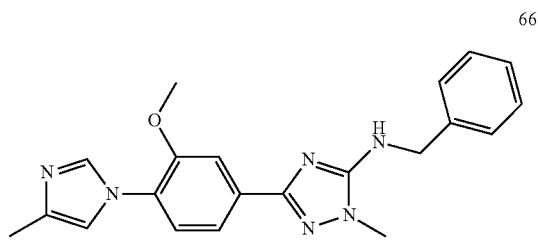 [SMILES: COc1cc(-c2nc(NCc3ccccc3)n(C)n2)ccc1-n1cnc(C)c1]

A mixture of intermediate 65 (1.5 g, 5.6 mmol), crude intermediate 29 and 30 (2.29 g), Cs$_2$CO$_3$ (5.5 g, 16.8 mmol) in H$_2$O (6 ml) and DME (10 ml) was flushed with N$_2$ for 5 min. Pd(PPh$_3$)$_4$ (0.52 g, 0.5 mmol) was then added and the r.m. was heated at 100° C. for 16 h. After cooling, H$_2$O was removed under reduced pressure and the r.m. was diluted with DCM. The o.l. was washed with brine, dried (MgSO$_4$), filtered and the solvent was evaporated. The residue was purified by RP preparative HPLC (RP Vydac Denali C18-10 μm, 250 g, 5 cm). Mobile phase (0.25% NH$_4$HCO$_3$ sol. in water, MeOH). The desired fractions were collected and combined and the solvent was removed under reduced pressure. Yield: 1.02 g of intermediate 66 (48.5%).

c) Preparation of Intermediate 67

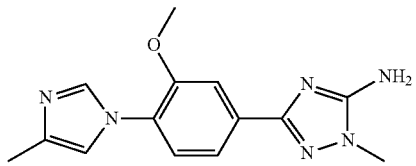

MeOH (100 ml) was added to Pd/C 10% (200 mg) under $N_2$ atmosphere. Subsequently, intermediate 66 (0.8 g, 2.1 mmol) was added. The r.m. was stirred at 25° C. under $H_2$ atmosphere until 1 eq of $H_2$ was absorbed. The catalyst was removed by filtration over diatomaceous earth. The filtrate was evaporated and the residue was triturated with $CH_3CN$ and filtered. Yield: 0.4 g of intermediate 67 (65.8%).

Example A29

Preparation of Intermediate 68

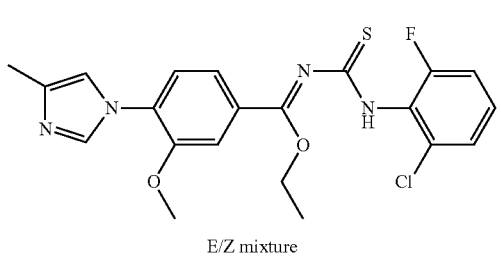

E/Z mixture (2-chloro-6-fluorophenyl)isothiocyanate (0.46 g, 3.0 mmol) was added dropwise to a sol. of intermediate 2a (0.78 g, 3.0 mmol) in MeCN (8 ml). The r.m. was stirred at 50° C. for 3 h and then at r.t. for 16 h. A precipitate was formed which was filtered and dried in vacuo at 60° C. Yield: 0.46 g of intermediate 68 (34.2%; E/Z mixture).

Example A30 a) Preparation of Intermediate 60

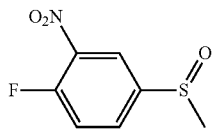

4-Fluorophenyl methyl sulfoxide ([658-14-0], 3 g, 19 mmol) was added to a 2 M $H_2SO_4$ aq. sol. at 5° C. Sodium nitrate (1.6 g, 19 mmol) was then added portionwise at the same temperature and the r.m. was stirred at r.t. overnight. The r.m. was poured out in $H_2O$ and the product was extracted with DCM. The o.l. was dried ($MgSO_4$), filtered and the solvent was removed under reduced pressure. The residue was purified by chromatography on silica gel (eluent: heptanes/EtOAc from 100/0 to 40/60). The product fractions were collected and evaporated under reduced pressure. Yield: 2.34 g of intermediate 69 (60%).

b) Preparation of Intermediate 70

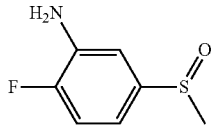

MeOH (45 ml) was added to Pd/C 10% (120 mg) under $N_2$ atmosphere. Subsequently, intermediate 69 (2.3 g, 11.5 mmol) was added. The r.m. was stirred at 25° C. under $H_2$ atmosphere until 3 eq of $H_2$ were absorbed. The catalyst was removed by filtration over diatomaceous earth. The filtrate was evaporated and the residue was purified by chromatography on silica gel (eluent: DCM/EtOAc from 95/5 to 25/75). The product fractions were collected and evaporated under reduced pressure. Yield: 0.79 g of intermediate 70 (40%).

Example A31

Preparation of Intermediate 71

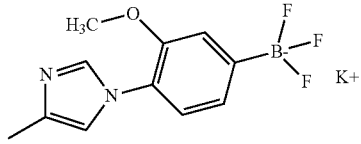

A crude mixture of intermediates 29 and 30 (22 g, approximately 70 mmol), was dissolved in acetone (150 ml) and a 4.5 M aq. sol. of $KHF_2$ (155.6 ml, 700 mmol) was added. The r.m. was stirred at r.t. for 1 h. The resulting brown precipitate was collected by filtration, and repeatedly (4x) triturated with acetone, to yield a white solid, which was dried in vacuo. Yield: 20 g of intermediate 71 (97%).

Example A32 a) Preparation of Intermediate 72

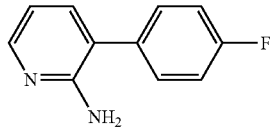

4-Fluorophenylboronic acid (1.21 g, 8.7 mmol) and $Pd(PPh_3)_4$ (0.42 g, 0.36 mmol) were added to a solution of 2-amino-3-bromopyridine (1.25 g, 7.20 mmol) in DMF (10 ml), water (4 ml) and $K_2CO_3$ (3.00 g, 21.70 mmol). The r.m. was stirred and heated at 160° C. for 30 min under microwave irradiation. The r.m. was cooled to r.t. and partitioned between water and DCM. The organic phase was separated, dried ($MgSO_4$), filtered and the solvent was evaporated in vacuo. The residue was purified by flash column chromatography over silica gel (eluent: DCM/MeOH from 100/0 to 98/2). The product fractions were collected and conc. in vacuo, yielding 1.20 g of intermediate 72 (88%).

b) Preparation of Intermediate 73

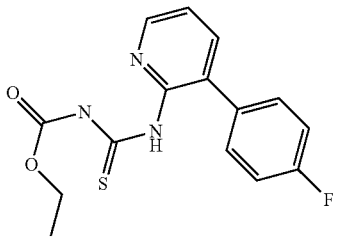

Ethoxycarbonyl isothiocyanate (1.92 g, 15 mmol) was added dropwise at r.t. to a mixture of intermediate 72 (2.4 g, 13 mmol) in dioxane (125 ml). The r.m. was stirred at r.t. for 6 h. The solvents were then evaporated under reduced pressure. The resulting solid was triturated in DIPE, filtered and dried in vacuo, yielding 2.9 g of intermediate 73 (71%).

c) Preparation of Intermediate 74

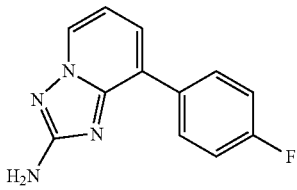

DIPEA (3.4 g, 26 mmol) was added dropwise at r.t. to a stirring mixture of hydroxylamine hydrochloride (3.05 g, 44 mmol) in MeOH (100 ml) and EtOH (10 ml). The r.m. was stirred at r.t. for 30 min. Subsequently, intermediate 73 (2.80 g, 8.8 mmol) was added portionwise and the r.m. was stirred at reflux for 16 h. The r.m. was cooled to r.t. and evaporated. The residue was dissolved in DCM and the solution was washed with brine. The combined organic layers were dried ($MgSO_4$), filtered and conc. in vacuo. The residue was purified by flash column chromatography over silica gel (eluent: DCM/MeOH from 100/0 to 98/2). The product fractions were collected and conc. in vacuo, yielding 1.4 g of intermediate 74 (70%).

d) Preparation of Intermediate 75

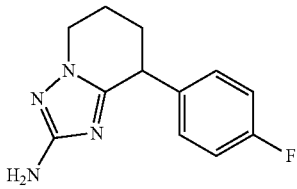

MeOH (100 ml) was added to Pt/$C_5$% (200 mg) under $N_2$ atmosphere. A mixture of intermediate 74 (1.20 g, 5.26 mmol) in HCl/iPrOH (6 N; q.s.) was added. The r.m. was stirred at 25° C. under $H_2$ atmosphere until 2 eq. of $H_2$ were absorbed. The catalyst was filtered off over diatomaceous earth and the filtrate was evaporated. The residue was suspended in DIPE, filtered and dried, yielding 1.1 g of intermediate 75 (78%).

e) Preparation of Intermediate 76

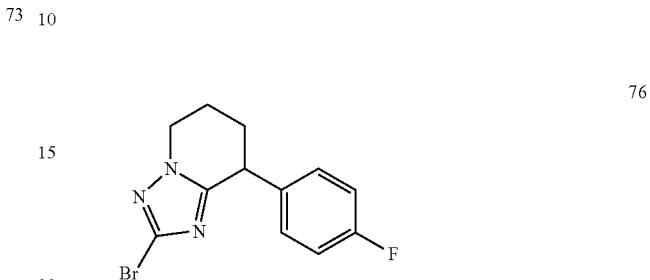

A solution of intermediate 75 (830 mg, 3.57 mmol) in AcOH (7.2 ml) was added to a mixture of $NaNO_2$ (277 mg, 4.13 mmol) in conc. $H_2SO_4$ (5.5 ml) at 10° C. The r.m. was stirred at r.t. for 30 min. Subsequently, the r.m. was added dropwise to a solution of CuBr (1.05 g, 7.34 mmol) in 48% HBr (7.2 ml). This mixture was stirred at r.t. for 1 h and was then carefully added to a stirred sat. aq. solution of $NaHCO_3$ and DCM. The organic phase was separated, dried ($MgSO_4$), filtered and the solvent was evaporated in vacuo. The combined organic layers were dried ($MgSO_4$), filtered and conc. in vacuo. The residue was purified by flash column chromatography over silica gel (eluent: DCM/MeOH from 100/0 to 98/2). The product fractions were collected and conc. in vacuo, yielding 570 mg of intermediate 76 (54%).

Example A33

Alternative Method for the Preparation of Intermediate 76 a) Preparation of Intermediate 77

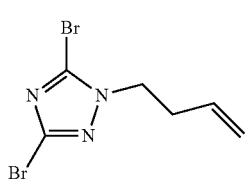

To a solution of 3,5-dibromo-1H-1,2,4-triazole (5.00 g, 22 mmol) in $CH_3CN$ (50 ml) was added 4-bromo-1-butene (3.27 g, 24 mmol) and DIPEA (4.00 ml, 24 mmol), the resulting solution was then heated at 90° C. for 3 h. The r.m. was then cooled and diluted with EtOAc (100 ml), washed with an aq. sat. sol. of $NaHCO_3$ followed by brine, dried ($MgSO_4$), filtered and conc. under reduced pressure. The residue was purified by flash column chromatography over silica gel (eluent: Heptane/DCM from 100/0 to 0/100). The product fractions were collected and conc. in vacuo, yielding 5.55 g of intermediate 77 (89%).

b) Preparation of Intermediate 78

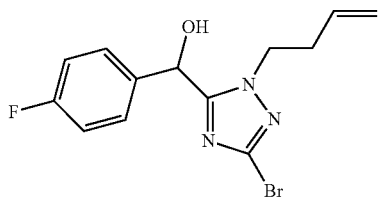
78

To a solution of intermediate 77 (4.50 g, 16 mmol) in THF (285 ml) at −78° C. was added n-butyl lithium (6.41 ml, 16 mmol, 2.5 M in hexanes). The r.m. was stirred for 20 min. at −78° C. Subsequently, 4-fluorobenzaldehyde (1.99 g, 16 mmol) in THF (56 ml) was added, and the solution was then stirred at −78° C. for 20 min. The r.m. was quenched by the addition of an aq. sat. solution of NH$_4$Cl (5 ml). The reaction was allowed to warm to r.t. and was then diluted by the addition of EtOAc (200 ml), washed with H$_2$O (2×100 ml). The organic layer was dried (MgSO$_4$), filtered and conc. under reduced pressure. The residue was purified by flash column chromatography over silica gel (eluent: DCM/MeOH (NH$_3$) from 100/0 to 97/3). The product fractions were collected and conc. in vacuo, yielding 4.20 g of intermediate 78 (80%).

c) Preparation of Intermediate 79

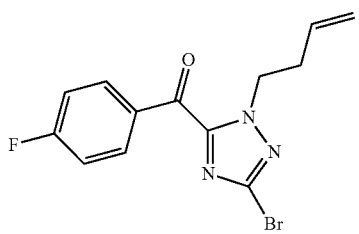
79

To a solution of intermediate 78 (2.00 g, 6.13 mmol) in DCM (200 ml) at 0° C. was added pyridine (0.74 ml, 9.20 mmol) and Dess-Martin periodinane (2.73 g, 6.44 mmol). The r.m. was stirred for 1 h at 0° C. The r.m. was then diluted with DCM (200 ml) and washed with a sat. aq. solution of NaHCO$_3$. The organic layer was dried (MgSO$_4$), and conc. under reduced pressure. The residue was purified by flash column chromatography over silica gel (eluent: DCM/MeOH (NH$_3$) from 100/0 to 97/3). The product fractions were collected and conc. in vacuo, yielding 1.65 g of intermediate 79 (83%).

d) Preparation of Intermediate 80

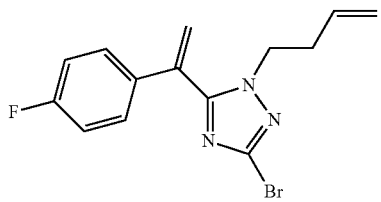
80

To a solution of intermediate 79 (1.00 g, 3.09 mmol) in THF (50 ml) at r.t. was added Tebbes reagent (6.17 ml, 3.085 mmol). The r.m. was then stirred for 18 h. The r.m. was diluted by the addition of Et$_2$O (400 ml) and quenched by the addition of an aq. solution of NaOH (30.8 ml, 0.5 M). The mixture was filtered through a pad of diatomaceous earth and conc. under reduced pressure. The residue was purified by flash column chromatography over silica gel (eluent: DCM/MeOH(NH$_3$) from 100/0 to 97/3). The product fractions were collected and conc. in vacuo, yielding 660 mg of intermediate 80 (66%).

e) Preparation of Intermediate 81

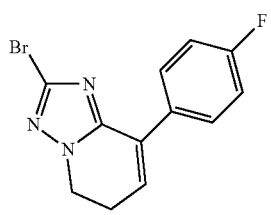
81

To a solution of intermediate 80 (550 mg, 1.71 mmol) in DCE (55 ml) was added Grubbs second generation catalyst (145 mg, 0.17 mmol). The r.m. was then heated at 60° C. for 2 h and conc. under reduced pressure. The residue was purified by flash column chromatography over silica gel (eluent: DCM/MeOH(NH$_3$) from 100/0 to 97/3). The product fractions were collected and conc. in vacuo, yielding 350 mg of intermediate 81 (69%).

f) Preparation of Intermediate 76

To a solution of intermediate 81 (250 mg, 0.85 mmol) in MeOH (55 ml) was added sodium borohydride (322 mg, 8.50 mmol). The r.m. was stirred at r. t. for 2 h. The r.m. was conc. under reduced pressure. The residue was then dissolved in DCM and washed with an aq. solution of HCl (0.5 M), dried (MgSO$_4$), and conc. under reduced pressure. The residue was purified by flash column chromatography over silica gel (eluent: DCM/MeOH(NH$_3$) from 100/0 to 97/3). The product fractions were collected and conc. in vacuo, yielding 220 mg of intermediate 76 (87%).

Example A34 a) Preparation of Intermediate 82

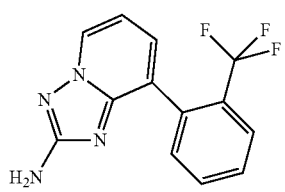
82

Intermediate 82 was prepared starting from 2-(trifluoromethyl)phenylboronic acid and 2-amino-3-bromopyridine, according to the synthesis protocol described in Example A32.a, A32.b and A32.c.

b) Preparation of Intermediate 83

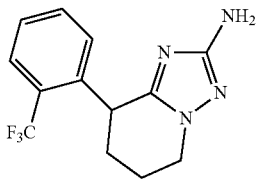

83

MeOH (150 ml) was added to Pd/C 10% (approximately 2 g) under a N$_2$ atmosphere. Subsequently, intermediate 82 (5.0 g, 18 mmol) and a mixture HCl/isopropanol (6 N) (3 ml, 18 mmol) were added. The r.m. was stirred at 50° C. under a H$_2$ atmosphere until 2 eq. of H$_2$ was absorbed. The catalyst was filtered off over diatomaceous earth and the filtrate was evaporated. The residue was partitioned between DCM and an aq. NH$_4$OH sol. The organic layer was separated, dried (MgSO$_4$), and conc. in vacuo. Yield: 3.5 g of intermediate 83 (69%), which was used as such in the next reaction step.

c) Preparation of Intermediate 84

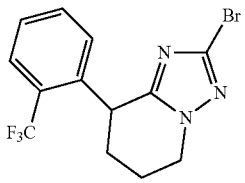

84

A solution of NaNO$_2$ (538 mg, 7.8 mmol) in water (30 ml) was added dropwise over 45 min. to a solution of intermediate 83 (1.1 g, 3.9 mmol) in a 40% aq. HBr solution (30 ml) cooled to 0° C. The mixture was allowed to warm to r.t., stirred for 15 min. and was then cooled to 0° C. Subsequently, CuBr (1.13 g, 7.8 mmol) was added portionwise, and the r.m. was stirred for 15 min at 0° C., 15 min at r.t., and 30 min at 0° C. The r.m. was diluted with EtOAc and then basified with an aq. NH$_4$OH sol. The 0.1 was separated, dried on (MgSO$_4$), filtered and conc. in vacuo. The residue was purified by flash column chromatography over silica gel (eluent: heptanes/EtOAC from 100/0 to 90/10). The product fractions were collected and conc. in vacuo, yielding 1.1 g of intermediate 84 (81%).

Example A35 a) Preparation of Intermediate 85

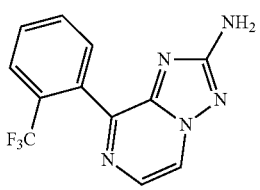

85

Intermediate 85 was prepared starting from 2-(trifluoromethyl)phenylboronic acid and 2-amino-3-chloropyrazine according to the 3-step preparation described in Example A32.a, A32.b and A32.c.

b) Preparation of Intermediate 86

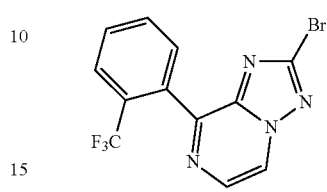

86

Isoamyl nitrite (4.2 g, 35.8 mmol) and CuBr (5.14 g, 35.8 mmol) were added to a mixture of intermediate 85 (5.0 g, 17.9 mmol) in CH$_3$CN (120 ml) at r.t. The r.m. was stirred at reflux for 1 h. The r.m. was cooled to r.t. and conc. Under reduced pressure. The residue was partitioned between DCM and an aq. solution of NH$_4$OH. The organic layer was separated, dried (MgSO$_4$), filtered and conc. in vacuo. The residue was purified by flash column chromatography over silica gel (eluent: DCM/MeOH from 100/0 to 99/1). The product fractions were collected and conc. in vacuo, yielding 2.5 g of intermediate 86 (41%).

Example A36 a) Preparation of Intermediate 87

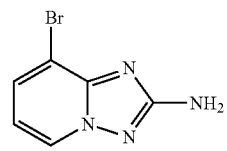

87

Intermediate 87 was prepared starting from 2-amino-3-bromopyridine according to the synthesis protocol described in Example A32.b and A32.c.

b) Preparation of Intermediate 88

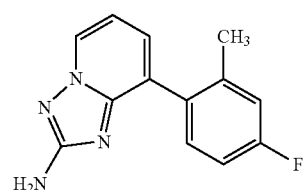

88

4-Fluoro-2-methyl-phenylboronic acid (1.74 g, 11.3 mmol) and Pd(PPh$_3$)$_4$ (1.08 g, 0.94 mmol) were added to a solution of intermediate 87 (2.0 g, 9.4 mmol) in dioxane (10 ml). To this mixture, an aq. sat. NaHCO$_3$ sol. (10 ml) was added, and the resulting mixture was stirred and heated at 150° C. for 10 min under microwave irradiation. The r.m. was cooled to r.t. and filtered through a pad of diatomaceous earth and conc. under reduced pressure. The residue was purified by flash column chromatography over silica gel (eluent: DCM/MeOH(NH$_3$) from 100/0 to 97/3). The product fractions were collected and conc. in vacuo, yielding 1.2 g of intermediate 88 (53%).

c) Preparation of Intermediate 89

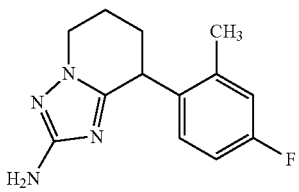
89

MeOH (150 ml) was added to Pd/C 10% (approximately 1 g) under a N₂ atmosphere. Subsequently, intermediate 88 (1.10 g, 4.54 mmol) and a mixture HCl/isopropanol (6N) (1.51 ml, 9.1 mmol) were added. The r.m. was stirred at 50° C. under a H₂ atmosphere until 2 eq. of H₂ was absorbed. The catalyst was filtered off over diatomaceous earth and the filtrate was evaporated. The residue was triturated with DIPE, yielding 900 mg of intermediate 89 (80%).

d) Preparation of Intermediate 90

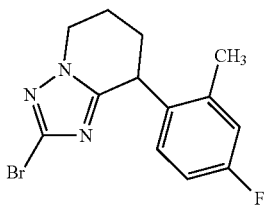
90

A solution of NaNO₂ (919 mg, 13.3 mmol) in water (50 ml) was added dropwise over 45 min. to a solution of intermediate 89 (1.64 g, 6.66 mmol) in a 40% aq. HBr sol. (50 ml) cooled to 0° C. The mixture was allowed to warm to r.t., stirred at r.t. for 15 min. and then cooled to 0° C. CuBr (1.92 g, 13.3 mmol) was added portionwise, and the r.m. was stirred for 60 min at 0° C. The r.m. was diluted with EtOAc and then carefully basified with an aq. NH₄OH sol. The mixture was extracted with EtOAc (3×), and the combined o.l was washed with brine, dried (MgSO₄), filtered and conc. in vacuo. The residue was purified by flash column chromatography over silica gel (eluent: DCM/MeOH(NH₃) from 100/0 to 97/3). The product fractions were collected and conc. in vacuo, yielding 1.45 g of intermediate 90 (70%).

Example A37 a) Preparation of Intermediate 91

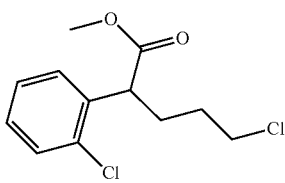
91

NaH (60% dispersion in mineral oil; 2.0 g, 49 mmol) was added to a solution of methyl-2-chlorophenylacetate (8.3 g, 45 mmol) in DMF (120 ml) at 0° C. The r.m. was stirred at 0° C. for 10 min and for 30 min at r.t. The r.m. was then cooled again to 0° C. and 1-chloro-3-iodopropane (5.1 ml, 48.1 mmol) was added dropwise under stirring. The r.m. was stirred at r.t. for 20 h. H₂O was then carefully added followed by Et₂O, and the layers were separated. The organic layer was washed with H₂O and brine, was dried (MgSO₄), and was then evaporated under reduced pressure to yield intermediate 91 (8.75 g, 75%) which was used as such in the next reaction step.

b) Preparation of Intermediate 92

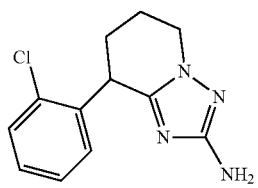
92

Aminoguanidine bicarbonate (15.4 g, 113 mmol) was added to a sol. of intermediate 91 (7.4 g, 28.3 mmol) in iPrOH (130 ml). The r.m. was heated in a sealed vessel for 48 h at 145° C. The r.m. was then cooled to r.t., the solid was filtered off and the filtrate was conc. under reduced pressure. The residue was dissolved in DCM, washed with an aq. sol. of NaHCO₃ and brine. The organic layer was dried (MgSO₄) and conc. in vacuo. The residue was purified by flash column chromatography over silica gel (eluent: DCM/MeOH from 100/0 to 98/2). The product fractions were collected and conc. in vacuo, yielding 1.5 g of intermediate 92 (21%).

c) Preparation of Intermediate 93

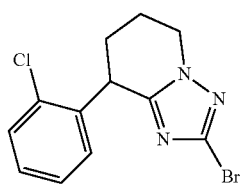
93

Intermediate 93 was prepared from intermediate 92 according to the procedure described in example A34.c Example A38 a) Preparation of Intermediate 94

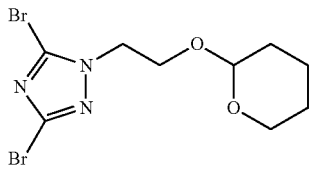
94

2-(2-Bromoethoxy)tetrahydro-2H-pyran (5.07 g, 24.24 mmol) and DIPEA (4.00 ml, 24.24 mmol) were added to a sol. of 3,5-dibromo-1H-1,2,4-triazole (5.00 g, 22.04 mmol) in CH₃CN (50 ml). The sol. was heated at 90° C. for 3 h. Subsequently, the mixture was cooled and diluted with EtOAc (100 ml). The resulting sol. was then washed with a sat. aq. solution of NaHCO₃ and brine. The organic layer was dried (MgSO₄) and conc. The residue was purified by flash column chromatography over silica gel (eluent: DCM/MeOH (NH₃) from 100/0 to 97/3). The product fractions were collected and conc. in vacuo, yielding 6.00 g of intermediate 94 (77%).

b) Preparation of Intermediate 95

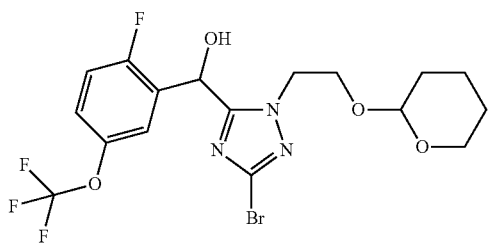

95 n-Butyl lithium (5.63 ml, 14.1 mmol, 2.5 M in hexanes) was added to a sol. of intermediate 94 (5.00 g, 14.1 mmol) in THF (250 ml) at −78° C. The sol. was stirred for 20 min. at −78° C. after which a sol. of 2-(fluoro-5-trifluoromethoxy-benzaldehyde (2.93 g, 14.1 mmol) in THF (50 ml) was added. The sol. was then stirred at −78° C. for 20 min. and quenched by the addition of a sat. aq. sol. of NH₄Cl (5 ml). The reaction was then allowed to warm to r.t., diluted with EtOAc (200 ml) and washed with H₂O (2×100 ml). The organic layer was dried (MgSO₄), filtered and conc. under reduced pressure. The residue was purified by flash column chromatography over silica gel (eluent: DCM/MeOH(NH₃) from 100/0 to 99/1). The product fractions were collected and conc. in vacuo, yielding 3.00 g of intermediate 95 (44%).

c) Preparation of Intermediate 96

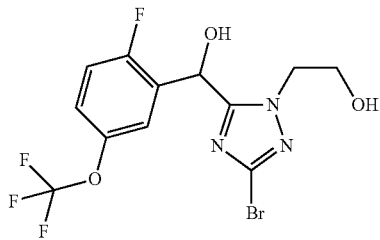

96 p-Toluenesulfonic acid (213 mg, 1.24 mmol) was added to a sol. of intermediate 95 (3.00 g, 6.19 mmol) in MeOH (150 ml) at r.t. The resulting sol. was stirred for 2 h. The r.m. was then conc. in vacuo and the residue dissolved in DCM (100 ml), washed with a sat. aq. solution of NaHCO₃, dried (MgSO4) and conc. under reduced pressure. The residue was purified by flash column chromatography over silica gel (eluent: DCM/MeOH(NH₃) from 100/0 to 97/3). The product fractions were collected and conc. in vacuo, yielding 2.48 g of intermediate 96 (99%).

d) Preparation of Intermediate 97

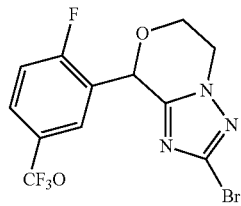

97 p-Toluenesulfonic acid (1.28 g, 6.75 mmol) was added to a solution of intermediate 96 (2.70 g, 6.75 mmol) in xylene (500 ml). The resulting sol. was refluxed for 25 h using a Dean-Stark apparatus. The sol. was then washed with an aq. sol. of 1 M NaOH and brine, dried (MgSO4), and conc. under reduced pressure. The residue was purified by flash column chromatography over silica gel (eluent: DCM/MeOH(NH₃) from 100/0 to 90/10). The product fractions were collected and conc. in vacuo, yielding 1.50 g of intermediate 97 (58%).

Example A39

Preparation of Intermediate 98

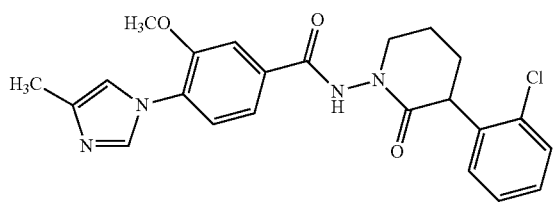

98

DIPEA (2.23 g, 17.2 mmol) and bis(2-oxo-3-oxazolidinyl) phosphinic chloride (1.65 g, 6.5 mmol) were added to a cooled (0° C.) sol. of intermediate 6 (1.0 g, 4.31 mmol) and 1-amino-3-(2-chlorophenyl)piperidin-2-one (1.4 g, 6.03 mmol) in DMF (40 ml). The r.m. was stirred at r.t. overnight, and then conc. in vacuo. The residue was partitioned between DCM and water. The organic layer was dried (MgSO₄), filtered and evaporated. The residue was purified by flash column chromatography over silica gel (eluent: DCM/MeOH from 100/0 to 97/3). The fractions containing product were collected and conc. in vacuo. The residue was purified further by RP preparative HPLC [Vydac Denali C18-10 µm, 250 g, 5 cm); mobile phase: a gradient of (0.25% NH₄HCO₃ sol. in water)/MeOH/CH₃CN]. The product fractions were collected and worked up. Yield 544 mg of intermediate 98 (29%).

Example A40 a) Preparation of Intermediate 99

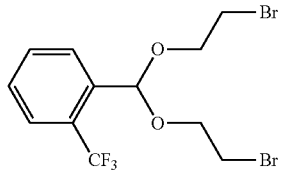

99

Bromo-ethanol (17.94 g, 143.6 mmol) was added to a sol. of 2-(trifluoromethyl)-benzaldehyde (5.00 g, 28.7 mmol) in toluene (107 ml). This solution was heated for 120 h in a Dean-Stark apparatus at reflux. Subsequently, the solution was cooled to r.t. and conc. in vacuo. The resulting residue was dissolved in EtOAc (100 ml) and washed with a sat. aq. sol. of NaHCO₃ and brine. The organic layer was dried (MgSO₄) and conc. under reduced pressure. The residue was purified by flash column chromatography over silica gel (eluent: Heptane/DCM, from 100/0 to 0/100). The product fractions were collected and conc. in vacuo, yielding 8.10 g of intermediate 99 (70%).

b) Preparation of Intermediate 100

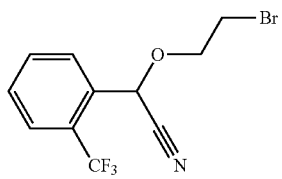

100

Trimethylsilyl cyanide (3.96 g, 39.9 mmol) and tetracyanoethylene (0.51 g, 3.99 mmol) were added to a sol. of intermediate 99 (8.10 g, 19.95 mmol) in CH₃CN (100 ml). The r.m. was heated at reflux in a sealed tube for 4 h, after which it was cooled to r.t. and conc. in vacuo. The resulting residue was dissolved in EtOAc (100 ml) and washed with a sat. aq. sol. of NaHCO₃ and brine. The organic layer was dried (MgSO₄), filtered, and conc. under reduced pressure. The residue was purified by flash column chromatography over silica gel (eluent: 100% DCM). The product fractions were collected and conc. in vacuo, yielding 2.10 g of intermediate 100 (34%).

c) Preparation of Intermediate 101

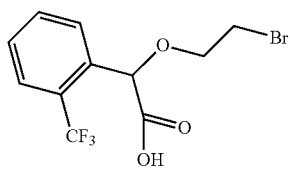

101

A solution of intermediate 100 (2.10 g, 6.82 mmol) in aq. HCl (5 M, 26 ml) was heated at reflux temperature for 15 h. Subsequently, the mixture was cooled to r.t., basified with NaOH (5 N), and washed with Et₂O (2×25 ml). The aq. sol. was then acidified again, and extracted with EtOAc (2×25 ml). The organic layer was dried (MgSO₄), filtered and evaporated. Yield: 1.40 g of intermediate 101 (63%).

d) Preparation of Intermediate 102

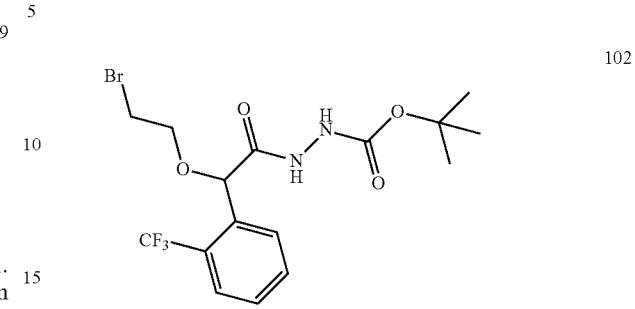

102

Bis(2-oxo-3-oxazolidinyl)phospinic chloride (1.64 g, 6.42 mmol) was added to a solution of intermediate 101 (1.40 g, 4.28 mmol) and tert-butylcarbazate (0.82 g, 5.99 mmol) in DCM (10 ml). Subsequently, DIPEA (2.95 ml, 17.12 mmol) was added. The r.m. was stirred at r.t. for 3 h, after which the reaction was diluted by the addition of water (10 ml) and the mixture was extracted with DCM (2×10 ml). The organic layer was dried (MgSO₄), filtered and conc. under reduced pressure. The residue was purified by flash column chromatography over silica gel (eluent: DCM/MeOH from 100/0 to 90/10). The product fractions were collected and conc. in vacuo, yielding 1.30 g of intermediate 102 (69%).

Example A41 a) Preparation of Intermediate 103

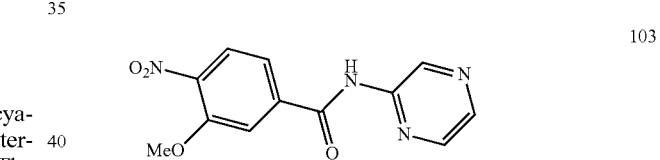

103

Pyridine (2.24 ml) was added to a solution of aminopyrazine (1.76 g, 18.6 mmol) in DCM (10 ml). Subsequently, 3-methoxy-4-nitro-benzoyl chloride (4.40 g, 20.4 mmol) was added. The r.m. was then stirred for 2 h, after which it was diluted by the addition of DCM (10 ml) and washed with a sat. aq. sol. of NaHCO₃ and brine. The organic layer was dried (MgSO₄), filtered and conc. under reduced pressure. The residue was purified by flash column chromatography over silica gel (eluent: DCM/MeOH(NH₃) from 100/0 to 97/3). The product fractions were collected and conc. in vacuo, yielding 3.5 g of intermediate 103 (69%).

b) Preparation of Intermediate 104

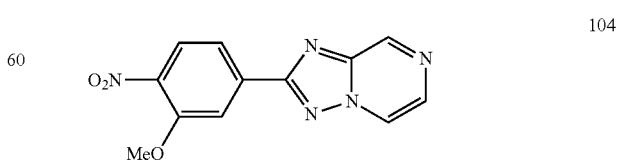

104

To a solution of intermediate 103 (1.50 g, 5.47 mmol) in DCE (10 ml) was added PCl₅ (1.70 g, 8.20 mmol) and the resulting solution was heated using microwave irradiation at 150° C. for 30 min, after which the r.m. was evaporated. The resulting residue was dissolved in THF (2 ml) and to this solution hydroxylamine (6.7 ml, 109.4 mmol) was added. The resulting solution was heated using microwave irradiation at 90° C. for 2 min. Subsequently, the mixture was partitioned between DCM and a sat. aq. sol. of NaHCO₃. The organic layer was dried (MgSO₄), filtered and conc. under reduced pressure. The resulting residue was dissolved in CH₃CN (32 ml) and POCl₃ (2.26 g, 14.5 mmol) was added. The resulting solution was heated using microwave irradiation at 150° C. for 10 min, after which it was diluted by the addition of EtOAc (50 ml) and washed with a sat. aq. solution of NaHCO₃. The organic layer was dried (MgSO₄), filtered and conc. under reduced pressure. The residue was purified by flash column chromatography over silica gel (eluent: DCM/MeOH(NH₃) from 100/0 to 97/3). The product fractions were collected and conc. in vacuo, yielding 1.10 g of intermediate 104 (76%).

c) Preparation of Intermediate 105

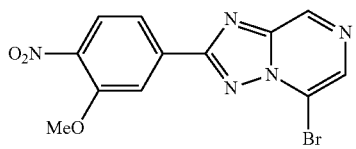

Bromine (0.25 ml, 4.87 mmol) was added to a solution of intermediate 104 (1.10 g, 4.06 mmol) in EtOH (55 ml). This solution was stirred at r.t. for 24 h, after which it was conc. under reduced pressure. The residue was dissolved in EtOAc (20 ml) and washed with a sat. aq. sol. of Na₂S₂O₃. The organic layer was dried (MgSO₄), filtered, and conc. under reduced pressure. The residue was purified by flash column chromatography over silica gel (eluent: DCM/MeOH(NH₃) from 100/0 to 97/3). The product fractions were collected and conc. in vacuo, yielding 0.41 g of intermediate 105 (29%).

d) Preparation of Intermediate 106

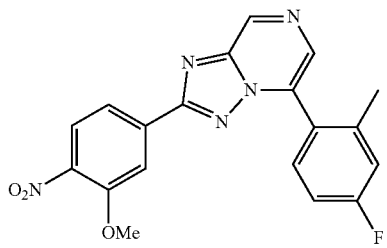

4-Fluoro-2-methylphenylboronic acid (0.484 g, 3.14 mmol) and Pd(PPh₃)₄ (0.33 g, 0.29 mmol) were added to a sol. of intermediate 105 (1.00 g, 2.87 mmol) in dioxane (4 ml) and a sat. aq. sol. of NaHCO₃ (4 ml). The resulting solution was heated using microwave irradiation at 150° C. for 10 min, after which the r.m. was filtered through diatomaceaous earth and evaporated. The residue was purified by flash column chromatography over silica gel (eluent: DCM/MeOH(NH₃) from 100/0 to 97/3). The product fractions were collected and conc. in vacuo, yielding 0.5 g of intermediate 106 (52%).

e) Preparation of Intermediate 107

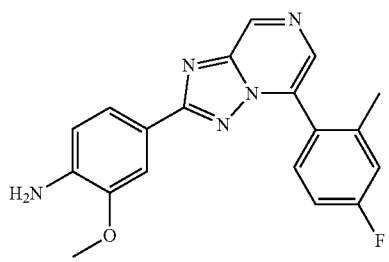

Iron filings (0.40 g, 7.45 mmol) were added to a sol. of intermediate 106 (0.55 g, 1.45 mmol) in acetic acid (15 ml). The resulting solution was heated at 80° C. for 15 min. Subsequently, the r.m. was filtered through diatomaceaous earth and the solid was washed with EtOAc. The organic layer was then washed with water and brine. The organic layer was dried (MgSO₄), filtered and conc. under reduced pressure. The residue was purified by flash column chromatography over silica gel (eluent: DCM). The product fractions were collected and conc. in vacuo, yielding 0.45 g of intermediate 107 (89%).

Example A42 a) Preparation of Intermediate 108

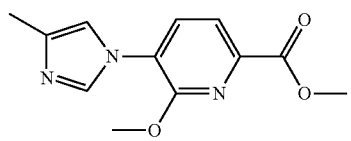

1,3-Bis(diphenylphosphino)propane (0.28 g, 0.69 mmol), KOAc (2.52 g, 25.74 mmol) and Pd(OAc)₂ (0.078 g, 0.34 mmol) were added to a sol. of intermediate 37 (4.60 g, 17.16 mmol) in THF (100 ml) and MeOH (10 ml). The mixture was heated at 100° C. under 50 atm CO pressure for 10 h. Subsequently, the mixture was conc. in vacuo and the residue was dissolved in DCM (150 ml) and washed with water. The organic layer was dried (MgSO₄); filtered and conc. under reduced pressure. The residue was purified by precipitation using DIPE. The solid was collected by filtration, yielding 2.34 g of intermediate 108 (34%).

b) Preparation of Intermediate 109

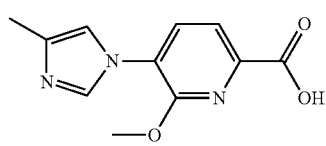

LiOH (0.27 g, 11.20 mmol) was added to a solution of intermediate 108 (2.31 g, 9.35 mmol) in THF (9 ml) and H₂O (3 ml). The mixture was stirred for 16 h at r.t. and was then evaporated to remove THF. The aq. layer was neutralised with an aq. 1 N HCl sol. The precipitate was collected by filtration Yield: 2.10 g of intermediate 109 (96%).

(c) Preparation of Intermediate 110

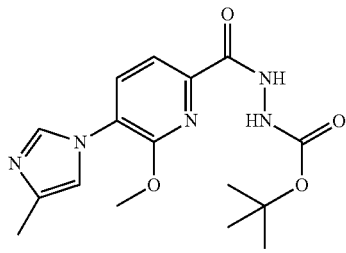

Tert-butyl carbazate (0.10 g, 0.76 mmol) and 1-(3-dimethylaminopropyl)-3-ethylcarbodiimide hydrochloride (0.146 g; 0.76 mmol) were added to a sol. of intermediate 109 (0.17 g, 0.73 mmol) in DCM (10 ml). The resulting solution was stirred at r.t. for 3 h. Then more tert-butyl carbazate (0.05 g) and 1-(3-dimethylaminopropyl)-3-ethylcarbodiimide hydrochloride (0.073 g) were added. The mixture was stirred for 20 h at r.t. Subsequently it was washed with water (10 ml). The organic layer was dried (MgSO$_4$), filtered and conc. The residue was purified by flash column chromatography over silica gel (eluent: DCM/MeOH(NH$_3$) 99/1). The product fractions were collected and evaporated, yielding 0.125 g of intermediate 110 (50%).

(d) Preparation of Intermediate 111

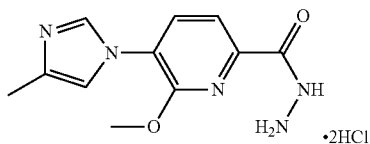

Aq. HCl (37%, 0.7 ml) was added to a sol. of intermediate 110 (0.13 g, 0.36 mmol) in MeOH (0.7 ml). The resulting sol. was stirred at r.t. for 30 min. The r.m. was diluted with DIPE and a solid precipitated, which was collected. Yield: 0.11 g of intermediate 111 as an HCl salt (96%; 0.2HCl).

Example A43 a) Preparation of Intermediate 112

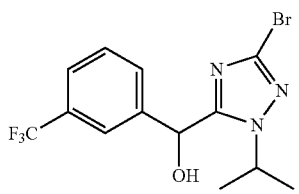

A 2.5 M sol. of nBuLi in hexanes (14.9 ml, 37.2 mmol) was added to a cooled (−78° C.) sol. of intermediate 12 (10.0 g, 37.2 mmol) in THF (660 ml). The r.m. was stirred at −78° C. for 15 min. Subsequently, a solution of 3-trifluorobenzaldehyde (6.47 g, 37.2 mmol) in THF (132 ml) was added dropwise. The r.m. was allowed to warm to r.t., and then quenched by the addition of a sat. aq. NH$_4$Cl sol. The mixture was extracted with EtOAc, and the o.l. was washed with a sat. aq. NH$_4$Cl sol. and brine. The organic layer was dried (MgSO$_4$), filtered and conc. under reduced pressure. The residue was purified by flash column chromatography over silica gel (eluent: DCM/MeOH(NH$_3$) from 100/0 to 97/3). The product fractions were collected and conc. in vacuo, yielding 5.0 g of intermediate 112 (36%).

(b) Preparation of Intermediate 113

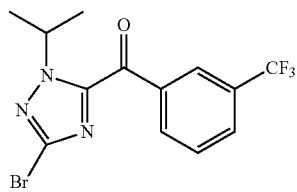

N-Methyl-morpholine N-oxide (1.6 g, 13.7 mmol) and tetrapropylammonium perruthenate (241 mg, 0.69 mmol) were added to a sol. of intermediate 112 (5.0 g, 13.7 mmol) in DCM (103 ml). The solution was stirred for 3 h at r.t., and was then filtered through a pad of diatomaceous earth. The filtrate was conc. The residue was purified by flash chromatography over silica gel (eluent: DCM). The desired fraction was collected and evaporated. Yield: 3.3 g of intermediate 113 (66%).

Example A44

Preparation of Intermediate 114

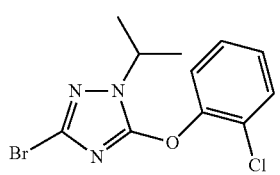

A mixture of 2-chlorophenol (0.72 g, 5.6 mmol), intermediate 12 (1.5 g, 5.6 mmol) and K$_2$CO$_3$ (1.54 g, 11 mmol) in DMF (20 ml) was heated at 160° C. for 45 min using microwave irradiation. The r.m. was cooled, poured onto H$_2$O and extracted with DCM. The combined organic extracts were dried (MgSO$_4$), filtered and conc. under reduced pressure. The residue was triturated in a solution of DIPE/n-heptane. The resulting solid was filtered and dried in vacuo at 50° C., yielding 0.995 g of intermediate 114 (56%).

Example A45

Preparation of Intermediate 115

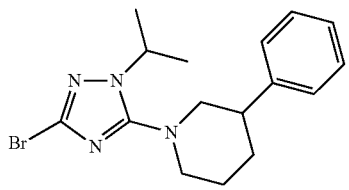

A mixture of intermediate 12 (3.34 g, 12.4 mmol), 3-phenyl-piperidine (2.0 g, 12.4 mmol) and $K_2CO_3$ (3.43 g, 24.8 mmol) in DMF (20 ml) was heated at 160° C. for 1 h in a microwave. The r.m. was cooled and conc. in vacuo. The residue was partitioned between DCM and water. The organic layer was separated, dried ($MgSO_4$), filtered and conc. under reduced pressure. The residue was purified by flash column chromatography over silica gel (eluent: n-heptane/EtOAc from 100/0 to 50/50). The product fractions were collected and conc. in vacuo, yielding 1.4 g of intermediate 115 (32%).

Example A46

(a) Preparation of Intermediate 116

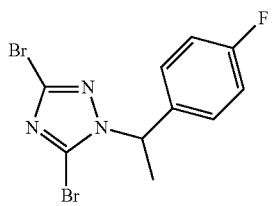

NaH (2.59 g, 64.6 mmol) was added to a stirred sol. of 3,5-dibromotriazole (9.78 g, 43.1 mmol) in DMF (122 ml) under $N_2$ atmosphere at r.t. After 30 min, 1-(1-bromo-ethyl)-4-fluoro-benzene (15 g, 51.7 mmol) was added slowly and the r.m. was stirred at r.t. for 30 min. The mixture cooled on an ice-bath and water was added carefully. The mixture was extracted with EtOAc (3×). The combined organic extracts were washed (brine) and dried ($Na_2SO_4$). Filtration and concentration under reduced pressure yielded a yellow oil, which solidified in water. Yield: 7.8 g of intermediate 116 (52%).

(b) Preparation of Intermediate 117

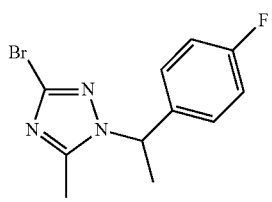

A stirred mixture of intermediate 116 (3.0 g, 8.6 mmol), methylboronic acid (669 mg, 11.7 mmol) and $Pd(PPh_3)_4$ (0.99 g, 0.86 mmol) in a mixture of dioxane (4 ml) and an aq. sat. $NaHCO_3$ sol. (4 ml), was heated at 150° C. for 15 min under microwave irradiation. The cooled mixture was filtered over diatomaceous earth. The filtrate was evaporated (reduced pressure). The crude was purified by column chromatography on silica gel (eluent: DCM/MeOH($NH_3$) from 100/0 to 97/3). The product fractions were collected and evaporated. Yield: 1.0 g of intermediate 117 (41%).

Example A47

(a) Preparation of Intermediate 118

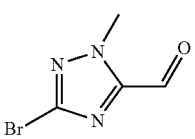

A 2.5 M sol. of nBuLi in hexanes (16.6 ml, 41.5 mmol) was added to a cooled (−78° C.) sol. of intermediate 31 (10.0 g, 41.5 mmol) in THF (583 ml). The r.m. was stirred for 15 min at −78° C. Subsequently, a solution of DMF (3.21 ml, 41.5 mmol) in THF (117 ml) was added dropwise. The r.m. was allowed to warm to r.t., and was then quenched by the addition of a sat. aq. $NH_4Cl$ sol. The mixture was diluted with EtOAc, and the o.l. was washed with a sat. aq. $NH_4Cl$ sol. and brine. The organic layer was dried ($MgSO_4$), filtered and conc. under reduced pressure. The residue was used as such in the next reaction step. Yield: 7.0 g of crude intermediate 118.

(b) Preparation of Intermediate 119

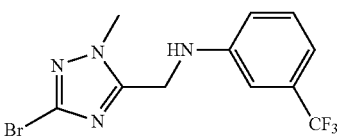

3-Trifluoromethylaniline (1.7 g, 10.5 mmol) was added to a sol. of intermediate 118 (2.0 g, 5.2 mmol) in THF (74 ml) at 0° C., and the solution was stirred at 0° C. for 15 min. Then, $NaBH(OAc)_3$ (3.35 g, 15.8 mmol) was added portionwise, and the r.m. was allowed to warm to r.t. and stirred overnight. The mixture was diluted with EtOAc, and the o.l. was washed with a sat. aq. $NH_4Cl$ sol. and brine. The organic layer was dried ($MgSO_4$), filtered and conc. under reduced pressure. The residue was purified by column chromatography on silica gel (eluent: DCM/MeOH from 100/0 to 99/1). The product fractions were collected and evaporated. Yield: 0.45 g of intermediate 119 (used as such in the next reaction steps).

Example A48

(a) Preparation of Intermediate 120

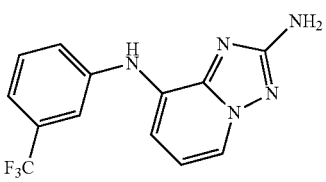

Intermediate 87 (1.0 g, 4.51 mmol), $Pd_2(dba)_3$ (413 mg, 0.45 mmol), X-Phos (473 mg, 0.99 mmol) and $Cs_2CO_3$ (4.4 g, 13.5 mmol) were added to a solution of 3-trifluoromethylaniline (1.09 g, 6.76 mmol) in 2-methyl-2-propanol (5 ml) under a N₂ atmosphere. The r.m. was heated at 100° C. for 4 h. Then the r.m. was cooled to r.t., water was added and the mixture was filtered over diatomaceous earth, then extracted with DCM. The combined organic layers were dried (MgSO₄), filtered and conc. in vacuo. The residue was purified by column chromatography on silica gel (eluent: DCM/MeOH(NH₃) from 100/0 to 98/2). The product fractions were collected and evaporated. The residue was solidified from DIPE/iPrOH. Yield: 0.68 g of intermediate 120 (51%).

(b) Preparation of Intermediate 121

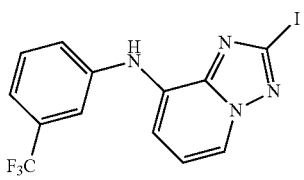

Intermediate 121 was prepared from intermediate 120 (0.68 g, 2.32 mmol) as described in example A35.b, replacing CuBr for CuI. Yield: 0.301 g of intermediate 121 (32%).

Example A49

Preparation of Intermediate 122

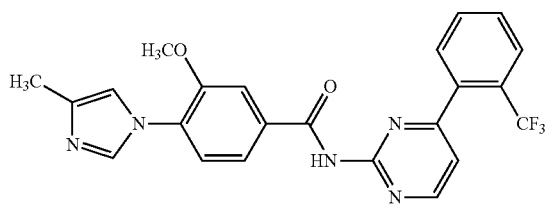

A mixture of the HCl salt of intermediate 5 (4.38 g, 14.4 mmol), 4-[2-(trifluoromethyl)phenyl]-2-pyrimidinamine (3.8 g, 15.9 mmol), Et₃N (2.92 g, 28.9 mmol), Xantphos (0.167 g, 0.29 mmol) and Pd(OAc)₂ (65 mg, 0.29 mmol) in toluene (40 ml) was heated in a stainless steel autoclave under a 20 atm CO atmosphere for 18 h at 110° C. The contents were allowed to cool and the solvent was evaporated under reduced pressure. The residue was purified by chromatography over silica gel (eluent: DCM/MeOH from 100/0 to 95/5). The product fractions were collected and evaporated. Yield: 0.98 g of intermediate 122 (15%).

Example A50

(a) Preparation of Intermediate 123

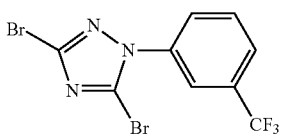

A mixture of Cu(OAc)₂ (7.97 g, 43.9 mmol) and pyridine (5.2 g, 65.8 mmol) in toluene (10 ml) was added to a mixture of 3,5-dibromotriazole (9.95 g g, 43.9 mmol), 3-trifluoromethylboronic acid (12.5 g, 65.8 mmol) and Na₂CO₃ (6.98 g, 65.8 mmol) in toluene (10 ml). The r.m. was stirred at 70° C. for 16 h. The r.m was cooled to r.t. and washed with a sat. aq. NH₄Cl sol. and water. The organic layer was dried (MgSO₄), filtered and conc. The residue was purified by chromatography over silica gel (eluent: heptanes/EtOAc from 100/0 to 60/40). The product fractions were collected and evaporated. Yield: 4.32 g of crude intermediate 123 (27%).

(b) Preparation of Intermediate 124

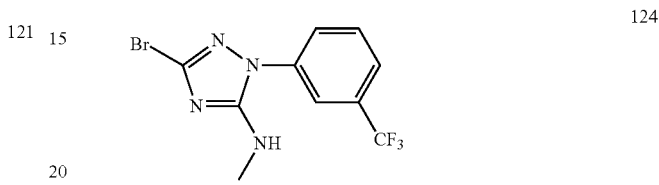

A mixture of intermediate 123 (1.5 g, 4.0 mmol), methylamine (2 N in THF, 3 ml, 6 mmol) and K₂CO₃ (838 mg, 6 mmol) in CH₃CN (10 ml) was heated at 140° C. for 20 min in a microwave. The r.m. was cooled and conc. in vacuo. The residue was partitioned between DCM and water. The organic layer was separated, dried (MgSO₄), filtered and conc. under reduced pressure. The residue was purified by flash column chromatography over silica gel (eluent: n-heptane/EtOAc from 100/0 to 75/25). The product fractions were collected and conc. in vacuo, yielding 0.88 g of intermediate 124 (68%).

Example A51

(a) Preparation of Intermediate 125

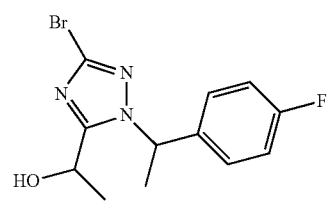

A 2.5 M sol. of nBuLi in hexanes (9.17 ml, 22.9 mmol) was added to a cooled (−78° C.) solution of intermediate 116 (8.0 g, 22.9 mmol) in THF (357 ml). The r.m. was stirred at −78° C. for 15 min. Subsequently, a cooled (−78° C.) solution of acetaldehyde (1.29 ml, 22.9 mmol) in THF (50 ml) was added dropwise. The r.m. was allowed to warm to r.t., and was then quenched by the addition of a sat. aq. NH₄Cl sol. The mixture was diluted with EtOAc, and the organic layer was washed with a sat. aq. NH₄Cl sol. and brine. The organic layer was dried (MgSO₄), filtered and conc. under reduced pressure. The residue was purified by chromatography over silica gel (eluent: DCM/MeOH from 100/0 to 97/3). The product fractions were collected and evaporated. Yield: 4.6 g of intermediate 125 (64%).

(b) Preparation of Intermediate 126

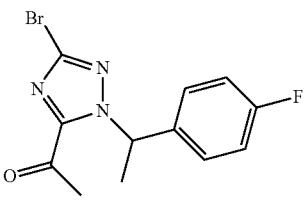

126

Intermediate 125 (4.6 g, 14.6 mmol) was oxidized using the procedure described in example A43.b. Yield: 4.3 g of intermediate 126 (94%).

Example A52

Preparation of Intermediate 127

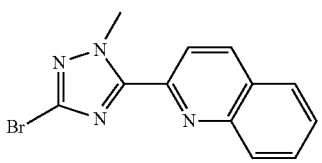

127

A 2.5 M sol. of nBuLi in hexanes (6.64 ml, 16.6 mmol) was added to a cooled (−70° C.) sol. of intermediate 31 (4.0 g, 16.6 mmol) in THF (200 ml). The r.m. was stirred for 2 min at −78° C., and then 2-chloroquinoline (2.72 g, 16.6 mmol) was added. The r.m. was allowed to warm to r.t. The mixture was conc. under reduced pressure, and the residue was partitioned between DCM and water. The organic layer was dried (MgSO₄), filtered and conc. under reduced pressure. The residue was purified by RP preparative HPLC [Vydac Denali C18-10 μm, 250 g, 5 cm); mobile phase: a gradient of (0.25% NH₄HCO₃ sol. in water)/CH₃CN]. The product fractions were collected and the solvent was evaporated. Yield: 0.19 g of intermediate 127 (4%).

Example A53

(a) Preparation of Intermediate 128

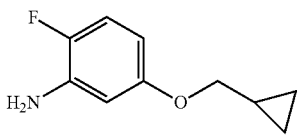

128

A mixture of 5-bromo-2-fluoroaniline (1.5 g, 7.9 mmol), cyclopropylmethanol (6.4 ml, 79 mmol), K₃PO₄ (3.35 g, 15.8 mmol), CuI (0.075 g, 0.4 mmol) and 8-hydroxyquinoline (0.11 g, 0.8 mmol) was flushed with N₂ for 5 min. The r.m. was heated in a closed vessel at 110° C. for 24 h. After cooling, H₂O and EtOAc were added and the two layers were separated. The o.l. was dried (MgSO₄), filtered and evaporated under reduced pressure. The crude product was purified by flash chromatography over silicagel (eluent: Heptanes/EtOAc from 100/0 to 85/15). The product fractions were combined and evaporated. Yield: 0.55 g of intermediate 128 (38%).

Intermediates 129 and 130 were prepared via the same procedure starting from 1-hydroxy-2-methoxyethane and (RS)-3-hydroxytetrahydrofuran respectively.

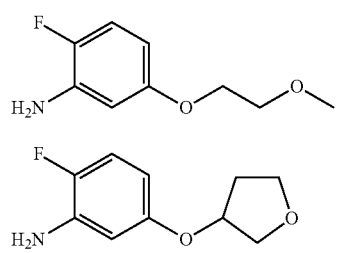

129

130

Example A54

(a) Preparation of Intermediate 131

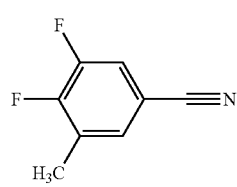

131

In a sealed tube, a mixture of 5-bromo-2,3-difluoroanisole (4.7 g, 21 mmol), Pd(PPh₃)₄ (1.2 g, 1.05 mmol) and zinc cyanide (2.5 g, 21 mmol) in DMF (47 ml) was heated at 100° C. for 2 h. DMF was evaporated under reduced pressure. The residue was diluted with EtOAc and the o.l. was washed with a sat. NaHCO₃ sol. The o.l. was dried (MgSO₄), filtered and evaporated under reduced pressure. The crude product was purified by flash chromatography over silicagel (eluent: Heptane/DCM from 90/10 to 50/50). The product fractions were collected and conc. in vacuo to become a white solid. Yield: 3.0 g of intermediate 131 (84%).

(b) Preparation of Intermediate 132

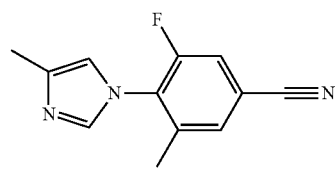

132

A mixture of intermediate 131 (3 g, 17.7 mmol), 4-methylimidazole (2.9 g, 35.5 mmol) and K₂CO₃ (4.9 g, 35.5 mmol) in DMSO (40 ml) was stirred at 80° C. for 1 h. After cooling, H₂O (5 ml) was added and the r.m. was extracted with EtOAc. The o.l. was separated, dried (MgSO₄), filtered and conc. in vacuo. The residue was purified by RP preparative HPLC [Vydac Denali C18-10 μm, 250 g, 5 cm); mobile phase: a gradient of (0.25% NH₄HCO₃ sol. in water)/

CH₃CN]. The product fractions were collected and the solvent was evaporated. Yield: 1.55 g of intermediate 132 (37.8%).

Example A55

(a) Preparation of Intermediate 133

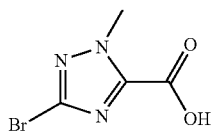

A 2.5 M sol. of nBuLi in hexanes (8.3 ml, 20.8 mmol) was added to a cooled (−78° C.) sol. of intermediate 31 (5.0 g, 20.8 mmol) in THF (74 ml). The r.m. was stirred for 20 min at −78° C., and was then quenched via the addition of dry ice (solid CO₂). The r.m. was allowed to warm to r.t., and the mixture was partitioned between water and EtOAc. The aq. layer was acidified by adding a 1 N aq. HCl solution, and then extracted with DCM. The organic layer was dried (MgSO₄), filtered and conc. under reduced pressure. The residue was used as such in the next reaction step. Yield: 3.5 g of intermediate 133 (82%).

(b) Preparation of Intermediate 134

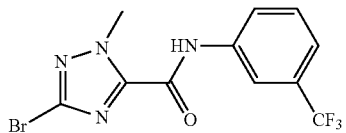

Bis(2-oxo-3-oxazolidinyl)phosphinic chloride (968 mg, 3.8 mmol) and DIPEA (1.75 ml, 10.1 mmol) were added to a solution of the lithium salt of intermediate 133 (2.36 mmol) and 3-trifluoromethylaniline (530 mg, 3.3 mmol) in DCM (6 ml). The r.m. was stirred at r.t. for 3 h. The mixture was washed with water. The o.l. was separated, dried (MgSO₄), filtered and conc. under reduced pressure. The residue was purified by flash chromatography over silicagel (eluent DCM/MeOH 100/0 to 90/10). The product fractions were combined and evaporated. The residue was triturated with heptane and dried. Yield: 656 mg of intermediate 134 (80%).

Example A56

Preparation of Intermediate 135

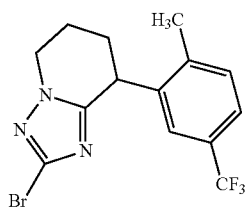

Intermediate 135 was prepared starting from 2-amino-3-bromopyridine according to the synthesis protocol described in Example A36.a-d.

B. Preparation of the Compounds

Example B1 a) Preparation of Compound 1

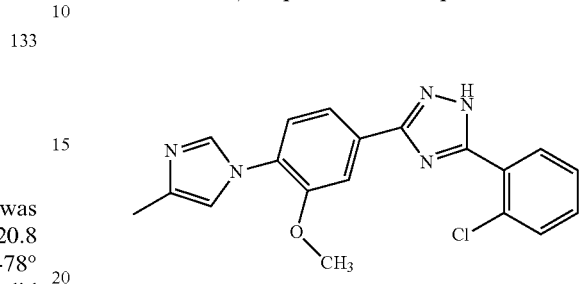

A stirred mixture of intermediate 2 (585 mg, 2.26 mmol), NH₄OAc (5.22 g, 67.7 mmol) and 2-chlorobenzoic acid hydrazide (397 mg, 2.26 mmol) in AcOH (15 ml) was heated at 150° C. for 1 h. The cooled r.m. was conc. under reduced pressure and sat. aq. NaHCO₃ was added to the residue. The contents were then extracted with EtOAc and the combined organic extracts washed with brine and dried (MgSO₄). Filtration and concentration gave the crude product which was purified by flash chromatography over silicagel (eluent, 100:0 to 90:10 DCM/MeOH, gradient elution). The product fractions were combined and evaporated. Yield: 450 mg of compound 1 (54.5%).

b) Preparation of Compound 2 and 23

Compound 2

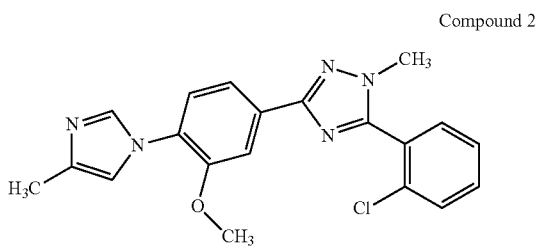

Compound 23

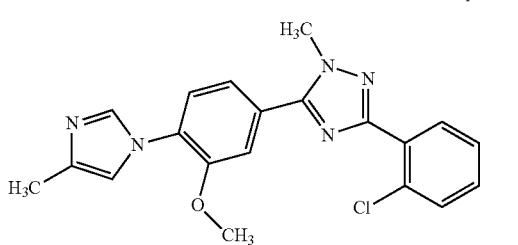

NaH (60% in mineral oil, 118 mg, 2.94 mmol) was added to an ice-cooled, stirred sol. of compound 1 (430 mg, 1.18 mmol) in anhydrous DMF (15 ml) under a N₂ atmosphere. MeI (81 μl, 1.29 mmol) was added and the r.m. was stirred at r.t. for 2 h. The reaction was quenched by MeOH (10 ml). The solvents were removed under reduced pressure. The resulting residue was partitioned between EtOAc/H₂O and the phases separated. The aq. phase was extracted with EtOAc and subsequently the combined organic extracts were washed with brine and dried (MgSO$_4$). Filtration and concentration under reduced pressure gave a residue which was purified by RP preparative HPLC [Vydac Denali C18-10 μm, 250 g, 5 cm); mobile phase: a gradient of (0.25% NH$_4$HCO$_3$ sol. in water)/MeOH]. The product fractions were collected and worked up to yield 82 mg of compound 2 (18%) and 33 mg of compound 23 (7%).

Example B2

Preparation of Compound 3

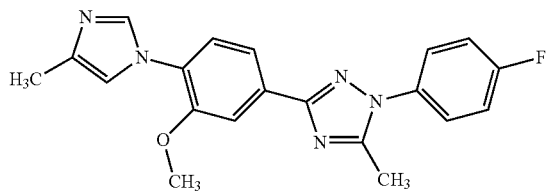 [SMILES: COc1cc(-c2nc(C)n(-c3ccc(F)cc3)n2)ccc1-n1cnc(C)c1]

A sol. of intermediate 14 (65 mg, 241 μmol) and 4-fluoroiodobenzene (536 mg, 2.41 mmol) in degassed DMF (5 ml) was reacted under a N$_2$ atmosphere. (1R,2R)-(−)-1,2-Diaminocyclohexane (8 mg, 72 μmol), CuI (7 mg, 36 μmol) and K$_3$PO$_4$ (307 mg, 1.45 mmol) were added and the r.m. was heated at 150° C. for 3 days. Subsequently, the mixture was cooled and the solvent was removed. The resulting residue was partitioned between EtOAc/H$_2$O and the phases were separated. The aq. phase was extracted with EtOAc. The combined organic extracts were washed with brine and dried (MgSO$_4$). Filtration and concentration under reduced pressure gave a residue which was purified by RP preparative HPLC [Vydac Denali C18-10 μm, 250 g, 5 cm); mobile phase: a gradient of (0.25% NH$_4$OAc sol. in water)/MeOH/MeCN]. The product fractions were collected and worked up to yield 12 mg of compound 3 (13.7%).

Example B3 a) Preparation of Compound 4

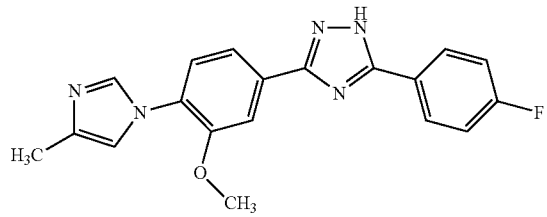 [SMILES: COc1cc(-c2n[nH]c(-c3ccc(F)cc3)n2)ccc1-n1cnc(C)c1]

A mixture of intermediate 1 (443 mg, 2.08 mmol), 4-fluorobenzoic acid hydrazide (320 mg, 2.08 mmol) and K$_2$CO$_3$ (143 mg, 1.04 mmol) in n-BuOH (15 ml) was heated in the microwave at 120° C. for 12 h. The solvent was removed under reduced pressure and the resulting residue partitioned between EtOAc/H$_2$O. The phases were separated. The aq. phase was extracted with EtOAc, and the combined organic extracts were washed with brine and dried (MgSO$_4$). Filtration and concentration under reduced pressure gave the crude product which was purified by column chromatography over silica gel (eluent: 100:0 to 90:10 DCM/MeOH, gradient elution). The product fractions were collected and evaporated to yield 450 mg of compound 4 (62.0%).

b) Preparation of Compound 5

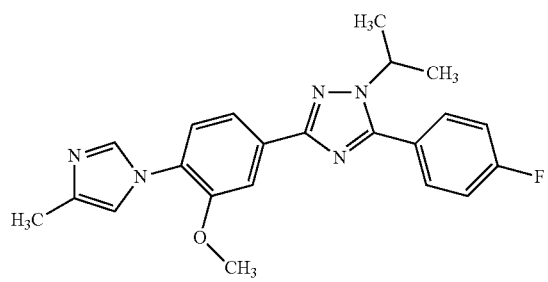 [SMILES: COc1cc(-c2nc(-c3ccc(F)cc3)n(C(C)C)n2)ccc1-n1cnc(C)c1]

NaH (60% in mineral oil, 86 mg, 2.15 mmol) was added to an ice-cooled, stirred sol. of compound 4 (250 mg, 0.716 mmol) in anhydrous DMF (15 ml) under a N$_2$ atmosphere. 2-iodopropane (107 μl, 1.079 mmol) was added and the r.m. was stirred at 70° C. for 8 h. Then the mixture was quenched by the addition of MeOH (10 ml). The solvents were removed under reduced pressure. The resulting residue was partitioned between EtOAc/H$_2$O and the phases separated. The aq. phase was extracted with DCM, and the combined organic extracts were washed with brine and dried (MgSO$_4$). Filtration and concentration under reduced pressure gave a residue which was purified by RP preparative HPLC [Vydac Denali C18-10 μm, 250 g, 5 cm); mobile phase: a gradient of (0.25% NH$_4$HCO$_3$ sol. in water)/MeCN]. The product fractions were collected and worked up to yield 66 mg of pure compound 5 (24%).

Example B4 a) Preparation of Compound 6

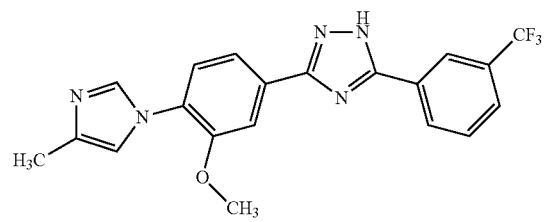 [SMILES: COc1cc(-c2n[nH]c(-c3cccc(C(F)(F)F)c3)n2)ccc1-n1cnc(C)c1]

A mixture of intermediate 8 (670 mg, 2.72 mmol), K$_2$CO$_3$ (189 mg, 1.37 mmol) and 3-trifluoromethylbenzonitrile (559 mg, 3.27 mmol) in EtOH (20 ml) was heated at 120° C. under microwave irradiation for 12 h. The r.m. was cooled and then the solvent was removed under reduced pressure. The resulting residue was partitioned between EtOAc and H$_2$O and the phases were separated. The aq. phase was extracted with DCM and the combined organic extracts were washed with brine and dried (MgSO$_4$). Filtration and concentration under reduced pressure gave a residue which was purified by flash chromatography over silicagel (eluent, 100:0 to 90:10 DCM/MeOH, gradient elution). The product fractions were collected and evaporated. Yield: 398 mg of compound 6 (50.0%).

b) Preparation of Compound 7 and 8

Compound 7

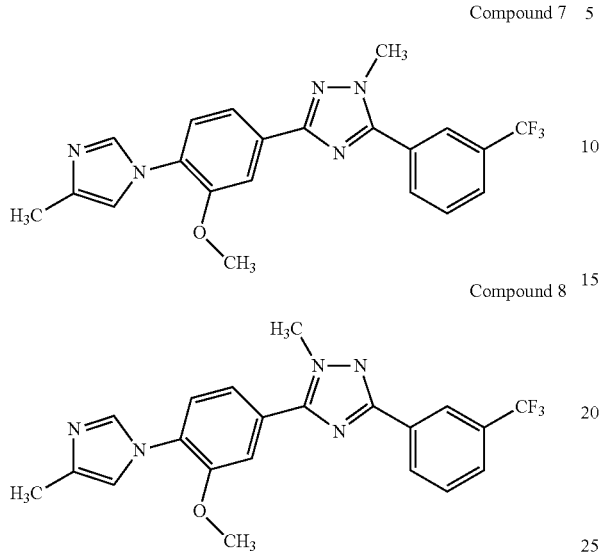

Compound 8

NaH (60% in mineral oil, 27 mg, 0.68 mmol) was added to an ice-cooled, stirred sol. of compound 6 (180 mg, 0.45 mmol) in anhydrous DMF (15 ml) under a $N_2$ atmosphere. MeI (35 µl, 0.56 mmol) was added and the r.m. was stirred at r.t. for 2 h. The reaction was quenched by the addition of MeOH (10 ml) and the solvents were removed under reduced pressure. The resulting residue was partitioned between EtOAc and $H_2O$ and the phases separated. The aq. phase was extracted with DCM, then the combined organic extracts washed with brine and dried ($MgSO_4$). Filtration and concentration under reduced pressure gave a residue which was purified by RP preparative HPLC [Vydac Denali C18-10 µm, 250 g, 5 cm); mobile phase: a gradient of (0.25% $NH_4HCO_3$ sol. in water)/MeCN]. The product fractions were collected and worked up to yield 49 mg of compound 7 (26%) and 74 mg of compound 8 (40%).

Example B5

Preparation of Compound 9

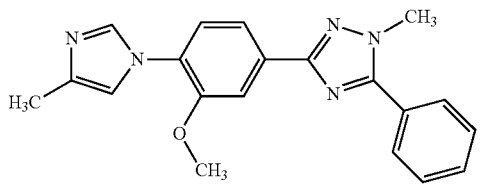 [SMILES: COc1cc(-c2nc(-c3ccccc3)n(C)n2)ccc1-n1cnc(C)c1]

4-Methyl imidazole (190 mg, 2.32 mmol), CuI (44 mg, 232 µmol) and $Cs_2CO_3$ (757 mg, 2.32 mmol) were added to a stirred sol. of intermediate 11 (as a mixture with intermediate 11a) (400 mg, 1.16 mmol) in degassed DMF (25 ml). $N_2$ was bubbled through the r.m. and the mixture was heated in a sealed tube at 120° C. for 48 h. DCM/$H_2O$ was added to the cooled r.m. and the phases were separated. The aq. phase was extracted with DCM and the combined organic extracts washed with brine and dried ($MgSO_4$). Filtration and concentration under reduced pressure gave the crude product which was purified by preparative SFC [Chiralpak Diacel (OD 20×250 mm); mobile phase: isocratic 89% $CO_2$, 11% MeOH with 0.2% isopropylamine, followed by a second run using isocratic 75% $CO_2$, 25% MeOH with 0.2% isopropylamine]. The product fractions were collected and worked up to yield 90 mg of compound 9 (22%).

Example B6

Preparation of Compound 10

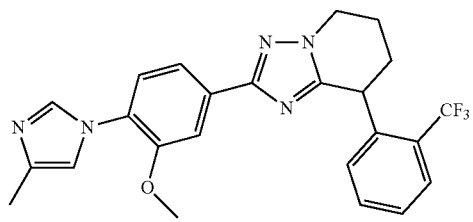 [SMILES: COc1cc(-c2nc3n(n2)CCCC3c2ccccc2C(F)(F)F)ccc1-n1cnc(C)c1]

A stirred mixture of intermediate 2 (653 mg, 2 mmol), NaOAc (0.4 g, 6.1 mmol) and N-1-amino-3-(2-trifluoromethylphenyl)piperidin-2-one (CAS [1123193-83-8], 507 mg, 2 mmol) in dioxane (25 ml) was heated at reflux temperature for 3 days. The cooled r.m. was conc. under reduced pressure. The residue was partitioned between DCM and $H_2O$. The o.l. was dried ($MgSO_4$), filtered and conc. to give a residue which was purified by flash chromatography over silicagel (eluent, 99:1 DCM/MeOH). The product fractions were combined and evaporated, and the residue triturated with DIPE. Yield: 60 mg of compound 10 (5%).

Example B7

Preparation of Compound 11

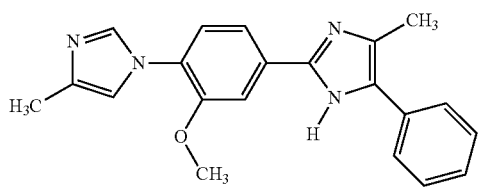 [SMILES: COc1cc(-c2nc(C)c(-c3ccccc3)[nH]2)ccc1-n1cnc(C)c1]

A microwave vessel was charged with intermediate 15 (108 mg, 0.5 mmol), 1-phenyl-propane-1,2-dione (74 mg, 0.5 mmol), $NH_4$(OAc) (385 mg, 5 mmol) and AcOH (4 ml). The r.m. was stirred and heated at 160° C. for 7 min. under microwave irradiation. The r.m. was cooled and poured into sat. aq. $Na_2CO_3$. The mixture was extracted with EtOAc. The o.l. was washed with $H_2O$, brine, and dried ($MgSO_4$). Filtration and concentration gave the crude product which was purified by flash chromatography over silicagel (eluent, 100:0 to 90:10 DCM/MeOH, gradient elution). The product fractions were collected and evaporated. Yield: 38 mg of compound 11 (22%).

Example B8 a) Preparation of Compound 12

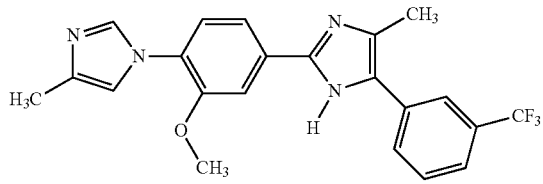 [SMILES: COc1cc(-c2nc(C)c(-c3cccc(C(F)(F)F)c3)[nH]2)ccc1-n1cnc(C)c1]

A microwave vessel was charged with intermediate 15 (1 g, 4.63 mmol), 1-[3-(trifluoromethyl)phenyl]-propane-1,2-dione (1 g, 4.63 mmol), NH$_4$(OAc) (3.57 g, 46.3 mmol) and AcOH (10 ml). The r.m. was stirred and heated at 160° C. for 7 min. under microwave irradiation. The r.m. was cooled and poured into a sat. aq. Na$_2$CO$_3$ sol. The mixture was extracted with DCM. The o.l. was washed with H$_2$O and dried (MgSO$_4$). Filtration and concentration under reduced pressure gave the crude product which was purified by flash chromatography over silicagel (eluent, 100:0 to 90:10 DCM/MeOH, gradient elution). The product fractions were collected and evaporated. The residue was purified further by preparative SFC (Chiralpak Diacel AD 20 mm, mobile phase: isocratic 80% CO$_2$, 20% MeOH with 0.2% isopropylamine). The product fractions were collected and worked up to yield 463 mg of compound 12 after trituration with DIPE (24%).

b) Preparation of Compound 13 and 14

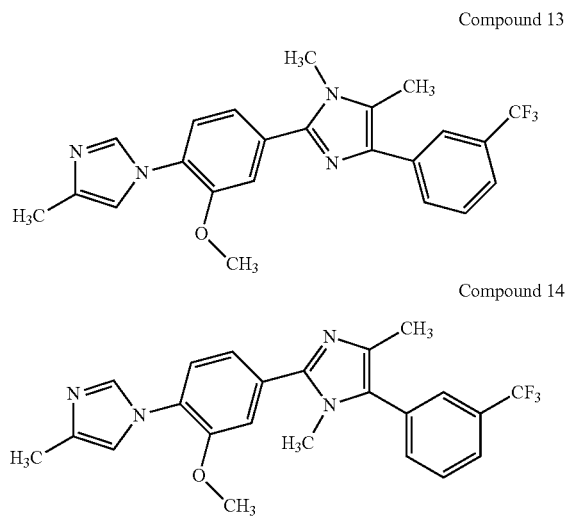

NaH (60% in mineral oil, 52 mg, 1.3 mmol) was added to an ice-cooled, stirred sol. of DMF (5 ml), and subsequently compound 12 (356 mg, 0.86 mmol) was added under an atmosphere of N$_2$. MeI (81 μl, 1.29 mmol) was then added and the r.m. was stirred at r.t. for 2 h. Then the mixture was conc. under reduced pressure and the resulting residue was partitioned between DCM and H$_2$O. The phases were separated and the o.l. was dried (MgSO$_4$), filtered and conc. under reduced pressure. The residue was purified by RP preparative HPLC [Vydac Denali C18-10 μm, 250 g, 5 cm); mobile phase: a gradient of (0.25% NH$_4$HCO$_3$ sol. in water)/MeCN]. The product fractions were collected and worked up. After crystallization from DIPE, pure compound 13 (20 mg, 5%) and compound 14 (170 mg, 46%) were obtained.

Example B9

Preparation of Compound 15 and 16

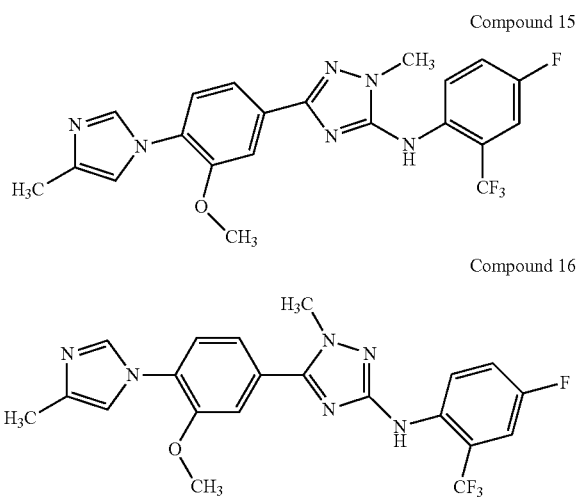

A mixture of intermediate 18 (0.86 g, 1.84 mmol), N-methyl-hydrazine (0.17 g, 3.7 mmol) in 2-methyl-2-propanol (20 ml) was stirred and heated at reflux temperature for 5 h. The r.m. was cooled to r.t. and the resulting precipitate was filtered off. The filtrate was conc. under reduced pressure and the residue was purified by RP preparative HPLC [Vydac Denali C18-10 μm, 250 g, 5 cm); mobile phase: a gradient of (0.25% NH$_4$HCO$_3$ sol. in water)/MeCN]. The product fractions were collected and worked up. Yield: 90 mg of compound 16 (11%). The precipitate obtained after filtration of the crude r.m. was heated at reflux in iPrOH (20 ml) for 7 days. The r.m. was conc. under reduced pressure. The residue was purified by flash chromatography over silica gel (eluent: DCM/MeOH from 98/2 to 96/4). The desired fraction was collected and the solvent was evaporated. The residue was crystallized from Et$_2$O. Yield: 57 mg of compound 15 (7%).

Example B10

Preparation of Compound 17

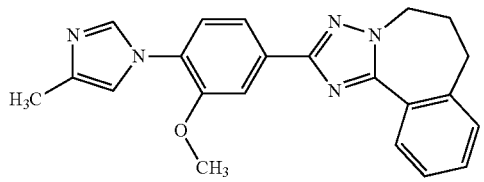 [SMILES: COc1cc(-c2nc3n(n2)CCCc2ccccc2-3)ccc1-n1cnc(C)c1]

A stirred mixture of intermediate 2 (268 mg, 0.81 mmol), NH$_4$OAc (1.87 g, 24.2 mmol) and intermediate 19 (237 mg, 0.54 mmol) in AcOH (5.8 ml) was heated at 120° C. for 2 h. The cooled r.m. was conc. and the residue was partitioned between DCM and water. This mixture was neutralized with Na$_2$CO$_3$ and the o.l. was separated, dried (MgSO$_4$), filtered and conc. under reduced pressure. The residue was purified by RP preparative HPLC [Vydac Denali C18-10 μm, 250 g, 5 cm); mobile phase: a gradient of (0.25% NH$_4$HCO$_3$ sol. in water)/MeOH]. The product fractions were collected and worked up. Yield: 43 mg of compound 17 (14%).

Example B11

Preparation of Compound 18

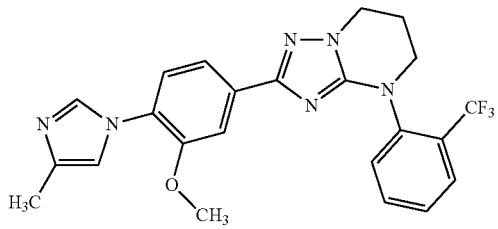 [SMILES: COc1cc(-c2nc3n(n2)CCCN3c2ccccc2C(F)(F)F)ccc1-n1cnc(C)c1]

Intermediate 24 (570 mg, 1.2 mmol) was added to phosphorus oxychloride (20 ml) and heated at 120° C. for 1 h. The r.m was conc. under reduced pressure, and then a sol. of NH$_4$OAc (93 mg, 1.2 mmol) in AcOH (10 ml) was added. The resulting r.m. was heated at 150° C. for 3 h. The cooled r.m. was conc. under reduced pressure and the residue was partitioned between DCM and a sat. aq. NaHCO$_3$ sol. The o.l. was separated, dried (MgSO$_4$), filtered and conc. under reduced pressure. The residue was purified by flash chromatography over silica gel (eluent: DCM/MeOH(NH$_3$) from 100/0 to 91/9). The desired fraction was collected and the solvent was evaporated. Yield: 162 mg of compound 18 (30%).

Example B12

Preparation of Compound 19

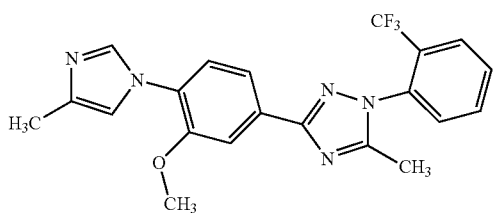 [SMILES: COc1cc(-c2nc(C)n(-c3ccccc3C(F)(F)F)n2)ccc1-n1cnc(C)c1]

Pyridine (0.282 ml, 3.5 mmol), and acetylchloride (0.078 ml, 1.1 mmol) were added to a suspension of intermediate 2 (332 mg, 1 mmol) in DCM (4 ml). The r.m. was stirred at r.t. for 1 h. Et$_3$N (0.5 ml, 3.6 mmol) and more acetylchloride (0.071 ml, 1 mmol) were added to the r.m. and stirring was continued at 60° C. for 1.5 h. The r.m. was cooled to r.t. and 2-(trifluoromethyl)-phenylhydrazine (587 mg, 3 mmol) was added, followed by Et$_3$N (0.42 ml, 3 mmol). The r.m. was stirred at 50° C. for 1 h, and then overnight at 65° C. The r.m. was cooled and water was added. The o.l. was separated and the aq. layer extracted with DCM. The combined o.l. were washed with brine, dried (MgSO$_4$), filtered and conc. under reduced pressure. The residue was purified by flash chromatography over silica gel (eluent: DCM/MeOH from 100/0 to 97/3). The desired fraction was collected and the solvent was evaporated. The residue was dissolved in a mixture of DIPE and MeCN, and a few drops of a 6 N HCl sol. in iPrOH were added. The resulting precipitate was filtered off, washed with DIPE, and dried. Yield: 190 mg of compound 19 (39%).

Example B13

Preparation of Compound 20

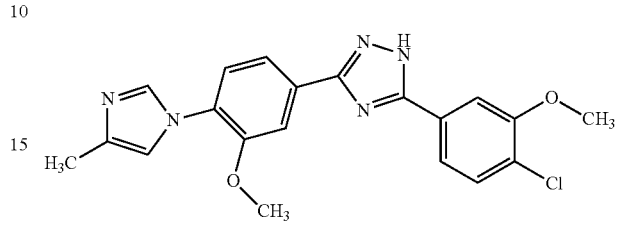

A stirred mixture of intermediate 8 (415 mg, 1.68 mmol), NH$_4$OAc (3.9 g, 50.6 mmol) and intermediate 25 (371 mg, 1.48 mmol) in AcOH (14 ml) was heated at 150° C. for 2 h. The cooled r.m. was conc. under reduced pressure and to the residue was added sat. aq. NaHCO$_3$. The contents were then extracted with EtOAc and the combined organic extracts washed with brine, then dried (MgSO$_4$). Filtration and concentration gave the crude product which was crystallized from DIPE/MeOH. Yield: 220 mg of impure compound 20 (37%), which was used as such in the next step. The mother liquor was conc. and the residue was purified by RP preparative HPLC [Vydac Denali C18-10 μm, 250 g, 5 cm); mobile phase: a gradient of (0.25% NH$_4$HCO$_3$ sol. in water)/MeOH]. The product fractions were collected and worked up, and the residue was purified further by RP preparative HPLC [Vydac Denali C18-10 μm, 250 g, 5 cm); mobile phase: a gradient of (0.25% NH$_4$HCO$_3$ sol. in water)/MeCN]. The product fractions were collected and worked up. Yield: 18 mg of pure compound 20 (3%).

Example B14

Preparation of Compound 21

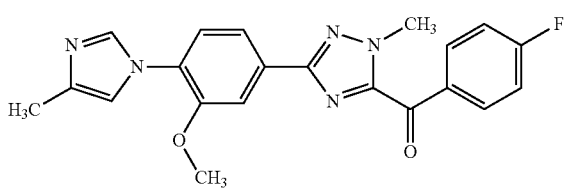 [SMILES: COc1cc(-c2nc(C(=O)c3ccc(F)cc3)n(C)n2)ccc1-n1cnc(C)c1]

A mixture of compound 22 (prepared according to Example B4) (50 mg, 132 μmol) and manganese(IV)oxide (125 mg, 1.4 mmol) in CHCl$_3$ (4 ml) was stirred and heated at 50° C. overnight. The r.m. was cooled and filtered over diatomaceaous earth. The filtrate was conc. under reduced pressure. The residue was purified by flash chromatography over silica gel (eluent: DCM/MeOH from 99/1 to 98/2). The desired fraction was collected and evaporated. Yield: 362 mg of compound 21 (69%).

Example B15

Preparation of Compound 24

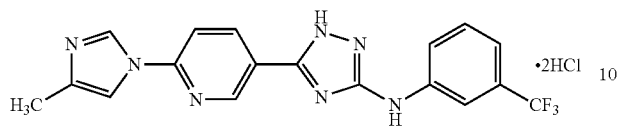

A mixture of intermediate 28 (281 mg, 732 µmol), 4-methyl-imidazole (180 mg, 2.2 mmol), and $Cs_2CO_3$ (715 mg, 2.2 mmol) in DMA (10 ml) was stirred and heated at 150° C. for 1 h. under microwave irradiation. The r.m. was cooled and $H_2O$ was added. The mixture was neutralized by the addition of a sat. aq. $NH_4Cl$ sol. and the resulting mixture was extracted with DCM. The combined o.l. were washed with brine, dried ($MgSO_4$), filtered and conc. under reduced pressure. The residue was purified by RP preparative HPLC [Shandon Hyperprep C18-8 µm, 250 g, 5 cm); mobile phase: a gradient of (0.25% $NH_4HCO_3$ sol. in water)/MeOH]. The desired fractions were collected and worked up. The residue was dissolved in a 1:1 mixture of DIPE and iPrOH, and water (0.5 ml) and a 6 N HCl sol. in iPrOH (3 ml) were added. The mixture was heated at 65° C. for 1 h, then cooled, and the solvents were evaporated. The residue was suspended in iPrOH/DIPE and the solid was filtered off and dried. Yield: 28 mg of compound 24 (8%; 0.2HCl).

Example B16

Preparation of Compound 39

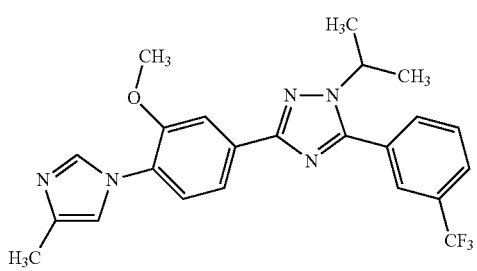 [SMILES: COc1cc(-c2nc(-c3cccc(C(F)(F)F)c3)n(C(C)C)n2)ccc1-n1cnc(C)c1]

A stirred mixture of intermediate 13 (500 mg, 1.5 mmol), crude intermediate 29 and 30 (564 mg) and $K_2CO_3$ (414 mg, 3 mmol) in $H_2O$ (3 ml) and dioxane (12 ml) was flushed with $N_2$ for 10 min. $Pd(PPh_3)_4$ (86 mg, 0.075 mmol) was then added and the r.m. was sealed and heated at 100° C. for 25 min. under microwave irradiation The r.m. was allowed to cool to r.t. and the mixture was partitioned between EtOAc and water. The o.l. was washed with brine, dried ($MgSO_4$), filtered and evaporated. The residue was purified by RP preparative HPLC [Vydac Denali C18-10 µm, 250 g, 5 cm); mobile phase: a gradient of (0.25% $NH_4HCO_3$ sol. in water)/MeOH]. The product fractions were collected and worked up. Yield: 118 mg of compound 39 (18%).

Example B17

Preparation of Compound 66

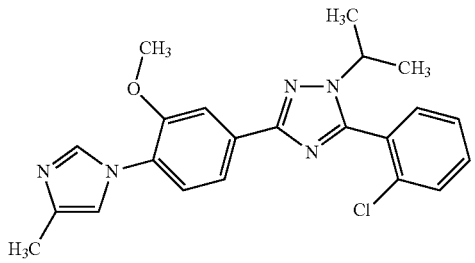 [SMILES: COc1cc(-c2nc(-c3ccccc3Cl)n(C(C)C)n2)ccc1-n1cnc(C)c1]

$Et_3N$ (0.837 ml, 6.0 mmol) was added to a sol. of intermediate 2 (500 mg, 1.5 mmol) and 2-chloro-benzoylchloride (0.21 ml, 1.65 mmol) in toluene (15 ml). The r.m. was stirred and heated at reflux for 2 h. Additional 2-chlorobenzoylchloride (0.19 ml, 1.5 mmol) was added to the r.m., and stirring was continued at reflux temperature for 1 h. Isopropyl-hydrazine (0.66 ml, 7.5 mmol) was added to the mixture and the r.m. was stirred at reflux for 3 h. The r.m. was cooled and conc. under reduced pressure. The residue was purified by flash chromatography over silica gel (eluent: DCM/MeOH from 100/0 to 95/5). The desired fraction was collected and the solvent was evaporated. The residue was triturated with diethylether. Yield: 75 mg of compound 66 (12%).

Example B18

Preparation of Compound 97

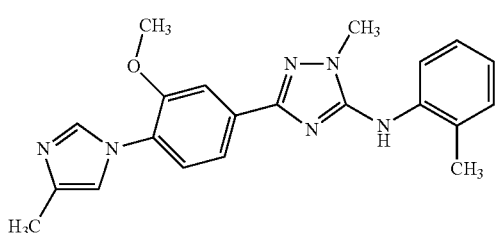

A solution of intermediates 29 and 30 (9 g, approximately 28 mmol), intermediate 33 (6.95 g, 26 mmol), and $Cs_2CO_3$ (25.4 g, 78.1 mmol), in a mixture of DME (160 ml) and $H_2O$ (40 ml) was flushed with $N_2$ for 5 min. $Pd(PPh_3)_4$ (3 g, 2.6 mmol) was added and the r.m. was refluxed for 16 h. After cooling, $H_2O$ was added and the r.m. was extracted with EtOAc and DCM. The combined o.l. were conc. under reduced pressure. EtOAc was added and the organic layer was extracted with an aq. 1N HCl sol. Insoluble material was filtered off. The aq, layer was washed with $Et_2O$, and subsequently basified with a 50% aq. NaOH sol. The suspension was extracted with EtOAc. The o.l. was dried ($MgSO_4$), filtered and evaporated under reduced pressure. The residue was purified by flash chromatography over silica gel (eluent: EtOAc/MeOH($NH_3$) from 100/0 to 95/5). The product fractions were collected and the solvent was removed under reduced pressure. Yield: 5.2 g of compound 97 (53.3%).

Example B19 a) Preparation of Compound 154

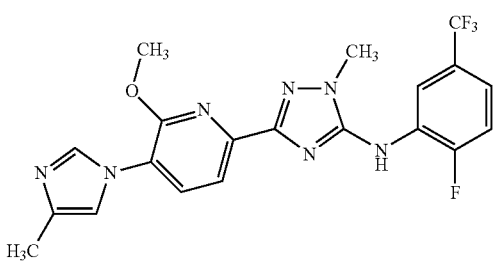 [SMILES: COc1nc(-c2nc(Nc3cc(C(F)(F)F)ccc3F)n(C)n2)ccc1-n1cnc(C)c1]

A sol. of intermediate 32 (0.339 g, 1 mmol), intermediate 38 (0.245 g, 0.78 mmol), and $Cs_2CO_3$ (0.77 g, 2.36 mmol) in a mixture of DME (3 ml) and $H_2O$ (1.5 ml) was flushed with $N_2$ for 5 min. $Pd(PPh_3)_4$ (0.085 g, 0.074 mmol) was added and the r.m. was flushed with $N_2$ for an additional 5 min. The r.m. was stirred at 90° C. for 6 h. The r.m. was cooled to r.t., DCM was added and the o.l. was washed with $H_2O$, dried ($MgSO_4$) filtered and evaporated under reduced pressure. The residue was purified by flash chromatography over silica gel (eluent: DCM/MeOH($NH_3$) from 100/0 to 98/2). The product was recrystallized from DIPE/iPrOH. The solid was filtered off, washed and dried. Yield: 0.17 g of compound 154 (38%).

b) Preparation of Compound 154 (Alternative Conditions)

A mixture of intermediate 32 (47 g, 138.6 mmol), and $Cs_2CO_3$ (104 g, 320 mmol), in a mixture of DME (200 ml) and $H_2O$ (200 ml) was flushed with $N_2$ for 5 min. $PdCl_2(dppf)$ (7.88 g, 10.7 mmol) was added and the r.m. was flushed with $N_2$ for an additional 5 min. The mixture was heated to 80° C. and a solution of intermediate 38 (35 g, 107 mmol) in DME (400 ml) was added dropwise over a 4 h period. After addition, the r.m. was stirred at 80° C. for an additional 30 min. The r.m was cooled to r.t., and the layers were separated. The aq. layer was extracted with DME (100 ml). The combined organic layers were conc. till a volume of approximately 250 ml, and a precipitate was formed. The precipitate was filtered off, washed with DME (50 ml), and dried in vacuo. The solid was dissolved in an aq. 4 N HCl sol. (600 ml). The resulting solution was washed with DCM (100 ml) and EtOAc (100 ml). The aq. layer was then cooled with ice and basified to pH 8-9 via the addition of a 50% aq NaOH sol. The resulting precipitate was filtered off, washed with water, and dried in vacuo. The product was recrystallized from iPrOH. The solid was filtered off, washed with DIPE, and dried. Yield: 23 g of compound 154 (48%).

Example B20

Preparation of Compound 157

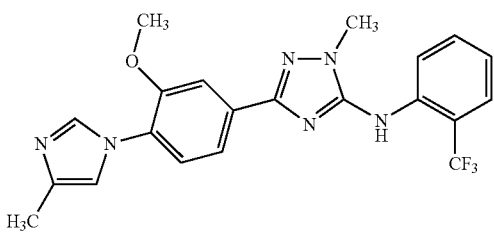 [SMILES: COc1cc(-c2nc(Nc3ccccc3C(F)(F)F)n(C)n2)ccc1-n1cnc(C)c1]

Methylhydrazine (0.58 ml, 10.8 mmol) was added to a solution of intermediate 39 (5 g, 10.8 mmol) in MeOH (116 ml). The r.m. was stirred at 50° C. for 1 h. After cooling the r.m. was conc. in vacuo. The residue was purified by flash chromatography over silica gel (eluent: DCM/MeOH from 100/0 to 98/2). The product fractions were collected and the solvent was removed under reduced pressure. The residue was crystallized from DIPE, filtered off and dried under vacuum. Yield: 2.37 g of compound 157 (51.2%).

Example B21

Preparation of Compound 223

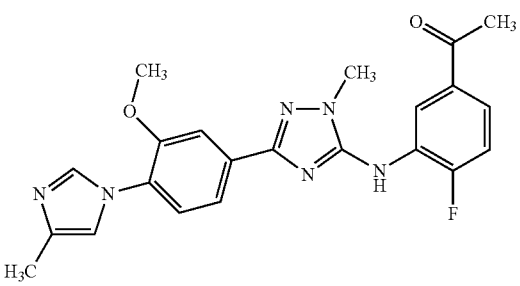 [SMILES: COc1cc(-c2nc(Nc3cc(C(C)=O)ccc3F)n(C)n2)ccc1-n1cnc(C)c1]

Methylhydrazine (0.28 ml, 5.3 mmol) was added to a solution of intermediate 60 (2.4 g, 5.3 mmol) in MeOH (82 ml). The r.m. was stirred at 50° C. for 3 h. After cooling the r.m. was conc. in vacuo. The residue was dissolved in DCM and a precipitate was formed and filtered. This material was recrystallized from $CH_3CN$, filtered and dried under vacuum. Yield: 0.97 g of compound 223 (43%).

Example B22

Preparation of Compound 175

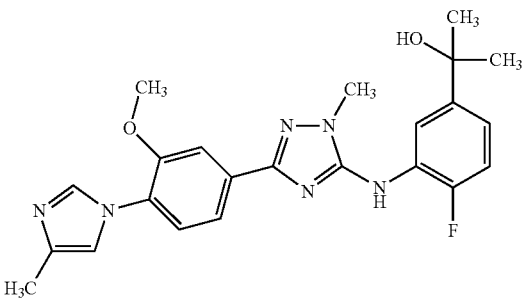 [SMILES: COc1cc(-c2nc(Nc3cc(C(C)(C)O)ccc3F)n(C)n2)ccc1-n1cnc(C)c1]

$CH_3MgBr$ (3 M in THF; 3.1 ml, 9.3 mmol) was added dropwise to a sol. of compound 223 (0.38 g, 0.92 mmol) in THF (5 ml) at 0° C. The r.m. was stirred at r.t. for 72 h. A sat. aq. sol. of $NH_4Cl$ was added dropwise to the r.m and the product was extracted with EtOAc. The o.l. was dried ($MgSO_4$), filtered and evaporated under reduced pressure. The crude was purified by column chromatography over silica gel (eluent: DCM/MeOH from 100/0 to 95/5). The pure fractions were collected and evaporated under reduced pressure, and the residue was recrystallized from DIPE/$CH_3CN$ to give product. Yield: 0.04 g of compound 175 (10%).

Example B23

Preparation of Compound 200

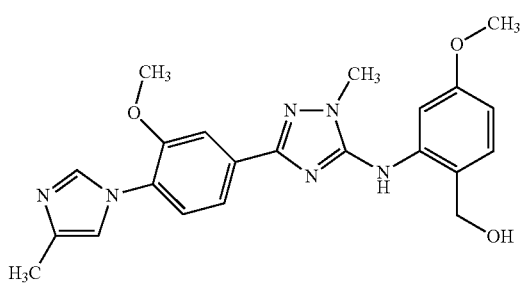 [SMILES: COc1ccc(CO)c(Nc2nc(-c3ccc(-n4cnc(C)c4)c(OC)c3)nn2C)c1]

LiAlH$_4$ (1 M in THF, 0.78 ml, 0.78 mmol) was added to a suspension of intermediate 63 in THF (5 ml), at r.t., under N$_2$. The resulting sol. was stirred at r.t. for 16 h. The reaction was quenched at 0° C. with H$_2$O (0.78 ml), NaOH 15% (0.78 ml) and water (2.4 ml), stirred for 30 min at r.t., and filtered through diatomaceous earth. The filtrate was evaporated under reduced pressure and the resulting residue partitioned between water and DCM. The two layers were separated. The aq. layer was extracted (DCM). The combined o.l. were dried (MgSO$_4$), filtered and evaporated. The residue was triturated (CH$_3$CN), to yield 0.038 g of compound 200 (34.5%).

Example B24

Preparation of Compound 232

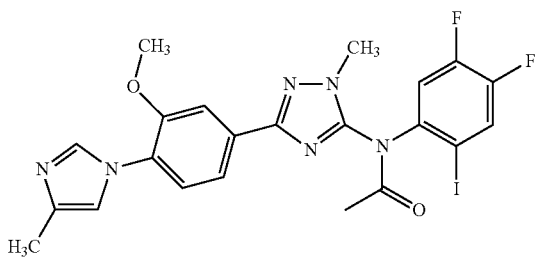 [SMILES: COc1cc(-c2nc(N(C(C)=O)c3cc(F)c(F)cc3I)n(C)n2)ccc1-n1cnc(C)c1]

A sol. of compound 120 (0.3 g, 0.57 mmol) in acetic anhydride (147 ml) was refluxed for 90 min. The r.m. was cooled down to r.t. and the solvent was evaporated under reduced pressure. DCM was added and the o.l. was washed with a sat. NaHCO$_3$ sol. The o.l. was dried (MgSO$_4$), filtered and evaporated under reduced pressure. The residue was purified by column chromatography over silica gel (eluent: DCM/MeOH from 100/0 to 98/2). The product fractions were evaporated. The residue was triturated (DIPE), filtered and dried in vacuo. Yield: 0.026 g of compound 232 (80.1%).

Example B25

Preparation of Compound 71

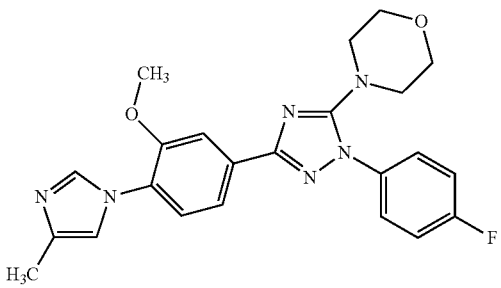 [SMILES: COc1cc(-c2nc(N3CCOCC3)n(-c3ccc(F)cc3)n2)ccc1-n1cnc(C)c1]

A mixture of intermediate 64 (0.4 g, 1.2 mmol), 4-morpholinecarbonitrile (0.72 ml, 7.05 mmol) and K$_2$CO$_3$ (0.081 g, 0.6 mmol) in n-BuOH (4 ml) was heated at 150° C. under microwave irradiation for 1 h. The r.m. was cooled and the solvent removed in vacuo. The residue was partitioned between H$_2$O and DCM. The organic layer was separated, dried (MgSO$_4$), filtered and evaporated. The residue was purified by RP preparative HPLC [Vydac Denali C18-10 μm, 250 g, 5 cm); mobile phase: a gradient of (0.25% NH$_4$HCO$_3$ sol. in water)/MeOH. The product fractions were collected and the solvent was evaporated. Yield: 0.073 g of compound 71 (14.3%).

Example B26

Preparation of Compound 130

A mixture of intermediate 67 (0.17 g, 0.59 mmol), 2-bromo-5-fluorotoluene (0.18 ml, 1.48 mmol), Cs$_2$CO$_3$ (0.48 g, 1.48 mmol), CuI (0.11 g, 0.59 mmol), and N,N'-dimethyl-ethylenediamine (0.13 ml, 1.18 mmol) in DMF (1.7 ml) was heated at 170° C. under microwave irradiation for 3 h. The r.m. was filtered over diatomaceous earth and washed with EtOAc. The o.l. was washed with al M NH$_4$OH-sol., brine, then dried (MgSO$_4$), filtered and the solvent was evaporated. The residue was purified by column chromatography over silica gel (eluent: DCM/MeOH from 100/0 to 96/4) The product fractions were isolated and evaporated under reduced pressure. The product was recrystallized from CH$_3$CN. Yield: 0.048 g of compound 130 (20.7%).

Example B27

Preparation of Compound 236

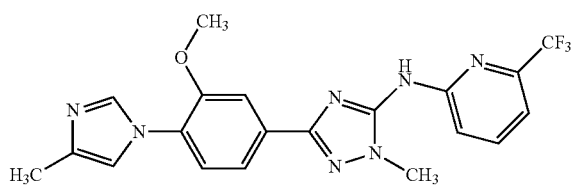

A mixture of intermediate 67 (0.21 g, 0.74 mmol), 2-chloro-6-(trifluomethyl)pyridine (0.54 g, 2.9 mmol), and $Cs_2CO_3$ (0.60 g, 1.85 mmol) in DMF was heated at 150° C. under microwave irradiation for 1.5 h. After cooling, $H_2O$ was added and the r.m. was extracted with EtOAc. The o.l. was washed with brine, dried ($MgSO_4$), filtered and evaporated under reduced pressure. The residue was purified by column chromatography over silica gel (eluent: DCM/MeOH from 100/0 to 97/3) The product fractions were isolated and evaporated under reduced pressure. The product was recrystallized from $CH_3CN$ and isolated by filtration as a white solid. Yield: 0.077 g of compound 236 (24.2%).

Example B28

Preparation of Compound 157 and intermediate 136

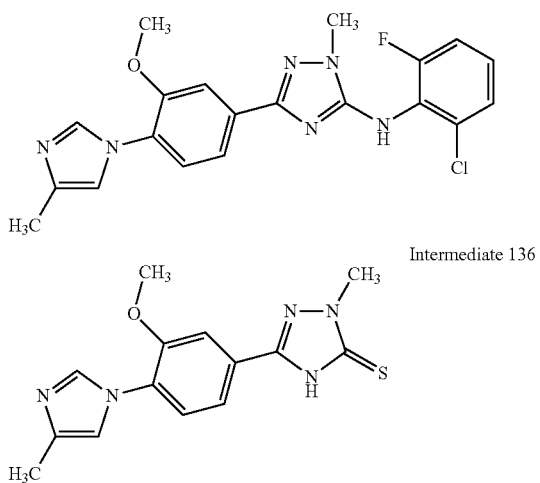

Methylhydrazine (0.055 ml, 1.02 mmol) was added to a solution of intermediate 68 (0.46 g, 1.03 mmol) in MeOH (12.5 ml). The r.m. was stirred at 60° C. for 1 h. After cooling the r.m. was conc. in vacuo. The resulting oil was purified by flash chromatography over silica gel (eluent: DCM/MeOH from 100/0 to 97/3). The purest fractions were collected and the solvent was evaporated. The residue was triturated ($CH_3CN$) and the solid was filtered off. Yield: 0.040 g of intermediate 136 (12.9%). The filtrate was evaporated and the residue purified by flash chromatography over silica gel (eluent: DCM/MeOH from 100/0 to 98/2). The product fractions were collected and the solvent was removed under reduced pressure. The residue was triturated ($CH_3CN$), filtered and dried. Yield: 0.079 g of compound 125 (18.6%).

Example B29

Preparation of Compound 249

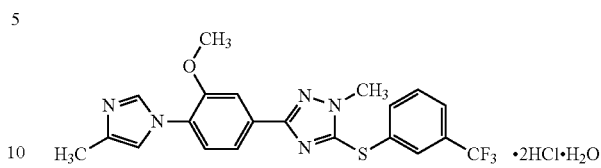

A mixture of intermediate 136 (0.040 g, 0.136 mmol), 3-iodobenzotrifluoride (0.038 ml, 0.27 mmol), $Cs_2CO_3$ (0.065 g, 0.20 mmol) and Xantphos (0.030 g, 0.051 mmol) in 1,4-dioxane (15 ml) was flushed with $N_2$ for 5 min. $Pd_2(dba)_3$ (0.012 g, 0.013 mmol) was then added and the r.m. was heated at 85° C. for 2 h. After cooling, the solvent was removed under reduced pressure. The residue was purified by chromatography over silica gel (eluent: DCM/MeOH from 100/0 to 98/2). The product fractions were collected and evaporated. Yield: 0.020 g of compound 249 (28.5%; 0.2HCl.$H_2O$).

Example B30

Preparation of Compound 251

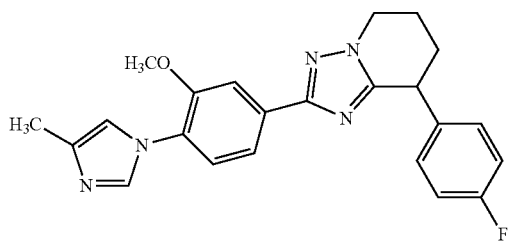 [SMILES: COc1cc(-c2nc3n(n2)CCCC3c2ccc(F)cc2)ccc1-n1cnc(C)c1]

A mixture of intermediate 76 (150 mg, 0.51 mmol), intermediates 29-30 (239 mg) and $Pd(PPh_3)_4$ (59 mg, 0.051 mmol) in a mixture of dioxane (4 ml) and a sat. aq. $NaHCO_3$ solution (4 ml) was heated at 150° C. for 15 min. under microwave irradiation. After cooling, the mixture was filtered over diatomaceous earth. The filtrate was evaporated under reduced pressure and the crude product was purified by column chromatography on silica gel (eluent: DCM/MeOH($NH_3$) from 100/0 to 97/3). The product fractions were evaporated. Yield: 0.12 g of compound 251 (59%).

Example B31 a) Preparation of Compound 258

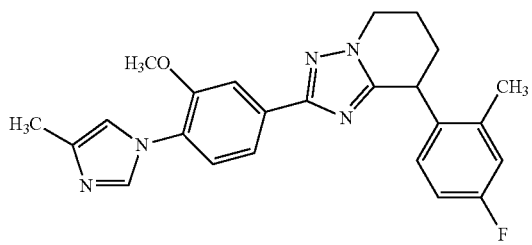

A mixture of intermediate 90 (570 mg, 1.84 mmol), intermediate 71 (763 mg, 2.21 mmol), $K_2CO_3$ (762 mg, 5.5 mmol) and $Pd(PPh_3)_4$ (212 mg, 0.18 mmol) in a mixture of $CH_3CN$ (32 ml) and $H_2O$ (8 ml) was heated at 150° C. for 15 min under microwave irradiation. After cooling, the mixture was filtered over diatomaceous earth. The filtrate was evaporated.

The crude product was purified by column chromatography on silica gel (eluent: DCM/MeOH(NH₃) from 100/0 to 97/3). The product fractions were collected and evaporated, yielding 0.45 g of compound 258 (59%).

b) Preparation of Compounds 332, 333, 315 and 314

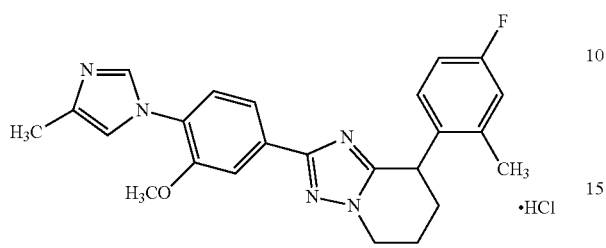

Compound 333: S-enantiomer; free base
Compound 332: R-enantiomer; free base
Compound 315: S-enantiomer; •HCl
Compound 314: R-enantiomer; •HCl Compound 258 (130 mg) was separated into its enantiomers by preparative SFC (Chiralpak Diacel OD 20×250 mm). Mobile phase (CO₂, MeOH with 0.2% 2-propylamine). The respective product fractions were collected and evaporated. The products were isolated to yield compound 332 and compound 333. Subsequently, the free bases were converted into their HCl salt forms by using a method known to the skilled person, yielding compound 314 (40 mg, R-enantiomer; .HCl) and compound 315 (40 mg, S-enantiomer; .HCl).

c) Preparation of Compound 269

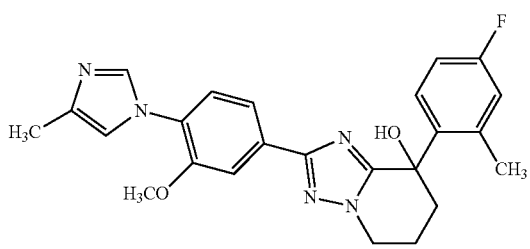

NaH (60% in mineral oil, 38 mg, 0.96 mmol) was added to a solution of compound 258 (200 mg, 0.48 mmol) in DMF (8 ml). Oxygen was bubbled through the mixture during a period of 24 h. The r.m. was diluted with EtOAc and washed (brine). The organic layer was dried (MgSO₄), filtered and conc. in vacuo. The residue was purified by chromatography over silica gel (eluent: DCM/MeOH(NH₃) from 100/0 to 97/3). The product fractions were evaporated. Yield: 0.125 g of compound 269 (60%).

d) Preparation of Compound 334

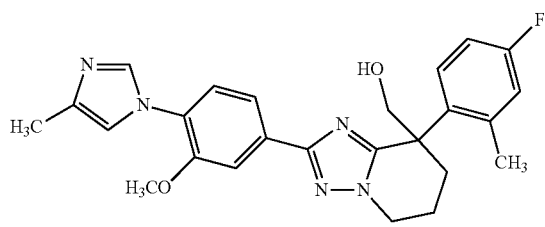 [SMILES: COc1cc(-c2nc3n(n2)CCCC3(CO)c2ccc(F)cc2C)ccc1-n1cnc(C)c1]

NaH (60% in mineral oil, 115 mg, 2.87 mmol) was added to a sol. of compound 258 (600 mg, 1.44 mmol) and paraformaldehyde (647 mg, 7.2 mmol) in DMF (24 ml). The r.m. was stirred at r.t. for 48 h, water was added and the aq. mixture was extracted with EtOAc. The organic layer was dried (MgSO₄), filtered and conc. in vacuo. The residue was purified by chromatography over silica gel (eluent: DCM/MeOH(NH₃) from 100/0 to 97/3). The product fractions were collected and evaporated. Yield: 45 mg of compound 334 (7%).

Example B32 a) Preparation of Compound 373

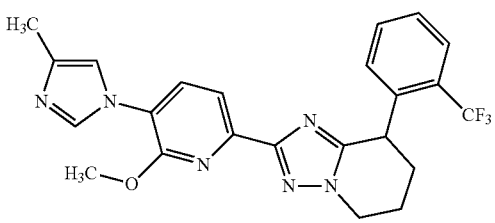 [SMILES: COc1nc(-c2nc3n(n2)CCCC3c2ccccc2C(F)(F)F)ccc1-n1cnc(C)c1]

5-Chloro-2-(2-trifluoromethylphenyl)pentanimidic acid ethyl ester hydrochloride (0.12 g, 0.34 mmol) and imidazole (0.28 g, 4.12 mmol) were added to a sol. of intermediate 111 (0.11 g, 0.34 mmol) in MeOH (1.5 ml). The sol. was stirred for 40 h at 30° C. The r.m. was conc. and the residue was dissolved in DCM (5 ml). The sol. was washed with a sat. aq. NaHCO₃ sol. The organic layer was dried (MgSO₄), filtered and conc. The residue was purified by flash column chromatography over silica gel (eluent: DCM/MeOH(NH₃) from 100/0 to 99/1). The product fractions were collected and conc. in vacuo, yielding 0.06 g of compound 373 (33%).

b) Preparation of Compounds 262 and 263

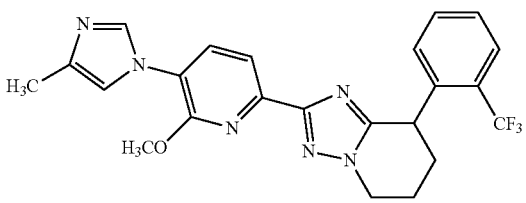

Compound 262: R-enantiomer
Compound 263: S-enantiomer

Compound 373 (200 mg) was separated into its enantiomers by preparative SFC (Chiralpak Diacel AS 20×250 mm). Mobile phase (CO₂, MeOH with 0.2% 2-propylamine). The respective product fractions were collected and evaporated, to yield compound 262 (50 mg, R-enantiomer) and compound 263 (50 mg, S-enantiomer).

Example B33 a) Preparation of Compound 281

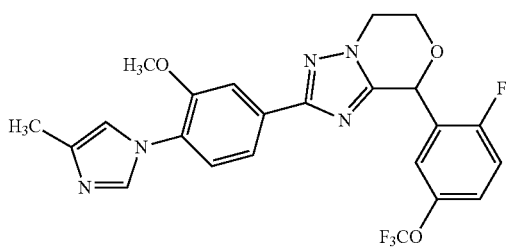 [SMILES: COc1cc(-c2nc3n(n2)CCOC3c2cc(OC(F)(F)F)ccc2F)ccc1-n1cnc(C)c1]

A mixture of intermediate 97 (250 mg, 0.65 mmol), intermediate 71 (231 mg, 0.79 mmol), $K_2CO_3$ (271 mg, 1.96 mmol) and $Pd(PPh_3)_4$ (76 mg, 0.065 mmol) in $CH_3CN$ (16 ml) and $H_2O$ (4 ml) was heated at 150° C. for 20 min under microwave irradiation. After cooling, the mixture was evaporated under reduced pressure, and the residue was partitioned between DCM and water. The organic layer was dried ($MgSO_4$), filtered and conc. The residue was purified by flash column chromatography over silica gel (eluent: DCM/MeOH ($NH_3$) from 100/0 to 97/3). The product fractions were collected and evaporated. Yield: 120 mg of compound 281 (37%).

b) Preparation of Compounds 165 and 128

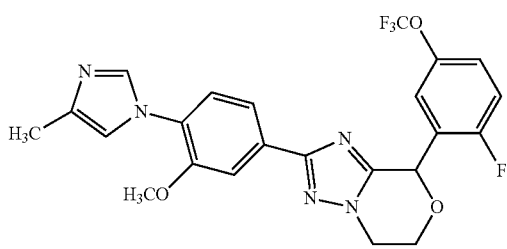

Compound 128: S-enantiomer
Compound 165: R-enantiomer

Compound 281 (87 mg) was separated into its enantiomers by preparative SFC (Chiralpak Diacel AD 20×250 mm). Mobile phase ($CO_2$, MeOH with 0.2% 2-propylamine). The respective product fractions were collected and evaporated to give compound 165 (20 mg, R-enantiomer) and compound 128 (24 mg, S-enantiomer).

Example B34 a) Preparation of Compound 294

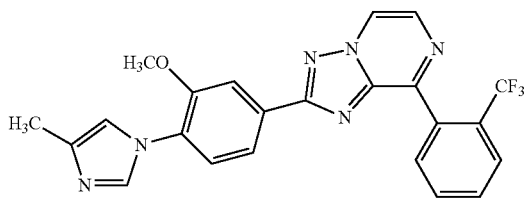 [SMILES: COc1cc(-c2nc3c(-c4ccccc4C(F)(F)F)nccn3n2)ccc1-n1cnc(C)c1]

A mixture of intermediate 86 (412 mg, 1.2 mmol), intermediates 29-30 (566 mg), $Cs_2CO_3$ (1.17 g, 3.6 mmol) and $Pd(PPh_3)_4$ (111 mg, 0.096 mmol) in DME (8 ml) and water (4 ml) was heated at 90° C. for 5 h. After cooling, the organic layer was separated and evaporated. The residue was partitioned between DCM and water. The organic layer was separated, dried ($MgSO_4$), filtered and evaporated. The residue was purified by chromatography over silica gel (eluent: DCM/MeOH from 100/0 to 99/1). The product fractions were evaporated. Yield: 325 mg of compound 294 (60%).

b) Preparation of Compound 278

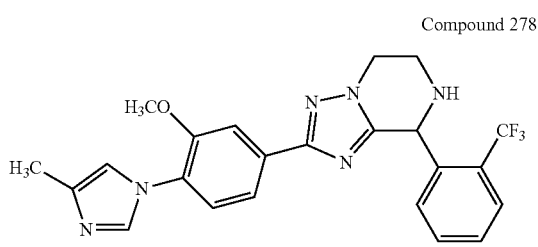 [SMILES: COc1cc(-c2nc3n(n2)CCNC3c2ccccc2C(F)(F)F)ccc1-n1cnc(C)c1]

Compound 278

MeOH (30 ml) was added to Pd/C 10% (50 mg) under a $N_2$ atmosphere. Subsequently, compound 294 (300 mg, 0.28 mmol) and a mixture HCl/isopropanol (6 N) (0.33 ml, 2 mmol) were added. The r.m. was stirred at 50° C. under a $H_2$ atmosphere until 2 eq. of $H_2$ was absorbed. The catalyst was filtered off over diatomaceous earth and the filtrate was evaporated. The residue was partitioned between DCM and an aq. $NH_4OH$ solution. The separated organic layer was dried ($MgSO_4$), filtered and evaporated. The residue was crystallized from DIPE/$CH_3CN$. Yield: 185 mg of compound 278 (61%).

c) Preparation of Compound 276

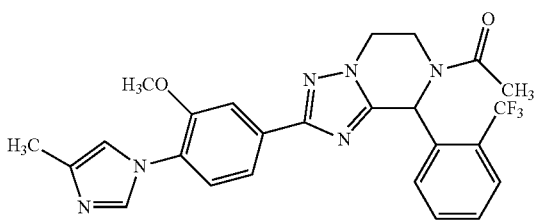 [SMILES: COc1cc(-c2nc3n(n2)CCN(C(C)=O)C3c2ccccc2C(F)(F)F)ccc1-n1cnc(C)c1]

Acetylchloride (13 mg, 0.17 mmol) was added to a sol. of compound 278 (75 mg, 0.17 mmol) and $Et_3N$ (0.034 ml, 0.25 mmol) in DCM (3.1 ml). The mixture was stirred at r.t. for 2 h. Water (1 ml) and a few drops of aq. $NH_4OH$ were added. The mixture was filtered over diatomaceous earth. The organic layer was evaporated and the residue was purified by chromatography over silica gel (eluent: DCM/MeOH from 100/0 to 99/1). The product fractions were evaporated. Yield: 25 mg of compound 276 (28%).

d) Preparation of Compound 275

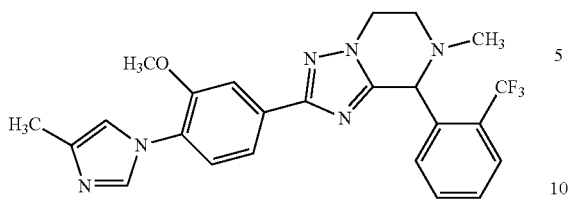

A 37% aq. formaldehyde sol. (0.02 ml) was added to a sol. of compound 278 (80 mg, 0.18 mmol) in MeOH (2.2 ml). The r.m. was stirred at r.t. for 1 h, and then 1 drop of AcOH was added followed by NaBH$_3$CN (16 mg, 0.25 mmol). The r.m. was stirred at r.t. for 2 h. Subsequently, 1 drop of water was added. The mixture was conc. and the residue was partitioned between DCM, water and a few drops of an aq. NH$_4$OH sol. The mixture was filtered over diatomaceous earth. The organic layer was evaporated. The residue was solidified from DIPE. Yield: 66 mg of compound 275 (80%).

Example B35

Preparation of Compound 279

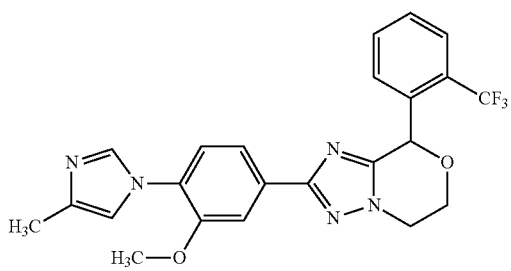 [SMILES: COc1cc(-c2nc3n(n2)CCOC3c2ccccc2C(F)(F)F)ccc1-n1cnc(C)c1]

HCl (4 M in dioxane, 14.6 ml, 58.3 mmol) was added to a sol. of intermediate 102 (1.30 g, 2.95 mmol) in EtOAc (16.2 ml). The solution was stirred for 1.5 h, after which it was conc. in vacuo. The residue was dissolved in EtOH (8 ml) and Et$_3$N (1.6 ml). A sol. of intermediate 2a (0.92 g, 3.54 mmol) in EtOH (8 ml) and Et$_3$N (1.6 ml) was added. The r.m. was refluxed for 24 h, then cooled to r.t. and washed with a sat. aq. sol. of NaHCO$_3$. The organic layer was dried (MgSO$_4$), filtered and conc. under reduced pressure. The residue was purified by flash column chromatography over silica gel (eluent: DCM/MeOH(NH3) from 100/0 to 97/3). The product fractions were collected and conc. in vacuo, yielding 0.15 g of compound 279 (12%).

Example B36

Preparation of Compound 295

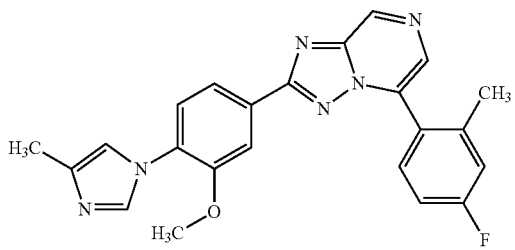 [SMILES: COc1cc(-c2nc3cncc(-c4ccc(F)cc4C)n3n2)ccc1-n1cnc(C)c1]

Compound 295 was prepared from intermediate 107 (0.36 g, 1.03 mmol) via a 3 step sequence as described for intermediate 37 in Example A14.b-d yielding 0.20 g of compound 295.

Example B37

Preparation of Compound 79

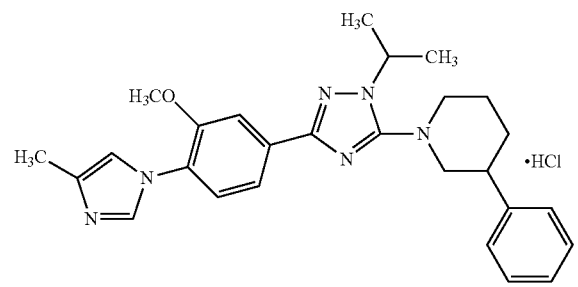 [SMILES: COc1cc(-c2nc(N3CCCC(c4ccccc4)C3)n(C(C)C)n2)ccc1-n1cnc(C)c1 ; Cl]

Bis(pinacolato)diboron (730 mg, 2.86 mmol), PdCl$_2$(dppf) (120 mg, 0.14 mmol), and KOAc (560 mg, 5.73 mmol) were added to a sol. of intermediate 5 (560 mg, 1.86 mmol) in DMF (20 ml). The r.m. was heated at 120° C. for 30 min under microwave irradiation and was then cooled to r.t. Subsequently, K$_2$CO$_3$ (593 mg, 4.29 mmol), intermediate 115 (500 mg, 1.43 mmol), Pd(PPh$_3$)$_4$ (83 mg, 0.072 mmol), and water (2.41 ml) were added and the r.m. was heated at 150° C. for 1 h under microwave irradiation. The r.m. was partitioned between DCM and water. The organic layer was separated and the o.l was dried (MgSO$_4$), filtered, and evaporated. The residue was purified by chromatography over silica gel (eluent: DCM/MeOH from 100/0 to 95/5). The product containing fractions were collected and evaporated. The residue was purified further by chromatography over silica gel (eluent: DCM/EtOAc from 100/0 to 50/50 to 0/100). The product fractions were collected and evaporated. Yield: 176 mg of compound 79 (25%) as an HCl salt.

Example B38 a) Preparation of Compound 91

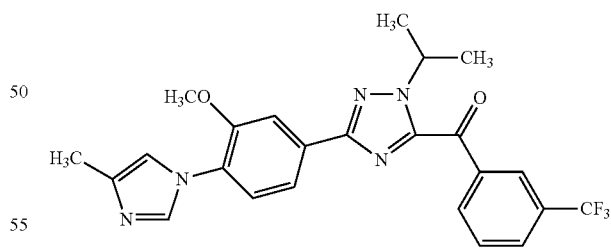

A sol. of intermediate 113 (615 mg, 1.7 mmol), intermediate 71 (500 mg, 1.7 mmol), K$_2$CO$_3$ (705 mg, 5.1 mmol) and Pd(PPh$_3$)$_4$ (196 mg, 0.17 mmol) in a mixture of CH$_3$CN (22 ml) and H$_2$O (6 ml) was flushed with N$_2$ for 5 min. The r.m. was heated at 150° C. for 20 min. under microwave irradiation. After cooling, the solvent was removed and the residue was partitioned between DCM and H$_2$O. The o.l. was separated, dried (MgSO$_4$), filtered and evaporated. The residue was purified by chromatography over silica gel (eluent: heptane/EtOAc from 50/50 to 0/100). The product fractions were collected and evaporated. The residue was triturated with heptane to yield: 0.30 g of compound 91 (38%).

b) Preparation of Compound 89

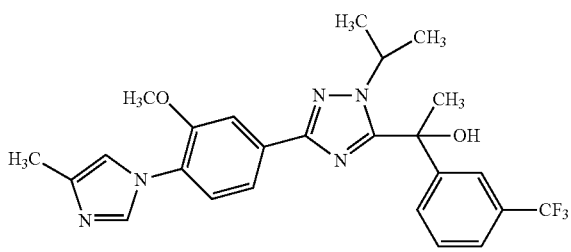 [SMILES: COc1cc(-c2nc(C(C)(O)c3cccc(C(F)(F)F)c3)n(C(C)C)n2)ccc1-n1cnc(C)c1]

To a sol. of compound 91 (90 mg, 0.19 mmol) in THF (13 ml) was added a sol. of MeMgBr in Et$_2$O (3 M, 0.32 ml, 0.96 mmol) at 0° C. The r.m. was stirred at 0° C. for 1 h, and then added dropwise to a sat. aq. NH$_4$Cl sol. The mixture was extracted with EtOAc. The separated o.l. was dried (MgSO$_4$), filtered and evaporated. The residue was purified by chromatography over silica gel (eluent: DCM/MeOH from 100/0 to 95/5). The product fractions were evaporated. Yield: 49 mg of compound 89 (53%).

Example B39 a) Preparation of Compound 290 and compound 291 compound 290

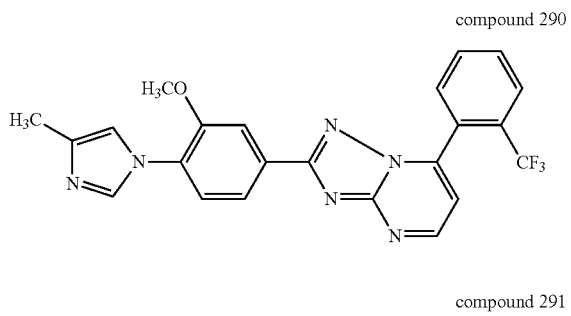

compound 291

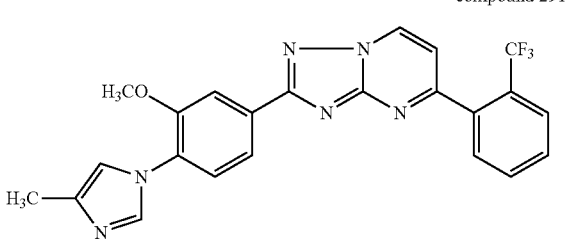

Starting from intermediate 122 (500 mg, 1.1 mmol), compounds 290 and 291 were obtained according to the procedure described in Example A41.b. Yield: 36 mg of compound 290 (6%) and 96 mg of compound 291 (17%)

b) Preparation of Compound 274

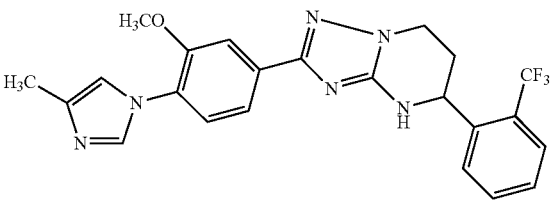 [SMILES: COc1cc(-c2nc3n(n2)CCC(c2ccccc2C(F)(F)F)N3)ccc1-n1cnc(C)c1]

Compound 291 (50 mg, 0.11 mmol) was added to a stirred mixture of 10% Pd/C (20 mg) in MeOH (40 ml). The r.m. was stirred at 25° C. under a H$_2$ atmosphere. After 2 eq. of H$_2$ were absorbed, the catalyst was removed by filtration over diatomaceous earth. The filtrate was evaporated under reduced pressure and the crude product was purified by column chromatography on silica gel (eluent: DCM/MeOH from 100/0 to 95/5). The product fractions were combined and evaporated to yield a light-brown solid. Yield: 35 mg of compound 274 (71%).

Example B40

Preparation of Compound 93

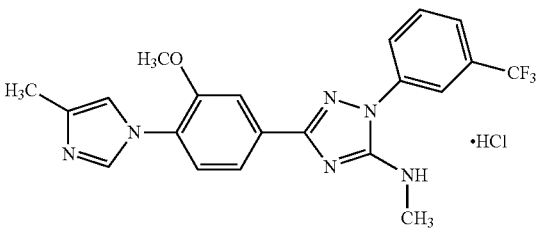 [SMILES: CNc1nc(-c2ccc(-n3cnc(C)c3)c(OC)c2)nn1-c1cccc(C(F)(F)F)c1 ; Cl]

A mixture of intermediate 124 (380 mg, 1.18 mmol), intermediates 29-30 (412 mg) and Pd(PPh$_3$)$_4$ (140 mg, 0.12 mmol) in a mixture of dioxane (4 ml) and a sat. aq. NaHCO$_3$ sol. (4 ml) was heated at 150° C. for 15 min under microwave irradiation. After cooling, the r.m. was filtered over diatomaceous earth and conc. under reduced pressure. The residue was purified by chromatography over silica gel (eluent: DCM/MeOH(NH$_3$) from 100/0 to 97/3). The product fractions were collected and evaporated. Yield: 210 mg of compound 93 as HCl salt (38%).

Example B41

Preparation of Compound 84

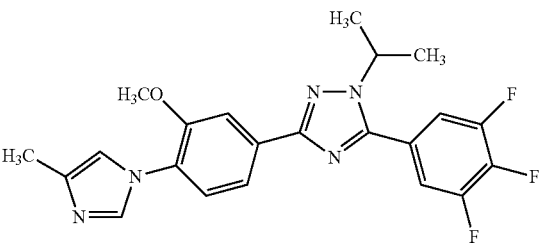 [SMILES: COc1cc(-c2nc(-c3cc(F)c(F)c(F)c3)n(C(C)C)n2)ccc1-n1cnc(C)c1]

Et$_3$N (4.18 ml, 30.1 mmol) was added to a sol. of intermediate 2 (1 g, 3.01 mmol) and 3,4,5-trifluorobenzoylchloride (761 mg, 3.91 mmol) in toluene (q.s.). The r.m. was heated at reflux for 2 h. Subsequently 1 more eq. 3,4,5-trifluorobenzoylchloride was added and the r.m. was refluxed for 1 h. Subsequently, isopropylhydrazine (1.14 g, 15 mmol) was

Example B42 a) Preparation of Compound 362

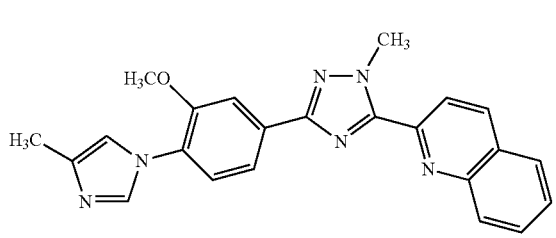 [SMILES: COc1cc(-c2nc(-c3ccc4ccccc4n3)n(C)n2)ccc1-n1cnc(C)c1]

A mixture of intermediate 127 (140 mg, 0.48 mmol), intermediate 71 (171 mg, 0.58 mmol), K₂CO₃ (201 mg, 1.45 mmol) and Pd(PPh₃)₄ (56 mg, 0.048 mmol) in a mixture of CH₃CN (4 ml) and H₂O (1 ml) was heated at 150° C. for 20 min under microwave irradiation. Then, more of intermediate 71 (171 mg, 0.58 mmol) and Pd(PPh₃)₄ (56 mg, 0.048 mmol) were added, and the r.m. was heated at 150° C. for 30 min under microwave irradiation. After cooling, the mixture was evaporated and the residue was partitioned between DCM and water. The o.l. was separated, dried (MgSO₄), filtered and conc. in vacuo. The residue was purified by chromatography over silica gel (eluent: DCM/MeOH(NH₃) from 100/0 to 99/1).). The product fractions were collected and evaporated. Yield: 106 mg of compound 362 (55%).

b) Preparation of Compound 365 and Compound 366

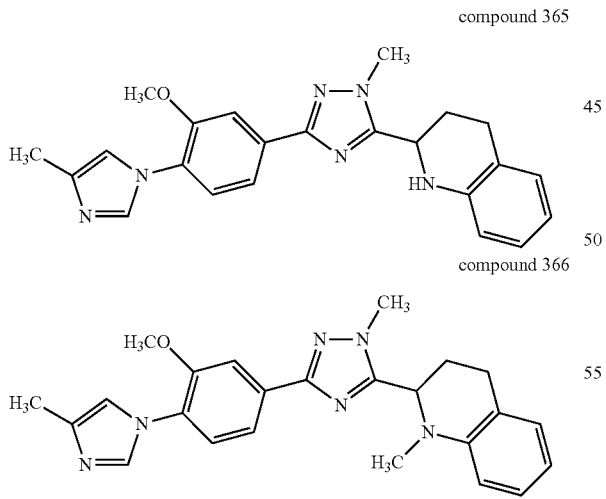

compound 365 compound 366

MeOH (40 ml) was added to Pt/C₅% (50 mg) under N₂ atmosphere. Compound 362 (100 mg, 0.252 mmol) was added. The r.m. was stirred at 50° C. under H₂ atmosphere until 2 eq. of H₂ were absorbed. The catalyst was filtered off over diatomaceous earth and the filtrate was evaporated. The residue was purified by RP preparative HPLC [Vydac Denali C18-10 µm, 250 g, 5 cm); mobile phase: a gradient of (0.25% NH₄HCO₃ sol. in water)/CH₃CN]. The product fractions were collected and evaporated. Yield: 3.6 mg of compound 365 (3.6%) and 4.6 mg of compound 366 (4.4%).

Example B43 a) Preparation of Compound 372

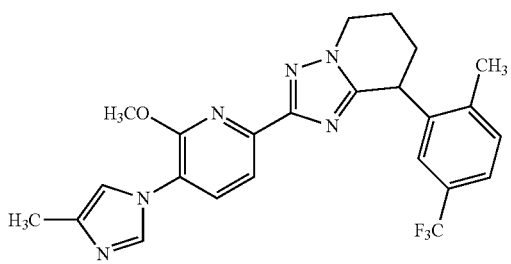 [SMILES: COc1nc(-c2nc3n(n2)CCCC3c2cc(C(F)(F)F)ccc2C)ccc1-n1cnc(C)c1]

A mixture of intermediate 135 (200 mg, 0.56 mmol), intermediate 38 (171 mg, 0.54 mmol) and Pd(PPh₃)₄ (64 mg, 0.056 mmol), in a mixture of dioxane (4 ml) and an aq. sat. NaHCO₃ sol. (4 ml) was heated at 150° C. for 20 min under microwave irradiation. After cooling, the mixture was evaporated under reduced pressure, and the residue was partitioned between DCM and water. The organic layer was dried (MgSO₄), filtered and conc. under reduced pressure. The residue was purified by flash column chromatography over silica gel (eluent: DCM/MeOH(NH₃) from 100/0 to 97/3). The product fractions were collected and evaporated. The residue was purified further by preparative SFC (Chiralpak Diacel OD 20×250 mm). Mobile phase (CO₂, CH₃CN). The product fractions were evaporated. Yield: 0.1 g of compound 372 (37%).

b) Preparation of Compounds 342 and 343

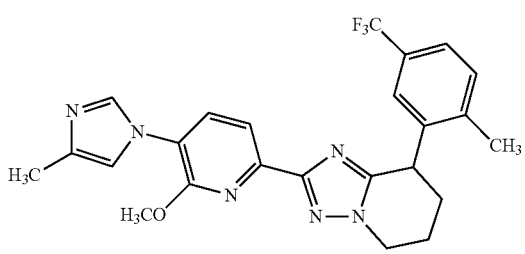

Compound 342: R-enantiomer
Compound 343: S-enantiomer

Compound 372 (100 mg) was separated into its enantiomers by preparative SFC (Chiralpak Diacel AD 20×250 mm). Mobile phase (CO₂, MeOH with 0.2% 2-propylamine). The respective product fractions were collected and evaporated to yield compound 342 (35 mg, R-enantiomer) and compound 343 (40 mg, S-enantiomer).

Compounds 1 to 379 in tables 1a, 1b, 1c, 1d, 1e, 1f and 1g list the compounds that were prepared by analogy to one of the above Examples. In case no salt form is indicated, the compound was obtained as a free base. In case no specific stereochemistry is indicated for a stereocenter, the compound was obtained as a racemic mixture of the R and the S enantiomers. 'Pr.' refers to the Example number according to which protocol the compound was synthesized. 'Co. No.' means compound number.

TABLE 1a
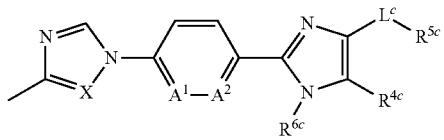
| Co. No. | Pr. | X | A¹ | A² | R⁴ᶜ | Lᶜ—R⁵ᶜ | R⁶ᶜ |
|---|---|---|---|---|---|---|---|
| 25 | B8a | CH | COCH₃ | CH | CH₃ | CH₃ | H |
| 13 | B8b | CH | COCH₃ | CH | | CH₃ | CH₃ |
| 26 | B8a | CH | COCH₃ | CH | CH₃ | | H |
| 11 | B7 | CH | COCH₃ | CH | CH₃ | | H |
| 27 | B7 | CH | CH | COCH₃ | CH₃ | | H |
| 28 | B7 | N | COCH₃ | CH | CH₃ | | H |
| 29 | B7 | CH | COCH₃ | CH | | | H |
| 12 | B8a | CH | COCH₃ | CH | CH₃ | | H |
| 14 | B8b | CH | COCH₃ | CH | CH₃ | | CH₃ |
TABLE 1b
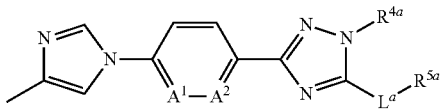
| Co. No. | Pr. | A¹ | A² | R⁴ᵃ | Lᵃ—R⁵ᵃ | Stereochemistry and salt forms |
|---|---|---|---|---|---|---|
| 63 | B2 | COCH₃ | CH | F₃C—(phenyl) | H | •2HCl |

TABLE 1b-continued

| Co. No. | Pr. | A¹ | A² | R⁴ᵃ | Lᵃ—R⁵ᵃ | Stereochemistry and salt forms |
|---|---|---|---|---|---|---|
| 65 | B2 | COCH₃ | CH | 3-(CF₃)phenyl | H | |
| 3 | B2 | COCH₃ | CH | 4-F-phenyl | CH₃ | |
| 19 | B12 | COCH₃ | CH | 2-(CF₃)phenyl | CH₃ | •2HCl |
| 30 | B12 | COCH₃ | CH | 3-(CF₃)phenyl | CH₃ | •2HCl |
| 69 | B40 | COCH₃ | N | 4-F-phenyl (isopropyl) | CH₃ | |
| 31 | B12 | COCH₃ | CH | 4-F-phenyl | isopropyl | •HCl |
| 32 | B12 | COCH₃ | CH | 3-(CF₃)phenyl | isopropyl | •HCl |
| 300 | B38b | COCH₃ | CH | 4-F-phenyl (isopropyl) | C(CH₃)₂OH | |
| 70 | B35 | COCH₃ | CH | H | 1-(2-CF₃-phenyl)-4-chlorobutyl | |
| 33 | B1a | COCH₃ | CH | H | cyclohexyl | |

TABLE 1b-continued
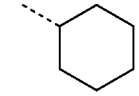
| Co. No. | Pr. | A¹ | A² | R$^{4a}$ | L$^a$—R$^{5a}$ | Stereochemistry and salt forms |
|---|---|---|---|---|---|---|
| 34 | B1b | COCH$_3$ | CH | CH$_3$ | 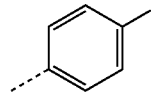 | |
| 71 | B25 | COCH$_3$ | CH | 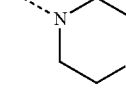 | 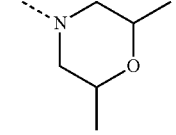 | |
| 35 | B9 | COCH$_3$ | CH | CH$_3$ |  | CIS |
| 301 | B38a | COCH$_3$ | CH | 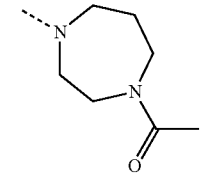 | 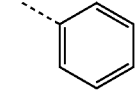 | •HCl •H$_2$O |
| 9 | B5 | COCH$_3$ | CH | CH$_3$ | 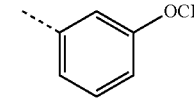 | |
| 36 | B2b | COCH$_3$ | CH | CH$_3$ |  | |
| 37 | B3b | COCH$_3$ | CH | 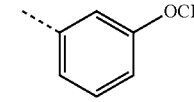 | 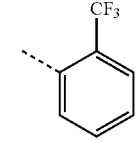 | |
| 38 | B4b | COCH$_3$ | CH | CH$_3$ | 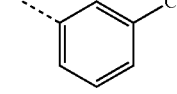 | |
| 7 | B4b | COCH$_3$ | CH | CH$_3$ |  | |
| 39 | B16 | COCH$_3$ | CH | 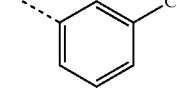 |  | |
| 68 | B16 | COCH$_3$ | N | 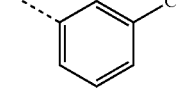 | | •2HCl |

TABLE 1b-continued
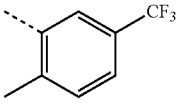
| Co. No. | Pr. | A¹ | A² | R⁴ᵃ | Lᵃ—R⁵ᵃ | Stereochemistry and salt forms |
|---|---|---|---|---|---|---|
| 72 | B1b | COCH₃ | CH | CH₃ | 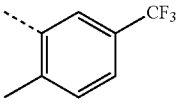 | |
| 73 | B3b | COCH₃ | CH | 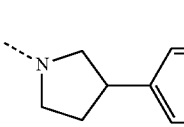 | 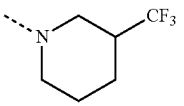 | |
| 74 | B37 | COCH₃ | CH | 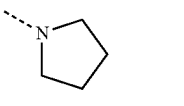 |  | •2HCl •2.5H₂O |
| 75 | B37 | COCH₃ | CH | 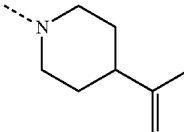 |  | 1.8HCl 1.5H₂O |
| 76 | B40 | COCH₃ | CH | 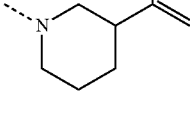 | 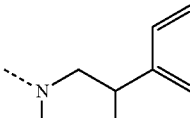 | |
| 77 | B37 | COCH₃ | CH | CH₃ | 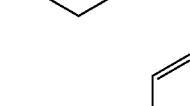 | |
| 78 | B37 | COCH₃ | CH | CH₃ | 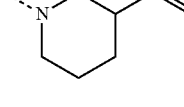 | •1.5HCl •2.5H₂O |
| 79 | B37 | COCH₃ | CH |  | | •HCl |
| 80 | B37 | COCH₃ | N | | | •HCl |

TABLE 1b-continued
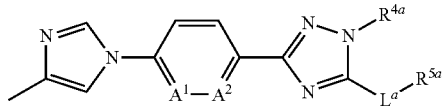
| Co. No. | Pr. | A¹ | A² | R⁴ᵃ | Lᵃ—R⁵ᵃ | Stereochemistry and salt forms |
|---|---|---|---|---|---|---|
| 365 | B42b | COCH₃ | CH | CH₃ | 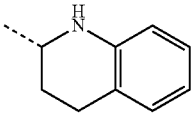 | |
| 366 | B42b | COCH₃ | CH | CH₃ | 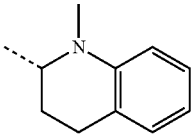 | |
| 81 | B37 | COCH₃ | CH | CH₃ | 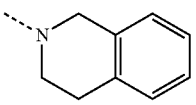 | |
| 82 | B37 | COCH₃ | CH |  | 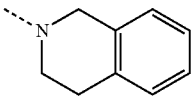 | •HCl |
| 349 | B18 | COCH₃ | CH | CH₃ | 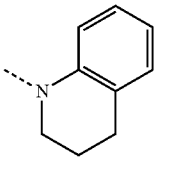 | •2HCl •H₂O |
| 325 | B18 | COCH₃ | CH | CH₃ | 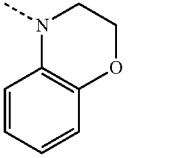 | •2HCl •H₂O |
| 327 | B18 | COCH₃ | CH | CH₃ | 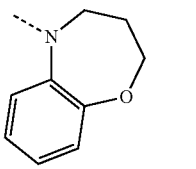 | |
| 4 | B3a | COCH₃ | CH | H | 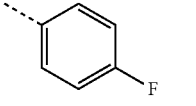 | |
| 40 | B4b | COCH₃ | CH | CH₃ | 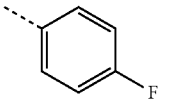 | |
| 5 | B3b | COCH₃ | CH | 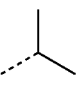 | 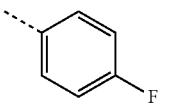 | |

TABLE 1b-continued
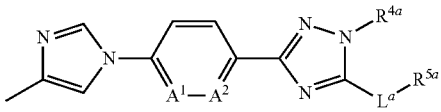
| Co. No. | Pr. | A¹ | A² | R⁴ᵃ | Lᵃ—R⁵ᵃ | Stereochemistry and salt forms |
|---|---|---|---|---|---|---|
| 83 | B3b | COCH₃ | CH |  | 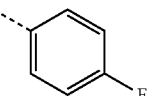 | •1.3HCl •H₂O |
| 41 | B3b | COCH₃ | CH | 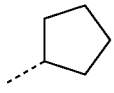 | 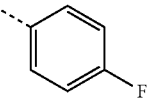 | |
| 42 | B3a | COCH₃ | N | H | 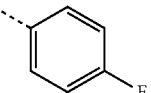 | |
| 84 | B41 | COCH₃ | CH |  | 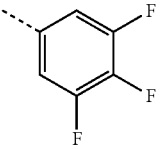 | |
| 2 | B1b | COCH₃ | CH | CH₃ | 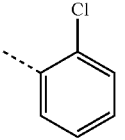 | |
| 85 | B3b | COCH₃ | CH | 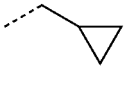 | 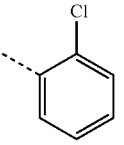 | •2H₂O •0.8HCl |
| 86 | B3b | COCH₃ | CH | 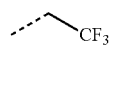 | 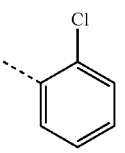 | •1.6H₂O<br>•1.2HCl |
| 87 | B3b | COCH₃ | CH | 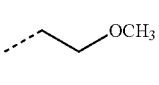 | 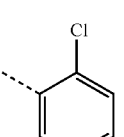 | |
| 66 | B17 | COCH₃ | CH |  | 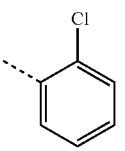 | |

TABLE 1b-continued
| Co. No. | Pr. | A¹ | A² | R⁴ᵃ | Lᵃ—R⁵ᵃ | Stereochemistry and salt forms |
|---|---|---|---|---|---|---|
| 88 | B1b | COCH₃ | CH | CH₃ | 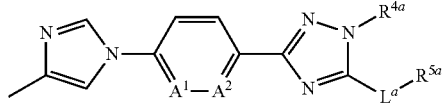 | |
| 67 | B17 | COCH₃ | CH | 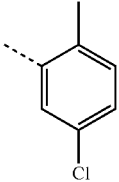 |  | •2HCl |
| 43 | B4b | COCH₃ | CH | CH₃ | 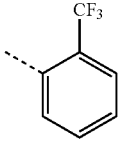 | |
| 326 | B42a | COCH₃ | CH | CH₃ | 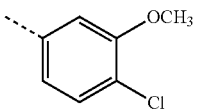 | |
| 44 | B4a | COCH₃ | CH | H | 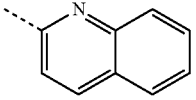 | |
| 22 | B4b | COCH₃ | CH | CH₃ | 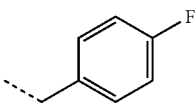 | |
| 45 | B4 | COCH₃ | CH | CH₃ | 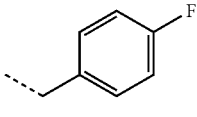 | (E) |
| 46 | B4 | COCH₃ | CH | CH₃ | 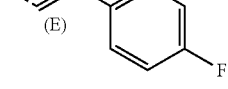 | |
| 89 | B38b | COCH₃ | CH | 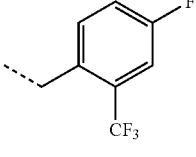 |  | |
| 47 | B4 | COCH₃ | CH | CH₃ | 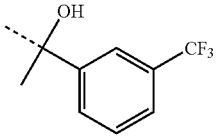 | |

TABLE 1b-continued
| Co. No. | Pr. | A¹ | A² | R⁴ᵃ | Lᵃ—R⁵ᵃ | Stereochemistry and salt forms |
|---|---|---|---|---|---|---|
| 90 | B1 | COCH₃ | CH | CH₃ | 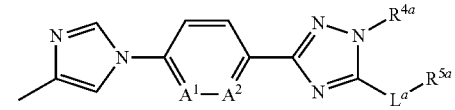 | |
| 21 | B14 | COCH₃ | CH | CH₃ | 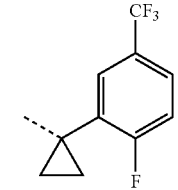 | |
| 91 | B38a | COCH₃ | CH | 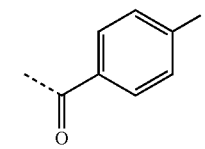 |  | |
| 92 | B40 | COCH₃ | N | 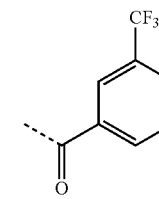 | 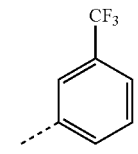 | •HCl |
| 93 | B40 | COCH₃ | CH |  | 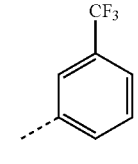 | •HCl |
| 94 | B18 | COCH₃ | CH | CH₃ |  | |
| 95 | B18 | COCH₃ | CH | CH₃ | 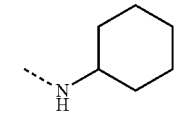 | CIS |
| 96 | B18 | COCH₃ | CH | CH₃ | 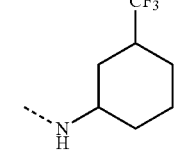 | TRANS |

TABLE 1b-continued
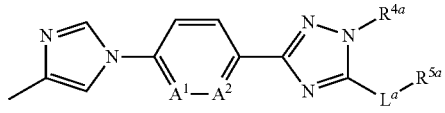
| Co. No. | Pr. | A¹ | A² | R$^{4a}$ | L$^a$—R$^{5a}$ | Stereochemistry and salt forms |
|---|---|---|---|---|---|---|
| 335 | B20 | COCH₃ | CH | CH₃ | 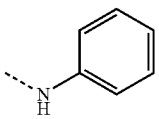 | |
| 97 | B18 | COCH₃ | CH | CH₃ | 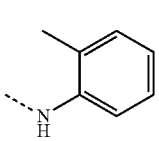 | |
| 98 | B18 | COCF₃ | CH | CH₃ | 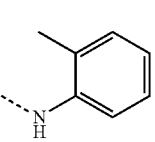 | |
| 99 | B18 | COCH₃ | CH | CH₃ | 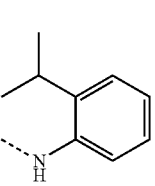 | |
| 100 | B19a | COCH₃ | N | CH₃ | 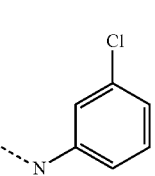 | |
| 101 | B18 | COCH₃ | CH | CH₃ | 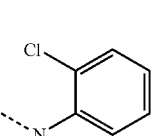 | •2HCl •H₂O |
| 102 | B20 | COCH₃ | CH | CH₃ | 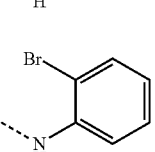 | |
| 103 | B20 | COCH₃ | CH | CH₃ | 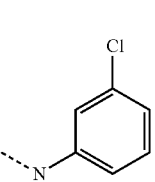 | |
| 104 | B20 | COCH₃ | CH | CH₃ | 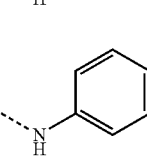 | |

TABLE 1b-continued
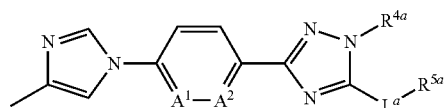
| Co. No. | Pr. | A¹ | A² | R⁴ᵃ | Lᵃ—R⁵ᵃ | Stereochemistry and salt forms |
|---|---|---|---|---|---|---|
| 105 | B20 | COCH₃ | CH | CH₃ | 2-F-phenyl-NH- | |
| 106 | B20 | COCH₃ | CH | CH₃ | 4-F-phenyl-NH- | |
| 107 | B20 | COCH₃ | N | CH₃ | 2-F-phenyl-NH- | |
| 108 | B20 | COCH₃ | CH | CH₃ | 4-Cl-phenyl-NH- | |
| 323 | B18 | COCH₃ | CH | CH₃ | 2-methyl-6-F-phenyl-NH- | |
| 350 | B20 | COCH₃ | CH | CH₃ | 5-methyl-2-F-phenyl-NH- | |
| 352 | B20 | COCH₃ | CH | CH₃ | 4-methyl-2-F-phenyl-NH- | |
| 109 | B20 | COCH₃ | CH | CH₃ | 2-Cl-4-F-phenyl-NH- | |
| 110 | B20 | COCH₃ | CH | CH₃ | 2-F-5-F-phenyl-NH- | |

TABLE 1b-continued
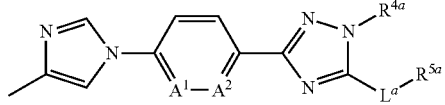
| Co. No. | Pr. | A¹ | A² | R⁴ᵃ | Lᵃ—R⁵ᵃ | Stereochemistry and salt forms |
|---|---|---|---|---|---|---|
| 111 | B18 | COCH₃ | CH | CH₃ | 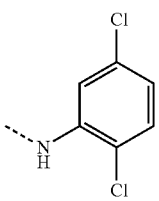 | |
| 112 | B18 | COCH₃ | CH | CH₃ | 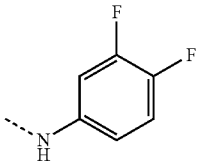 | |
| 113 | B20 | COCH₃ | CH | CH₃ | 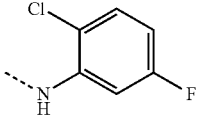 | |
| 114 | B20 | COCH₃ | CH | CH₃ | 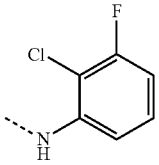 | |
| 302 | B19a | COCH₃ | N | CH₃ | 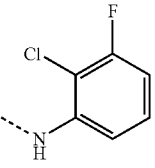 | |
| 115 | B20 | COCH₃ | CH | CH₃ | 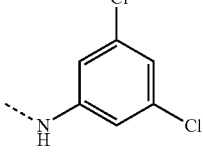 | |
| 116 | B20 | COCH₃ | CH | CH₃ | 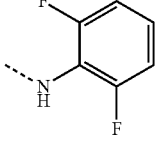 | |
| 117 | B19a | COCH₃ | N | CH₃ | 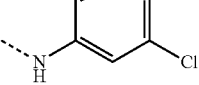 | |

TABLE 1b-continued
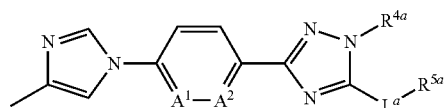
| Co. No. | Pr. | A¹ | A² | R$^{4a}$ | L$^a$—R$^{5a}$ | Stereochemistry and salt forms |
|---|---|---|---|---|---|---|
| 303 | B20 | COCH₃ | CH | CH₃ | 2-F, 5-Br anilino | |
| 118 | B20 | COCH₃ | CH | CH₃ | 2-F, 3-Cl anilino | |
| 119 | B20 | COCH₃ | CH | CH₃ | 2-Cl, 3-Cl anilino | |
| 120 | B20 | COCH₃ | CH | CH₃ | 2-F, 4-F, 5-I anilino | |
| 121 | B20 | COCH₃ | CH | CH₃ | 2-Cl, 4-F, 5-F anilino | |
| 122 | B20 | COCH₃ | CH | CH₃ | 2-F, 3-Cl, 6-F anilino | |
| 123 | B20 | COCH₃ | CH | CH₃ | 2-F, 5-Cl anilino | |
| 48 | B9 | COCH₃ | CH | CH₃ | 3-F, 4-F, 5-F anilino | |

TABLE 1b-continued

| Co. No. | Pr. | A¹ | A² | R⁴ᵃ | Lᵃ—R⁵ᵃ | Stereochemistry and salt forms |
|---|---|---|---|---|---|---|
| 124 | B20 | COCH₃ | CH | CH₃ | 2,3-difluorophenyl-NH- | |
| 125 | B28 | COCH₃ | CH | CH₃ | 2-chloro-6-fluorophenyl-NH- | |
| 126 | B20 | COCH₃ | CH | CH₃ | 4-chloro-2-fluorophenyl-NH- | |
| 127 | B20 | COCH₃ | CH | CH₃ | 3-bromo-2,6-difluorophenyl-NH- | |
| 318 | B18 | COCH₃ | CF | CH₃ | 2-methylphenyl-NH- | |
| 129 | B26 | COCH₃ | CH | CH₃ | 3-chloro-2-methylphenyl-NH- | |
| 130 | B26 | COCH₃ | CH | CH₃ | 4-fluoro-2-methylphenyl-NH- | |
| 304 | B18 | COCH₃ | CH | CH₃ | 3-fluoro-2-methylphenyl-NH- | |
| 131 | B20 | COCH₃ | CH | CH₃ | 2-methyl-5-(trifluoromethyl)phenyl-NH- | |

TABLE 1b-continued

| Co. No. | Pr. | A¹ | A² | R⁴ᵃ | Lᵃ—R⁵ᵃ | Stereochemistry and salt forms |
|---|---|---|---|---|---|---|
| 132 | B19a | COCH₃ | N | CH₃ | 2-CF₃-phenyl-NH- | |
| 133 | B20 | COCH₃ | CH | isobutyl | 3-CF₃-phenyl-NH- | |
| 134 | B20 | COCH₃ | CH | CH₃ | 2-F,4-CF₃-phenyl-NH- | |
| 135 | B20 | COCH₃ | CH | CH₂CH₃ | 2-F,5-CF₃-phenyl-NH- | |
| 351 | B20 | COCH₃ | CH | CH₃ | 2-CF₃,5-CH₃-phenyl-NH- | |
| 319 | B20 | C—CH₃ | N | CH₃ | 2-F,5-CF₃-phenyl-NH- | |
| 320 | B18 | COCH₃ | CF | CH₃ | 2-F,5-CF₃-phenyl-NH- | |
| 136 | B20 | COCH₃ | CH | -C(CH₃)₂OH | 2-F,5-CF₃-phenyl-NH- | |
| 137 | B20 | COCH₃ | CH | -CH₂CH₂CN | 2-F,5-CF₃-phenyl-NH- | |
| 138 | B20 | COCH₃ | N | CH₃ | 2-CF₃,3-F-phenyl-NH- | |

TABLE 1b-continued

| Co. No. | Pr. | A¹ | A² | R⁴ᵃ | Lᵃ—R⁵ᵃ | Stereochemistry and salt forms |
|---|---|---|---|---|---|---|
| 139 | B18 | COCF₃ | CH | CH₃ | 2-F, 5-CF₃ anilino | |
| 140 | B20 | COCH₃ | CH | CH₃ | 2,3-diF, 5-CF₃ anilino | |
| 141 | B20 | COCH₃ | CH | CH₃ | 2,5-diF, 4-CF₃ anilino | |
| 142 | B20 | COCH₃ | CH | CH₃ | 2-CF₃, 4,5-diF anilino | |
| 143 | B20 | COCH₃ | CH | CH₃ | 2-CF₃, 5-Cl anilino | |
| 144 | B20 | COCH₃ | CH | CH₃ | 2-CF₃, 5-CF₃ anilino | |
| 145 | B20 | COCH₃ | CH | CH₂CF₃ | 5-CF₃ anilino | |
| 146 | B20 | COCH₃ | CH | CH₃ | 3-CF₃ anilino | |
| 147 | B20 | COCH₃ | CH | CH₂CH₃ | 2-CF₃ anilino | |
| 148 | B18 | COCH₃ | CH | CH₃ | 2-F, 3-CF₃ anilino | |

TABLE 1b-continued

| Co. No. | Pr. | A¹ | A² | R$^{4a}$ | L$^a$—R$^{5a}$ | Stereochemistry and salt forms |
|---|---|---|---|---|---|---|
| 149 | B20 | CH | CH | CH₃ | 2-CF₃, 4-F anilino | |
| 150 | B20 | COCH₃ | CH | CH₃ | 3,5-bis(CF₃) anilino | |
| 151 | B20 | COCH₃ | CH | CH₃ | 4-CF₃ anilino | |
| 152 | B20 | COCH₃ | CH | CH₃ | 3-CF₃, 4-F anilino | |
| 153 | B19a | COCH₃ | N | CH₃ | 3-CF₃ anilino | |
| 154 | B19a B19b | COCH₃ | N | CH₃ | 2-F, 5-CF₃ anilino | |
| 15 | B9 | COCH₃ | CH | CH₃ | 4-F, 2-CF₃ anilino | |
| 49 | B9 | COCH₃ | CH | iPr | 4-F, 2-CF₃ anilino | |
| 155 | B20 | COCH₃ | CH | CH₃ | 3-F, 2-CF₃ anilino | |

TABLE 1b-continued
| Co. No. | Pr. | A¹ | A² | R⁴ᵃ | Lᵃ—R⁵ᵃ | Stereochemistry and salt forms |
|---|---|---|---|---|---|---|
| 156 | B20 | COCH₃ | CH | CH₃ | 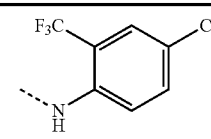 | |
| 157 | B20 | COCH₃ | CH | CH₃ | 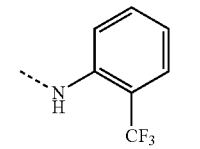 | |
| 158 | B19a | COCH₃ | N | CH₃ | 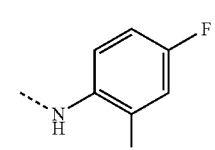 | |
| 159 | B20 | COCH₃ | CH | CH₃ | 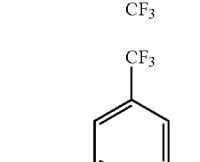 | |
| 160 | B19a | COCH₃ | N | CH₃ | 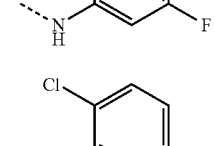 | |
| 161 | B20 | COCH₃ | CH | CH₃ | 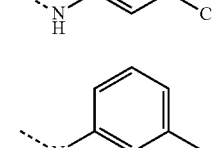 | |
| 162 | B20 | COCH₃ | CH | CH₃ | 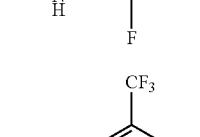 | |
| 163 | B20 | COCH₃ | CH | CH₃ | 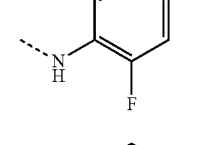 | |
| 164 | B20 | COCH₃ | CH | CH₃ | 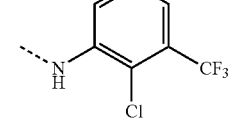 | |

TABLE 1b-continued

| Co. No. | Pr. | A¹ | A² | R⁴ᵃ | Lᵃ—R⁵ᵃ | Stereochemistry and salt forms |
|---|---|---|---|---|---|---|
| 357 | B20 | COCH₃ | CH | CH₃ | 2-F, 5-tBu anilino | |
| 358 | B20 | COCH₃ | CH | CH₃ | 2-F, 5-(tetrahydrofuran-3-yloxy) anilino | |
| 321 | B18 | C—CN | CH | CH₃ | 2-CF₃ anilino | |
| 322 | B18 | C—CN | CH | CH₃ | 5-CF₃, 2-F anilino | |
| 167 | B19a | COCH₃ | N | CH₃ | 2-F, 3-CF₃ anilino | |
| 168 | B20 | COCH₃ | CH | CH₃ | 2-CF₃, 5-F anilino | |
| 169 | B20 | COCH₃ | CH | CH₃ | 2-CF₃, 3-Cl anilino | |
| 170 | B20 | CH | N | CH₃ | 2-CF₃, 4-F anilino | |
| 171 | B19a | COCH₃ | N | CH₃ | 3-CF₃, 4-F anilino | |

TABLE 1b-continued

| Co. No. | Pr. | A¹ | A² | R⁴ᵃ | Lᵃ—R⁵ᵃ | Stereochemistry and salt forms |
|---|---|---|---|---|---|---|
| 172 | B20 | COCH₃ | CH | CH₃ | 2,4-difluoro-5-(trifluoromethyl)anilino | |
| 173 | B20 | COCH₃ | CH | CH₃ | 5-fluoro-2-methylanilino | •2HCl |
| 174 | B20 | COCH₃ | CH | CH₃ | 5-chloro-2-methylanilino | |
| 175 | B22 | COCH₃ | CH | CH₃ | 2-fluoro-5-(2-hydroxypropan-2-yl)anilino | |
| 176 | B20 | COCH₃ | CH | isobutyl | 2-(trifluoromethyl)anilino | |
| 177 | B18 | COCH₃ | CH | CH₃ | 2-chloro-5-(trifluoromethyl)anilino | |
| 178 | B20 | COCH₃ | CH | isobutyl | 2-fluoro-5-(trifluoromethyl)anilino | |
| 179 | B20 | COCH₃ | CH | sec-butyl | 2-fluoro-5-(trifluoromethyl)anilino | |
| 180 | B20 | COCH₃ | CH | CH₃ | 5-(dimethylamino)-2-fluoroanilino | |
| 181 | B20 | COCH₃ | CH | CH₃ | 3-(trifluoromethoxy)anilino | |

TABLE 1b-continued
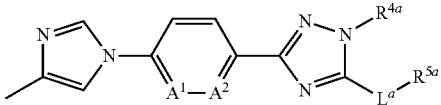
| Co. No. | Pr. | A¹ | A² | R⁴ᵃ | Lᵃ—R⁵ᵃ | Stereochemistry and salt forms |
|---|---|---|---|---|---|---|
| 182 | B20 | COCH₃ | CH | CH₃ | 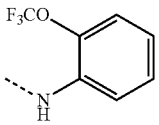 | •2HCl •1.4H₂O |
| 183 | B20 | COCH₃ | CH | CH₃ | 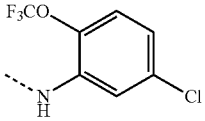 | |
| 184 | B20 | COCH₃ | N | CH₃ | 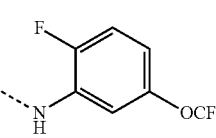 | |
| 185 | B20 | COCH₃ | CH | CH₃ | 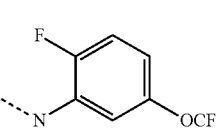 | |
| 186 | B20 | COCH₃ | CH | CH₃ | 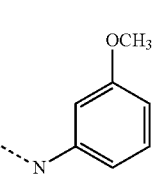 | |
| 187 | B20 | COCH₃ | CH | CH₃ | 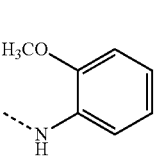 | |
| 367 | B18 | COCH₃ | CH | CH₃ | 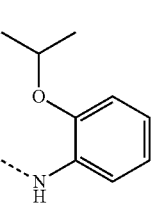 | |
| 188 | B20 | COCH₃ | CH | CH₃ | 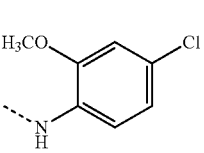 | |
| 189 | B18 | COCH₃ | CH | CH₃ | 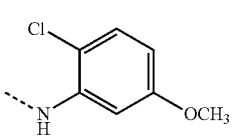 | |

TABLE 1b-continued

| Co. No. | Pr. | A¹ | A² | R⁴ᵃ | Lᵃ—R⁵ᵃ | Stereochemistry and salt forms |
|---|---|---|---|---|---|---|
| 190 | B20 | COCH₃ | CH | CH₃ | 5-F, 2-OCH₃ anilino | |
| 191 | B20 | COCH₃ | CH | CH₃ | 4-Cl, 3-OCH₃ anilino | |
| 192 | B20 | COCH₃ | CH | CH₃ | 5-Cl, 2-OCH₃ anilino | |
| 193 | B20 | COCH₃ | CH | CH₃ | 4-F, 3-OCH₃ anilino | |
| 194 | B20 | COCH₃ | CH | CH₃ | 3-Cl, 2-OCH₃ anilino | |
| 195 | B20 | COCH₃ | CH | CH₃ | 2-F, 5-OCH₃ anilino | |
| 196 | B20 | COCH₃ | CH | CH₃ | 2,6-diF, 3-OCH₃ anilino | |
| 354 | B20 | COCH₃ | CH | CH₃ | 5-OCH₂CH₃, 2-F anilino | |

TABLE 1b-continued
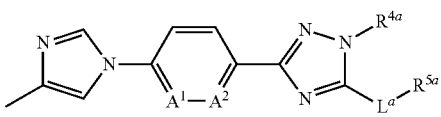
| Co. No. | Pr. | A¹ | A² | R⁴ᵃ | Lᵃ—R⁵ᵃ | Stereochemistry and salt forms |
|---|---|---|---|---|---|---|
| 355 | B20 | COCH₃ | CH | CH₃ | 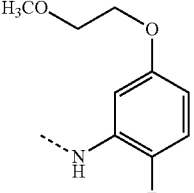 | |
| 356 | B20 | COCH₃ | CH | CH₃ | 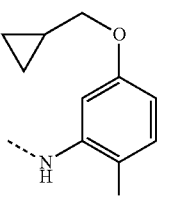 | |
| 197 | B20 | COCH₃ | CH | CH₃ | 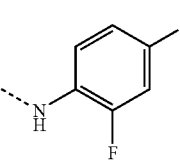 | |
| 353 | B19b | COCH₃ | N | CH₃ | 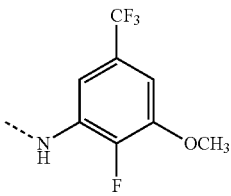 | |
| 198 | B20 | COCH₃ | CH | CH₃ | 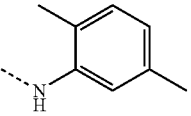 | |
| 199 | B18 | COCH₃ | CH | CH₃ | 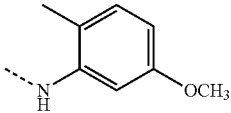 | |
| 328 | B18 | COCH₃ | CH | CH₃ | 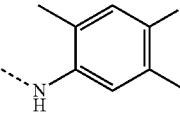 | |
| 200 | B23 | COCH₃ | CH | CH₃ | 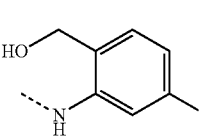 | |

TABLE 1b-continued
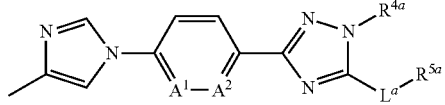
| Co. No. | Pr. | A¹ | A² | R$^{4a}$ | L$^a$—R$^{5a}$ | Stereochemistry and salt forms |
|---|---|---|---|---|---|---|
| 307 | B20 | COCH$_3$ | CH | CH$_3$ | 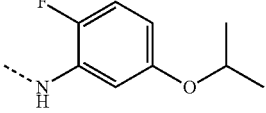 | |
| 201 | B19a | COCH$_3$ | N | CH$_3$ | 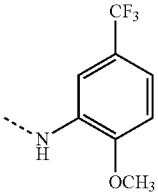 | |
| 202 | B20 | COCH$_3$ | CH | CH$_3$ | 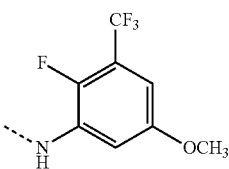 | |
| 203 | B20 | COCH$_3$ | CH | CH$_3$ | 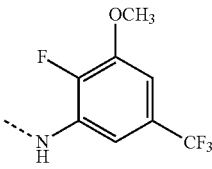 | |
| 324 | B20 | COCH$_3$ | CH | CH$_3$ | 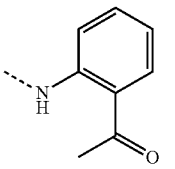 | •HCl |
| 308 | B20 | COCH$_3$ | CH | CH$_3$ | 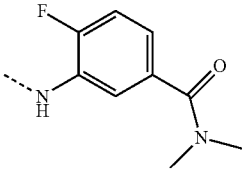 | |
| 309 | B20 | COCH$_3$ | CH | CH$_3$ | 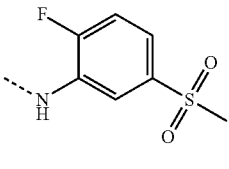 | |
| 204 | B20 | COCH$_3$ | CH | CH$_3$ | 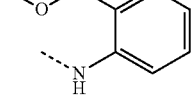 | •HCl •0.12H$_2$O |

TABLE 1b-continued
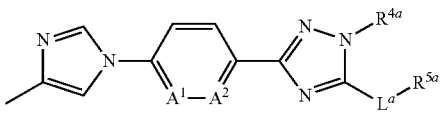
| Co. No. | Pr. | A¹ | A² | R⁴ᵃ | Lᵃ—R⁵ᵃ | Stereochemistry and salt forms |
|---|---|---|---|---|---|---|
| 205 | B20 | COCH₃ | CH | CH₃ | 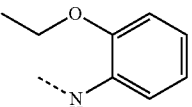 | |
| 206 | B20 | CH | CH | CH₃ | 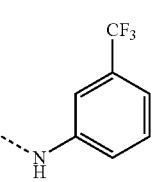 | |
| 207 | B20 | CH | CH | CH₃ | 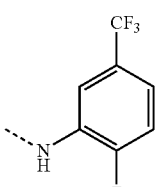 | |
| 208 | B20 | COCH₃ | CH | CH₃ | 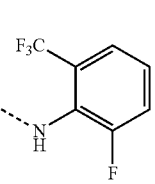 | |
| 209 | B20 | COCH₃ | CH | (CH₂)₂OCH₃ | 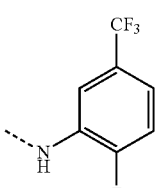 | |
| 210 | B20 | COCH₃ | CH | CH₃ | 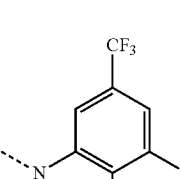 | |
| 211 | B20 | COCH₃ | CH | CH₃ | 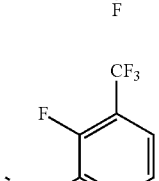 | |

TABLE 1b-continued
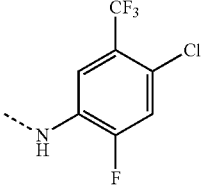
| Co. No. | Pr. | A¹ | A² | R⁴ᵃ | Lᵃ—R⁵ᵃ | Stereochemistry and salt forms |
|---|---|---|---|---|---|---|
| 212 | B20 | COCH₃ | CH | CH₃ | 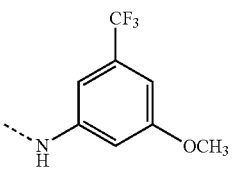 | |
| 213 | B20 | COCH₃ | CH | CH₃ | 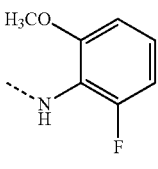 | |
| 214 | B20 | COCH₃ | CH | CH₃ | 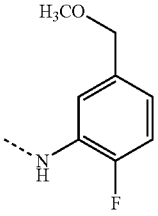 | |
| 331 | B18 | COCH₃ | CH | CH₃ | 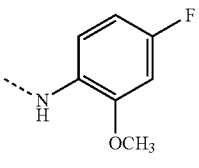 | |
| 215 | B20 | COCH₃ | CH | CH₃ | 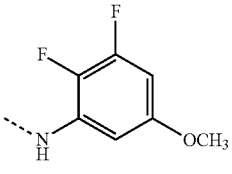 | |
| 216 | B20 | COCH₃ | CH | CH₃ | 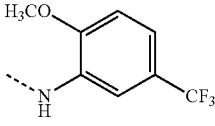 | |
| 217 | B18 | COCH₃ | CH | CH₃ | 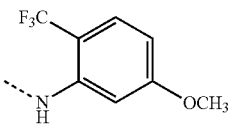 | |
| 218 | B20 | COCH₃ | CH | CH₃ | | |

TABLE 1b-continued

| Co. No. | Pr. | A¹ | A² | R⁴ᵃ | Lᵃ—R⁵ᵃ | Stereochemistry and salt forms |
|---|---|---|---|---|---|---|
| 219 | B20 | COCH₃ | CH | CH₃ | 2-fluoro-3-methoxyphenyl-NH– | |
| 220 | B20 | COCH₃ | CH | CH₃ | 2-methoxy-4-fluoro-5-trifluoromethylphenyl-NH– | |
| 310 | B20 | COCH₃ | CH | CH₃ | 2-(difluoromethoxy)phenyl-NH– | |
| 221 | B20 | COCH₃ | CH | CH₃ | 3-acetamido-4-fluorophenyl-NH– | |
| 222 | B20 | COCH₃ | CH | CH₃ | 3-acetamidophenyl-NH– | |
| 223 | B21 | COCH₃ | CH | CH₃ | 3-acetyl-4-fluorophenyl-NH– | |
| 224 | B20 | COCH₃ | CH | CH₃ | 3-cyanophenyl-NH– | |

TABLE 1b-continued
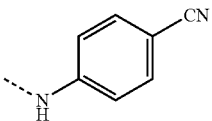
| Co. No. | Pr. | A¹ | A² | R$^{4a}$ | L$^a$—R$^{5a}$ | Stereochemistry and salt forms |
|---|---|---|---|---|---|---|
| 225 | B20 | COCH₃ | CH | CH₃ | 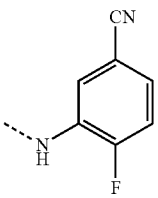 | |
| 226 | B20 | COCH₃ | CH | CH₃ | 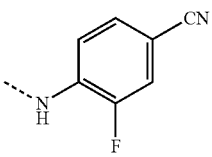 | |
| 227 | B20 | COCH₃ | CH | CH₃ | 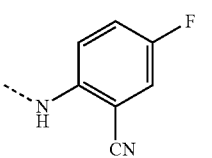 | |
| 228 | B20 | COCH₃ | CH | CH₃ |  | |
| 229 | B20 | COCH₃ | CH | CH₃ | 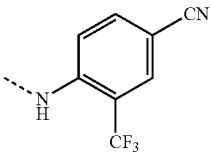 | |
| 230 | B20 | COCH₃ | CH | CH₃ | 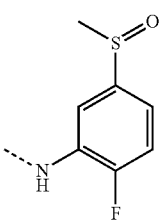 | |
| 330 | B20 | COCH₃ | CH | CH₃ | 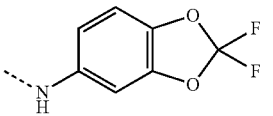 | |
| 231 | B20 | COCH₃ | CH | CH₃ | | |

TABLE 1b-continued

| Co. No. | Pr. | A¹ | A² | R⁴ᵃ | Lᵃ—R⁵ᵃ | Stereochemistry and salt forms |
|---|---|---|---|---|---|---|
| 317 | B20 | COCH₃ | CH | CH₃ | 4-NH-2,2-difluoro-benzo[1,3]dioxole | |
| 50 | B9 | COCH₃ | CH | CH₃ | NH-(4-fluoro-2-trifluoromethyl-phenyl) | |
| 337 | B19a | COCH₃ | N | CH₃ | NH-(2-fluoro-5-trifluoromethyl-phenyl) | |
| 232 | B24 | COCH₃ | CH | CH₃ | N(COCH₃)-(2-iodo-4,5-difluoro-phenyl) | |
| 233 | B20 | COCH₃ | CH | CH₃ | NH-(2-trifluoromethyl-pyridin-3-yl) | |
| 234 | B20 | COCH₃ | CH | CH₃ | NH-(2-chloro-pyridin-4-yl) | |
| 235 | B18 | COCH₃ | CH | CH₃ | NH-(2-trifluoromethyl-pyridin-4-yl) | |
| 236 | B27 | COCH₃ | CH | CH₃ | NH-(6-trifluoromethyl-pyridin-2-yl) | |

TABLE 1b-continued

| Co. No. | Pr. | A¹ | A² | R⁴ᵃ | Lᵃ—R⁵ᵃ | Stereochemistry and salt forms |
|---|---|---|---|---|---|---|
| 237 | B20 | COCH₃ | CH | CH₃ | pyridin-3-yl-NH- | |
| 238 | B20 | COCH₃ | CH | CH₃ | (6-methylpyridin-3-yl)-NH- | |
| 239 | B20 | COCH₃ | CH | CH₃ | (2-methylpyridin-4-yl)-NH- | |
| 240 | B20 | COCH₃ | CH | CH₃ | (3-trifluoromethylpyridin-2-yl)-NH- | |
| 241 | B20 | COCH₃ | CH | CH₃ | (2-methoxypyridin-3-yl)-NH- | |
| 242 | B20 | COCH₃ | CH | CH₃ | (1-methyl-6-oxo-1,6-dihydropyridin-3-yl)-NH- | |
| 243 | B20 | COCH₃ | CH | CH₃ | (1-methyl-2-oxo-1,2-dihydropyridin-3-yl)-NH- | |
| 244 | B20 | COCH₃ | CH | CH₃ | (5-tert-butyl-1-methyl-1H-pyrazol-3-yl)-NH- | |
| 245 | B18 | COCH₃ | CH | CH₃ | benzyl-NH- | |
| 311 | B38a | COCH₃ | CH | CH₃ | -CH₂-NH-(3-trifluoromethylphenyl) | |

TABLE 1b-continued

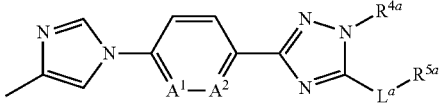

| Co. No. | Pr. | A¹ | A² | R⁴ᵃ | Lᵃ—R⁵ᵃ | Stereochemistry and salt forms |
|---|---|---|---|---|---|---|
| 51 | B9 | COCH₃ | CH | CH₃ | 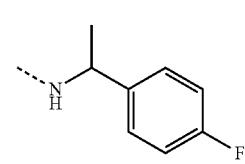 S-enantiomer | S-enantiomer |
| 329 | B38a | COCH₃ | CH | CH₃ | 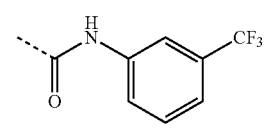 | |
| 246 | B37 | COCH₃ | CH | CH₃ | 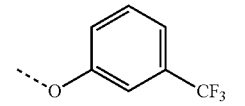 | |
| 247 | B37 | COCH₃ | CH | 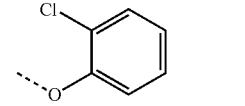 | 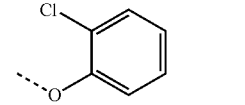 | |
| 248 | B37 | COCH₃ | CH | CH₃ | 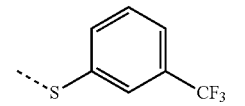 | |
| 249 | B29 | COCH₃ | CH | CH₃ | 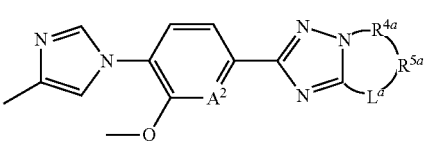 | •2HCl •H₂O |

TABLE 1c

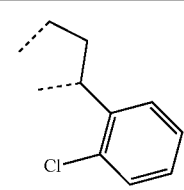

| Co. No. | Pr. | A² | R⁴ᵃ/R⁵ᵃ/Lᵃ | Salt forms/ Stereochemistry/ Optical Rotation (OR) |
|---|---|---|---|---|
| 250 | B6 | CH | 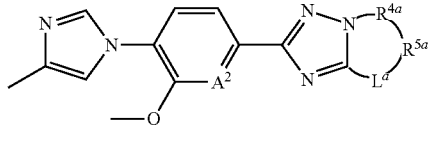 | |

TABLE 1c-continued

| Co. No. | Pr. | A² | R⁴ᵃ/R⁵ᵃ/Lᵃ | Salt forms/ Stereochemistry/ Optical Rotation (OR) |
|---|---|---|---|---|
| 344 | B30 | CH | 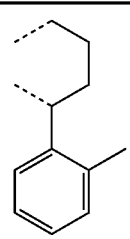 | |

TABLE 1c-continued
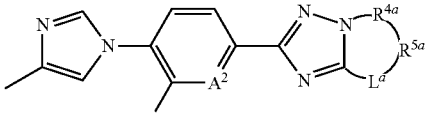
| Co. No. | Pr. | A² |  | Salt forms/ Stereochemistry/ Optical Rotation (OR) |
|---|---|---|---|---|
| 251 | B30 | CH | 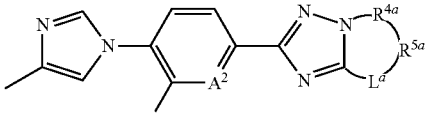 | |
| 252 | B30 | CH |  | |
| 253 | B30 | N | 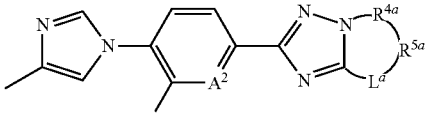 | |
| 254 | B31b | CH |  | R-enantiomer OR: +61.64° (589 nm; 20° C.; 0.4656 w/v %; MeOH) |
| 255 | B31b | CH | 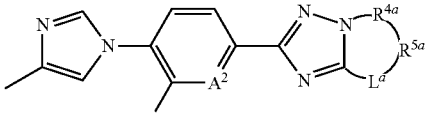 | S-enantiomer OR: −61.54° (589 nm; 20° C.; 0.4306 w/v %; MeOH) |
| 256 | B11 | CH |  | |
| 257 | B30 | CH | 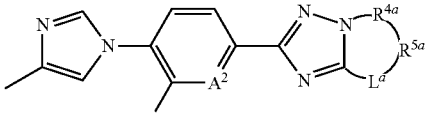 | |
| 312 | B30 | CH |  | |
| 336 | B30 | CH | 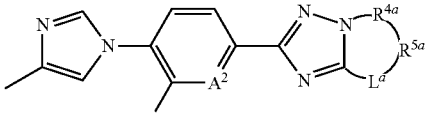 | |
| 10 | B6 | CH |  | |

TABLE 1c-continued

| Co. No. | Pr. | A² | (R⁴ᵃ/R⁵ᵃ/Lᵃ group) | Salt forms/ Stereochemistry/ Optical Rotation (OR) |
|---|---|---|---|---|
| 378 | B31a | CH | 2-methyl-3-fluorophenyl | |
| 379 | B31a | N | 2-methyl-3-fluorophenyl | |
| 258 | B31a | CH | 2-methyl-4-fluorophenyl | |
| 332 | B31b | CH | 2-methyl-4-fluorophenyl, R | R-enantiomer OR: +74.19° (589 nm; 20° C.; 0.3464 w/v %; MeOH) |
| 314 | B31b | CH | 2-methyl-4-fluorophenyl, R | •HCl R-enantiomer |
| 333 | B31b | CH | 2-methyl-4-fluorophenyl, S | S-enantiomer OR: −72.59° (589 nm; 20° C.; 0.3582 w/v %; MeOH) |
| 315 | B31b | CH | 2-methyl-4-fluorophenyl, S | •HCl S-enantiomer |
| 313 | B30 | N | 2-methyl-4-fluorophenyl | |
| 360 | B31b | N | 2-methyl-4-fluorophenyl, R | R-enantiomer |

TABLE 1c-continued
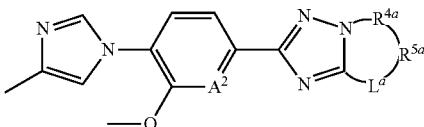
| Co. No. | Pr. | A² | R⁴ᵃ R⁵ᵃ Lᵃ structure | Salt forms/ Stereochemistry/ Optical Rotation (OR) |
|---|---|---|---|---|
| 361 | B31b | N |  | S-enantiomer S-enantiomer |
| 362 | B30 | N | 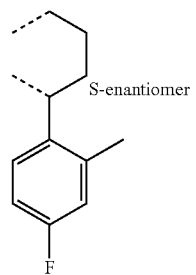 | CIS |
| 363 | B30 | CH | 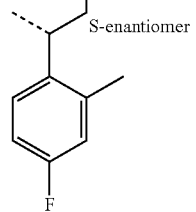 | CIS |
| 368 | B30 | N | 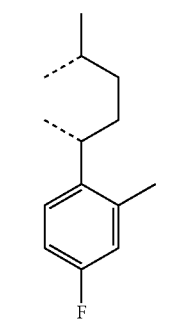 | CIS |
| 369 | B30 | CH | 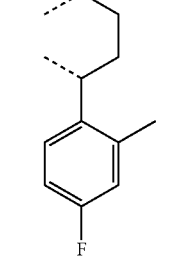 | CIS |
| 259 | B30 | CH | 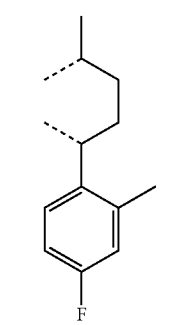 | |
| 364 | B30 | CH | 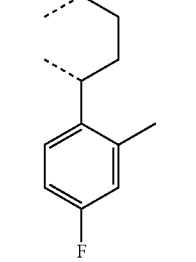 | |
| 375 | B34b | CH | 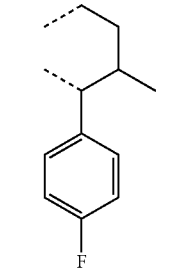 | |
| 260 | B32b | CH | 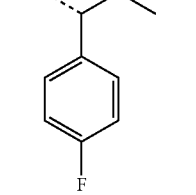 | R-enantiomer OR: +89.14° (589 nm; 20° C.; 0.1896 w/v %; MeOH) R-enantiomer |

TABLE 1c-continued

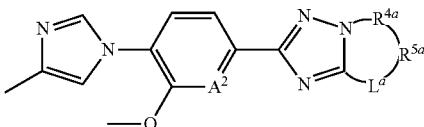

| Co. No. | Pr. | A² | [R⁴ᵃ/R⁵ᵃ/Lᵃ ring] | Salt forms/ Stereochemistry/ Optical Rotation (OR) |
|---|---|---|---|---|
| 261 | B32b | CH | 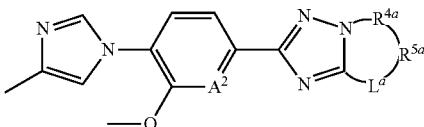 | S-enantiomer OR: −84.27° (589 nm; 20° C.; 0.089 w/v %; MeOH) |
| 262 | B32b | N | 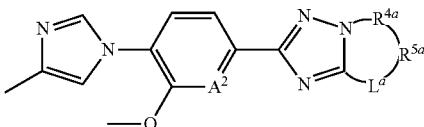 | R-enantiomer OR: +79.31° (589 nm; 20° C.; 0.3316 w/v %; MeOH) |
| 263 | B32b | N | 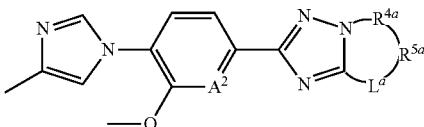 | S-enantiomer OR: −79.81° (589 nm; 20° C.; 0.3546 w/v %; MeOH) |
| 373 | B32a | N | 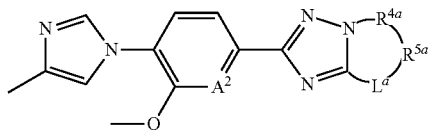 | |
| 264 | B30 | CH | 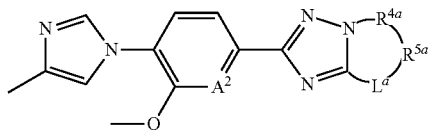 | |

| Co. No. | Pr. | A² | [R⁴ᵃ/R⁵ᵃ/Lᵃ ring] | Salt forms/ Stereochemistry/ Optical Rotation (OR) |
|---|---|---|---|---|
| 338 | B31b | CH | 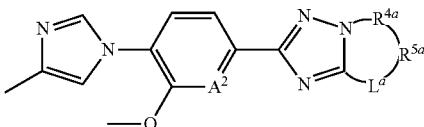 | R-enantiomer |
| 339 | B31b | CH | 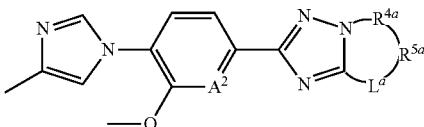 | R-enantiomer •HCl |
| 340 | B31b | CH | 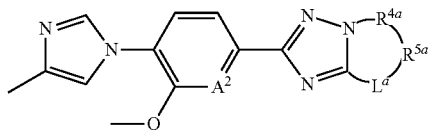 | S-enantiomer |
| 341 | B31b | CH | 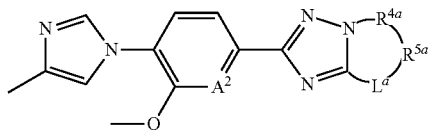 | S-enantiomer •HCl |
| 342 | B43b | N | 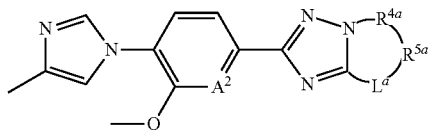 | R-enantiomer |

TABLE 1c-continued

| Co. No. | Pr. | A² | R⁴ᵃ-R⁵ᵃ-Lᵃ group | Salt forms/ Stereochemistry/ Optical Rotation (OR) |
|---|---|---|---|---|
| 343 | B43b | N | 2-methyl-5-trifluoromethylphenyl substituent | S-enantiomer S-enantiomer |
| 265 | B30 | CH | 2-fluoro-5-trifluoromethoxyphenyl substituent | |
| 266 | B34b | CH | 2-trifluoromethoxyphenyl substituent | |
| 267 | B34b | CH | 3-trifluoromethoxyphenyl substituent | |
| 268 | B30 | CH | 4-trifluoromethylphenyl substituent | |
| 372 | B43a | N | 2-methyl-5-trifluoromethylphenyl substituent | |
| 269 | B31c | CH | 4-fluoro-2-methylphenyl with OH | |
| 334 | B31d | CH | 4-fluoro-2-methylphenyl with CH₂OH | |
| 270 | B10 | CH | spirocyclohexyl | |
| 271 | B10 | CH | spirocyclohexyl | •1.8 HCl •2.2 H₂O |
| 18 | B11 | CH | 2-trifluoromethylphenylamino | |

TABLE 1c-continued
| Co. No. | Pr. | A² | R⁴ᵃ/R⁵ᵃ/Lᵃ | Salt forms/ Stereochemistry/ Optical Rotation (OR) |
|---|---|---|---|---|
| 274 | B39b | CH |  | |
| 275 | B34d | CH | 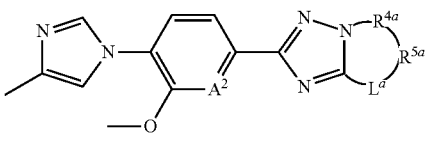 | |
| 276 | B34c | CH |  | |
| 277 | B34c | CH | 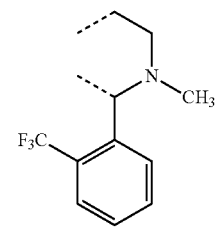 | |
| 278 | B34b | CH | 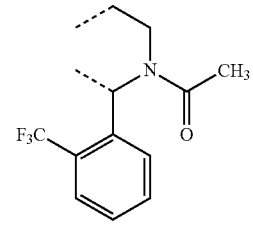 | |
| 345 | B33a | CH | 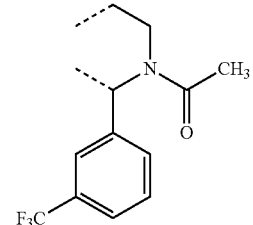 | |
| 347 | B33a | N | 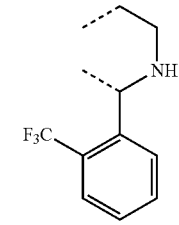 | |
| 279 | B35 | CH | 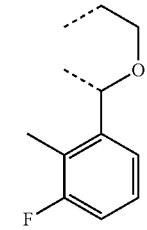 | |
| 316 | B33b | CH | 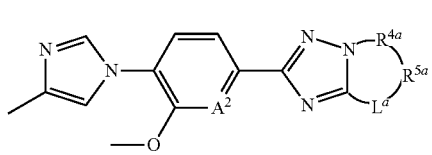 | R-enantiomer |
| 306 | B33b | CH |  | S-enantiomer |
| 280 | B33a | CH | 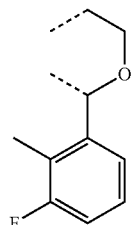 | |

TABLE 1c-continued

| Co. No. | Pr. | A² | R⁴ᵃ–R⁵ᵃ–Lᵃ group | Salt forms/ Stereochemistry/ Optical Rotation (OR) |
|---|---|---|---|---|
| 370 | B33a | N | 2-methyl-5-(trifluoromethyl)phenyl ethoxy | |
| 371 | B33a | CH | 2-methyl-5-(trifluoromethyl)phenyl ethoxy | |
| 305 | B33b | CH | 4-fluoro-2-methylphenyl ethoxy | R-enantiomer R-enantiomer |
| 166 | B33b | CH | 4-fluoro-2-methylphenyl ethoxy | S-enantiomer S-enantiomer |
| 346 | B33a | CH | 2-(trifluoromethoxy)phenyl ethoxy | |
| 348 | B33a | N | 2-(trifluoromethoxy)phenyl ethoxy | |
| 374 | B33a | N | 2-fluoro-5-(trifluoromethoxy)phenyl ethoxy | |
| 281 | B33a | CH | 2-fluoro-5-(trifluoromethoxy)phenyl ethoxy | |
| 165 | B33b | CH | 2-fluoro-5-(trifluoromethoxy)phenyl ethoxy | R-enantiomer R-enantiomer |
| 128 | B33b | CH | 2-fluoro-5-(trifluoromethoxy)phenyl ethoxy | S-enantiomer S-enantiomer |

TABLE 1c-continued
| Co. No. | Pr. | A² | R⁴ᵃ/R⁵ᵃ/Lᵃ | Salt forms/ Stereochemistry/ Optical Rotation (OR) |
|---|---|---|---|---|
| 282 | B33a | CH |  | |
| 376 | B33a | CH | 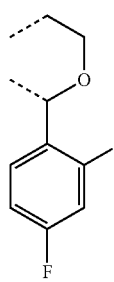 | |
| 283 | B35 | CH | 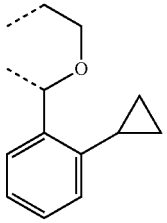 | |
| 284 | B35 | CH | 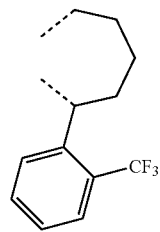 | |
| 285 | B35 | CH | 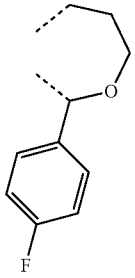 | |
| 17 | B10 | CH | 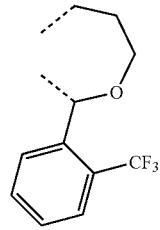 | |
| 286 | B34a | CH | 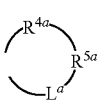 | |
| 287 | B34a | CH | 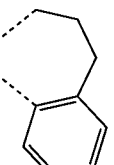 | |
| 288 | B34a | CH | 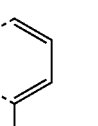 | |
| 289 | B34a | CH | 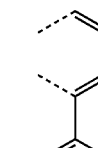 | |
| 290 | B39a | CH | 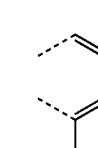 | |

TABLE 1c-continued
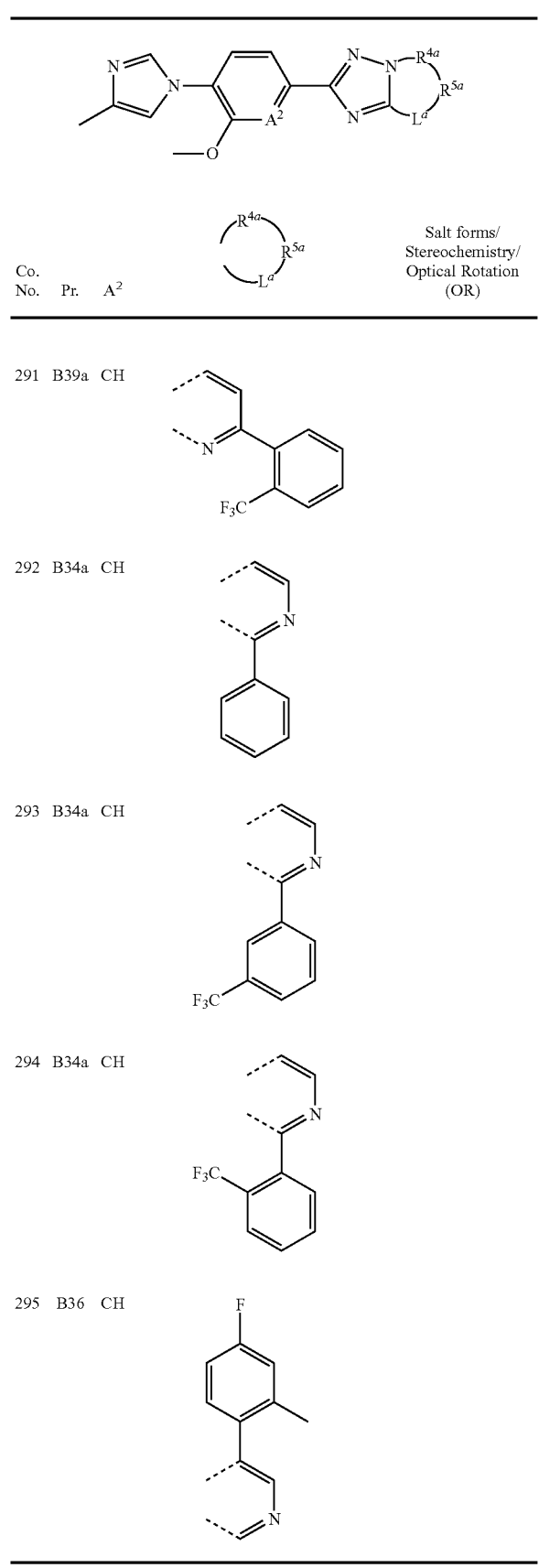
TABLE 1d
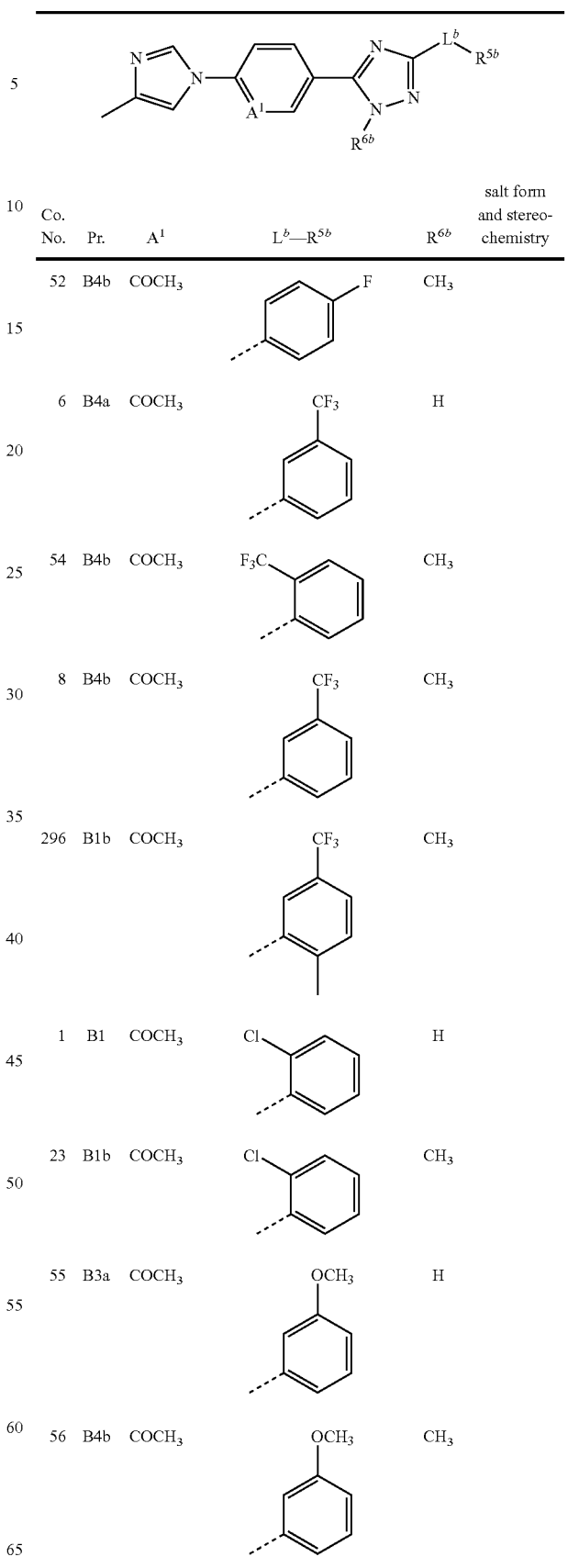

TABLE 1d-continued

| Co. No. | Pr. | A¹ | L$^b$—R$^{5b}$ | R$^{6b}$ | salt form and stereo-chemistry |
|---|---|---|---|---|---|
| 57 | B4b | COCH₃ | 2-CF₃, 4-F-benzyl | CH₃ | |
| 297 | B1a | COCH₃ | 4-Cl, 3-methylphenyl | H | |
| 298 | B1b | COCH₃ | 4-Cl, 3-methylphenyl | CH₃ | |
| 20 | B13 | COCH₃ | 2-OCH₃, 3-Cl-phenyl | H | |
| 58 | B4b | COCH₃ | 2-OCH₃, 3-Cl-phenyl | CH₃ | |
| 59 | B4b | COCH₃ | (E)-4-F-styryl | CH₃ | (E) |
| 60 | B4b | COCH₃ | 1-(4-F-phenyl)cyclopropyl | CH₃ | |
| 24 | B15 | N | 3-CF₃-phenyl-NH- | H | •2HCl |
| 16 | B9 | COCH₃ | 2-CF₃, 4-F-phenyl-NH- | CH₃ | |
| 61 | B9 | COCH₃ | 3,4,5-triF-phenyl-NH- | CH₃ | |
| 62 | B9 | COCH₃ | 1-(4-F-phenyl)ethyl-NH- | CH₃ | S-enantiomer |
| 53 | B9 | COCH₃ | 2-CF₃, 4-F-phenyl-N(CH₃)- | CH₃ | |
| 64 | B9 | COCH₃ | 2,6-dimethylmorpholin-4-yl | CH₃ | CIS |

TABLE 1e

| Co. No. | Pr. | X | A¹ | L$^c$—R$^{5c}$ | R$^{4c}$ | R$^{6c}$ |
|---|---|---|---|---|---|---|
| 299 | B7 | N | COCH₃ | phenyl | CH₃ | H |

TABLE 1f

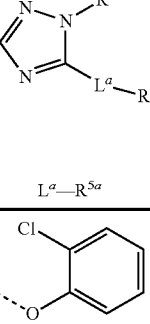

| Co. No. | Pr. | X | A¹ | A³ | $L^a$—$R^{5a}$ | $R^{4a}$ |
|---|---|---|---|---|---|---|
| 272 | B16 | N | COCH₃ | CH | 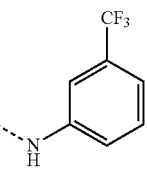 | CH₃ |
| 273 | B18 | N | COCH₃ | CH | 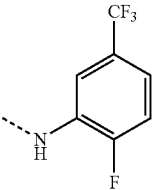 | CH₃ |
| 377 | B20 | CH | COCH₃ | CF | 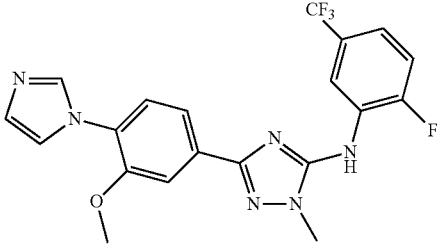 | CH₃ |

TABLE 1g

| Co. No. | Pr. | Structure |
|---|---|---|
| 359 | B20 | 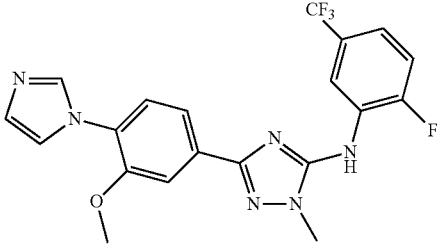 [SMILES: COc1cc(-c2nc(Nc3cc(C(F)(F)F)ccc3F)n(C)n2)ccc1-n1ccnc1] |

Analytical Part
LCMS (Liquid Chromatography/Mass Spectrometry)
General Procedure A The LC measurement was performed using an Acquity HPLC (Ultra Performance Liquid Chromatography) (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds (sec) using a dwell time of 0.02 sec. The capillary needle voltage was 3.5 kV and the source temperature (temp) was maintained at 140° C. $N_2$ was used as the nebulizer gas. Data acquisition was performed with a Waters-Micromass MassLynx-Openlynx data system.

General Procedure B

The HPLC measurement was performed using an Alliance HT 2790 (Waters) system comprising a quaternary pump with degasser, an autosampler, a column oven (set at 40° C., unless otherwise indicated), a DAD and a column as specified in the respective methods below. Flow from the column was split to a MS spectrometer. The MS detector was configured with an electrospray ionization source. Mass spectra were acquired by scanning from 100 to 1000 in 1 sec using a dwell time of 0.1 sec. The capillary needle voltage was 3 kV and the source temp was maintained at 140° C. $N_2$ was used as the nebulizer gas. Data acquisition was performed with a Waters-Micromass MassLynx-Openlynx data system.

General Procedure C

The HPLC measurement was performed using an Agilent 1100 series liquid chromatography system comprising a binary pump with degasser, an autosampler, a column oven, a UV detector and a column as specified in the respective methods below. Flow from the column was split to a MS spectrometer which was configured with an electrospray ionization source. The capillary voltage was 3 kV, the quadrupole temp was maintained at 100° C. and the desolvation temp was 300° C. $N_2$ was used as nebulizer gas. Data acquisition was performed with an Agilent Chemstation data system.

LCMS Method 1

In addition to general procedure A: Reversed phase HPLC was carried out on a bridged ethylsiloxane/silica hybrid (BEH) C18 column (1.7 μm, 2.1×50 mm; Waters Acquity) with a flow rate of 0.8 ml/min. 2 Mobile phases (25 mM NH₄OAc in H₂O/CH₃CN 95/5; mobile phase B: CH₃CN) were used to run a gradient from 95% A and 5% B to 5% A and 95% B in 1.3 minutes (min) and hold for 0.3 min. An injection volume of 0.5 μl was used. Cone voltage was 10 V for positive and 20 V for negative ionization mode.

LCMS Method 2

In addition to general procedure A: Reversed phase HPLC was carried out on a BEH C18 column (1.7 μm, 2.1×50 mm; Waters Acquity) with a flow rate of 0.8 ml/min. 2 Mobile phases (mobile phase A: 0.1% formic acid in H₂O/MeOH 95/5; mobile phase B: MeOH) were used to run a gradient condition from 95% A and 5% B to 5% A and 95% B in 1.3 min and hold for 0.2 min. An injection volume of 0.5 μl was used. Cone voltage was 10 V for positive ionization mode and 20 V for negative ionization mode.

LCMS Method 3

In addition to general procedure B: Column heater was set at 45° C. Reversed phase HPLC was carried out on an Atlantis C18 column (3.5 μm, 4.6×100 mm) with a flow rate of 1.6 ml/min. 2 Mobile phases (mobile phase A: 70% MeOH+30% H₂O; mobile phase B: 0.1% formic acid in H₂O/MeOH 95/5) were employed to run a gradient from 100% B to 5% B+95% A in 9 min and hold these conditions for 3 min. An injection volume of 10 μl was used. Cone voltage was 10 V for positive and 20 V for negative ionization mode.

LCMS Method 4

In addition to general procedure A: Reversed phase HPLC (Ultra Performance Liquid Chromatography) was carried out on a BEH C18 column (1.7 μm, 2.1×50 mm; Waters Acquity) with a flow rate of 0.8 ml/min. 2 Mobile phases (25 mM NH₄OAc/CH₃CN 95/5; mobile phase B: CH₃CN) were used to run a gradient from 95% A and 5% B to 5% A and 95% B in 1.3 min and hold for 0.3 min. An injection volume of 0.5 μl was used. Cone voltage was 30 V for positive and 30 V for negative ionization mode.

LCMS Method 5

In addition to general procedure B: Reversed phase HPLC was carried out on an Xterra MS C18 column (3.5 μm, 4.6× 100 mm) with a flow rate of 1.6 ml/min. 3 Mobile phases (mobile phase A: 95% 25 mM NH₄OAc+5% CH₃CN; mobile phase B: CH₃CN; mobile phase C: MeOH) were employed to run a gradient condition from 100% A to 1% A, 49% B and 50% C in 6.5 min, to 1% A and 99% B in 1 min and hold these conditions for 1 min and reequilibrate with 100% A for 1.5 min. Injection volume was 10 μl. Cone voltage was 10 V for positive and 20 V for negative ionization mode.

LCMS Method 6

In addition to general procedure C: Reversed phase HPLC was carried out on a YMC-Pack ODS-AQ C18 column (4.6× 50 mm) with a flow rate of 2.6 ml/min. A gradient run was used from 95% $H_2O$ and 5% $CH_3CN$ to 95% $CH_3CN$ in 4.80 min and was hold for 1.20 min. Mass spectra were acquired by scanning from 100 to 1400. Injection volume was 10 μl. Column temperature was 35° C.

LCMS Method 7

In addition to general procedure B: Reversed phase HPLC was carried out on an Xterra MS C18 column (3.5 μm, 4.6× 100 mm) with a flow rate of 1.6 ml/min. 3 Mobile phases (mobile phase A: 95% 25 mM $NH_4OAc$+5% $CH_3CN$; mobile phase B: $CH_3CN$; mobile phase C: MeOH) were employed to run a gradient condition from 100% A to 50% B and 50% C in 6.5 min, to 100% B in 1 min, 100% B for 1 min and reequilibrate with 100% A for 1.5 min. An injection volume of 10 μl was used. Cone voltage was 10 V for positive ionization mode and 20 V for negative ionization mode.

Melting Points

Unless otherwise indicated, melting points (m.p.) were determined with a DSC823e (Mettler-Toledo). Melting points were measured with a temp gradient of 30° C./min. Maximum temp was 400° C. Values are peak values.

The m.p. for compounds 108-110, 113-115, 118, 119, 126, 135-137, 141, 147, 156, 161, 163, 164, 176, 179, 188, 190, 192, 194, 209, 215, 219, 225-227, 229, 230, 234, 237, 238, 241-243, 308, 309, 330, 335, 351, 352, 354-357, were determined in open capillary tubes on a Mettler FP62 apparatus. M.p. were measured with a temp ranging from 50° C. to 300° C., using a gradient of 10° C./minute. The m.p. value was read from a digital display.

The results of the analytical measurements are shown in table 2.

TABLE 2

Retention time ($R_t$) in min., $[M + H]^+$ peak (protonated molecule), LCMS method and m.p. (melting point in ° C.). (n.d. means not determined)

| Co. No. | $R_t$ | $[M + H]^+$ | LCMS Method | m.p. (° C.) |
|---|---|---|---|---|
| 1 | 1.00 | 366 | 2 | n.d. |
| 2 | 0.95 | 380 | 4 | 149.3 |
| 3 | 5.48 | 364 | 5 | 157.3 |
| 4 | 0.87 | 350 | 4 | n.d. |
| 5 | 1.08 | 392 | 4 | n.d. |
| 6 | 1.01 | 400 | 4 | n.d. |
| 7 | 1.05 | 414 | 4 | n.d. |
| 8 | 1.10 | 414 | 4 | 127.9 |
| 9 | 0.92 | 346 | 4 | 115.8 |
| 10 | 1.08 | 454 | 4 | 218.0 |
| 11 | 0.90 | 345 | 1 | n.d. |
| 12 | 1.11 | 413 | 1 | n.d. |
| 13 | 1.03 | 427 | 4 | 130.7 |
| 14 | 1.07 | 427 | 4 | 132.9 |
| 15 | 5.78 | 447 | 5 | 147.7 |
| 16 | 6.91 | 447 | 3 | 170.5 |
| 17 | 1.01 | 372 | 4 | n.d. |
| 18 | 0.97 | 455 | 4 | 211.6 |
| 19 | 0.97 | 414 | 4 | n.d. |
| 20 | 0.95 | 396 | 4 | 262.6 |
| 21 | 1.05 | 392 | 2 | 145.3 |
| 22 | 6.08 | 378 | 3 | 123.7 |
| 23 | 0.95 | 380 | 4 | n.d. |
| 24 | 0.93 | 386 | 1 | n.d. |
| 25 | 0.68 | 283 | 1 | n.d. |
| 26 | 0.91 | 325 | 1 | n.d. |
| 27 | 0.67 | 345 | 2 | n.d. |
| 28 | 0.84 | 346 | 4 | 159.1 |
| 29 | 5.14 | 373 | 3 | 205.0 |
| 30 | 1.05 | 414 | 4 | 230.4 |
| 31 | 1.09 | 392 | 4 | n.d. |
| 32 | 1.19 | 442 | 4 | 202.2 |
| 33 | 4.31 | 338 | 5 | 211.9 |
| 34 | 1.00 | 352 | 4 | 122.3 |
| 35 | 0.88 | 383 | 4 | n.d. |
| 36 | 0.93 | 376 | 4 | n.d. |
| 37 | 1.09 | 404 | 4 | n.d. |
| 38 | 1.17 | 414 | 2 | n.d. |
| 39 | 1.19 | 442 | 4 | n.d. |
| 40 | 0.93 | 364 | 4 | 156.8 |
| 41 | 1.16 | 418 | 2 | n.d. |
| 42 | n.d. | n.d. | n.d. | 267.1 |
| 43 | 1.01 | 410 | 4 | n.d. |
| 44 | 5.07 | 364 | 5 | n.d. |
| 45 | 1.02 | 390 | 4 | 190.7 |
| 46 | 1.05 | 446 | 4 | n.d. |
| 47 | 1.00 | 404 | 4 | n.d. |
| 48 | 7.14 | 415 | 3 | n.d. |
| 49 | 1.16 | 475 | 4 | n.d. |
| 50 | 1.10 | 461 | 4 | 128.2 |
| 51 | 0.95 | 407 | 4 | n.d. |
| 52 | 0.96 | 364 | 4 | 151.3 |
| 53 | 1.01 | 461 | 4 | 135.3 |
| 54 | 1.14 | 414 | 2 | n.d. |
| 55 | 1.07 | 362 | 2 | n.d. |
| 56 | 0.92 | 376 | 4 | n.d. |
| 57 | 1.03 | 446 | 4 | n.d. |
| 58 | 1.02 | 410 | 4 | n.d. |
| 59 | 0.99 | 390 | 4 | 172.9 |
| 60 | 1.00 | 404 | 4 | n.d. |
| 61 | 6.88 | 415 | 3 | 292.9 |
| 62 | 0.91 | 407 | 4 | n.d. |
| 63 | 0.97 | 400 | 4 | 150.3 |
| 64 | 0.96 | 383 | 4 | 193.8 |
| 65 | 1.08 | 400 | 4 | n.d. |
| 66 | 1.12 | 409 | 4 | 159.0 |
| 67 | 1.13 | 442 | 4 | n.d. |
| 68 | 6.17 | 443 | 5 | n.d. |
| 69 | 0.94 | 393 | 4 | n.d. |
| 70 | 1.18 | 504 | 4 | n.d. |
| 71 | 0.96 | 435 | 4 | n.d. |
| 72 | 1.09 | 428 | 4 | 136.1 |
| 73 | 1.25 | 456 | 4 | n.d. |
| 74 | 1.30 | 511 | 4 | n.d. |
| 75 | 6.51 | 449 | 5 | n.d. |
| 76 | 1.19 | 447 | 4 | n.d. |
| 77 | 1.15 | 429 | 4 | 170.3 |
| 78 | 1.17 | 429 | 4 | n.d. |
| 79 | 1.54 | 457 | 4 | n.d. |
| 80 | 6.66 | 458 | 5 | n.d. |
| 81 | 6.09 | 401 | 5 | 135.71 |
| 82 | 1.22 | 429 | 4 | n.d. |
| 83 | 1.08 | 392 | 4 | n.d. |
| 84 | 1.16 | 428 | 4 | 122.23 |
| 85 | 1.11 | 420 | 4 | n.d. |
| 86 | 1.08 | 448 | 4 | n.d. |
| 87 | 0.98 | 424 | 4 | n.d. |
| 88 | 0.99 | 394 | 2 | 135.7 |
| 89 | 1.19 | 486 | 4 | n.d. |
| 90 | 1.12 | 472 | 4 | 124.5 |
| 91 | 1.34 | 470 | 4 | n.d. |
| 92 | 0.95 | 430 | 4 | 218.4 |
| 93 | 0.93 | 429 | 2 | n.d. |
| 94 | 0.97 | 367 | 4 | 156.0 |
| 95 | 5.84 | 435 | 5 | 188.8 |
| 96 | 1.05 | 435 | 4 | 207.7 |
| 97 | 0.95 | 375 | 4 | 159.4 |
| 98 | 1.09 | 429 | 4 | 150.2 |
| 99 | 5.96 | 403 | 5 | 185.6 |

TABLE 2-continued

Retention time (R$_t$) in min., [M + H]$^+$ peak (protonated molecule), LCMS method and m.p. (melting point in ° C.). (n.d. means not determined)

| Co. No. | R$_t$ | [M + H]$^+$ | LCMS Method | m.p. (° C.) |
|---|---|---|---|---|
| 100 | 5.89 | 396 | 5 | n.d. |
| 101 | 5.86 | 395 | 5 | n.d. |
| 102 | 1.03 | 439 | 4 | n.d. |
| 103 | 1.02 | 395 | 4 | 212.72 |
| 104 | 0.96 | 379 | 4 | 222.18 |
| 105 | 0.93 | 379 | 4 | 158.6 |
| 106 | 0.94 | 379 | 4 | 221.5 |
| 107 | 0.85 | 380 | 4 | 204.7 |
| 108 | 2.36 | 395 | 6 | 231.8 |
| 109 | 2.21 | 413 | 6 | 163.2 |
| 110 | 2.10 | 397 | 6 | 196.0 |
| 111 | 1.12 | 429 | 4 | n.d. |
| 112 | 0.98 | 397 | 4 | n.d. |
| 113 | 2.35 | 413 | 6 | 181.1 |
| 114 | 2.22 | 413 | 6 | 168.4 |
| 115 | 2.68 | 430 | 6 | 273.0 |
| 116 | 0.84 | 397 | 4 | n.d. |
| 117 | 5.74 | 414 | 5 | 210.7 |
| 118 | 2.27 | 413 | 6 | 201.5 |
| 119 | 2.42 | 430 | 6 | 159.3 |
| 120 | 1.09 | 523 | 4 | 231.6 |
| 121 | 1.07 | 431 | 4 | 193.6 |
| 122 | 0.95 | 431 | 4 | 224.4 |
| 123 | 6.07 | 413 | 5 | 221.9 |
| 124 | 0.95 | 397 | 4 | 194.7 |
| 125 | 0.90 | 413 | 4 | n.d. |
| 126 | 2.30 | 413 | 6 | 249.3 |
| 127 | 0.96 | 475 | 4 | 231.5 |
| 128 | 1.06 | 490 | 4 | n.d. |
| 129 | 1.04 | 409 | 4 | 190.9 |
| 130 | 0.95 | 393 | 4 | 189.7 |
| 131 | 1.09 | 443 | 4 | 189.3 |
| 132 | 0.96 | 430 | 4 | 171.6 |
| 133 | 6.41 | 457 | 7 | 224.1 |
| 134 | 1.10 | 447 | 4 | 224.0 |
| 135 | 2.54 | 461 | 6 | 191.3 |
| 136 | 2.61 | 505 | 6 | 235.7 |
| 137 | 2.37 | 486 | 6 | 221.0 |
| 138 | 0.96 | 448 | 4 | 183.6 |
| 139 | 1.21 | 501 | 2 | n.d. |
| 140 | 1.11 | 465 | 4 | 237.0 |
| 141 | 2.36 | 465 | 6 | 158.7 |
| 142 | 1.09 | 465 | 4 | 157.2 |
| 143 | 1.15 | 463 | 4 | 174.9 |
| 144 | 6.24 | 497 | 7 | 177.9 |
| 145 | 1.16 | 497 | 4 | n.d. |
| 146 | 1.26 | 429 | 4 | n.d. |
| 147 | 2.37 | 443 | 6 | 152.8 |
| 148 | 1.07 | 447 | 4 | 242.6 |
| 149 | 1.03 | 417 | 4 | 186.6 |
| 150 | 6.77 | 497 | 5 | n.d. |
| 151 | 6.22 | 429 | 5 | 232.9 |
| 152 | 6.30 | 447 | 5 | 238.7 |
| 153 | 1.01 | 430 | 4 | 238.1 |
| 154 | 1.02 | 448 | 4 | 230.1 |
| 155 | 0.92 | 447 | 2 | 171.4 |
| 156 | 2.52 | 463 | 6 | 141.1 |
| 157 | 1.03 | 429 | 4 | 159.3 |
| 158 | 0.96 | 448 | 4 | 164.3 |
| 159 | 6.49 | 447 | 5 | 253.0 |
| 160 | 1.08 | 464 | 4 | 199.5 |
| 161 | 2.19 | 393 | 6 | 154.0 |
| 162 | 1.07 | 447 | 4 | 198.3 |
| 163 | 2.52 | 463 | 6 | 174.7 |
| 164 | 2.42 | 443 | 6 | 176.7 |
| 165 | 1.06 | 490 | 4 | n.d. |
| 166 | 0.98 | 420 | 4 | n.d. |
| 167 | 1.01 | 448 | 4 | 245.3 |
| 168 | 5.95 | 447 | 7 | 159.8 |
| 169 | 1.08 | 463 | 4 | n.d. |
| 170 | 0.90 | 418 | 4 | 228.4 |
| 171 | 1.03 | 448 | 4 | 235.2 |
| 172 | 1.08 | 465 | 4 | 230.5 |
| 173 | 1.00 | 393 | 4 | n.d. |
| 174 | 1.05 | 409 | 4 | 164.7 |
| 175 | 0.85 | 437 | 4 | 193.8 |
| 176 | 2.54 | 457 | 6 | 134.4 |
| 177 | 1.16 | 463 | 4 | 173.1 |
| 178 | 2.67 | 475 | 6 | n.d. |
| 179 | 2.81 | 489 | 6 | 139.0 |
| 180 | 5.84 | 422 | 5 | 213.2 |
| 181 | 1.09 | 445 | 4 | 229.0 |
| 182 | 5.94 | 445 | 5 | n.d. |
| 183 | 6.39 | 479 | 5 | 214.0 |
| 184 | 6.01 | 464 | 5 | 229.6 |
| 185 | 6.38 | 463 | 5 | 211.4 |
| 186 | 0.92 | 391 | 4 | n.d. |
| 187 | 0.97 | 391 | 4 | n.d. |
| 188 | 2.42 | 425 | 6 | 123.7 |
| 189 | 0.93 | 425 | 2 | n.d. |
| 190 | 2.25 | 409 | 6 | 164.6 |
| 191 | 6.07 | 425 | 5 | 262.8 |
| 192 | 2.40 | 425 | 6 | 201.3 |
| 193 | 0.93 | 409 | 4 | 234.1 |
| 194 | 2.28 | 425 | 6 | 137.7 |
| 195 | 0.84 | 409 | 4 | 208.8 |
| 196 | 0.85 | 427 | 4 | 211.7 |
| 197 | 2.03 | 409 | 6 | n.d. |
| 198 | 1.01 | 389 | 4 | 182.6 |
| 199 | 0.96 | 405 | 4 | 157.4 |
| 200 | 0.84 | 421 | 4 | 235.2 |
| 201 | 1.04 | 460 | 4 | 225.6 |
| 202 | 1.11 | 477 | 4 | n.d. |
| 203 | 1.02 | 477 | 2 | 232.0 |
| 204 | 5.71 | 405 | 5 | n.d. |
| 205 | 2.31 | 405 | 6 | n.d. |
| 206 | 1.05 | 399 | 4 | 251.2 |
| 207 | 1.05 | 417 | 4 | 240.5 |
| 208 | 5.40 | 447 | 5 | 222.7 |
| 209 | 2.68 | 491 | 6 | 143.1 |
| 210 | 1.17 | 481 | 4 | n.d. |
| 211 | 0.98 | 465 | 4 | 212.53 |
| 212 | 1.15 | 481 | 4 | 275.1 |
| 213 | 6.37 | 459 | 5 | 234.7 |
| 214 | 0.86 | 409 | 4 | 184.6 |
| 215 | 2.12 | 409 | 6 | 180.1 |
| 216 | 0.89 | 427 | 4 | 211.6 |
| 217 | 1.10 | 459 | 4 | 210.6 |
| 218 | 1.07 | 459 | 4 | n.d. |
| 219 | 2.16 | 409 | 6 | 289.7 |
| 220 | 1.11 | 477 | 4 | 229.1 |
| 221 | 1.77 | 436 | 6 | n.d. |
| 222 | 1.76 | 418 | 6 | n.d. |
| 223 | 5.32 | 421 | 5 | n.d. |
| 224 | 0.90 | 386 | 4 | n.d. |
| 225 | 2.05 | 386 | 6 | 272.8 |
| 226 | 2.04 | 404 | 6 | 237.9 |
| 227 | 2.03 | 404 | 6 | 249.7 |
| 228 | 1.97 | 404 | 6 | n.d. |
| 229 | 2.03 | 404 | 6 | 251.5 |
| 230 | 2.20 | 454 | 6 | 174.5 |
| 231 | 1.06 | 441 | 4 | n.d. |
| 232 | 1.05 | 565 | 4 | n.d. |
| 233 | 0.87 | 430 | 4 | 209.5 |
| 234 | 1.89 | 396 | 6 | 257.9 |
| 235 | 0.91 | 430 | 4 | 254.4 |
| 236 | 1.02 | 430 | 4 | 240.0 |
| 237 | 1.29 | 362 | 6 | 218.0 |
| 238 | 1.31 | 376 | 6 | 259.4 |
| 239 | 1.27 | 376 | 6 | n.d. |
| 240 | 1.04 | 430 | 4 | n.d. |
| 241 | 1.93 | 392 | 6 | 185.6 |
| 242 | 1.53 | 392 | 6 | 233.1 |
| 243 | 1.79 | 392 | 6 | 191.6 |
| 244 | 0.88 | 421 | 4 | n.d. |
| 245 | 0.90 | 375 | 4 | 196.0 |
| 246 | 1.12 | 430 | 4 | 105.3 |
| 247 | 1.24 | 424 | 4 | 163.1 |

TABLE 2-continued

Retention time (R$_t$) in min., [M + H]$^+$ peak (protonated molecule), LCMS method and m.p. (melting point in ° C.). (n.d. means not determined)

| Co. No. | R$_t$ | [M + H]$^+$ | LCMS Method | m.p. (° C.) |
|---|---|---|---|---|
| 248 | 1.06 | 396 | 4 | 134.7 |
| 249 | 1.14 | 446 | 4 | 78.4 |
| 250 | 1.02 | 406 | 4 | n.d. |
| 251 | 0.99 | 404 | 4 | 190.5 |
| 252 | 0.99 | 404 | 4 | n.d. |
| 253 | 5.35 | 404 | 5 | 191.0 |
| 254 | 1.05 | 420 | 4 | n.d. |
| 255 | 1.05 | 420 | 4 | n.d. |
| 256 | 1.05 | 420 | 4 | n.d. |
| 257 | 0.99 | 404 | 4 | 162.1 |
| 258 | 1.04 | 418 | 4 | 241.8 |
| 259 | 1.01 | 422 | 4 | 209.9 |
| 260 | 1.10 | 454 | 4 | 187.0 |
| 261 | 1.09 | 454 | 4 | 188.2 |
| 262 | 1.02 | 455 | 4 | 189.0 |
| 263 | 1.02 | 455 | 4 | 191.1 |
| 264 | 1.11 | 468 | 4 | 250.4 |
| 265 | 1.11 | 488 | 4 | 234.0 |
| 267 | 1.10 | 470 | 4 | 156.1 |
| 268 | 1.09 | 454 | 4 | 233.4 |
| 269 | 0.94 | 434 | 4 | n.d. |
| 270 | 1.08 | 378 | 4 | 142.9 |
| 271 | 6.05 | 378 | 5 | n.d. |
| 272 | 1.05 | 397 | 4 | n.d. |
| 273 | 1.31 | 430 | 4 | n.d. |
| 274 | 0.99 | 455 | 4 | n.d. |
| 275 | 6.02 | 469 | 5 | 154.26 |
| 276 | 5.36 | 497 | 5 | n.d. |
| 277 | 5.59 | 497 | 5 | 193.8 |
| 278 | 0.92 | 455 | 4 | 183.0 |
| 279 | 1.02 | 456 | 4 | n.d. |
| 280 | 0.99 | 420 | 4 | 173.7 |
| 281 | 1.07 | 490 | 4 | 232.1 |
| 282 | 0.93 | 424 | 4 | n.d. |
| 283 | 1.19 | 468 | 4 | n.d. |
| 284 | 1.10 | 421 | 4 | 171.7 |
| 285 | 1.19 | 470 | 4 | 167.8 |
| 286 | 1.06 | 416 | 2 | n.d. |
| 287 | 1.27 | 466 | 4 | 140.7 |
| 288 | 1.15 | 466 | 4 | n.d. |
| 289 | 1.20 | 465 | 4 | n.d. |
| 290 | 1.09 | 451 | 4 | 191.0 |
| 291 | 1.11 | 451 | 4 | 193.4 |
| 292 | 1.26 | 383 | 4 | 184.1 |
| 293 | 1.25 | 451 | 4 | 184.2 |
| 294 | 1.03 | 451 | 4 | 176.9 |
| 295 | 1.04 | 415 | 4 | 210.7 |
| 296 | 1.19 | 428 | 4 | 111.9 |
| 297 | 1.03 | 380 | 4 | 235.2 |
| 298 | 1.05 | 394 | 2 | 132.8 |
| 299 | 0.80 | 346 | 4 | 252.1 |
| 300 | 5.89 | 436 | 5 | 191.5 |
| 301 | 0.84 | 438 | 4 | n.d. |
| 302 | 0.97 | 414 | 4 | 183.4 |
| 303 | 2.40 | 458 | 6 | 208.8 |
| 304 | 0.98 | 393 | 4 | 200.4 |
| 305 | 0.98 | 420 | 4 | n.d. |
| 306 | 1.02 | 456 | 4 | n.d. |
| 307 | 6.03 | 437 | 5 | 193.8 |
| 308 | 1.82 | 450 | 6 | 197.2 |
| 309 | 1.84 | 457 | 6 | 219.7 |
| 310 | 0.99 | 427 | 4 | n.d. |
| 311 | 5.83 | 443 | 5 | 166.9 |
| 312 | 1.00 | 440 | 4 | 192.7 |
| 313 | n.d. | n.d. | — | 217.7 |
| 314 | 0.99 | 418 | 2 | n.d. |
| 315 | 0.98 | 418 | 2 | n.d. |
| 316 | 1.02 | 456 | 4 | n.d. |
| 317 | 0.98 | 441 | 2 | 223.77 |
| 318 | 5.42 | 393 | 5 | 195.86 |
| 319 | 0.94 | 432 | 4 | 201.0 |
| 320 | 1.06 | 465 | 4 | 195.9 |
| 321 | 1.03 | 424 | 4 | n.d. |
| 322 | 1.05 | 442 | 4 | 249.7 |
| 323 | 0.97 | 393 | 4 | 195.8 |
| 324 | 1.03 | 403 | 4 | n.d. |
| 325 | 0.96 | 403 | 4 | 155.9 |
| 326 | 1.15 | 397 | 4 | 197.9 |
| 327 | 5.75 | 417 | 5 | 153.2 |
| 328 | 1.18 | 461 | 4 | 157.1 |
| 329 | 1.16 | 457 | 4 | 177.1 |
| 330 | 1.78 | 441 | 6 | 187.4 |
| 331 | 0.92 | 423 | 4 | 157.2 |
| 332 | 1.02 | 418 | 4 | n.d. |
| 333 | 1.02 | 418 | 4 | n.d. |
| 334 | 0.93 | 448 | 4 | n.d. |
| 335 | 2.09 | 361 | 6 | 205.5 |
| 336 | 0.99 | 454 | 2 | 217.7 |
| 337 | 0.96 | 462 | 2 | n.d. |
| 338 | 1.10 | 468 | 4 | n.d. |
| 340 | 1.10 | 468 | 4 | n.d. |
| 342 | 1.05 | 469 | 4 | n.d. |
| 343 | 1.05 | 469 | 4 | n.d. |
| 344 | 1.03 | 400 | 4 | n.d. |
| 345 | 1.00 | 420 | 4 | n.d. |
| 346 | 1.04 | 472 | 4 | 142.2 |
| 347 | 0.95 | 421 | 4 | 204.9 |
| 348 | 0.98 | 473 | 4 | 194.8 |
| 349 | 5.93 | 401 | 5 | 148.6 |
| 350 | 2.22 | 393 | 6 | n.d. |
| 351 | 2.43 | 443 | 6 | 140.8 |
| 352 | 2.21 | 393 | 6 | 240.9 |
| 353 | 5.84 | 478 | 5 | 220.3 |
| 354 | 2.31 | 423 | 6 | 191.0 |
| 355 | 2.13 | 453 | 6 | 180.4 |
| 356 | 2.45 | 449 | 6 | 159.2 |
| 357 | 2.76 | 435 | 6 | 205.5 |
| 358 | 2.18 | 465 | 6 | n.d. |
| 360 | 0.98 | 419 | 4 | n.d. |
| 361 | 0.98 | 419 | 4 | n.d. |
| 362 | 1.11 | 433 | 4 | n.d. |
| 363 | 1.10 | 432 | 4 | 197.3 |
| 364 | 1.00 | 434 | 4 | 179.3 |
| 365 | 5.62 | 401 | 5 | n.d. |
| 366 | 5.92 | 415 | 5 | n.d. |
| 367 | 1.11 | 419 | 4 | 141.4 |
| 368 | 0.97 | 419 | 4 | 203.3 |
| 369 | 1.04 | 418 | 4 | 222.8 |
| 370 | 1.03 | 471 | 4 | 223.8 |
| 371 | 1.09 | 470 | 4 | 235.9 |
| 373 | 0.96 | 455 | 2 | n.d. |
| 374 | 1.01 | 491 | 4 | 219.9 |
| 375 | 1.08 | 472 | 4 | n.d. |
| 376 | 1.04 | 428 | 4 | n.d. |
| 377 | 6.18 | 465 | 5 | 237.8 |
| 378 | 1.00 | 418 | 2 | n.d. |
| 379 | 0.96 | 419 | 4 | n.d. |

NMR

For a number of compounds, $^1$H NMR spectra were recorded on a Bruker DPX-360, on a Bruker DPX-400 or on a Bruker Avance 600 spectrometer with standard pulse sequences, operating at 360 MHz, 400 MHz and 600 MHz respectively, using CHLOROFORM-d (deuterated chloroform, CDCl$_3$) or DMSO-d$_6$ (deuterated DMSO, dimethyl-d6 sulfoxide) as solvents. Chemical shifts (δ) are reported in parts per million (ppm) relative to tetramethylsilane (TMS), which was used as internal standard.

The results are shown in Table 2-b.

| Co. No. | NMR result |
|---|---|
| 3 | (600 MHz, DMSO-$d_6$) δ ppm 2.16 (s, 3 H) 2.52 (s, 3 H) 3.92 (s, 3 H) 7.19 (s, 1 H) 7.45 (t, J = 8.80 Hz, 2 H) 7.48 (d, J = 8.22 Hz, 1 H) 7.72 (dd, J = 7.92, 1.76 Hz, 1 H) 7.74 (dd, J = 8.95, 4.84 Hz, 2 H) 7.78 (d, J = 1.47 Hz, 1 H) 7.84 (s, 1 H). |
| 4 | (600 MHz, DMSO-$d_6$) δ ppm 2.17 (s, 3 H), 3.95 (s, 3 H), 7.21 (s, 1 H), 7.38 (t, J = 8.6 Hz, 2 H), 7.54 (d, J = 8.1 Hz, 1 H), 7.76 (dd, J = 8.1, 1.7 Hz, 1 H), 7.85 (s, 1 H), 7.86 (d, J = 1.7 Hz, 1 H), 8.14 (dd, J = 8.7, 5.5 Hz, 2 H), 14.59 (br. s., 1 H). |
| 5 | (400 MHz, DMSO-$d_6$) δ ppm 1.50 (d, J = 6.5 Hz, 6 H), 2.17 (d, J = 1.0 Hz, 3 H), 3.92 (s, 3 H), 4.67 (spt, J = 6.5 Hz, 1 H), 7.19 (t, J = 1.2 Hz, 1 H), 7.45 (t, J = 8.8 Hz, 2 H), 7.48 (d, J = 8.1 Hz, 1 H), 7.73 (dd, J = 8.1, 1.7 Hz, 1 H), 7.75-7.80 (m, 3 H), 7.83 (d, J = 1.3 Hz, 1 H). |
| 9 | (600 MHz, DMSO-$d_6$) δ ppm 2.17 (s, 3 H), 3.92 (s, 3 H), 4.04 (s, 3 H), 7.19 (br. s., 1 H), 7.48 (d, J = 8.1 Hz, 1 H), 7.58-7.63 (m, 3 H), 7.73 (dd, J = 8.1, 1.7 Hz, 1 H), 7.79 (d, J = 1.7 Hz, 1 H), 7.84 (br. s., 1 H), 7.85-7.87 (m, 2 H). |
| 10 | (400 MHz, CDCl$_3$) δ ppm 1.90-2.05 (m, 1 H) 2.10-2.21 (m, 1 H) 2.23-2.33 (m, 4 H) 2.41-2.53 (m, 1 H) 3.90 (s, 3 H) 4.32-4.41 (m, 2 H) 4.74 (dd, J = 7.87, 6.26 Hz, 1 H) 6.93 (s, 1 H) 7.00 (d, J = 7.67 Hz, 1 H) 7.24 (d, J = 7.67 Hz, 1 H) 7.39 (t, J = 7.67 Hz, 1 H) 7.47 (t, J = 7.06 Hz, 1 H) 7.65-7.76 (m, 4 H). |
| 11 | (360 MHz, CDCl3) δ ppm 2.27 (s, 3 H), 2.51 (s, 3 H) 3.73 (s, 3 H) 6.94 (s, 1 H) 7.20 (d, J = 8.05 Hz, 1 H) 7.27-7.31 (m, 1 H) 7.41 (t, J = 7.68 Hz, 2 H) 7.53 (dd, J = 8.05, 1.46 Hz, 1 H) 7.58-7.69 (m, 2 H) 7.70 (d, J = 1.10 Hz, 1 H) 7.71 (d, J = 1.46 Hz, 1 H). |
| 12 | (400 MHz, DMSO-$d_6$) δ ppm 2.18 (s, 3 H) 2.50 (s, 3 H) 3.92 (s, 3 H) 7.05-7.12 (m, 1 H) 7.40 (d, J = 8.07 Hz, 1 H) 7.54 (d, J = 7.67 Hz, 1 H) 7.58-7.69 (m, 2 H) 7.73 (d, J = 1.21 Hz, 1 H) 7.78 (d, J = 1.61 Hz, 1 H) 7.97-8.10 (m, 2 H) 12.24 (br. s., 1 H). |
| 13 | (400 MHz, DMSO-$d_6$) δ ppm 2.17 (s, 3 H), 2.20 (s, 3 H) 3.61 (s, 3 H) 3.92 (s, 3 H) 7.20 (s, 1 H) 7.39 (dd, J = 8.28, 1.82 Hz, 1 H) 7.49-7.53 (m, 2 H) 7.76-7.83 (m, 4 H) 7.84 (d, J = 1.21 Hz, 1 H). |
| 18 | (360 MHz, CDCl$_3$) δ ppm 2.28 (s, 3 H) 2.39 (br. s., 2 H) 3.67 (br. s., 2 H) 3.87 (s, 3 H) 4.30 (br. s., 2 H) 6.91 (s, 1 H) 7.19 (d, J = 8.8 Hz, 1 H) 7.46-7.54 (m, 2 H) 7.55-7.61 (m, 2 H) 7.61-7.69 (m, 1 H) 7.70 (s, 1 H) 7.79 (d, J = 7.7 Hz, 1 H). |
| 19 | (600 MHz, DMSO-$d_6$) δ ppm 2.34 (s, 3 H), 2.37 (d, J = 1.0 Hz, 3 H), 3.95 (s, 3 H), 7.70 (d, J = 8.2 Hz, 1 H), 7.77 (s, 1 H), 7.79 (dd, J = 8.2, 1.6 Hz, 1 H), 7.84 (d, J = 1.6 Hz, 1 H), 7.87 (d, J = 7.8 Hz, 1 H), 7.90 (t, J = 7.7 Hz, 1 H), 7.97 (t, J = 7.6 Hz, 1 H), 8.06 (d, J = 7.9 Hz, 1 H), 9.42 (s, 1 H), 15.23 (br. s., 1 H). |
| 25 | (360 MHz, DMSO-$d_6$) δ ppm 2.01-2.23 (m, 9 H) 3.88 (s, 3 H) 7.14 (s, 1 H) 7.38 (d, J = 8.42 Hz, 1 H) 7.51 (d, J = 8.05 Hz, 1 H) 7.66 (s, 1 H) 7.79 (s, 1 H) 12.18 (br. s., 1 H). |
| 26 | (360 MHz, DMSO-$d_6$) δ ppm 0.90 (d, J = 6.6 Hz, 6 H), 1.89 (spt, J = 6.6 Hz, 1 H), 2.14 (s, 3 H), 2.15 (s, 3 H), 2.37 (d, J = 7.0 Hz, 2 H), 3.89 (s, 3 H), 7.15 (s, 1 H), 7.39 (d, J = 8.1 Hz, 1 H), 7.53 (dd, J = 8.1, 1.5 Hz, 1 H), 7.67 (d, J = 1.5 Hz, 1 H), 7.79 (d, J = 1.1 Hz, 1 H), 12.12 (br. s., 1 H). |
| 27 | (400 MHz, DMSO-$d_6$) δ ppm 2.19 (s, 3 H), 2.49 (s, 3 H), 4.05 (s, 3 H), 7.23 (t, J = 7.4 Hz, 1 H), 7.28 (dd, J = 8.4, 2.1 Hz, 1 H), 7.34 (d, J = 2.1 Hz, 1 H), 7.41 (t, J = 7.6 Hz, 2 H), 7.55 (s, 1 H), 7.71 (d, J = 7.7 Hz, 2 H), 8.15 (d, J = 8.4 Hz, 1 H), 8.25 (d, J = 1.4 Hz, 1 H), 11.65 (br. s., 1 H). |
| 30 | (600 MHz, DMSO-$d_6$) δ ppm 2.37 (d, J = 1.1 Hz, 3 H), 2.61 (s, 3 H), 3.98 (s, 3 H), 7.72 (d, J = 8.2 Hz, 1 H), 7.79 (t, J = 1.4 Hz, 1 H), 7.84 (dd, J = 8.2, 1.6 Hz, 1 H), 7.88 (t, J = 7.9 Hz, 1 H), 7.89 (d, J = 1.6 Hz, 1 H), 7.95 (d, J = 7.9 Hz, 1 H), 8.06 (d, J = 7.9 Hz, 1 H), 8.10 (s, 1 H), 9.44 (d, J = 1.6 Hz, 1 H), 15.21 (br. s., 1 H). |
| 31 | (600 MHz, DMSO-$d_6$) δ ppm 1.27 (d, J = 6.8 Hz, 6 H), 2.37 (d, J = 1.1 Hz, 3 H), 3.11 (spt, J = 6.8 Hz, 1 H), 3.96 (s, 3 H), 7.47 (t, J = 8.8 Hz, 2 H), 7.71 (dd, J = 8.8, 5.1 Hz, 2 H), 7.71 (d, J = 8.4 Hz, 1 H), 7.78 (t, J = 1.4 Hz, 1 H), 7.82 (dd, J = 8.1, 1.6 Hz, 1 H), 7.84 (d, J = 1.6 Hz, 1 H), 9.44 (d, J = 1.6 Hz, 1 H). |
| 34 | (400 MHz, DMSO-$d_6$) δ ppm 1.22-1.34 (m, J = 12.6, 12.6, 12.4, 2.9, 2.9 Hz, 2 H), 1.35-1.47 (m, J = 12.5, 12.3, 12.3, 3.1 Hz, 2 H), 1.72 (d, J = 12.2 Hz, 1 H), 1.81 (dt, J = 12.7, 3.2 Hz, 2 H), 1.89 (d, J = 12.7 Hz, 2 H), 2.16 (s, 3 H), 2.93 (tt, J = 11.5, 3.5 Hz, 1 H), 3.88 (s, 3 H), 3.89 (s, 3 H), 7.14-7.17 (m, J = 1.2, 1.2 Hz, 1 H), 7.43 (d, J = 8.1 Hz, 1 H), 7.63 (dd, J = 8.1, 1.7 Hz, 1 H), 7.68 (d, J = 1.7 Hz, 1 H), 7.80 (d, J = 1.3 Hz, 1 H). |
| 36 | (360 MHz, DMSO-$d_6$) δ ppm 2.16 (s, 3 H), 3.86 (s, 3 H), 3.92 (s, 3 H), 4.04 (s, 3 H), 7.17 (dd, J = 7.7, 2.2 Hz, 1 H), 7.19 (s, 1 H), 7.37 (s, 1 H), 7.40 (d, J = 7.7 Hz, 1 H), 7.45-7.56 (m, 2 H), 7.73 (dd, J = 8.1, 1.5 Hz, 1 H), 7.78 (d, J = 1.5 Hz, 1 H), 7.84 (s, 1 H). |
| 37 | (600 MHz, DMSO-$d_6$) δ ppm 1.50 (d, J = 6.46 Hz, 6 H) 2.17 (d, J = 0.88 Hz, 3 H) 3.85 (s, 3 H) 3.92 (s, 3 H) 4.71 (spt, J = 6.46 Hz, 1 H) 7.15-7.20 (m, 2 H) 7.21-7.23 (m, 1 H) 7.24-7.27 (m, J = 7.63, 0.88, 0.73, 0.73 Hz, 1 H) 7.48 (d, J = 8.22 Hz, 1 H) 7.52 (t, J = 7.92 Hz, 1 H) 7.73 (dd, J = 7.92, 1.76 Hz, 1 H) 7.78 (d, J = 1.76 Hz, 1 H) 7.83 (d, J = 1.17 Hz, 1 H). |
| 38 | (360 MHz, DMSO-$d_6$) δ ppm 2.16 (s, 3 H), 3.73 (s, 3 H), 3.91 (s, 3 H), 7.19 (s, 1 H), 7.49 (d, J = 8.1 Hz, 1 H), 7.70 (dd, J = 8.1, 1.5 Hz, 1 H), 7.76 (d, J = 1.5 Hz, 1 H), 7.81 (dd, J = 6.9, 1.5 Hz, 1 H), 7.84 (d, J = 1.1 Hz, 1 H), 7.86-7.94 (m, 2 H), 8.01 (dd, J = 6.9, 1.5 Hz, 1 H). |
| 39 | (600 MHz, DMSO-$d_6$) δ ppm 1.52 (d, J = 6.5 Hz, 6 H), 2.17 (s, 3 H), 3.93 (s, 3 H), 4.68 (spt, J = 6.5 Hz, 1 H), 7.19 (s, 1 H), 7.49 (d, J = 8.1 Hz, 1 H), 7.75 (dd, J = 8.1, 1.7 Hz, 1 H), 7.79 (d, J = 1.7 Hz, 1 H), 7.84 (d, J = 1.4 Hz, 1 H), 7.86 (d, J = 7.8 Hz, 1 H), 7.99 (d, J = 7.9 Hz, 1 H), 8.04 (d, J = 7.8 Hz, 1 H), 8.06 (s, 1 H). |
| 40 | (600 MHz, DMSO-$d_6$) δ ppm 2.17 (d, J = 1.0 Hz, 3 H), 3.92 (s, 3 H), 4.03 (s, 3 H), 7.18 (t, J = 1.2 Hz, 1 H), 7.44 (t, J = 8.9 Hz, 2 H), 7.48 (d, J = 8.1 Hz, 1 H), 7.72 (dd, J = 8.0, 1.7 Hz, 1 H), 7.78 (d, J = 1.7 Hz, 1 H), 7.83 (d, J = 1.3 Hz, 1 H), 7.92 (dd, J = 8.8, 5.3 Hz, 2 H). |

| Co. No. | NMR result |
|---|---|
| 41 | (400 MHz, DMSO-$d_6$) δ ppm 1.60-1.71 (m, 2 H), 1.88-2.00 (m, 2 H), 2.00-2.15 (m, 4 H), 2.17 (s, 3 H), 3.92 (s, 3 H), 4.83 (quin, J = 7.2 Hz, 1 H), 7.18 (t, J = 1.2 Hz, 1 H), 7.44 (t, J = 8.8 Hz, 2 H), 7.48 (d, J = 8.1 Hz, 1 H), 7.72 (dd, J = 8.1, 1.7 Hz, 1 H), 7.77 (d, J = 1.7 Hz, 1 H), 7.79 (dd, J = 8.8, 5.4 Hz, 2 H), 7.83 (d, J = 1.4 Hz, 1 H). |
| 42 | (360 MHz, DMSO-$d_6$) δ ppm 2.18 (s, 3 H), 4.13 (s, 3 H), 7.27-7.43 (m, 3 H), 7.84 (d, J = 7.7 Hz, 1 H), 8.00 (s, 1 H), 8.03 (d, J = 7.7 Hz, 1 H), 8.15 (dd, J = 8.8, 5.9 Hz, 2 H), 14.73 (br. s., 1 H). |
| 48 | (400 MHz, DMSO-$d_6$) δ ppm 2.16 (s, 3 H), 3.83 (s, 3 H), 3.91 (s, 3 H), 7.16 (s, 1 H), 7.47 (d, J = 8.1 Hz, 1 H), 7.60-7.68 (m, 3 H), 7.69 (d, J = 1.7 Hz, 1 H), 7.81 (d, J = 1.4 Hz, 1 H), 9.48 (s, 1 H). |
| 51 | (400 MHz, DMSO-$d_6$) δ ppm 1.52 (d, J = 7.0 Hz, 3 H), 2.16 (s, 3 H), 3.66 (s, 3 H), 3.86 (s, 3 H), 4.99 (qd, J = 7.2, 7.1 Hz, 1 H), 6.93 (d, J = 7.9 Hz, 1 H), 7.14 (t, J = 8.9 Hz, 2 H), 7.13 (br. s., 1 H), 7.37 (d, J = 8.1 Hz, 1 H), 7.46-7.54 (m, 3 H), 7.59 (d, J = 1.6 Hz, 1 H), 7.78 (br. s., 1 H). |
| 52 | (600 MHz, DMSO-$d_6$) δ ppm 2.18 (d, J = 1.2 Hz, 3 H), 3.94 (s, 3 H), 4.06 (s, 3 H), 7.23 (t, J = 1.2 Hz, 1 H), 7.32 (t, J = 8.9 Hz, 2 H), 7.51 (dd, J = 8.1, 1.8 Hz, 1 H), 7.59 (d, J = 8.1 Hz, 1 H), 7.62 (d, J = 1.8 Hz, 1 H), 7.89 (d, J = 1.4 Hz, 1 H), 8.09 (dd, J = 8.8, 5.6 Hz, 2 H). |
| 54 | (360 MHz, DMSO-$d_6$) δ ppm 2.18 (d, J = 0.73 Hz, 3 H) 3.93 (s, 3 H) 4.11 (s, 3 H) 7.24 (t, J = 1.10 Hz, 1 H) 7.52 (dd, J = 8.05, 1.83 Hz, 1 H) 7.60 (d, J = 8.05 Hz, 1 H) 7.64 (d, J = 1.83 Hz, 1 H) 7.71 (t, J = 7.68 Hz, 1 H) 7.80 (t, J = 7.32 Hz, 1 H) 7.87-7.95 (m, 3 H). |
| 61 | (400 MHz, DMSO-$d_6$) δ ppm 2.17 (d, J = 0.8 Hz, 3 H), 3.92 (s, 3 H), 3.96 (s, 3 H), 7.22 (t, J = 1.2 Hz, 1 H), 7.41 (dd, J = 11.1, 6.2 Hz, 2 H), 7.46 (dd, J = 8.1, 1.8 Hz, 1 H), 7.57 (d, J = 10.3 Hz, 1 H), 7.56 (d, J = 2.0 Hz, 1 H), 7.87 (d, J = 1.4 Hz, 1 H), 9.80 (s, 1 H). |
| 62 | (400 MHz, DMSO-$d_6$) δ ppm 1.40 (d, J = 6.9 Hz, 3 H), 2.17 (s, 3 H), 3.74 (s, 3 H), 3.88 (s, 3 H), 4.65-4.76 (m, 1 H), 6.57 (d, J = 8.6 Hz, 1 H), 7.11 (t, J = 8.8 Hz, 2 H), 7.19 (s, 1 H), 7.34 (dd, J = 8.1, 1.7 Hz, 1 H), 7.41-7.47 (m, 3 H), 7.50 (d, J = 8.1 Hz, 1 H), 7.84 (s, 1 H). |
| 65 | (600 MHz, CDCl$_3$) δ ppm 2.32 (s, 3 H), 4.00 (s, 3 H), 6.99 (s, 1 H), 7.37 (d, J = 8.5 Hz, 1 H), 7.69 (d, J = 4.7 Hz, 2 H), 7.78 (s, 1 H), 7.88-7.91 (m, 2 H), 7.95-7.99 (m, 1 H), 8.08 (s, 1 H), 8.66 (s, 1 H). |
| 66 | (600 MHz, CDCl$_3$) δ ppm 1.52 (d, J = 6.6 Hz, 6 H), 2.31 (s, 3 H), 3.96 (s, 3 H), 4.29 (spt, J = 6.6 Hz, 1 H), 6.97 (s, 1 H), 7.32 (d, J = 8.4 Hz, 1 H), 7.43 (t, J = 7.6 Hz, 1 H), 7.46-7.53 (m, 2 H), 7.56 (d, J = 7.9 Hz, 1 H), 7.76 (s, 1 H), 7.82-7.88 (m, 2 H). |
| 67 | (600 MHz, DMSO-$d_6$) δ ppm 1.43 (d, J = 6.5 Hz, 6 H), 2.38 (s, 3 H), 3.96 (s, 3 H), 4.23 (spt, J = 6.5 Hz, 1 H), 7.71 (d, J = 8.2 Hz, 1 H), 7.77 (s, 1 H), 7.79 (d, J = 7.2 Hz, 1 H), 7.81 (dd, J = 8.2, 1.6 Hz, 1 H), 7.84 (d, J = 1.6 Hz, 1 H), 7.89 (t, J = 7.6 Hz, 1 H), 7.92 (t, J = 7.3 Hz, 1 H), 8.03 (d, J = 7.5 Hz, 1 H), 9.44 (d, J = 1.5 Hz, 1 H), 15.37 (br. s., 1 H). |
| 97 | (400 MHz, DMSO-$d_6$) δ ppm 2.15 (d, J = 1.0 Hz, 3 H), 2.27 (s, 3 H), 3.76 (s, 3 H), 3.87 (s, 3 H), 6.99 (td, J = 7.4, 1.3 Hz, 1 H), 7.14 (t, J = 1.2 Hz, 1 H), 7.18 (td, J = 7.7, 1.6 Hz, 1 H), 7.22 (d, J = 7.5 Hz, 1 H), 7.40 (d, J = 8.1 Hz, 1 H), 7.40 (d, J = 8.2 Hz, 1 H), 7.56 (dd, J = 8.1, 1.6 Hz, 1 H), 7.63 (d, J = 1.7 Hz, 1 H), 7.79 (d, J = 1.3 Hz, 1 H), 8.10 (s, 1 H). |
| 98 | (360 MHz, CDCl$_3$) δ ppm 2.31 (d, J = 0.7 Hz, 3 H) 2.35 (s, 3 H) 3.71 (s, 3 H) 5.95 (s, 1 H) 6.95 (t, J = 1.1 Hz, 1 H) 7.02 (td, J = 7.3, 1.1 Hz, 1 H) 7.18-7.26 (m, 2 H) 7.39 (dd, J = 8.8, 1.1 Hz, 1 H) 7.42 (d, J = 8.4 Hz, 1 H) 7.69 (d, J = 1.5 Hz, 1 H) 8.08 (dd, J = 8.4, 1.8 Hz, 1 H) 8.12 (quin, J = 1.5 Hz, 1 H). |
| 107 | (360 MHz, DMSO-$d_6$) δ ppm 2.16 (s, 3 H) 3.84 (s, 3 H) 4.00 (s, 3 H) 6.97-7.09 (m, 1 H) 7.13-7.22 (m, 1 H) 7.22-7.31 (m, 2 H) 7.67 (d, J = 8.1 Hz, 1 H) 7.80-7.91 (m, 2 H) 7.94 (d, J = 1.5 Hz, 1 H) 8.76 (s, 1 H). |
| 128 | (360 MHz, CDCl$_3$) δ ppm 2.30 (s, 3 H) 3.92 (s, 3 H) 4.15-4.28 (m, 1 H) 4.31-4.56 (m, 3 H) 6.17 (s, 1 H) 6.95 (s, 1 H) 7.13-7.32 (m, 4 H) 7.66-7.73 (m, 3 H). |
| 129 | (360 MHz, DMSO-$d_6$) δ ppm 2.15 (s, 3 H) 2.30 (s, 3 H) 3.77 (s, 3 H) 3.87 (s, 3 H) 7.10-7.23 (m, 3 H) 7.34 (dd, J = 7.0, 2.2 Hz, 1 H) 7.41 (d, J = 8.1 Hz, 1 H) 7.55 (dd, J = 8.1, 1.5 Hz, 1 H) 7.62 (d, J = 1.5 Hz, 1 H) 7.80 (d, J = 1.5 Hz, 1 H) 8.42 (s, 1 H). |
| 138 | (360 MHz, CDCl$_3$) δ ppm 2.31 (s, 3 H) 3.82 (s, 3 H) 4.18 (s, 3 H) 6.69-6.91 (m, 2 H) 7.02 (s, 1 H) 7.47 (td, J = 8.3, 5.7 Hz, 1 H) 7.53-7.58 (m, 1 H) 7.64 (d, J = 7.7 Hz, 1 H) 7.81 (d, J = 8.1 Hz, 1 H) 7.85 (d, J = 1.1 Hz, 1 H). |
| 154 | (360 MHz, DMSO-$d_6$) δ ppm 2.17 (s, 3 H) 3.89 (s, 3 H) 4.02 (s, 3 H) 7.28 (s, 1 H) 7.33-7.44 (m, 1 H) 7.53 (dd, J = 11.0, 8.8 Hz, 1 H) 7.65 (d, J = 7.7 Hz, 1 H) 7.87-8.00 (m, 2 H) 8.59 (dd, J = 7.7, 2.2 Hz, 1 H) 9.21 (s, 1 H). |
| 155 | (400 MHz, DMSO-$d_6$) δ ppm 2.15 (s, 3 H), 3.77 (s, 3 H), 3.87 (s, 3 H), 7.11-7.18 (m, 2 H), 7.29 (d, J = 8.4 Hz, 1 H), 7.41 (d, J = 8.1 Hz, 1 H), 7.55 (dd, J = 8.1, 1.6 Hz, 1 H), 7.64 (td, J = 8.4, 6.1 Hz, 1 H), 7.63 (d, J = 1.7 Hz, 1 H), 7.80 (d, J = 1.4 Hz, 1 H), 8.73 (s, 1 H). |
| 157 | (360 MHz, CDCl$_3$) δ ppm 2.31 (s, 3 H) 3.77 (s, 3 H) 3.95 (s, 3 H) 6.50 (br. s., 1 H) 6.97 (s, 1 H) 7.13 (t, J = 7.5 Hz, 1 H) 7.31 (d, J = 8.8 Hz, 1 H) 7.55 (t, J = 7.9 Hz, 1 H) 7.63 (d, J = 7.7 Hz, 1 H) 7.73-7.77 (m, 3 H) 7.81 (d, J = 8.4 Hz, 1 H). |
| 162 | (360 MHz, DMSO-d6) d ppm 2.16 (s, 3 H) 3.86 (s, 3 H) 3.89 (s, 3 H) 7.18 (s, 1 H) 734-743 (m, 1 H) 7.47 (d, J = 8.1 Hz, 1 H) 7.53 (dd, J = 10.6, 8.8 Hz, 1 H) 7.59 (dd, J = 8.1, 1.8 Hz, 1 H) 7.69 (d, J = 1.5 Hz, 1 H) 7.82 (d, J = 1.1 Hz, 1 H) 8.52 (dd, J = 7.7, 2.2 Hz, 1 H) 9.20 (s, 1 H). |

| Co. No. | NMR result |
|---|---|
| 167 | (360 MHz, DMSO-d$_6$) δ ppm 2.17 (s, 3 H) 3.87 (s, 3 H) 4.01 (s, 3 H) 7.28 (s, 1 H) 7.31-7.45 (m, 2 H) 7.69 (d, J = 8.1 Hz, 1 H) 7.91 (d, J = 8.1 Hz, 1 H) 7.94 (s, 1 H) 8.13-8.28 (m, 1 H) 9.14 (s, 1 H). |
| 173 | (400 MHz, DMSO-d$_6$) δ ppm 2.27 (s, 3 H) 2.36 (s, 3 H) 3.85 (s, 3 H) 3.93 (s, 3 H) 6.79 (td, J = 8.4 2.6 Hz, 1 H) 7.19-7.28 (m, 1 H) 7.43 (dd, J = 11.3, 2.8 Hz, 1 H) 7.65 (d, J = 8.1 Hz, 1 H) 7.68 (dd, J = 8.1, 1.6 Hz, 1 H) 7.74 (d, J = 1.2 Hz, 1 H) 7.75 (t, J = 1.2 Hz, 1 H) 8.43 (br. s., 1 H) 9.40 (d, J = 1.6 Hz, 1 H) 15.35 (br. s., 1 H). |
| 184 | (360 MHz, DMSO-d$_6$) δ ppm 2.17 (s, 3 H) 3.88 (s, 3 H) 4.02 (s, 3 H) 7.01 (dt, J = 8.7, 3.3 Hz, 1 H) 7.28 (s, 1 H) 7.42 (dd, J = 11.0, 9.1 Hz, 1 H) 7.66 (d, J = 7.7 Hz, 1 H) 7.91-7.98 (m, 2 H) 8.20 (dd, J = 7.0, 2.6 Hz, 1 H) 9.15 (s, 1 H). |
| 198 | (360 MHz, DMSO-d$_6$) δ ppm 2.15 (s, 3 H) 2.21 (s, 3 H) 2.25 (s, 3 H) 3.74 (s, 3 H) 3.87 (s, 3 H) 6.81 (d, J = 7.3 Hz, 1 H) 7.09 (d, J = 7.7 Hz, 1 H) 7.15 (s, 1 H) 7.17 (br. s., 1 H) 7.41 (d, J = 8.1 Hz, 1 H) 7.55 (dd, J = 8.1, 1.5 Hz, 1 H) 7.63 (d, J = 1.5 Hz, 1 H) 7.80 (d, J = 1.1 Hz, 1 H) 8.09 (s, 1 H). |
| 199 | (360 MHz, CDCl$_3$) δ ppm 2.27 (s, 3 H) 2.31 (s, 3 H) 3.74 (s, 3 H) 3.79 (s, 3 H) 3.94 (s, 3 H) 5.89 (s, 1 H) 6.55 (dd, J = 8.1, 2.6 Hz, 1 H) 6.97 (s, 1 H) 7.05-7.14 (m, 2 H) 7.30 (d, J = 8.4 Hz, 1 H) 7.71-7.76 (m, 3 H). |
| 200 | (400 MHz, CHLOROFORM-d) δ ppm 2.30 (s, 3 H), 2.93 (br. s., 1 H), 3.76 (s, 3 H), 3.85 (s, 3 H), 3.94 (s, 3 H), 4.78 (s, 2 H), 6.50 (dd, J = 8.3, 2.6 Hz, 1 H), 6.96 (s, 1 H), 7.03 (d, J = 8.3 Hz, 1 H), 7.29 (d, J = 8.1 Hz, 1 H), 7.71 (d, J = 1.4 Hz, 1 H), 7.75 (dd, J = 8.1, 1.6 Hz, 1 H), 7.77 (d, J = 1.6 Hz, 1 H), 7.83 (d, J = 2.6 Hz, 1 H), 8.14 (s, 1 H). |
| 203 | (360 MHz, DMSO-d$_6$) δ ppm 2.16 (s, 3 H) 3.85 (s, 3 H) 3.89 (s, 3 H) 3.95 (s, 3 H) 7.14 (dd, J = 6.8 1.6 Hz, 1 H) 7.17 (s, 1 H) 7.47 (d, J = 8.1 Hz, 1 H) 7.58 (dd, J = 8.2, 1.6 Hz, 1 H) 7.68 (d, J = 1.5 Hz, 1 H) 7.82 (d, J = 1.1 Hz, 1 H) 8.06 (dd, J = 6.4, 1.3 Hz, 1 H) 9.15 (br. s., 1 H). |
| 211 | (360 MHz, DMSO-d$_6$) δ ppm 2.14 (s, 3 H) 3.83 (s, 3 H) 3.84 (s, 3 H) 7.14 (s, 1 H) 7.38 (d, J = 8.1 Hz, 1 H) 7.40-7.49 (m, 2 H) 7.57 (d, J = 1.5 Hz, 1 H) 7.61-7.73 (m, 1 H) 7.79 (d, J = 1.1 Hz, 1 H) 9.14 (s, 1 H). |
| 258 | (360 MHz, CDCl$_3$) δ ppm 1.89-2.15 (m, 2 H) 2.15-2.36 (m, 2 H) 2.30 (s, 3 H) 2.41 (s, 3 H) 3.92 (s, 3 H) 4.24-4.44 (m, 2 H) 4.54 (t, J = 6.0 Hz, 1 H) 6.69 (dd, J = 8.6, 5.7 Hz, 1 H) 6.81 (td, J = 8.4, 2.6 Hz, 1 H) 6.91-6.97 (m, 2 H) 7.26 (d, J = 7.3 Hz, 1 H) 7.71-7.76 (m, 3 H). |
| 261 | (360 MHz, CDCl$_3$) δ ppm 1.86-2.06 (m, 1 H) 2.08-2.23 (m, 1 H) 2.23-2.36 (m, 1 H) 2.29 (s, 3 H) 2.41-2.55 (m, 1 H) 3.90 (s, 3 H) 4.36-4.43 (m, 2 H) 4.69-4.79 (m, 1 H) 6.90-6.97 (m, 1 H) 7.01 (d, J = 8.1 Hz, 1 H) 7.23-7.28 (m, 1 H) 7.40 (t, J = 7.7 Hz, 1 H) 7.48 (t, J = 7.5 Hz, 1 H) 7.66-7.72 (m, 2 H) 7.72-7.77 (m, 2 H). |
| 263 | (360 MHz, CDCl$_3$) δ ppm 1.89-2.05 (m, 1 H) 2.05-2.22 (m, 1 H) 2.23-2.37 (m, 4 H) 2.39-2.56 (m, 1 H) 4.16 (s, 3 H) 4.40-4.48 (m, 2 H) 4.76 (dd, J = 7.7, 6.6 Hz, 1 H) 6.94-7.01 (m, 2 H) 7.39 (t, J = 7.5 Hz, 1 H) 7.46 (t, J = 7.1 Hz, 1 H) 7.56 (d, J = 7.7 Hz, 1 H) 7.69-7.76 (m, 2 H) 7.81 (d, J = 1.1 Hz, 1 H). |
| 264 | (360 MHz, CDCl$_3$) δ ppm 1.90-2.06 (m, 1 H) 2.06-2.27 (m, 2 H) 2.30 (s, 3 H) 2.33-2.43 (m, 1 H) 2.46 (s, 3 H) 3.91 (s, 3 H) 4.25-4.47 (m, 2 H) 4.59 (t, J = 6.6 Hz, 1 H) 6.95 (d, J = 1.1 Hz, 1 H) 7.07 (s, 1 H) 7.25-7.30 (m, 1 H) 7.34 (d, J = 8.1 Hz, 1 H) 7.45 (d, J = 8.1 Hz, 1 H) 7.63-7.78 (m, 3 H). |
| 265 | (360 MHz, CDCl$_3$) δ ppm 1.97-2.12 (m, 1 H) 2.12-2.27 (m, 2 H) 2.30 (s, 3 H) 2.36-2.53 (m, 1 H) 3.92 (s, 3 H) 4.35 (t, J = 6.0 Hz, 2 H) 4.61 (t, J = 7.0 Hz, 1 H) 6.89 (dd, J = 6.2, 2.2 Hz, 1 H) 6.95 (s, 1 H) 7.06-7.20 (m, 2 H) 7.29 (d, J = 8.4 Hz, 1 H) 7.67-7.78 (m, 3 H). |
| 266 | (360 MHz, CDCl$_3$) δ ppm 2.00-2.25 (m, 3 H), 2.30 (s, 3 H), 2.33-2.43 (m, 1 H), 3.91 (s, 3 H), 4.35 (t, J = 5.9 Hz, 2 H), 4.68 (t, J = 6.5 Hz, 1 H), 6.95 (s, 1 H), 6.98 (d, J = 7.3 Hz, 1 H), 7.18-7.24 (m, 1 H), 7.27-7.38 (m, 3 H), 7.68-7.76 (m, 3 H). |
| 267 | (360 MHz, DMSO-d$_6$) δ ppm 1.87-2.13 (m, 3 H) 2.15 (s, 3 H) 2.24-2.39 (m, 1 H) 3.86 (s, 3 H) 4.19-4.42 (m, 2 H) 4.49 (t, J = 7.0 Hz, 1 H) 7.16 (s, 1 H) 7.23-7.33 (m, 3 H) 7.42 (d, J = 8.1 Hz, 1 H) 7.49 (t, J = 7.9 Hz, 1 H) 7.59 (dd, J = 8.1, 1.8 Hz, 1 H) 7.66 (d, J = 1.8 Hz, 1 H) 7.80 (d, J = 1.5 Hz, 1 H). |
| 269 | (360 MHz, CDCl$_3$) δ ppm 1.95 (s, 3 H) 2.01-2.15 (m, 1 H) 2.22-2.28 (m, 2 H) 2.31 (s, 3 H) 2.43-2.62 (m, 1 H) 3.76 (s, 3 H) 4.15-4.30 (m, 1 H) 4.44 (s, 1 H) 6.84 (dd, J = 9.5, 2.6 Hz, 1 H) 6.88-6.97 (m, 2 H) 7.14 (d, J = 8.1 Hz, 1 H) 7.59-7.70 (m, 3 H) 7.76 (s, 1 H). |
| 275 | (360 MHz, DMSO-d$_6$) δ ppm 2.14 (s, 3 H) 2.20 (s, 3 H) 3.09 (td, J = 11.8, 4.2 Hz, 1 H) 3.30-3.42 (m, 1 H) 3.84 (s, 3 H) 4.32-4.40 (m, 1 H) 4.41-4.51 (m, 1 H) 4.83 (s, 1 H) 7.13 (s, 1 H) 7.37 (d, J = 8.4 Hz, 1 H) 7.47 (dd, J = 8.2, 1.6 Hz, 1 H) 7.53-7.61 (m, 3 H) 7.61-7.69 (m, 1 H) 7.78 (d, J = 1.5 Hz, 1 H) 7.82 (d, J = 8.1 Hz, 1 H). |
| 279 | (360 MHz, CDCl$_3$) δ ppm 2.30 (d, J = 0.7 Hz, 3 H) 3.91 (s, 3 H) 4.15-4.27 (m, 1 H) 4.33-4.45 (m, 2 H) 4.47-4.59 (m, 1 H) 6.30 (s, 1 H) 6.94 (t, J = 1.1 Hz, 1 H) 7.27-7.33 (m, 2 H) 7.48-7.59 (m, 2 H) 7.66-7.76 (m, 3 H) 7.77-7.83 (m, 1 H). |
| 280 | (360 MHz, CDCl$_3$) δ ppm 2.30 (s, 3 H) 2.44 (s, 3 H) 3.92 (s, 3 H) 4.07-4.18 (m, 1 H) 4.25-4.51 (m, 3 H) 6.10 (s, 1 H) 6.87 (td, J = 8.4, 2.9 Hz, 1 H) 6.95 (t, J = 1.1 Hz, 1 H) 6.98 (dd, J = 9.7, 2.4 Hz, 1 H) 7.07 (dd, J = 8.6, 5.7 Hz, 1 H) 7.29 (d, J = 8.4 Hz, 1 H) 7.67-7.78 (m, 3 H). |
| 317 | (360 MHz, DMSO-d$_6$) δ ppm 2.16 (s, 3 H) 3.83 (s, 3 H) 3.87 (s, 3 H) 7.06 (dd, J = 8.2, 0.9 Hz, 1 H) 7.14-7.23 (m, 2 H) 7.43 (d, J = 8.4 Hz, 1 H) 7.49 (dd, J = 8.4, 0.7 Hz, 1 H) 7.59 (dd, J = 8.1, 1.5 Hz, 1 H) 7.66 (d, J = 1.8 Hz, 1 H) 7.81 (d, J = 1.5 Hz, 1 H) 9.36 (s, 1 H). |

-continued

| Co. No. | NMR result |
|---|---|
| 318 | (360 MHz, DMSO-d$_6$) δ ppm 2.17 (s, 3 H) 2.27 (s, 3 H) 3.79 (s, 6 H) 7.00 (td, J = 7.3, 1.1 Hz, 1 H) 7.14-7.25 (m, 3 H) 7.32 (dd, J = 8.8, 1.5 Hz, 1 H) 7.43 (d, J = 7.3 Hz, 1 H) 7.67 (dd, J = 8.4, 7.7 Hz, 1 H) 7.89 (d, J = 1.1 Hz, 1 H) 8.17 (s, 1 H). |
| 322 | (360 MHz, CDCl$_3$) δ ppm 2.33 (s, 3 H) 3.89 (s, 3 H) 6.57 (d, J = 3.7 Hz, 1 H) 7.13 (s, 1 H) 7.18-7.34 (m, 2 H) 7.50 (d, J = 8.8 Hz, 1 H) 7.82 (d, J = 1.1 Hz, 1 H) 8.37 (dd, J = 8.4, 1.8 Hz, 1 H) 8.49 (d, J = 1.8 Hz, 1 H) 8.65 (dd, J = 7.9, 1.6 Hz, 1 H). |
| 333 | (360 MHz, CDCl$_3$) δ ppm 1.90-2.03 (m, 1 H) 2.03-2.14 (m, 1 H) 2.15-2.27 (m, 1 H) 2.27-2.37 (m, 4 H) 2.41 (s, 3 H) 3.92 (s, 3 H) 4.24-4.45 (m, 2 H) 4.54 (t, J = 6.0 Hz, 1 H) 6.69 (dd, J = 8.4, 5.9 Hz, 1 H) 6.75-6.86 (m, 1 H) 6.89-6.99 (m, 2 H) 7.27 (d, J = 7.7 Hz, 1 H) 7.64-7.79 (m, 3 H). |
| 343 | (360 MHz, CDCl$_3$) δ ppm 1.92-2.05 (m, 1 H) 2.06-2.29 (m, 2 H) 2.31 (s, 3 H) 2.32-2.44 (m, 1 H) 2.46 (s, 3 H) 4.17 (s, 3 H) 4.33-4.53 (m, 2 H) 4.61 (t, J = 6.6 Hz, 1 H) 7.00 (s, 1 H) 7.04 (s, 1 H) 7.34 (d, J = 8.1 Hz, 1 H) 7.44 (d, J = 8.1 Hz, 1 H) 7.59 (d, J = 8.1 Hz, 1 H) 7.76 (d, J = 7.7 Hz, 1 H) 7.86 (s, 1 H). |
| 353 | (360 MHz, DMSO-d$_6$) δ ppm 2.17 (s, 3 H) 3.88 (s, 3 H) 3.95 (s, 3 H) 4.02 (s, 3 H) 7.14 (dd, J = 7.0, 1.8 Hz, 1 H) 7.28 (s, 1 H) 7.64 (d, J = 7.7 Hz, 1 H) 7.83-8.01 (m, 2 H) 8.12 (dd, J = 6.4, 2.0 Hz, 1 H) 9.17 (s, 1 H). |

Pharmacology

A) Screening of the Compounds of the Invention for γ-Secretase-Modulating Activity A1) Method 1

Screening was carried out using SKNBE2 cells carrying the APP 695-wild type, grown in Dulbecco's Modified Eagle's Medium/Nutrient mixture F-12 (DMEM/NUT-mix F-12) (HAM) provided by Gibco (cat no. 31330-38) containing 5% Serum/Fe supplemented with 1% non-essential amino acids. Cells were grown to near confluency.

The screening was performed using the assay as described in Citron et al (1997) Nature Medicine 3: 67. Briefly, cells were plated in a 96-well plate at about $10^5$ cells/ml one day prior to addition of compounds. Compounds were added to the cells in Ultraculture (Lonza, BE12-725F) supplemented with 1% glutamine (Invitrogen, 25030-024) for 18 h. The media were assayed by two sandwich ELISAs, for Aβ42 and Aβtotal. Toxicity of the compounds was assayed by WST-1 cell proliferation reagent (Roche, 1 644 807) according to the manufacturer's protocol.

To quantify the amount of Aβ42 in the cell supernatant, commercially available Enzyme-Linked-Immunosorbent-Assay (ELISA) kits were used (Innotest® β-Amyloid$_{(1-42)}$, Innogenetics N.V., Ghent, Belgium). The Aβ42 ELISA was performed essentially according to the manufacturer's protocol. Briefly, the standards (dilutions of synthetic Aβ1-42) were prepared in polypropylene Eppendorf with final concentrations of 8000 down to 3.9 pg/ml (1/2 dilution step). Samples, standards and blanks (100 μl) were added to the anti-Aβ42-coated plate supplied with the kit (the capture antibody selectively recognizes the C-terminal end of the antigen). The plate was allowed to incubate 3 h at 25° C. in order to allow formation of the antibody-amyloid complex. Following this incubation and subsequent wash steps a selective anti-Aβ-antibody conjugate (biotinylated 3D6) was added and incubated for a minimum of 1 hour (h) in order to allow formation of the antibody-Amyloid-antibody-complex. After incubation and appropriate wash steps, a Streptavidine-Peroxidase-Conjugate was added, followed 30 minutes later by an addition of 3,3',5,5'-tetramethylbenzidine (TMB)/peroxide mixture, resulting in the conversion of the substrate into a coloured product. This reaction was stopped by the addition of sulfuric acid (0.9 N) and the colour intensity was measured by means of photometry with an ELISA-reader with a 450 nm filter.

To quantify the amount of Aβtotal in the cell supernatant, samples and standards were added to a 6E10-coated plate. The plate was allowed to incubate overnight at 4° C. in order to allow formation of the antibody-amyloid complex. Following this incubation and subsequent wash steps a selective anti-Aβ-antibody conjugate (biotinylated 4G8) was added and incubated for a minimum of 1 h in order to allow formation of the antibody-Amyloid-antibody-complex. After incubation and appropriate wash steps, a Streptavidine-Peroxidase-Conjugate was added, followed 30 minutes later by an addition of Quanta Blu fluorogenic peroxidase substrate according to the manufacturer's instructions (Pierce Corp., Rockford, Ill.).

To obtain the values reported in Table 3a, the data were calculated as percentage of the maximum amount of amyloid Beta 42 measured in the absence of the test compound. The sigmoidal dose response curves were analyzed using non-linear regression analysis with percentage of the control plotted against the log concentration of the compound. A 4-parameter equation was used to determine the IC$_{50}$. The values reported in Table 3a are averaged IC$_{50}$ values.

The IC$_{50}$ values are shown in Table 3a:

| Co. No. | IC$_{50}$ Aβ42 (μM) | IC$_{50}$ Aβtotal (μM) | Co. No. | IC$_{50}$ Aβ42 (μM) | IC$_{50}$ Aβtotal (μM) | Co. No. | IC$_{50}$ Aβ42 (μM) | IC$_{50}$ Aβtotal (μM) |
|---|---|---|---|---|---|---|---|---|
| 24 | 1.45 | >3 | 12 | 0.09 | >3 | 3 | 0.49 | >3 |
| 11 | 0.11 | >3 | 28 | >3 | >3 | 9 | 0.79 | >30 |
| 25 | 2.51 | >3 | 13 | 1.05 | >3 | 299 | >3 | >3 |
| 26 | 0.76 | >3 | 14 | 0.50 | >3 | 15 | 0.25 | 11.48 |
| 27 | 0.17 | >10 | 29 | 0.19 | >3 | | | |

A2) Method 2

Screening was carried out using SKNBE2 cells carrying the APP 695-wild type, grown in Dulbecco's Modified Eagle's Medium/Nutrient mixture F-12 (DMEM/NUT-mix F-12) (HAM) provided by Invitrogen (cat no. 10371-029) containing 5% Serum/Fe supplemented with 1% non-essential amino acids, 1-glutamine 2 mM, Hepes 15 mM, penicillin 50 U/ml (units/ml) en streptomycin 50 μg/ml. Cells were grown to near confluency.

The screening was performed using a modification of the assay as described in Citron et al (1997) Nature Medicine 3: 67. Briefly, cells were plated in a 384-well plate at $10^4$ cells/well in Ultraculture (Lonza, BE12-725F) supplemented with 1% glutamine (Invitrogen, 25030-024), 1% non-essential amino acid (NEAA), penicillin 50 U/ml en streptomycin 50 µg/ml in the presence of test compound at different test concentrations. The cell/compound mixture was incubated overnight at 37° C., 5% $CO_2$. The next day the media were assayed by two sandwich immuno-assays, for Aβ42 and Aβtotal.

Aβtotal and Aβ42 concentrations were quantified in the cell supernatant using the Aphalisa technology (Perkin Elmer). Alphalisa is a sandwich assay using biotinylated antibody attached to streptavidin coated donorbeads and antibody conjugated to acceptor beads. In the presence of antigen, the beads come into close proximity. The excitation of the donor beads provokes the release of singlet oxygen molecules that trigger a cascade of energy transfer in the acceptor beads, resulting in light emission. To quantify the amount of Aβ42 in the cell supernatant, monoclonal antibody specific to the C-terminus of Aβ42 (JRF/cAβ42/26) was coupled to the receptor beads and biotinylated antibody specific to the N-terminus of Aβ (JRF/AβN/25) was used to react with the donor beads. To quantify the amount of Aβ total in the cell supernatant, monoclonal antibody specific to the N-terminus of Aβ (JRF/AβN/25) was coupled to the receptor beads and biotinylated antibody specific to the mid region of Aβ (biotinylated 4G8) was used to react with the donor beads.

To obtain the values reported in Table 3b, the data were calculated as percentage of the maximum amount of amyloid Beta 42 measured in the absence of the test compound.

The sigmoidal dose response curves were analyzed using non-linear regression analysis with percentage of the control plotted against the log concentration of the compound. A 4-parameter equation was used to determine the $IC_{50}$.

The IC50 values are shown in Table 3b (Aβtot means Aβtotal).

| Co. No. | $IC_{50}$ Aβ42 (µM) | $IC_{50}$ Aβtot (µM) |
|---|---|---|
| 2 | 0.468 | >10 |
| 3 | 0.417 | >10 |
| 4 | 0.646 | >10 |
| 5 | 0.170 | >10 |
| 6 | 0.309 | >10 |
| 7 | 0.117 | >10 |
| 8 | 4.266 | >10 |
| 9 | 0.603 | >10 |
| 10 | 0.025 | 8.318 |
| 11 | 0.182 | >10 |
| 12 | 0.033 | 3.631 |
| 13 | 0.724 | >10 |
| 14 | 0.282 | 5.248 |
| 15 | 0.050 | >10 |
| 16 | 0.309 | >10 |
| 17 | 0.407 | >10 |
| 18 | 0.076 | >10 |
| 19 | 0.162 | >10 |
| 20 | 0.257 | >10 |
| 21 | 6.918 | >10 |
| 22 | 0.479 | >10 |
| 23 | 5.012 | >10 |
| 24 | 1.047 | 6.607 |
| 25 | 6.457 | >10 |
| 27 | <3 | >3 |
| 28 | >3 | >3 |
| 29 | 0.170 | >10 |
| 30 | 0.295 | >10 |
| 31 | 0.447 | >10 |
| 32 | 0.191 | 6.761 |
| 33 | 0.269 | >10 |
| 34 | 0.240 | >10 |
| 35 | 0.776 | >10 |
| 36 | 0.575 | >10 |
| 37 | 0.085 | 11.22 |
| 38 | 0.158 | >10 |
| 39 | 0.105 | 7.943 |
| 40 | 0.355 | >10 |
| 41 | 0.407 | >10 |
| 42 | 0.380 | >10 |
| 43 | 0.148 | >10 |
| 45 | 0.085 | >10 |
| 46 | 0.138 | 8.51 |
| 47 | 0.302 | 3.24 |
| 48 | 0.245 | 6.918 |
| 49 | 0.040 | 6.026 |
| 50 | 0.110 | >10 |
| 51 | 0.324 | >10 |
| 52 | 5.754 | >10 |
| 53 | >10 | >10 |
| 54 | 4.169 | >10 |
| 55 | 0.234 | >10 |
| 56 | >10 | >10 |
| 57 | 0.851 | >10 |
| 58 | >10 | >10 |
| 59 | 2.951 | >10 |
| 60 | 8.511 | >10 |
| 61 | 4.786 | >10 |
| 62 | 3.236 | >10 |
| 63 | 1.349 | >10 |
| 64 | >10 | >10 |
| 65 | 2.239 | >10 |
| 66 | 0.562 | >10 |
| 67 | 0.200 | 9.550 |
| 68 | 0.135 | >10 |
| 69 | 1.259 | >10 |
| 70 | 0.309 | >10 |
| 71 | 1.148 | >10 |
| 72 | 0.288 | >10 |
| 73 | 0.200 | 9.550 |
| 74 | 0.251 | 6.457 |
| 75 | 0.676 | 6.46 |
| 76 | 0.851 | 12.59 |
| 77 | 0.145 | 8.32 |
| 78 | 0.050 | 8.51 |
| 79 | 0.036 | 6.61 |
| 80 | 0.056 | 10 |
| 81 | 0.224 | >10 |
| 82 | 0.603 | 7.76 |
| 83 | 0.257 | >10 |
| 84 | 0.316 | >10 |
| 85 | 0.309 | >10 |
| 86 | 0.195 | >10 |
| 87 | 0.759 | >10 |
| 88 | 0.209 | >10 |
| 89 | 0.501 | 7.943 |
| 90 | 0.562 | 8.913 |
| 91 | 2.344 | >10 |
| 92 | 0.933 | >10 |
| 93 | 0.282 | >10 |
| 94 | 0.871 | >10 |
| 95 | 0.912 | >10 |
| 96 | 0.339 | >10 |
| 97 | 0.049 | >10 |
| 98 | 0.288 | >10 |
| 99 | 0.019 | >10 |
| 100 | 0.028 | >10 |
| 101 | 0.041 | >10 |
| 102 | 0.056 | >10 |
| 103 | 0.036 | 6.31 |
| 104 | 0.115 | 8.32 |
| 105 | 0.132 | >10 |
| 106 | 0.132 | >10 |
| 107 | 0.148 | >10 |
| 108 | 0.151 | 7.762 |
| 109 | 0.117 | >10 |
| 110 | 0.091 | >10 |
| 111 | 0.013 | >10 |
| 112 | 0.129 | 9.12 |
| 113 | 0.060 | >10 |
| 114 | 0.056 | >10 |
| 115 | 0.102 | >10 |
| 116 | 0.200 | >10 |

| Co. No. | IC$_{50}$ Aβ42 (μM) | IC$_{50}$ Aβtot (μM) |
|---|---|---|
| 117 | 0.060 | >10 |
| 118 | 0.089 | >10 |
| 119 | 0.054 | >10 |
| 120 | 0.123 | >10 |
| 121 | 0.123 | >10 |
| 122 | 0.066 | >15 |
| 123 | 0.058 | >10 |
| 124 | 0.151 | >10 |
| 125 | 0.085 | >10 |
| 126 | 0.162 | >10 |
| 127 | 0.066 | >10 |
| 128 | 0.028 | >10 |
| 129 | 0.025 | >10 |
| 130 | 0.060 | >10 |
| 131 | 0.008 | 6.310 |
| 132 | 0.135 | >10 |
| 133 | 0.031 | 2.344 |
| 134 | 0.110 | >10 |
| 135 | 0.026 | >10 |
| 136 | 0.076 | 3.020 |
| 137 | 0.041 | >10 |
| 138 | 0.050 | >10 |
| 139 | 0.794 | >10 |
| 140 | 0.020 | >10 |
| 141 | 0.047 | >10 |
| 142 | 0.059 | >10 |
| 143 | 0.030 | >10 |
| 144 | 0.009 | >10 |
| 145 | 0.038 | 2.239 |
| 146 | 0.015 | 4.074 |
| 147 | 0.041 | >10 |
| 148 | 0.023 | >10 |
| 149 | 1.698 | >10 |
| 150 | 0.013 | >10 |
| 151 | 0.027 | 4.074 |
| 152 | 0.019 | >10 |
| 153 | 0.008 | >10 |
| 154 | 0.017 | >10 |
| 155 | 0.095 | >10 |
| 156 | 0.033 | >10 |
| 157 | 0.063 | >15 |
| 158 | 0.040 | >10 |
| 159 | 0.021 | >10 |
| 160 | 0.006 | >10 |
| 161 | 0.078 | >10 |
| 162 | 0.011 | 3.63 |
| 163 | 0.062 | >10 |
| 164 | 0.030 | >10 |
| 165 | 0.138 | >10 |
| 166 | 0.065 | >10 |
| 167 | 0.038 | >15 |
| 168 | 0.071 | >10 |
| 169 | 0.041 | >10 |
| 170 | 3.236 | >10 |
| 171 | 0.042 | >15 |
| 172 | 0.062 | >10 |
| 173 | 0.060 | >10 |
| 174 | 0.020 | 7.413 |
| 175 | 0.089 | >10 |
| 176 | 0.046 | >10 |
| 177 | 0.010 | >10 |
| 178 | 0.021 | 7.94 |
| 179 | 0.019 | 5.012 |
| 180 | 0.022 | >10 |
| 181 | 0.025 | 5.754 |
| 182 | 0.035 | 8.511 |
| 183 | 0.013 | >10 |
| 184 | 0.013 | >15 |
| 185 | 0.017 | >10 |
| 186 | 0.078 | >10 |
| 187 | 0.178 | >10 |
| 188 | 0.178 | >10 |
| 189 | 0.019 | >10 |
| 190 | 0.214 | >10 |
| 191 | 0.028 | >10 |
| 192 | 0.041 | 9.550 |
| 193 | 0.063 | >10 |
| 194 | 0.065 | >10 |
| 195 | 0.095 | >10 |
| 196 | 0.129 | >10 |
| 197 | 0.135 | >10 |
| 198 | 0.013 | >10 |
| 199 | 0.016 | >10 |
| 200 | 0.158 | >10 |
| 201 | 0.015 | >15 |
| 202 | 0.025 | >10 |
| 203 | 0.010 | >10 |
| 204 | 0.110 | >10 |
| 205 | 0.100 | >10 |
| 206 | 0.166 | 8.128 |
| 207 | 0.123 | >10 |
| 208 | 0.178 | >10 |
| 209 | 0.052 | 9.55 |
| 210 | 0.035 | >10 |
| 211 | 0.025 | >10 |
| 212 | 0.017 | >10 |
| 213 | 0.005 | 8.91 |
| 214 | 0.170 | >10 |
| 215 | 0.269 | >10 |
| 216 | 0.076 | >10 |
| 217 | 0.026 | 6.457 |
| 218 | 0.014 | >10 |
| 219 | 0.091 | >10 |
| 220 | 0.063 | >10 |
| 221 | 0.708 | >10 |
| 222 | 1.148 | >10 |
| 223 | 0.126 | >10 |
| 224 | 0.646 | >10 |
| 225 | 1.445 | >10 |
| 226 | 0.417 | >10 |
| 227 | 0.676 | 0.891 |
| 228 | 4.467 | >10 |
| 229 | 0.295 | >10 |
| 230 | 0.302 | >10 |
| 231 | 0.056 | 5.888 |
| 232 | 1.413 | >10 |
| 233 | 0.603 | >10 |
| 234 | 0.955 | >10 |
| 235 | 0.132 | >10 |
| 236 | 0.575 | >10 |
| 237 | 3.162 | >10 |
| 238 | 1.585 | >10 |
| 239 | 4.467 | >10 |
| 240 | 0.794 | >10 |
| 241 | 0.741 | >10 |
| 242 | >10 | >10 |
| 243 | 8.318 | >10 |
| 244 | 0.083 | >10 |
| 245 | 0.646 | >10 |
| 246 | 0.269 | 9.77 |
| 247 | 0.363 | 8.13 |
| 248 | 0.389 | >10 |
| 249 | 0.646 | >10 |
| 250 | 0.135 | >10 |
| 251 | 0.245 | >10 |
| 252 | 0.240 | >10 |
| 253 | 0.170 | >10 |
| 254 | 0.234 | >10 |
| 255 | 0.032 | 9.33 |
| 256 | 0.021 | >10 |
| 257 | 0.148 | >10 |
| 258 | 0.062 | >10 |
| 259 | 0.158 | >10 |
| 260 | 0.457 | >15 |
| 261 | 0.024 | >15 |
| 262 | 0.324 | >10 |
| 263 | 0.029 | >10 |
| 264 | 0.015 | >10 |
| 265 | 0.019 | >10 |
| 266 | 0.074 | >3 |
| 267 | 0.049 | >10 |
| 268 | 0.141 | >10 |

-continued

| Co. No. | IC$_{50}$ Aβ42 (μM) | IC$_{50}$ Aβtot (μM) |
|---|---|---|
| 269 | 0.148 | >10 |
| 270 | 0.170 | >10 |
| 271 | 0.309 | >10 |
| 272 | 7.586 | >10 |
| 273 | 0.155 | 10.00 |
| 274 | 0.155 | 8.71 |
| 275 | 0.269 | >10 |
| 276 | 0.832 | >10 |
| 277 | 0.661 | >10 |
| 278 | 0.398 | >10 |
| 279 | 0.062 | >10 |
| 280 | 0.191 | >10 |
| 281 | 0.076 | >10 |
| 282 | 0.380 | >10 |
| 283 | 0.078 | 7.943 |
| 284 | 0.229 | >10 |
| 285 | 0.076 | >10 |
| 286 | 0.145 | 10 |
| 287 | 0.355 | >10 |
| 288 | 0.151 | >10 |
| 289 | 0.708 | >10 |
| 290 | 0.224 | >10 |
| 291 | 0.045 | 9.772 |
| 292 | 2.344 | >10 |
| 293 | 2.344 | >10 |
| 294 | 0.537 | >10 |
| 295 | 0.537 | >10 |
| 296 | 1.514 | 6.03 |
| 297 | 0.263 | >10 |
| 298 | 3.090 | >10 |
| 299 | 8.128 | >10 |
| 300 | 0.871 | >10 |
| 301 | >10 | >10 |
| 302 | 0.071 | >10 |
| 303 | 0.040 | >10 |
| 304 | 0.042 | >10 |
| 305 | 0.646 | >10 |
| 306 | 0.071 | >10 |
| 307 | 0.008 | >10 |
| 308 | 1.698 | >10 |
| 309 | 1.072 | >10 |
| 310 | 0.044 | >10 |
| 311 | 0.186 | 7.41 |
| 312 | 0.123 | >10 |
| 313 | 0.068 | >10 |
| 314 | 0.288 | >10 |
| 315 | 0.029 | >10 |
| 316 | 0.661 | >10 |
| 317 | 0.034 | 7.94 |
| 318 | 0.240 | >10 |
| 319 | 0.490 | >10 |
| 320 | 0.045 | >10 |
| 321 | 0.182 | >15 |
| 322 | 0.036 | >15 |
| 323 | 0.051 | >10 |
| 324 | 1.318 | >10 |
| 325 | 0.182 | >10 |
| 326 | 3.090 | >10 |
| 327 | 1.175 | >10 |
| 328 | 0.007 | 0.145 |
| 329 | 3.090 | 0.851 |
| 330 | 0.603 | 0.068 |
| 331 | 0.056 | >10 |
| 332 | 0.234 | >10 |
| 333 | 0.026 | >10 |
| 334 | 0.263 | >10 |
| 335 | 0.200 | >10 |
| 336 | 0.129 | >10 |
| 337 | 0.263 | >10 |
| 339 | 0.155 | >10 |
| 341 | 0.012 | 7.762 |
| 342 | 0.162 | >10 |
| 343 | 0.015 | >10 |
| 344 | 0.052 | >10 |
| 345 | 0.107 | >10 |
| 346 | 0.095 | >10 |
| 347 | 0.126 | >10 |
| 348 | 0.079 | >10 |
| 349 | 0.257 | >10 |
| 350 | 0.044 | n.d. |
| 351 | 0.028 | n.d. |
| 352 | 0.060 | n.d. |
| 353 | 0.017 | >10 |
| 354 | 0.022 | n.d. |
| 355 | 0.135 | n.d. |
| 356 | 0.020 | n.d. |
| 357 | 0.007 | n.d. |
| 358 | 0.062 | n.d. |
| 359 | 0.095 | >10 |
| 360 | 0.240 | n.d. |
| 361 | 0.042 | n.d. |
| 363 | 0.407 | n.d. |
| 364 | 0.083 | n.d. |
| 365 | 0.447 | n.d. |
| 366 | 0.513 | n.d. |
| 367 | 0.078 | n.d. |
| 368 | 0.066 | n.d. |
| 369 | 0.123 | n.d. |
| 370 | 0.036 | n.d. |
| 371 | 0.040 | n.d. |
| 374 | 0.062 | n.d. |

B) Demonstration of In Vivo Efficacy

B1) Method 1

Aβ42 lowering agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ42 lowering agents can be administered in any standard form using any standard method. For example, but not limited to, Aβ42 lowering agents can be in the form of liquid, tablets or capsules that are taken orally or by injection. Aβ42 lowering agents can be administered at any dose that is sufficient to significantly reduce levels of Aβ42 in the blood, blood plasma, serum, cerebrospinal fluid (CSF), or brain.

To determine whether acute administration of an Aβ42 lowering agent would reduce Aβ42 levels in vivo, non-transgenic rodents, e.g. mice or rats were used. Alternatively, two to three month old Tg2576 mice expressing APP695 containing the "Swedish" variant can be used or a transgenic mouse model developed by Dr. Fred Van Leuven (K.U. Leuven, Belgium) and co-workers, with neuron-specific expression of a clinical mutant of the human amyloid precursor protein [V717I] (Moechars et al., 1999 J. Biol. Chem. 274, 6483). Young transgenic mice have high levels of Aβ in the brain but no detectable Aβ deposition. At approximately 6-8 months of age, the transgenic mice start to display spontaneous, progressive accumulation of β-amyloid (Aβ) in the brain, eventually resulting in amyloid plaques within the subiculum, hippocampus and cortex. Animals treated with the Aβ42 lowering agent were examined and compared to those untreated or treated with vehicle and brain levels of soluble Aβ42 and total Aβ would be quantitated by standard techniques, for example, using ELISA. Treatment periods varied from hours (h) to days and were adjusted based on the results of the Aβ42 lowering once a time course of onset of effect could be established.

A typical protocol for measuring Aβ42 lowering in vivo is shown but it is only one of many variations that could be used to optimize the levels of detectable Aβ. For example, Aβ42 lowering compounds were formulated in 20% of Captisol® (a sulfobutyl ether of β-cyclodextrin) in water or 20% hydroxypropyl cyclodextrin. The Aβ42 lowering agents were administered as a single oral dose or by any acceptable route of administration to overnight fasted animals. After 4 h, the animals were sacrificed and Aβ42 levels were analysed.

Blood was collected by decapitation and exsanguinations in EDTA-treated collection tubes. Blood was centrifuged at 1900 g for 10 minutes (min) at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains were resuspended in 10 volumes of 0.4% DEA (diethylamine)/50 mM NaCl pH 10 (for non-transgenic animals) or 0.1% 3-[(3-cholamidopropyl)-dimethyl-ammonio]-1-propanesulfonate (CHAPS) in tris buffered saline (TBS) (for transgenic animals) containing protease inhibitors (Roche-11873580001 or 04693159001) per gram of tissue, e.g. for 0.158 g brain, add 1.58 ml of 0.4% DEA. All samples were sonicated for 30 seconds on ice at 20% power output (pulse mode). Homogenates were centrifuged at 221.300×g for 50 min. The resulting high speed supernatants were then transferred to fresh tubes and were optionally further purified before the next step. A portion of the supernatant was neutralized with 10% 0.5 M Tris-HCl and this was used to quantify Aβtotal.

The obtained supernatants were purified with Water Oasis HLB reverse phase columns (Waters Corp., Milford, Mass.) to remove non-specific immunoreactive material from the brain lysates prior subsequent Aβ detection. Using a vacuum manifold, all solutions were passed through the columns at a rate of approximately 1 ml per min, so the vacuum pressure was adjusted accordingly throughout the procedure. Columns were preconditioned with 1 ml of 100% MeOH, before equilibration with 1 ml of $H_2O$, Non-neutralized brain lysates were loaded onto the columns. The loaded samples were then washed twice with the first wash performed with 1 ml of 5% MeOH, and the second wash with 1 ml of 30% MeOH. Finally, the Aβ was eluted from the columns and into 100×30 mm glass tubes, with a solution of 90% MeOH with 2% $NH_4OH$. The eluate was then transferred into 1.5 ml tubes and concentrated in a speed-vac concentrator on high heat for about 1.5-2 h at 70° C. The concentrated Aβ was then resuspended in UltraCULTURE General Purpose Serum-Free Medium (Cambrex Corp., Walkersville, Md.) plus Protease Inhibitors added according to the manufacturers recommendation.

To quantify the amount of Aβ42 in the soluble fraction of the brain homogenates, commercially available Enzyme-Linked-Immunosorbent-Assay (ELISA) kits were used (e.g. Innotest® β-Amyloid$_{(1-42)}$, Innogenetics N.V., Ghent, Belgium). The Aβ42 ELISA was performed using the plate provided with the kit only. Briefly, the standards (a dilution of synthetic Aβ1-42) were prepared in 1.5 ml Eppendorf tube in Ultraculture, with final concentrations ranging from 25000 to 1.5 pg/ml. Samples, standards and blanks (60 μl) were added to the anti-Aβ42-coated plate (the capture antibody selectively recognizes the C-terminal end of the antigen). The plate was allowed to incubate overnight at 4° C. in order to allow formation of the antibody-amyloid complex. Following this incubation and subsequent wash steps a selective anti-Aβ-antibody conjugate (biotinylated detection antibody, e.g., biotinylated 4G8 (Covance Research Products, Dedham, Mass.) was added and incubated for a minimum of 1 h in order to allow formation of the antibody-Amyloid-antibody-complex. After incubation and appropriate wash steps, a Streptavidine-Peroxidase-Conjugate was added, followed 50 min later by an addition of Quanta Blu fluorogenic peroxidase substrate according to the manufacturer's instructions (Pierce Corp., Rockford, Ill.). A kinetic reading was performed every 5 min for 30 min (excitation 320/emission 420). To quantify the amount of Aβtotal in the soluble fraction of the brain homogenates, samples and standards were added to JRF/rAβ/2-coated plate. The plate was allowed to incubate overnight at 4° C. in order to allow formation of the antibody-amyloid complex. The ELISA was then performed as for Aβ42 detection.

In this model at least 20% Aβ42 lowering compared to untreated animals would be advantageous.

The results are shown in table 4a (dose 30 mg/kg oral dosing):

| Co. No. | Aβ42 (% Ctrl) Mean | Aβtotal (% Ctrl) Mean |
|---|---|---|
| 11 | 4 | −4 |
| 9 | 24 | 0 |
| 15 | 42 | 3 |
| 39 | 17 | 0 |
| 32 | 6 | 2 |
| 68 | 29 | −3 |
| 146 | 27 | 14 |

B2) Method 2

Aβ42 lowering agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ42 lowering agents can be administered in any standard form using any standard method. For example, but not limited to, Aβ42 lowering agents can be in the form of liquid, tablets or capsules that are taken orally or by injection. Aβ42 lowering agents can be administered at any dose that is sufficient to significantly reduce levels of Aβ42 in the blood, blood plasma, serum, cerebrospinal fluid (CSF), or brain.

To determine whether acute administration of an Aβ42 lowering agent would reduce Aβ42 levels in vivo, non-transgenic rodents, e.g. mice or rats were used. Animals treated with the Aβ42 lowering agent were examined and compared to those untreated or treated with vehicle and brain levels of soluble Aβ42 and total Aβ were quantitated by standard techniques, for example, using ELISA. Treatment periods varied from hours (h) to days and were adjusted based on the results of the Aβ42 lowering once a time course of onset of effect could be established.

A typical protocol for measuring Aβ42 lowering in vivo is shown but it is only one of many variations that could be used to optimize the levels of detectable Aβ. For example, Aβ42 lowering compounds were formulated in 20% of Captisol® (a sulfobutyl ether of β-cyclodextrin) in water or 20% hydroxypropyl β cyclodextrin. The Aβ42 lowering agents were administered as a single oral dose or by any acceptable route of administration to overnight fasted animals. After 4 h, the animals were sacrificed and Aβ42 levels were analysed.

Blood was collected by decapitation and exsanguinations in EDTA-treated collection tubes. Blood was centrifuged at 1900 g for 10 minutes (min) at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains from non-transgenic animals were resuspended in 8 volumes of 0.4% DEA (diethylamine)/50 mM NaCl containing protease inhibitors (Roche-11873580001 or 04693159001) per gram of tissue, e.g. for 0.158 g brain, add 1.264 ml of 0.4% DEA. All samples were homogenized in the FastPrep-24 system (MP Biomedicals) using lysing matrix D (MPBio #6913-100) at 6 m/s for 20 seconds. Homogenates were centrifuged at 221.300×g for 50 min. The resulting high speed supernatants were then transferred to fresh eppendorf tubes. Nine parts of supernatant were neutralized with 1 part 0.5 M Tris-HCl pH 6.8 and used to quantify Aβtotal and Aβ42.

To quantify the amount of Aβtotal and Aβ42 in the soluble fraction of the brain homogenates, Enzyme-Linked-Immunosorbent-Assays were used. Briefly, the standards (a dilution of synthetic Aβ1-40 and Aβ1-42, Bachem) were prepared in 1.5 ml Eppendorf tube in Ultraculture, with final concentrations ranging from 10000 to 0.3 pg/ml. The samples and standards were co-incubated with HRPO-labelled N-terminal antibody for Aβ42 detection and with the biotinylated mid-domain antibody 4G8 for Aβtotal detection. 50 μl of conjugate/sample or conjugate/standards mixtures were then added to the antibody-coated plate (the capture antibodies selectively recognize the C-terminal end of Aβ42, antibody JRF/cAβ42/26, for Aβ42 detection and the N-terminus of Aβ, antibody JRF/rAβ/2, for Aβtotal detection). The plate was allowed to incubate overnight at 4° C. in order to allow formation of the antibody-amyloid complex. Following this incubation and subsequent wash steps the ELISA for Aβ42 quantification was finished by addition of Quanta Blu fluorogenic peroxidase substrate according to the manufacturer's instructions (Pierce Corp., Rockford, Ill.). A reading was performed after 10 to 15 min (excitation 320/emission 420).

For Aβtotal detection, a Streptavidine-Peroxidase-Conjugate was added, followed 60 min later by an additional wash step and addition of Quanta Blu fluorogenic peroxidase substrate according to the manufacturer's instructions (Pierce Corp., Rockford, Ill.). A reading was performed after 10 to 15 min (excitation 320 nm/emission 420 nm).

In this model at least 20% Aβ42 lowering compared to untreated animals would be advantageous.

The results are shown in Table 4b (dose 30 mg/kg oral dosing):

| Co. No. | Aβ42 (% Ctrl) _Mean | Aβtotal (% Ctrl) _Mean | Co. No. | Aβ42 (% Ctrl) _Mean | Aβtotal (% Ctrl) _Mean | Co. No. | Aβ42 (% Ctrl) _Mean | Aβtotal (% Ctrl) _Mean |
|---|---|---|---|---|---|---|---|---|
| 12 | −22 | −21 | 123 | 36 | 31 | 136 | −14 | 1 |
| 15 | 37 | −5 | 180 | 51 | 10 | 264 | 49 | 8 |
| 18 | 5 | −5 | 177 | 51 | 11 | 198 | 55 | 6 |
| 146 | 17 | 2 | 132 | 39 | −1 | 265 | 55 | 22 |
| 152 | 10 | −9 | 144 | 38 | 9 | 203 | 54 | 6 |
| 279 | 26 | 9 | 125 | 2 | 11 | 99 | 58 | −2 |
| 158 | 44 | 3 | 169 | 57 | 9 | 269 | 37 | −5 |
| 80 | −20 | −19 | 185 | 40 | 9 | 211 | 32 | −1 |
| 153 | 14 | −6 | 117 | 44 | 17 | 175 | 3 | 0 |
| 150 | −6 | −8 | 184 | 69 | 15 | 320 | 23 | 8 |
| 213 | 9 | 7 | 260 | −1 | −9 | 304 | 48 | 11 |
| 162 | 35 | 2 | 261 | 46 | 6 | 307 | 19 | −2 |
| 100 | 12 | −4 | 182 | 55 | 14 | 306 | 22 | −2 |
| 148 | 37 | 12 | 322 | −5 | −4 | 315 | 49 | 10 |
| 130 | 20 | 8 | 167 | 52 | −1 | 302 | 31 | −3 |
| 154 | 54 | −5 | 214 | −15 | 0 | 303 | 33 | 23 |
| 199 | 39 | 5 | 140 | 33 | 8 | 310 | 45 | 20 |
| 157 | 39 | 3 | 138 | 46 | 17 | 128 | 47 | 24 |
| 105 | 24 | −7 | 97 | 40 | 10 | 330 | −9 | −2 |
| 255 | 21 | 11 | 114 | 53 | 9 | 337 | 30 | 3 |
| 111 | 33 | 15 | 161 | 45 | 8 | 343 | 64 | 18 |
| 181 | 28 | 9 | 244 | 7 | 5 | 353 | 63 | 2 |
| 217 | 35 | −4 | 263 | 62 | 12 | 361 | 32 | −8 |
| 129 | 56 | 9 | 204 | 41 | 2 | | | |

COMPOSITION EXAMPLES

"Active ingredient" (a.i.) as used throughout these examples relates to a compound of formula (I), including any stereochemically isomeric form thereof, a pharmaceutically acceptable salt thereof or a solvate thereof; in particular to any one of the exemplified compounds.

Typical examples of recipes for the formulation of the invention are as follows:

1. Tablets

| | |
|---|---|
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| | |
|---|---|
| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A compound of formula (I)

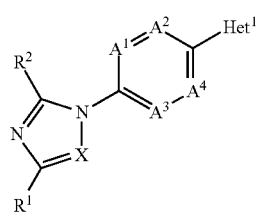

or a stereoisomeric form thereof, wherein
$R^1$ is $C_{1-4}$alkyl;
$R^2$ is hydrogen;
X is CH;
$A^1$ is $CR^{3a}$; wherein $R^{3a}$ is $C_{1-4}$alkyloxy optionally substituted with one or more halo substituents;
$A^2$ is N;
$A^3$ and $A^4$ are each CH;
$Het^1$ is formula (a)

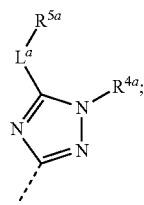

$R^{4a}$ is hydrogen; $Ar^1$; or $C_{1-6}$alkyl optionally substituted with one or more halo substituents;
wherein in the definition of $R^{4a}$, $Ar^1$ is phenyl optionally substituted with one or more substituents each independently selected from the group consisting of halo and $C_{1-4}$alkyl optionally substituted with one or more halo substituents;
$R^{5a}$ is $Ar^2$;
wherein
$Ar^2$ is phenyl optionally substituted with one or more substituents each independently selected from the group consisting of halo and $C_{1-4}$alkyl optionally substituted with one or more halo substituents;

$L^a$ represents $NR^9$
p represents 1 or 2; and,
$R^9$ is hydrogen,
or a pharmaceutically acceptable addition salt thereof.

2. The compound according to claim 1 or a stereoisomeric form thereof, wherein
$A^1$ is $CR^{3a}$ wherein $R^{3a}$ is $C_{1-4}$-alkyloxy;
$R^{4a}$ is $C_{1-6}$alkyl;
or a pharmaceutically acceptable addition salt thereof.

3. The compound according to claim 1 or a stereoisomeric form thereof, wherein
$Ar^2$ is phenyl optionally substituted with one or more substituents each independently selected from the group consisting of halo and methyl optionally substituted with one or more halo substituents
or a pharmaceutically acceptable addition salt thereof.

4. The compound according to claim 1, wherein
$A^1$ represents C—O—CH$_3$.

5. The compound according to claim 1, wherein
$A^1$ is $CR^{3a}$; wherein $R^{3a}$ is $C_{1-4}$-alkyloxy;
$R^{4a}$ is $C_{1-6}$alkyl;
$R^{5a}$ is phenyl substituted with one, two or three substituents each independently selected from the group consisting of halo and $C_{1-4}$-alkyl optionally substituted with one or more halo substituents;
and,
$L^a$ represents NH.

6. The compound according to claim 1, wherein the compound is
N-[3-fluoro-2-(trifluoromethyl)phenyl]-3-[6-methoxy-5-(4-methyl-1H-imidazol-1-yl)-2-pyridinyl]-1-methyl-1H-1,2,4-triazol-5-amine,
N-[2-fluoro-3-(trifluoromethyl)phenyl]-3-[6-methoxy-5-(4-methyl-1H-imidazol-1-yl)-2-pyridinyl]-1-methyl-1H-1,2,4-triazol-5-amine,
or
N-[2-fluoro-5-(trifluoromethyl)phenyl]-3-[6-methoxy-5-(4-methyl-1H-imidazol-1-yl)-2-pyridinyl]-1-methyl-1H-1,2,4-triazol-5-amine,
or a pharmaceutically acceptable addition salt thereof.

7. A pharmaceutical composition comprising a pharmaceutically acceptable carrier and, as active ingredient, a therapeutically effective amount of a compound as defined in any one of claims 1, 2, 3, 4, 5, or 6.

8. The compound according to claim 1, wherein the compound is N-[2-fluoro-5-(trifluoromethyl)phenyl]-3-[6-methoxy-5-(4-methyl-1H-imidazol-1-yl)-2-pyridinyl]-1-methyl-1H-1,2,4-triazol-5-amine or a pharmaceutically acceptable addition salt thereof.

9. The compound according to claim 8, wherein the compound is N-[2-fluoro-5-(trifluoromethyl)phenyl]-3-[6-methoxy-5-(4-methyl-1H-imidazol-1-yl)-2-pyridinyl]-1-methyl-1H-1,2,4-triazol-5-amine.

10. A compound of formula (I)

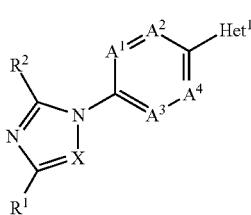

or a stereoisomeric form thereof, wherein
$R^1$ methyl;
$R^2$ is hydrogen;

X is CH;
A$^1$ is CR$^{3a}$; wherein R$^{3a}$ is —OCH$_3$ optionally substituted with one or more halo substituents;
A$^2$ is N;
A$^3$ and A$^4$ each are CH;
Het$^1$ is a heterocycle, having formula (a)

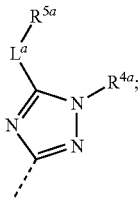
(a)

R$^{4a}$ is Ar$^1$; or C$_{1-6}$alkyl
wherein Ar$^1$ is phenyl optionally substituted with one or more substituents each independently selected from the group consisting of halo, and C$_{1-4}$-alkyl optionally substituted with one or more halo substituents;
R$^{5a}$ is Ar$^2$;
wherein
  Ar$^2$ is phenyl optionally substituted with one or more substituents each independently selected from the group consisting of halo and C$_{1-4}$-alkyl optionally substituted with one or more halo substituents
L$^a$ represents NR$^9$;
p represents 1 or 2; and,
R$^9$ is hydrogen;
or a pharmaceutically acceptable addition salt thereof.

11. The compound according to claim 10 or a stereoisomeric form thereof, wherein
A$^1$ is CR$^{3a}$ wherein R$^{3a}$ is —OCH$_3$;
R$^{4a}$ is C$_{1-6}$alkyl
or a pharmaceutically acceptable addition salt thereof.

12. The compound according to claim 10 or a stereoisomeric form thereof, wherein
Ar$^2$ is phenyl substituted with one or more substituents each independently selected from the group consisting of halo and C$_{1-4}$-alkyl optionally substituted with one or more halo substituents;
or a pharmaceutically acceptable addition salt thereof.

13. The compound according to claim 10, wherein A$^1$ represents C—O—CH$_3$.

14. The compound according to claim 10, wherein
R$^{4a}$ is C$_{1-6}$alkyl; and
R$^{5a}$ is phenyl substituted with one, two or three substituents each independently selected from the group consisting of halo, and C$_{1-4}$-alkyl optionally substituted with one or more halo substituents.

* * * * *